US011572569B2

(12) United States Patent
Long et al.

(10) Patent No.: US 11,572,569 B2
(45) Date of Patent: Feb. 7, 2023

(54) TRANSGENIC PLANTS WITH INCREASED PHOTOSYNTHESIS EFFICIENCY AND GROWTH

(71) Applicants: The Board of Trustees of the University of Illinois, Urbana, IL (US); The Regents of the University of California, Oakland, CA (US)

(72) Inventors: Stephen P. Long, Urbana, IL (US); Johannes Kromdijk, Champaign, IL (US); Katarzyna Glowacka, Champaign, IL (US); Krishna K. Niyogi, Oakland, CA (US); Laurie Leonelli, White Plains, NY (US); Stephane T. Gabilly, Walnut Creek, CA (US)

(73) Assignees: The Board of Trustees of The University Of Illinois, Urbana, IL (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/304,633

(22) PCT Filed: May 26, 2017

(86) PCT No.: PCT/US2017/034840
§ 371 (c)(1),
(2) Date: Nov. 26, 2018

(87) PCT Pub. No.: WO2017/205834
PCT Pub. Date: Nov. 30, 2017

(65) Prior Publication Data
US 2019/0161765 A1 May 30, 2019

Related U.S. Application Data

(60) Provisional application No. 62/342,248, filed on May 27, 2016.

(51) Int. Cl.
*C12N 15/82* (2006.01)
*C07K 14/415* (2006.01)
*C12N 9/02* (2006.01)

(52) U.S. Cl.
CPC .. *C12N 15/8269* (2013.01); *C12Y 110/99003* (2013.01); *C12Y 114/1309* (2013.01); *C07K 14/415* (2013.01); *C12N 9/0055* (2013.01); *C12N 9/0073* (2013.01)

(58) Field of Classification Search
CPC .......... C07K 14/415; C12Y 110/99003; C12Y 114/1309
See application file for complete search history.

(56) References Cited

U.S. PATENT DOCUMENTS

2006/0150283 A1  7/2006  Alexandrov et al.
2020/0283788 A1  9/2020  Long et al.

FOREIGN PATENT DOCUMENTS

| CA | 2300692 A1 | 8/2000 | |
|----|-----------|---------|---|
| CA | 2302828 A1 | 10/2000 | |
| CN | 109207508 A | 1/2019 | |
| EP | 1059354 A2 | 12/2000 | |
| EP | 1033405 A3 * | 8/2001 | ........... C07K 14/415 |
| WO | WO 1997/17447 | 5/1997 | |
| WO | WO-0040695 A2 | 7/2000 | |
| WO | WO 2008/069496 A1 | 6/2008 | |
| WO | WO-2016030885 A1 | 3/2016 | |

OTHER PUBLICATIONS

Kromdijk et al (Improving photosynthesis and crop productivity by accelerating recovery from photoprotection. Science. 354:857-861, 2016) (Year: 2016).*
And Luchi et al (A Stress-Inducible Gene for 9-cis-Epoxycarotenoid Dioxygenase Involved in Abscisic Acid Biosynthesis under Water Stress in Drought-Tolerant Cowpea. Plant Physiology, vol. 123, pp. 553-562, 2000) (Year: 2000).*
Zhang et al (MsZEP, a novel zeaxanthin epoxidase gene from alfalfa (*Medicago sativa*), confers drought and salt tolerance in transgenic tobacco. Plant Cell Rep 35:439-453, published online Nov. 2015). (Year: 2015).*
Kromdijk et al (Improving photosynthesis and crop productivity by accelerating recovery from photoprotection. Science. 354:857-861. Nov. 2016 (Year: 2016).*
Hieber et al (Significance of the Lipid Phase in the Dynamics and Functions of the Xanthophyll Cycle as Revealed by PsbS Overexpression in Tobacco and In-vitro De-epoxidation in Monogalactosyldiacylglycerol Micelles. Plant Cell Physiol. 45(1): 92-102, 2004), (Year: 2004).*
Lambrev et al (On the relationship between non-photochemical quenching and photoprotection of Photosystem II. / Biochimica et Biophysica Acta 1817:760-769, 2012). (Year: 2012).*
Pinnola et al (Zeaxanthin Binds to Light-Harvesting Complex Stress-Related Protein to Enhance Nonphotochemical Quenching in Physcomitrella patens. The Plant Cell, vol. 25: 3519-3534, 2013). (Year: 2013).*
Coesel et al (Evolutionary Origins and Functions of the Carotenoid Biosynthetic Pathway in Marine Diatoms. PLOS ONE. 3: 1-16, 2008). (Year: 2008).*

(Continued)

*Primary Examiner* — Charles Logsdon
*Assistant Examiner* — Wayne Zhong
(74) *Attorney, Agent, or Firm* — Tom Hunter; Weaver Austin Villeneuve & Sampson LLP

(57) ABSTRACT

The present disclosure provides a transgenic plant comprising one or more nucleotide sequences encoding polypeptides selected from photosystem II subunit S (PsbS), zeaxanthin epoxidase (ZEP), and violaxanthin de-epoxidase (VDE), operably linked to at least one expression control sequence. Expression vectors for making transgenic plants, and methods for increasing biomass production and/or carbon fixation and/or growth in a plant comprising increasing expression of at least one of PsbS, ZEP and VDE polypeptides are also provided.

22 Claims, 52 Drawing Sheets

Specification includes a Sequence Listing.

(56) References Cited

OTHER PUBLICATIONS

Liu et al (Comparative analysis of carotenoid accumulation in two goji (Lycium barbarum L. and L. ruthenicum Murr.) fruits. BMC Plant Biology, 14:269, 2014). (Year: 2014).*
Iuchi et al (A Stress-Inducible Gene for 9-cis-Epoxycarotenoid Dioxygenase Involved in Abscisic Acid Biosynthesis under Water Stress in Drought-Tolerant Cowpea. Plant Physiology, vol. 123, pp. 553-562, 2000). (Year: 2000).*
Izumi et al (RBCS1A and RBCS3B, two major members within the *Arabidopsis* RBCS multigene family, function to yield sufficient Rubisco content for leaf photosynthetic capacity. Journal of Experimental Botany, vol. 63, No. 5, pp. 2159-2170, 2012). (Year: 2012).*
Vogl et al (A Toolbox of Diverse Promoters Related to Methanol Utilization: Functionally Verified Parts for Heterologous Pathway Expression in Pichia pastoris. ACS Synth. Biol. 5, 172-186, published 2015). (Year: 2015).*
Hieber et al., "Significance of the lipid phase in the dynamics and functions of the xanthophyll cycle as revealed by PsbS overexpression in tobacco and in-vitro deepoxidation in monogalactosyldiacylglycerol micelles," *Plant Cell Physiology*, vol. 45, No. 1, pp. 92-102, 2004.
Murchie et al., "Manipulation of Photoprotection to Improve Plant Photosynthesis," *Plant Physiology*, vol. 155, No. 1, pp. 86-92, 2011.
Zhu et al., "The slow reversibility of photosystem II thermal energy dissipation on transfer from high to low light may cause large losses in carbon gain by crop canopies: A theoretical analysis," *Journal of Experimental Botany*, vol. 55, No. 400, pp. 1167-1175, 2004.
Zia et al., "Acclimation- and mutation-induced enhancement of PsbS levels affects the kinetics of non-photochemical quenching in *Arabidopsis thaliana*," *Planta*, vol. 233, No. 6, pp. 1253-1264, 2011.
PCT International Search Report and Written Opinion dated Jul. 26, 2017 issued in PCT/US2017/034840.
PCT International Preliminary Report on Patentability dated Nov. 27, 2018 issued in PCT/US2017/034840.
EP Office Action dated Jan. 15, 2020 issued in EP 17729973.2.
EP Office Action dated Oct. 29, 2020 issued in EP 17729973.2.
Busch (2014) "Opinion: the red-light response of stomatai movement is sensed by the redox state of the photosynthetic electron transport chain," Photosynth. Res., 119:131-140 [11 pages], Epub Mar. 13, 2013, doi: 10.1007/s11120-013-9805-6.
Glowacka et al. (2018) "Photosystem II Subunit S overexpression increases the efficiency of water use in a field-grown crop," Nat. Commun., 9: 868 [9 pages], doi: 10.1038/s41467-018-03231-x.
Huang et al. (2019) "The *Arabidopsis* Transcriptome Responds Specifically and Dynamically to High Light Stress" Cell Reports, 29: 4186-99.
Müller et al. (2001) "Non-photochemical quenching. A response to excess light energy." *Plant Physiol.*, 125: 1558-1566, doi: 10.1104/pp.125.4.1558.
Ruban (2016) "Nonphotochemical chlorophyll fluorescence quenching: mechanism and effectiveness in protecting plants from photodamage." *Plant Physiol.* 170: 1903-1916, doi: 10.1104/pp.15.01935.
JP Office Action dated Jun. 22, 2021 issued in JP 2018-561589.
Ali, S. B. et al., "Genetic and Epigenetic Characterization of the cry1Ab Coding Region and its 3' Flanking Genomic Region in MON810 Maize using Next-Generation Sequencing", European Food Research and Technology, 2018, vol. 244, pp. 1473-1485.
Anderson, J. et al., "Antagonistic Interaction Between Abscisic Acid and Jasmonate-ethylene Signaling Pathways Modulates Defense Gene Expression and Disease Resistance in *Arabidopsis*", The Plant cell, Dec. 2004, vol. 16, No. 12, pp. 3460-3479.
Arnoux, P. et al., "A Structural Basis for the pH-dependent Xanthophyll Cycle in *Arabidopsis thaliana*", The Plant cell, Jul. 2009, vol. 21, No. 7, pp. 2036-2044.
Audran, C. et al., "Localisation and expression of zeaxanthin epoxidase mRNA in *Arabidopsis* in response to drought stress and during seed development", 2001, 28, pp. 1161-1173.
Barrero, J. et al., "A Mutational Analysis of the ABA1 Gene of *Arabidopsis thaliana* Highlights the Involvement of ABA in Vegetative Development", Journal of Experimental Botany, Aug. 2005, vol. 56, No. 418, pp. 2071-2083.
Barrero, J. M. et al., "The ABA1 Gene and Carotenoid Biosynthesis are Required for Late Skotomorphogenic Growth in *Arabidopsis thaliana*", Plant, Cell and Environment, Feb. 2008, vol. 31, No. 2, pp. 227-234.
Bugos, R. C. et al., "Xanthophyll Cycle Enzymes are Members of The Lipocalin Family, The First Identified from Plants", The Journal of Biological Chemistry, Jun. 19, 1998, vol. 273, No. 25, pp. 15321-15324.
Cheng, C. et al., "AraportH: A Complete Reannotation of the *Arabidopsis thaliana* Reference Genome", Feb. 2017, vol. 89, No. 4, pp. 789-804.
EP Office Action dated Nov. 19, 2021, in Application No. EP17729973.2.
Hall, M. et al., "Thioredoxin Targets of The Plant Chloroplast Lumen and their Implications for Plastid Function", Proteomics, Mar. 2010, vol. 10, No. 5, pp. 987-1001.
Havaux, M. et al., "Photodamage of The Photosynthetic Apparatus and its Dependence on the Leaf Developmental Stage in The npq1 *Arabidopsis* Mutant Deficient in the Xanthophyll Cycle Enzyme Violaxanthin De-epoxidase", Plant Physiology, Sep. 2000, vol. 124, No. 1, pp. 273-284.
Havaux, M. et al., "The Effect of Zeaxanthin as the Only Xanthophyll on the Structure and Function of the Photosynthetic Apparatus in *Arabidopsis thaliana*", The Journal of Biological Chemistry, Apr. 2, 2004, vol. 279, No. 14, pp. 13878-13888.
Hieber, A. D. et al., "Overexpression of Violaxanthin De-epoxidase: Properties of C-terminal Deletions on Activity and pH-dependent Lipid Binding", Planta, Jan. 2002, vol. 214, No. 3, pp. 476-483.
Jakab, G. et al., "Enhancing *Arabidopsis* Salt and Drought Stress Tolerance by Chemical Priming for its Abscisic Acid Responses", Plant Physiology, Sep. 2005, vol. 139, No. 1, pp. 267-274.
Kalituho, L. et al., "The Transiently Generated Nonphotochemical Quenching of Excitation Energy in *Arabidopsis* Leaves Is Modulated by Zeaxanthin", Plant Physiology, Apr. 2007, vol. 143, pp. 1861-1870.
Kayoko, Y. et al., "Empirical Analysis of Transcriptional Activity in the *Arabidopsis* Genome", Science, Oct. 31, 2003, vol. 302, No. 5646, pp. 842-846.
Koornneef, M. et al., "In Vivo Inhibition of Seed Development and Reserve Protein Accumulation in Recombinants of Abscisic Acid Biosynthesis and Responsiveness Mutants in *Arabidopsis thaliana*", Plant Physiology, Jun. 1989, vol. 90, No. 2, pp. 463-469.
KR Office Action dated Apr. 1, 2022, in Application No. KR1020187037434 with English translation.
Lu, Y et al., "Identification of Potential Targets for Thylakoid Oxidoreductase AtVKOR/LTO1 in Chloroplasts", Protein and Peptide Letters, 2015, vol. 22, No. 3, pp. 219-225.
Merlot, S. et al., "Use of Infrared Thermal Imaging to Isolate *Arabidopsis* Mutants Defective in Stomatai Regulation", The Plant Journal: for Cell and Molecular Biology, Jun. 2002, vol. 30, No. 4, pp. 601-609.
Müller-Moulé, P. et al., "Ascorbate Deficiency Can Limit Violaxanthin De-epoxidase Activity in Vivo", Plant Physiology, Mar. 2002, vol. 128, No. 3, pp. 970-977.
Morillon, R. et al., "The Role of ABA and the Transpiration Stream in the Regulation of the Osmotic Water Permeability of Leaf Cells", Proceedings of the National Academy of Sciences of the United States of America, Nov. 20, 2001, vol. 98, No. 24, pp. 14138-14143.
Niyogi, K. et al., "Arabidopsis Mutants Define a Central Role for The Xanthophyll Cycle in the Regulation of Photosynthetic Energy Conversion", The Plant Cell, Jul. 1998, vol. 10, No. 7, pp. 1121-1134.
Nowicka, B. et al., "New Transgenic Line of *Arabidopsis thaliana* with Partly Disabled Zeaxanthin Epoxidase Activity Displays Changed Carotenoid Composition, Xanthophyll Cycle Activity and Non-photochemical Quenching Kinetics", Journal of Plant Physiology, 2009, vol. 166, pp. 1045-1056.
Park, H.Y. et al., "Overexpression of *Arabidopsis* Zep Enhances Tolerance to Osmotic Stress", Biochemical and Biophysical Research Communications, Oct. 10, 2008, vol. 375, No. 1, pp. 80-85.

(56) References Cited

OTHER PUBLICATIONS

Raz, V. et al., "Sequential Steps for Developmental Arrest in *Arabidopsis* Seeds", Development (Cambridge, England), Jan. 2001, vol. 128, vol. 2, pp. 243-252.

Sato, S. et al., "Structural analysis of *Arabidopsis thaliana* chromosome 5. X. Sequence features of the regions of 3,076,755 bp covered by sixty P1 and TAC clones". DNA Research, Feb. 28, 2000, vol. 7, No. 1, pp. 31-63.

Schubert, M. et al., "Proteome Map of The Chloroplast Lumen of *Arabidopsis thaliana*", The Journal of Biological Chemistry, Mar. 8, 2002, vol. 277, No. 10, pp. 8354-8365.

Takahashi, N. et al., "Hydrotropism in Abscisic Acid, Wavy, and Gravitropic Mutants of *Arabidopsis Thaliana*", Planta, Dec. 2002, vol. 216, No. 2, pp. 203-211.

Theologis, A. et al., "Sequence and Analysis of Chromosome 1 of the Plant *Arabidopsis thaliana*", Nature, Dec. 2000, vol. 408, No. 6814, pp. 816-820.

Ton, J. et al., "Beta-amino-butyric Acid-induced Resistance Against Necrotrophic Pathogens is Based on ABA-dependent Priming for Callose", The Plant journal: for cell and molecular biology, Apr. 2004, vol. 38, No. 1, pp. 119-130.

Ton, J. et al., "Dissecting the Beta-aminobutyric Acid-induced Priming Phenomenon in *Arabidopsis*", Mar. 2005, vol. 17, No. 3, pp. 987-999.

U.S. Non Final office Action dated Apr. 8, 2022 in U.S. Appl. No. 16/808,881.

U.S. Restriction Requirement dated Oct. 7, 2021, in U.S. Appl. No. 16/808,881.

Willing, E. M. et al., "Genome Expansion of Arabis Alpina Linked with Retrotransposition and Reduced Symmetric DNA Methylation", Nature plants, Feb. 2, 2015, vol. 1, No. 14023, pp. 1-7.

Xiong, L. et al., "Regulation of Osmotic Stress-responsive Gene Expression by the LOS6/ABA1 Locus in *Arabidopsis*", The Journal of Biological Chemistry, Mar. 8, 2002, vol. 277, No. 10, pp. 8588-8596.

Yamamoto, H. Y. "Functional Roles of the Major Chloroplast Lipids in the Violaxanthin Cycle", Planta, Aug. 2006, vol. 224, No. 3, pp. 719-724.

Zhang, L. et al., "Global Analysis of Gene Expression Profiles in Physic Nut (*Jatropha Curcas* L.) Seedlings Exposed to Salt Stress", PLoS One, May 16, 2014, vol. 9, No. 5, pp. 1-9.

* cited by examiner

Fitted time constants induction NPQ:

| NPQ | first induction (single exponential) | second induction (2-phase exponential) | | third induction (2-phase exponential) | |
|---|---|---|---|---|---|
| | τ (s) | τ₁ (s) | τ₂ (s) | τ₁ (s) | τ₂ (s) |
| N2-23 | 63.4 | 13.5 | 127.3 | 10.1 | 55.3 |
| N2-34 | 49.3 | 11.3 | 111.1 | 10.2 | 53.8 |
| N2-56 | 91.4 | 12.9 | 384.5 | 10.0 | 32.5 |
| WT | 82.7 | 5.5 | 115.3 | 4.3 | 37.2 |

Fitted time constants relaxation NPQ:

| | first relaxation (2-phase exponential) | | second relaxation (2-phase exponential) | | dark relaxation (2-phase exponential) | |
|---|---|---|---|---|---|---|
| | $\tau_1$ (s) | $\tau_2$ (s) | $\tau_1$ (s) | $\tau_2$ (s) | $\tau_1$ (s) | $\tau_2$ (s) |
| N2-23 | 1175.3 | 5.6 | 470.1 | 7.7 | 792.6 | 13.3 |
| N2-34 | 511.5 | 14.6 | 461.5 | 9.9 | 692.6 | 19.4 |
| N2-56 | 445.9 | 0.3 | 461.4 | 9.9 | 774.6 | 13.2 |
| WT | 564.9 | 10.4 | 886.4 | 9.2 | 2641.4 | 21.4 |

Fitted time constants dark relaxation $\phi_{PSII}$:

| | dark relaxation (2-phase exponential) | |
|---|---|---|
| | $\tau_1$ (s) | $\tau_2$ (s) |
| N2-23 | 20.4 | 103.0 |
| N2-34 | 14.2 | 85.6 |
| N2-56 | 7.9 | 70.3 |
| WT | 29.1 | 349.4 |

FIG. 16

| Plants | Date of first coppicing (early flowering stage) | Wet weight (Grams) of 36 plants | Dry weight (Grams) of 36 plants | Percentage of wet weight |
|---|---|---|---|---|
| 515 (ZEP/PSBS) | Day1+19 | 5,791 | 311 (-0.6%) | 5.37 |
| 675 (ZEP/VDE) | Day1+19 | 6,823 | 399 (+27.5%) | 5.85 |
| 770 (PSBS) | Day1+19 | 5,463 | 306 (-2.2%) | 5.60 |
| null | Day1+19 | 5,623 | 313 | 5.56 |

Photosystem II subunit S (PSBS)
CLUSTAL O(1.2.4) multiple sequence alignment

```
(SEQ ID NO: 10) XP_008466710.1    MAAQTMLLTSGVCVGHGVCLKRELSLRP------NNNQFTRLFFNPLPNHSVSL-PARGF
(SEQ ID NO: 11) XP_004150442.1    MAAQTMLLTSGVCVGHGVCLKRELSLRP------NYTQFTRLFFNPLPSHSVSL-PPRGF
(SEQ ID NO: 12) XP_006393723.1    -MAQTMMLTSGVSANQFLRNKSPLAQ--------PKVHHLFLSGNSPVVIPS-RRQSL
(SEQ ID NO: 13) NP_175092.1       -MAQTMLLTSGVTAGHFLRNKSPLAQ--------PKVHHLFLSGNSPVALPS-RRQSF
(SEQ ID NO: 14) XP_002891292.1    -MAQTMLLTSGVSAGQFLRNKSPLAQ--------PKVHHLFLSGNSPVVLPS-RRQSF
(SEQ ID NO: 15) XP_010500150.1    -MAQTMLLTSGVSAGQFLRNKNPLAQ--------PKVHHLFLSGTSPVALPS-RRQSF
(SEQ ID NO: 16) XP_006304103.1    -MAQTMLLTSGVSAGQFLRNKNPLAQ--------PKVHQLFLSGTSPVALPS-RRQSF
(SEQ ID NO: 17) JAU12851.1        -MAQTMLLTSGVSANQFLRNKNPLAQ--------PKIQHLFLSGNSPVALPS-RRPSF
(SEQ ID NO: 18) XP_013681211.1    -MAQTMLLTSGISANHFLRNKNPLAQ--------PKVHHLFLSGNSPVTLPS-RIPSL
(SEQ ID NO: 19) XP_018447609.1    -MAQTMLLTSGISANHFLRNKNPLAQ--------PKVHHLFLSGNSPVTLPS-RRPSL
(SEQ ID NO: 20) XP_009109479.1    -MAQTMLLTSGISANFFLRNKNPLAQ--------PKVHHLFLSGNSPVTLPS-RRPSL
(SEQ ID NO: 21) XP_018467982.1    -MAQTMLLTSGVSANTFLRNKNPLAQ--------PKVHHLFLSGNSHVTLPS-RRPSL
(SEQ ID NO: 22) XP_013592876.1    -MAQTMLLTSGVSANQFLRNKNPLAQ--------PKVHHLFLSGNSHVVLPS-RRPSL
(SEQ ID NO: 23) XP_009123055.1    -MAQTMLLTSGVSANQFLRNKNPLAQ--------PKVHHFFLSGNSHVVLPS-RRPSL
(SEQ ID NO: 24) XP_008783427.1    -MVHAVFT--SGLGAHLPDSKREPLLQSLRRLRPTPFSHLLLSQPSHKQLPSPSYSSYT
(SEQ ID NO: 25) JAT63827.1        -MAQSMLM--SSLGSRIVETKGEPLLQFQIRRLRPTPATHLLLPPPTRRHPLP---PSYA
(SEQ ID NO: 26) GAU40978.1        -MAQTMLLMSSVSSIYSSTYSVPLNKDPLLQCQRLRSRI--SDVSFNPLSSNSKSL-SSRTF
(SEQ ID NO: 27) AKG94171.1        -MAQTMLLMSSVSSIYSSTYSVPLNKDPLLQLQRLKPRF--SDISFSPLSSNSKSF-SSRTF
(SEQ ID NO: 28) XP_010692414.1    -MAQAMLLMPSVSTTNTIDLKRNALLKIQIQKIKPKSSSSHLFFSPLSSSS-S---SSSTF
(SEQ ID NO: 29) GAV71974.1        -MAQTMLLMCGISTSHVVDLRRDPLFHVQIQKLRPKSF-SHLFFNPLSNNGFS---LAQKF
                                        :                                .    :   .  :
```

FIG. 24A

| | | |
|---|---|---|
| (SEQ ID NO: 10) | XP_008466710.1 | TPLAVFKSRTKAPPKKV-EKPKQKVEDGIFGTSGGIGFTKQNELFVGRVAMIGFAASLLG |
| (SEQ ID NO: 11) | XP_004150442.1 | TTLAVFKSRTKAPPKKV-EKPKQKVEDGIFGTSGGIGFTKQNELFVGRVAMIGFAASLLG |
| (SEQ ID NO: 12) | XP_006393723.1 | VPLALFKPKTKAAPKKV-EKVKPKVEDGIFGTSGGIGFTKANELFVGRVAMIGFAASLLG |
| (SEQ ID NO: 13) | NP_175092.1 | VPLALFKPKTKAAPKKV-EKPKSKVEDGIFGTSGGIGFTKANELFVGRVAMIGFAASLLG |
| (SEQ ID NO: 14) | XP_002891292.1 | VPLALFKPKTKAAPKKV-EKPKKKVEDGIFGTSGGIGFTKANELFVGRVAMIGFAASLLG |
| (SEQ ID NO: 15) | XP_010500150.1 | VPLALFKPKTKAAPKKV-VKPKDKVEDGIFGTSGGIGFTKANELFVGRVAMIGFAASLLG |
| (SEQ ID NO: 16) | XP_006304103.1 | VPLALFKPKTKAAPKKV-EKVKPKVEDGIFGTSGGIGFTKQNELFVGRVAMIGFAASLLG |
| (SEQ ID NO: 17) | JAU12851.1 | VPLALFKPKTKAAPKKV-EKAKPKVEDGIFGTSGGIGFTKQNELFVGRVAMIGFAASLLG |
| (SEQ ID NO: 18) | XP_013681211.1 | VPLAIFKPKTKAAPKKV-EKVKPKVEDGIFGTSGGIGFTKQNELFVGRVAMIGFAASLLG |
| (SEQ ID NO: 19) | XP_018447609.1 | VPLAIFKPKTKAAPKKV-EKVKPKVEDGIFGTSGIGFTKQNELFVGRVAMIGFAASLLG |
| (SEQ ID NO: 20) | XP_009109479.1 | VPLAIFKPKTKAAPKKV-EKVKPKVEDGIFGTSGGIGFTKQNELFVGRVAMIGFAASLLG |
| (SEQ ID NO: 21) | XP_018467982.1 | VPLAIFKPKTKAAPKKV-EKVKPKVEDGIFGTSGGIGFTKQNELFVGRVAMIGFAASLLG |
| (SEQ ID NO: 22) | XP_013592876.1 | VPLAIFKPKTKAAPKKV-EKAKPKVEDGIFGTSGGIGFTKQNELFVGRVAMIGFAASLLG |
| (SEQ ID NO: 23) | XP_009123055.1 | VPLAIFKPKTKAAPKKV-EKAKPKVEDGIFGTSGGIGFTKQNELFVGRVAMIGFAASLLG |
| (SEQ ID NO: 24) | XP_008783427.1 | PVLAIFKSKTKAAPKKV-EKGNFKVEDGIFGTSGGIGFTKQNELFVGRVAMIGFAASLLG |
| (SEQ ID NO: 25) | JAT63827.1 | PTLALFKSKTKAAPKKV-V-KPKPKVEDGIFGTSGGFGFTKQNELFVGRVAMIGFAASLLG |
| (SEQ ID NO: 26) | GAU40978.1 | TTLALFKSKTKAPAKV-VPKQKPKVEDGVFGTSGGFGFTKQNELFVGRVAMIGFAASLLG |
| (SEQ ID NO: 27) | AKG94171.1 | KTLALFKPKTKAPVKKV-EKPKLKVEDGLFGTSGGIGFTKENELFVGRVAMIGFAASLLG |
| (SEQ ID NO: 28) | XP_010692414.1 | KTIALFKSKTKAAPKKVATTAKPKVEDGIFGTSGGIGFTKQNELFVGRVAMIGFAASLLG |
| (SEQ ID NO: 29) | GAV71974.1 | NTLALFKPKTKAAPKKV-EKPKLKVEDGIFGTSGGIGFTKQNELFVGRVAMIGFAASLLG |
| | | *  *:*** ::*.* * . *       * *  *::.****  **** |

FIG. 24A
(Continued)

```
(SEQ ID NO: 10) XP_008466710.1  EALTGKGILAQLNLETGIPITEAEPLLLFFILFTLLGAIGALGDRGKFIDDPEPATGLER
(SEQ ID NO: 11) XP_004150442.1  EALTGKGILAQLNLETGIPITEAEPLLLFFILFTLLGAIGALGDRGKFIDDPEPATGLER
(SEQ ID NO: 12) XP_006393723.1  EAVTGKGILAQLNLETGIPIYEAEPLLLFFILFTLLGAIGALGDRGKFVDDPPTPTGLEK
(SEQ ID NO: 13) NP_175092.1     EALTGKGILAQLNLETGIPIYEAEPLLLFFILFTLLGAIGALGDRGKFVDDPP---TGLEK
(SEQ ID NO: 14) XP_002891292.1  EALTGKGILAQLNLETGIPIYEAEPLLLFFILFTLLGAIGALGDRGQFVDDPP---TGLEK
(SEQ ID NO: 15) XP_010500150.1  EALTGKGILAQLNLETGIPIYEAEPLLLFFILFTLLGAIGALGDRGKFVDDPP---TGLEK
(SEQ ID NO: 16) XP_006304103.1  EALTGKGILAQLNLETGIPIYEAEPLLLFFILFTLLGAIGALGDRGKFVDDPP---TGLEK
(SEQ ID NO: 17) JAU12851.1      EALTGKGILAQLNLETGIPIYEAEPLLLFFILFTLLGAIGALGDRGKFVDDPP---TGLEK
(SEQ ID NO: 18) XP_013681211.1  EALTGKGILAQLNLETGIPIYEAEPLLLFFILFTLLGAIGALGDRGKFVDDPP---TGLEK
(SEQ ID NO: 19) XP_018447609.1  EALTGKGILAQLNLETGIPIYEAEPLLLFFILFTLLGAIGALGDRGKFVDDPP---TGLEK
(SEQ ID NO: 20) XP_009109479.1  EALTGKGILAQLNLETGIPIYEAEPLLLFFILFTLLGAIGALGDRGKFVDDPP---TGLEK
(SEQ ID NO: 21) XP_018467982.1  EALTGKGILAQLNLETGIPIYEAEPLLLFFILFTLLGAIGALGDRGKFVDDPP---TGLEK
(SEQ ID NO: 22) XP_013592876.1  EALTGKGILAQLNLETGIPIYEAEPLLLFFILFTLLGAIGALGDRGKFVDDPP---TGLEK
(SEQ ID NO: 23) XP_009123055.1  EALTGKGILAQLNLETGIPIYEAEPLLLFFILFTLLGAIGALGDRGKFVDDPP---TGLEK
(SEQ ID NO: 24) XP_008783427.1  EALTGKGILAQLNLETGIPIYEAEPLLLFFILFTLLGAIGALGDRGKFVDDPP---TGLEK
(SEQ ID NO: 25) JAT63827.1      EALTGKGILAQLNLETGIPIYEAEPLLLFFILFTLLGAIGALGDRGKFVDDEP--TT--G
(SEQ ID NO: 26) GAU40978.1      EGLTGKGILSQLNLETGIPIYEAEPLLLFFILFTLLGAIGALGDRGKFVDDEP---TGLEK
(SEQ ID NO: 27) AKG94171.1      EGLTGKGILSQLNLETGIPIYEAEPLLLFFILFTLLGAIGALGDRGRFVDDEP--TT--G
(SEQ ID NO: 28) XP_010692414.1  EGLTGKGILSQLNLETGIPIYEAEPLLLFFILFTLLGAIGALGDRGRFVDDPP---TGLEK
(SEQ ID NO: 29) GAV71974.1      EAVTGKGILSQLNLETGIPIYEAEPLLLFFILFTLLGAIGALGDRGRFVDDEP---TGLEK
                                *  ***** ********* *********************** ****:    *   *
```

FIG. 24A
(Continued)

| (SEQ ID NO: 10) | XP_008466710.1 | AVIPPGKSFRSALGLKEGGPLFGFTKANELFVGRLAQLGIAFSLIGEIITGKGALAQLNI |
| (SEQ ID NO: 11) | XP_004150442.1 | AVIPPGKSFRSALGLKEGGPLFGFTKANELFVGRLAQLGFAFSLIGEIITGKGALAQLNI |
| (SEQ ID NO: 12) | XP_006393723.1 | AVIAPGKNVRSALGLKEGGPLFGFTKANELFVGRLAQLGFAFSLIGEIITGKGALAQLNI |
| (SEQ ID NO: 13) | NP_175092.1 | AVIAPGKNVRSALGLKEQGPLFGFTKANELFVGRLAQLGIAFSLIGEIITGKGALAQLNI |
| (SEQ ID NO: 14) | XP_002891292.1 | AVIAPGKNVRSALGLKEQGPLFGFTKANELFVGRLAQLGIAFSLIGEIITGKGALAQLNI |
| (SEQ ID NO: 15) | XP_010500150.1 | AVIPPGKGVRSALGLKEGGPLFGFTKANELFVGRLAQLGIAFSLIGEIITGKGALAQLNI |
| (SEQ ID NO: 16) | XP_006304103.1 | AVIPPGKGVRSALGLKEQGPLFGFTKANELFVGRLAQLGIAFSLIGEIITGKGALAQLNI |
| (SEQ ID NO: 17) | JAU12851.1 | AVIPPGKGVRSALGLKEQGPLFGFTKSNELFVGRLAQLGIAFSLIGEIITGKGALAQLNI |
| (SEQ ID NO: 18) | XP_013681211.1 | AVIPPGKGVRSALGLKEQGPLFGFTKANELFVGRLAQLGIAFSLIGEIITGKGALAQLNI |
| (SEQ ID NO: 19) | XP_018447609.1 | AVIPPGKGVRSALGLKEQGPLFGFTKANELFVGRLAQLGIAFSLIGEIITGKGALAQLNI |
| (SEQ ID NO: 20) | XP_009109479.1 | AVIPPGKGVRSALGLKEQGPLFGFTKANELFVGRLAQLGIAFSLIGEIITGKGALAQLNI |
| (SEQ ID NO: 21) | XP_018467982.1 | AVIPPGKGVRSALGLKEQGPLFGFTKANELFVGRLAQLGIAFSIIGEIVTGKGALAQLNI |
| (SEQ ID NO: 22) | XP_013592876.1 | AVIPPGKGVRSALGLKEQGPLFGFTKANELFVGRLAQLGIAFSIIGEIITGKGALAQLNI |
| (SEQ ID NO: 23) | XP_009123055.1 | AVIPPGKGIRSALGLKEGGPLFGFTKSNELFVGRLAQLGIAFSIIGEIVTGKGALAQLNI |
| (SEQ ID NO: 24) | XP_008783427.1 | AVVPPGKGFRSSLGLREGGPLFGFTKSNELFVGRLAQLGFVFFSLIGEIITGKGALAQLNV |
| (SEQ ID NO: 25) | JAT63827.1 | GVIPPGKGFRAALGLSEGGPLFGFTKSNELFVGRLAQLGFVFSLIGEIITGKGALAQLNI |
| (SEQ ID NO: 26) | GAU40978.1 | GVIPPGKGFRQALGLREGGPLFGFTKSNELFVGRLAQLGFAFSLIGEIITGKGALAQLNI |
| (SEQ ID NO: 27) | AKG94171.1 | AVIPPGKNVRSALGLREGGPLFGFTKSNELFVGRLAQLGFAFSIIGEIITGKGALAQLNI |
| (SEQ ID NO: 28) | XP_010692414.1 | AVIPPGKGIRGALGLIREGGPLFGFTKSNELFVGRLAQLGIAFSIIGEIITGKGALAQLNI |
| (SEQ ID NO: 29) | GAV71974.1 | .*:.*.. : .*. * *:.** .***.*:.****.. ..*  |

FIG. 24A
(Continued)

| SEQ ID | Accession | Sequence |
|---|---|---|
| (SEQ ID NO: 10) | XP_008466710.1 | ETGVPINEIEPLVLLNVVFFFIAAVNPGTGKFVTDEEDDE |
| (SEQ ID NO: 11) | XP_004150442.1 | ETGVPINEIEPLVLLNVVFFFIAAVNPGTGKFVTDEEDDE |
| (SEQ ID NO: 12) | XP_006393723.1 | ETGIPIQDIEPLVLLNVAFFFAAINPGNGKFITDEGEDM |
| (SEQ ID NO: 13) | NP_175092.1 | ETGIPIQDIEPLVLLNVAFFFAAINPGNGKFITDDGEES |
| (SEQ ID NO: 14) | XP_002891292.1 | ETGIPIQDIEPLVLLNVAFFFAAINPGNGKFITDDGEES |
| (SEQ ID NO: 15) | XP_010500150.1 | ETGIPIQDIEPLVLLNVAFFFAAINPGNGKFITDDGEES |
| (SEQ ID NO: 16) | XP_006304103.1 | ETGIPIQDIEPLVLLNVAFFFAAINPGNGKFITDDGEES |
| (SEQ ID NO: 17) | JAU12851.1 | ETGIPIQDIEPLVLLNVAFFFAAINPGNGKFITDDGEES |
| (SEQ ID NO: 18) | XP_013681211.1 | ETGIPIQDIEPLVLLNVAFFFAAINPGNGKFITDDGEES |
| (SEQ ID NO: 19) | XP_018447609.1 | ETGIPIQDIEPLVLLNVAFFFAAINPGNGKFITDDGEES |
| (SEQ ID NO: 20) | XP_009109479.1 | ETGIPIQDIEPLVLLNVAFFFAAINPGNGKFITDDGEES |
| (SEQ ID NO: 21) | XP_018467982.1 | ETGIPIQDIEPLVLLNVAFFFAAINPGNGKFITDDGEES |
| (SEQ ID NO: 22) | XP_013592876.1 | ETGIPIQDIEPLVLFNVIFFFAAINPGNGKFITDDGEES |
| (SEQ ID NO: 23) | XP_009123055.1 | ETGIPIQDIEPLVLFNVIFFFAAINPGNGKFITDDGEER |
| (SEQ ID NO: 24) | XP_008783427.1 | ETGVPINEIEPLVLFNVVFFFLAALNPGTGKFVTDVEEE |
| (SEQ ID NO: 25) | JAT63827.1 | ETGVPISDIEPLVLLNVVFFFLAALNPGTGQFVTDDGED- |
| (SEQ ID NO: 26) | GAU40978.1 | ETGVPITEIEPLVLFNVIFFFLAALNPGTGTFVTDEEED- |
| (SEQ ID NO: 27) | AKG94171.1 | ETGVPINEIEPLVLFNVIFFFIAAINPGTGKFVTDEEED- |
| (SEQ ID NO: 28) | XP_010692414.1 | ETGVPVNEIEPLVLFNVLFFFIAAINPGTGKFITDEEE-- |
| (SEQ ID NO: 29) | GAV71974.1 | ETGIPINEIEPLVLFNVIFFFFAALNPGTGKFVTDEEAED |
|  |  | ***:*:. :. :*****:.: ****.* *:**.* |

FIG. 24A (Continued)

```
Zeaxanthin epoxidase (ZEP)
CLUSTAL O(1.2.4) multiple sequence alignment (SEQ ID NO: 30)  XP_010547517.1   ----------------------------------------MGSTLFCSPVNPSLSKLDFSRTHLLSPADKHFFLDLPSFMGK
(SEQ ID NO: 31)  KFK28343.1       ----------------------------------------MGSTPFCYTINPSPSKLDFTKTHL----AKQFYLDLSSFTGK
(SEQ ID NO: 32)  XP_010444704.1   ----------------------------------------MGSTPFCYSINPSPSKLDFTRTHVFSPVSKQFYLDLSSFTGK
(SEQ ID NO: 33)  XP_010484561.1   ----------------------------------------MGSTPFCYSINPSPSKLDFTRTHVFSPVSKQFYLDLSSFTGK
(SEQ ID NO: 34)  XP_006280131.1   ----------------------------------------MGSTPFCYSINPSPSKLDFTRTHVFSPVAKQFYLDLSSFTGK
(SEQ ID NO: 35)  NP_851285.1      ----------------------------------------MGSTLFCYSINPSPSKLDFTRTHVFSPVSKQFYLDLSSFSGK
(SEQ ID NO: 36)  XP_002865032.1   ----------------------------------------MGSTPFCYSINPSPSKLDFTRTHVVSPVAKQFYLDLSSFSGK
(SEQ ID NO: 37)  XP_018441511.1   ----------------------------------------MGSTLFCYSINPSPSKLDFTKTHVFSPVAKQFYLDFPSFAA-
(SEQ ID NO: 38)  CDY01444.1       MKCTSHIKLPLRASRIEMGSSTPFCYSINPSPSKLDFTRTHAFSPVAKQFYLDLPSFAGK
(SEQ ID NO: 39)  XP_009103460.1   ----------------------------------------MGCSTPFCYSINPSPSKLDFTKTHAFSPVAKQFYLDLPSFAGK
(SEQ ID NO: 40)  ACM68704.1       ----------------------------------------MGCSTPFCYSINPSPSKLDFTRTHAFSPLAKQFYLDLSSLAGK
(SEQ ID NO: 41)  JAU06164.1       ----------------------------------------MGSTPFCYSTNPSPSKLDFTRTHVFSPVAKQFYLDLSSCAGK
(SEQ ID NO: 42)  XP_006393901.1   ----------------------------------------MGSTPFCYSINPSPSKLDFTRTHVFSPVAKQFYLDLSSCAGK
(SEQ ID NO: 43)  AAV85824.1       ----------------------------------------MALTRFHNPFNLSSSS--LSRTCFPVPAFREYLVEISPCQRI
(SEQ ID NO: 44)  KGN61963.1       ----------------------------------------MASAVFYSSVQ--PSI--FSRTHIPIPISKDSFEEFGHSINY
(SEQ ID NO: 45)  NP_001268202.1   ----------------------------------------MATTL----FQNPSTF--FTGTQFPVSIPKYVPTESSACLHC
(SEQ ID NO: 46)  CMP01999.1       ----------------------------------------MASSTLFGNTL--TAV--SSRTHFPTPIFNNS-LELLSSTHS
(SEQ ID NO: 47)  XP_011043539.1   ----------------------------------------MASSAFFCNSINPSTSV--FSRTHFSFPIFSTVEFSSFAQY
(SEQ ID NO: 48)  XP_002523587.1   ----------------------------------------MASSTLFCNLINPSISV--FSRTHLPFPIVSSSSMEILSSHC
(SEQ ID NO: 49)  XP_012079233.1   ----------------------------------------MASSTLFCNLINPSISV--FSRTHLPFPIVSSSSMEILSSAHC
                                                                                                    :  *            :       ::
```

```
(SEQ ID NO: 30) XP_010547517.1  VR----GKSSVMSRRRVVGVKATAAVE-------EE-RRETAAEKEKLRVLVAGGGIGGL
(SEQ ID NO: 31) KFK28343.1       S---GAGLSGIKNRRGVVGVGVKASATAL------V-EEEKRETVTEKKKKSRVLVAGGGIGGL
(SEQ ID NO: 32) XP_010444704.1   SAGGG---GGFRSRRALVGVKATALV------EEKRES---GTEKKKKSRVLVAGGGIGGL
(SEQ ID NO: 33) XP_010484561.1   SGVGA---GGFRSLRALVGVKAATALV-----EEEQKRESVTDKTKKKSRVLVAGGGIGGL
(SEQ ID NO: 34) XP_006280131.1   SGVGGGLSGFRSRRTLVGVKAATALV------EEEQKPGEVT-ERKKKSRVLVAGGGIGGL
(SEQ ID NO: 35) NP_851285.1      P---G-GVSGFRSRRALLGVKAATALV------EKEEKREAVT-EKKKKSRVLVAGGGIGGL
(SEQ ID NO: 36) XP_002865032.1   S---GGGLSGFRSRKTLVGVKAATALV------EKEEKREAVT-EKKKKSRVLVAGGGIGGL
(SEQ ID NO: 37) XP_018441511.1   -----GKLRLRKRRALVGAKAET-------LLEEKRETVTEKKKKPRVLVAGGGIGGL
(SEQ ID NO: 38) CDY01444.1       S---GGGLSGFRSRRTLIGVKAAAATL-----VAEEEKRETVTESKKKPRVLVAGGGIGGL
(SEQ ID NO: 39) XP_009103460.1   S---GGGLSGLRKKRRALVGVKA--ATL----LAEEEKRETVTESKKKPRVLVAGGGIGGL
(SEQ ID NO: 40) ACM68704.1       S---GGGLSGLRKRRALVGVKA--ATL----LAEEEKRETVTESKKKPRVLVAGGGIGGL
(SEQ ID NO: 41) JAU06164.1       S---GGGLSGFRSPRTLVGVKAAAATA-----LVEEEKREVV-AEKKKSRVLVAGGGIGGL
(SEQ ID NO: 42) XP_006393901.1   S---GGGLSGFRSRRALVGVRA--ATA----LVEEEKREIA-KEKKKPRVLVAGGGIGGL
(SEQ ID NO: 43) AAV85824.1       S---GGGLSGFRSRRALVGVRA--ATA----LVEEEKREIA-KEKKKPRVLVAGGGIGGL
(SEQ ID NO: 44) KGN61963.1       GCNFGGKSACGRRKKLTQVKAAVTEAPPAEGAAG---EISRSLPTKNVRILVAGGGIGGL
(SEQ ID NO: 45) NP_001268202.1   KHYFRSNPCG-QKKRVAQKATLAEATPAPP-------APSLPSKKVRILVAGGGIGGL
(SEQ ID NO: 46) CMP01999.1       NYHFRGKASK-QKKRFLQVKATVAGTQSDSKSDEKNKVDANQQEKKKARILVAGGGIGGL
(SEQ ID NO: 47) XP_011043539.1   NYNFKTKTSTS--AKKLKVEAVVTETPAVSKS------EGKQSEQRKLKVLVAGGGIGGL
(SEQ ID NO: 48) XP_002523587.1   NFHFKTKKSDHQNKRFTQVKAVVTESPTVAES------NGKLSEQKKLRILVAGGGIGGL
(SEQ ID NO: 49) XP_012079233.1   NFHFRSKKSE-QNKKLTQVKAVVTESTSVAQS------DEKQPEQRKPRILVAGGGIGGL
                                                       .*                 .:  .:    *************
```

| | | |
|---|---|---|
| (SEQ ID NO: 30) | XP_010547517.1 | VFALAAKRRKGFDVAVFEKDLSAIRGEGQYRGPIQIQSNALAALEALEAIDMGVAEEVMEAGCI |
| (SEQ ID NO: 31) | KFK28343.1 | VFALAAKKKGFDVLVFEKDLSAIRGEGQYRGPIQIQSNALAALEALEAIDIAVAEEVMEAGCI |
| (SEQ ID NO: 32) | XP_010444704.1 | VFALAAKKKGFDVLVFEKDLSAIRGEGQYRGPIQIQSNALAALEALEAIDTDVAEQVMEAGCI |
| (SEQ ID NO: 33) | XP_010484561.1 | VFALAAKKKGFDVLVFEKDLSAIRGEGQYRGPIQIQSNALAALEALEAIDTDVAEQVMAGCI |
| (SEQ ID NO: 34) | XP_006280131.1 | VFALAAKKKGFDVLVFEKDLSAIRGEGQYRGPIQIQSNALAALEALEAIDNDVAEQVMEAGCI |
| (SEQ ID NO: 35) | NP_851285.1 | VFALAAKKKGFDVVVFEKDLSAIRGEGKYRGPIQIQSNALAALEALEAIDIEVAEQVMEAGCI |
| (SEQ ID NO: 36) | XP_002850832.1 | VFALAAKKKGFDVLVFEKDLSAIRGEGQYRGPIQIQSNALAALEALEAIDTDVAEQVMEAGCI |
| (SEQ ID NO: 37) | XP_018441511.1 | VFALAAKKKGFDVLVFEKDLSAIRGEGQYRGPIQIQSNALAALEALEAIDTGVAEEVMEAGCI |
| (SEQ ID NO: 38) | CDY01444.1 | VFALAAKKKGFDVLVFEKDLSAIRGEGQYRGPIQIQSNALAALEALEAIDIGVAEEVMEAGCI |
| (SEQ ID NO: 39) | XP_009103460.1 | VFALAAKKKGFDVLVFEKDLSAIRGEGQYRGPIQIQSNALAALEALEAIDIDVAEEVMEAGCI |
| (SEQ ID NO: 40) | ACM68704.1 | VFALAAKKKGFDVVVFEKDLSAIRGEGQYRGPIQIQSNALAALEALEAIDLDVAEEVMEAGCI |
| (SEQ ID NO: 41) | JAU06164.1 | VFALAAKKKGFDVVVFEKDMSAIRGEGQYRGPIQIQSNALAALEALEAVDMEVAEEVMRAGCI |
| (SEQ ID NO: 42) | XP_006393901.1 | VFALAAKRKGFDVLVFEKDLSAVRGEGQYRGPIQIQSNALAALEALEAIDMEVAEKVMEAGCI |
| (SEQ ID NO: 43) | AAV85824.1 | VLALAAKKKGFDVVFEKDLSAIRGEGQYRGPIQIQSNALAALEALEAIDLDVAEEVMRVGCI |
| (SEQ ID NO: 44) | KGN61963.1 | VFALAAKKKGFDVVFEKDLSAIRGEGQYRGPIQIQSNALAALEALEAIDLDVAEEVMEAGCI |
| (SEQ ID NO: 45) | NP_001268202.1 | VFALAAKNKGFDVVFEKDLSAIRGEGQYRGPIQIQSNALAALEALEAIDMEVAEEVMRAGCI |
| (SEQ ID NO: 46) | CMP01999.1 | VFALAAKRKGFDVMFEKDLSAIRGEGQYRGPIQIQSNALAALEALEAIDLDVAEEVMRAGCI |
| (SEQ ID NO: 47) | XP_011043539.1 | VFALAAKRKGFEVLVFEKDLSAIRGEGQYRGPIQVQSNALAALEALEAIDLEVAEEVMEAGCI |
| (SEQ ID NO: 48) | XP_002523587.1 | VFALAAKRKGFEVLVFEKDLSAVRGEGQYRGPIQIQSNALAALEALEAIDLEVAEEVMRAGCI |
| (SEQ ID NO: 49) | XP_012079233.1 | VFALAAKRKGFEVLVFEKDLSAVRGEGQYRGPIQIQSNALAALEALEAIDLEVAEEVMEAGCI |

FIG. 24B
(Continued)

```
(SEQ ID NO: 30)  XP_010547517.1  TGDRINGLVDGVSGSWYVKFDTFTPAAERGLPVTRVISRMTLQQILARAVGEDVIQNESN
(SEQ ID NO: 31)  KFK28343.1      TGDRINGLVDGVSGTWYVKFDTFTPAASRGLPVTRVISRMTLQQILARAVGEEVIRNESN
(SEQ ID NO: 32)  XP_010444704.1  TGDRINGLVDGISGTWYVKFDTFTPAASRGLPVTRVISRMTLQQILARAVGEEVIRNESN
(SEQ ID NO: 33)  XP_010484561.1  TGDRINGLVDGISGTWYVKFDTFTPAASRGLPVTRVISRMTLQQILARAVGEEVIRNESN
(SEQ ID NO: 34)  XP_006280131.1  TGDRINGLVDGVSGTWYVKFDTFTPAASRGLPVTRVISRMTLQQILARAVGEEVIRNESN
(SEQ ID NO: 35)  NP_851285.1     TGDRINGLVDGISGTWYVKFDTFTPAASRGLPVTRVISRMTLQQILARAVGEDVIRNESN
(SEQ ID NO: 36)  XP_002865032.1  TGDRINGLVDGVSGTWYVKFDTFTPAASRGLPVTRVISRMTLQQILARAVGEEIIRNESN
(SEQ ID NO: 37)  XP_018441511.1  TGDRINGLVDGVSGTWYVKFDTFTPAASRGLPVTRVISRMTLQQILARAVGEEIIRNESN
(SEQ ID NO: 38)  CDY01444.1      TGDRINGLVDGVSGTWYVKFDTFTPAASRGLPVIRVISRMTLQQILARAVGEEIIRNESN
(SEQ ID NO: 39)  XP_009103460.1  TGDRINGLVDGVSGTWYVKFDTFTPAASRGLPVTRVISRMTLQQILARAVGEEIIRNESN
(SEQ ID NO: 40)  ACM68704.1      TGDRINGLVDGVSGTWYVKFDTFTPAAERGLPVTRVISRMTLQQILARAVGEEVIRNESN
(SEQ ID NO: 41)  JAU06164.1      TGDRINGLVDGVSGNWYIKFDTFTPAAERGLPVTRVISRMSLQQILARAVGDDVIINDSN
(SEQ ID NO: 42)  XP_006393901.1  TGDRINGLVDGVSGDWYVKFDTFTPAAERGLPVTRVISRMTLQQILARAVGEDIIMNGSN
(SEQ ID NO: 43)  AAV85824.1      TGDRINGLVDGVSGSWYIKFDTFTPAAERGLPVTRVISRMTLQQILARAVGEDIIFNESN
(SEQ ID NO: 44)  KGN61963.1      TGDRINGLVDGISGTWYVKFDTFTPAAERGLPVTRVISRMTLQQILARSVGDDTILNDSN
(SEQ ID NO: 45)  NP_001268202.1  TGDRINGLVDGVSGTWYCKFDTFTPAAERGLPVTRVISRMTLQQILACAVGEDVIMNASN
(SEQ ID NO: 46)  CMP01999.1      TGDRINGLVDGVSGTWYVKFDTFTPAAERGLPVTRVISRMTLQQILALAVGEDVIRNESN
(SEQ ID NO: 47)  XP_010435539.1
(SEQ ID NO: 48)  XP_002523587.1
(SEQ ID NO: 49)  XP_012079233.1
                                 ************:**.********.***********:*********.:***:*..*.**
```

FIG. 24B
(Continued)

| | | |
|---|---|---|
| (SEQ ID NO: 30) | XP_010547517.1 | VVSFSESEDKVTVVLENGECYQGDLLVGADGIWSKVRSQLFGHEEATYSGYTCYTGIADF |
| (SEQ ID NO: 31) | KFK28343.1 | VVDFEDSGDKVTVVLENGQRYEGDLLVGADGIWSKVRNNLFGRSEATYSGYTCYTGIADF |
| (SEQ ID NO: 32) | XP_010444704.1 | VVDFEDSGDKVTVVLENGERYEGDLLVGADGIWSKVRNNLFGRSEASYSGYTCYTGIADF |
| (SEQ ID NO: 33) | XP_010484561.1 | VVDFEDSGDKVTVVLENGERYEGDLLVGADGIWSKVRNNLFGRSEASYSGYTCYTGIADF |
| (SEQ ID NO: 34) | XP_006280131.1 | VVDFEDSGDKVTVVLENGQRYEGDLLVGADGIWSKVRNNLFGRSEAEYSGYTCYTGIADF |
| (SEQ ID NO: 35) | NP_851285.1 | VVDFEDSGDKVTVVLENGQRYEGDLLVGADGIWSKVRNNLFGRSEATYSGYTCYTGIADF |
| (SEQ ID NO: 36) | XP_002865032.1 | VVDFEDSGDKVTVVLENGQRYEGDLLVGADGIWSKVRNNLFGRSEATYSGYTCYTGIADF |
| (SEQ ID NO: 37) | XP_018441511.1 | VVDFQDSGDKVTVVLENGERYEGDLLVGADGIWSKVRNNLFGRSEATYSGYTCYTGIADF |
| (SEQ ID NO: 38) | CDY01444.1 | VVDFEDSGDKVTVVLENGQRYEGDLLVGADGIWSKVRNNLFGRSEATYSGYTCYTGIADF |
| (SEQ ID NO: 39) | XP_009103460.1 | VVDFEDSGDKVTVVLENGQRYEGDLLVGADGIWSKVRNNLFGRSEATYSGYTCYTGIADF |
| (SEQ ID NO: 40) | ACM68704.1 | VVDFEDSGDKVTVVLENGQRYEGDLLVGADGIWSKVRKNLFGRSEATYSGYTCYTGIADF |
| (SEQ ID NO: 41) | JAU06164.1 | VVDFEDSGDKVTVVLENGQRYEGDLLVGADGIWSKVRKNLFGRSEATYSGYTCYTGIADF |
| (SEQ ID NO: 42) | XP_006393901.1 | VVDFEDSGERVKVTVLENGQHEGDLLVGADGIWSKVRKSLFGPKEATYSGYTCYTGIADF |
| (SEQ ID NO: 43) | AAV85824.1 | VVDFEDSGDKVTVVLENGQQYEGDLLIGADGIWSKVRKSLFGPKEATYSGYTCYTGIADF |
| (SEQ ID NO: 44) | KGN61963.1 | VVDFEDDGNKVTVILENGQRYEGDLLVGADGIWSKVRKNLFGPKDAVYSGYTCYTGIADF |
| (SEQ ID NO: 45) | NP_001268202.1 | VVDFEDDGNKVTVVLENGKRFEGDLLVGADGIWSKVRKNLFGPKEAVYSGYTCYTGIADF |
| (SEQ ID NO: 46) | CMP01999.1 | VVSFQDDGDKVTVVLENGQQFEGDLLVGADGIWSKVRKNLFGPKEATYSGYTCYTGIADF |
| (SEQ ID NO: 47) | XP_011043539.1 | VINFQDNEDKVTVTLENGQQYEGDLLVGADGIWSKVRKNLFGPKEAVYSGYTCYTGIADF |
| (SEQ ID NO: 48) | XP_002523587.1 | VVSFQDDGDKVTVTVTLENGQHFEGDLLVGADGIWSKVRKNLFGPKDATYSDYTCYTGIADF |
| (SEQ ID NO: 49) | XP_012079233.1 | *:.*: .:.*:*. :.**: .:*.*****:*:.:.:*.****** |

FIG. 24B
(Continued)

| | | |
|---|---|---|
| (SEQ ID NO: 30) | XP_010547517.1 | VPADIESVGYRVFLGHKQYFVSSDVGGGKMQWYAFHEEPAGGRDAPDGRKKRLLEIFQGW |
| (SEQ ID NO: 31) | KFK28343.1 | IPADIESVGYRVFLGHKQYFVSSDVGGGKMQWYAFYEEPAGGVDAPNGMKKRLFEIFEGW |
| (SEQ ID NO: 32) | XP_010444704.1 | IPADIESVGYRVFLGNKQYFVSSDVGGGKMQWYAFHEEPAGGADAPNGMKKRLFEIFEGW |
| (SEQ ID NO: 33) | XP_010484561.1 | IPADIESVGYRVFLGHKQYFVSSDVGGGKMQWYAFHEEPAGGADAPNGMKKRLFEIFDGW |
| (SEQ ID NO: 34) | XP_006280131.1 | IPADIESVGYRVFLGHKQYFVSSDVGGGKMQWYAFHEEPAGGTDAPNGMKKRLFEIFDGW |
| (SEQ ID NO: 35) | NP_851285.1 | IPADIESVGYRVFLGHKQYFVSSDVGGGKMQWYAFHEEPAGGADAPNGMKKRLFEIFDGW |
| (SEQ ID NO: 36) | XP_002865032.1 | VPADIESVGYRVFLGHKQYFVSSDVGGGKMQWYAFHEEPAGGVDAPNGMKKRLFEIFDGW |
| (SEQ ID NO: 37) | XP_018441511.1 | VPADIESVGYRVFLGHKQYFVSSDVGGGKMQWYAFHEEAAGGVDAPNGMKKRLFEIFEGW |
| (SEQ ID NO: 38) | CDY01444.1 | VPADIESVGYRVFLGHKQYFVSSDVGGGKMQWYAFHEEAAGGVDAPNGMKKRLFEIFEGW |
| (SEQ ID NO: 39) | XP_009103460.1 | VPADIESVGYRVFLGHKQYFVSSDVGGGKMQWYAFHEEPAGGVDAPNGMKKRLFDIFEGW |
| (SEQ ID NO: 40) | ACM68704.1 | VPADIESVGYRVFLGHKQYFVSSDVGGGKMQWYAFHEEPAGGVDAPNGMKKRLFDIFEGW |
| (SEQ ID NO: 41) | JAU06164.1 | IPADIETVGYRVFLGHKQYFVSSDVGAGKMQWYAFHKEPPGGADAPNGKKERLFKIFEGW |
| (SEQ ID NO: 42) | XP_006393901.1 | VPADIDSVGYRVFLGHKQYFVSSDVGAGKMQWYAFYNEPAGGVDGPEGKKERLFKIFGGW |
| (SEQ ID NO: 43) | AAV85824.1 | VPADIESVGYRVFLGHKQYFVSSDVGGGKMQWYAFHKEPAGGVDTPQGKKERLFKIFGGW |
| (SEQ ID NO: 44) | KGN61963.1 | VPADIESVGYRVFLGHKQYFVSSDVGAGKMQWYAFHEEPAGGVDGPEGKKERLFKIFGGW |
| (SEQ ID NO: 45) | NP_001268202.1 | VPADIESVGYRVFLGHKQYFVSSDVGGGKMQWYAFHEEPAGGVDTPQGKKERLFKIFGGW |
| (SEQ ID NO: 46) | CMP01999.1 | VPADIESVGYRVFLGHKQYFVSSDVGAGKMQWYAFHEEPAGGVDGPEGKKERLFKIFGGW |
| (SEQ ID NO: 47) | XP_011043539.1 | VPVDIETVGYRVFLGHKQYFVSSDVGAGKMQWYAFHKESPGGMDAPHGKKDRLLKIFEGW |
| (SEQ ID NO: 48) | XP_002523587.1 | VPVDIESVGYRVFLGHKQYFVSSDVGAGKMQWYAFHNEPPGGVDSPNGKKERLLKIFEGW |
| (SEQ ID NO: 49) | XP_012079233.1 | VPADIESVGYRVFLGHKQYFVSSDVGAGKMQWYAFHKEPPGGVDRPNGKKERLLKIFEGW |
| | | .*.*:*:******:****** *.:.:* *::. .:::*:**.* |

FIG. 24B
(Continued)

| | | |
|---|---|---|
| (SEQ ID NO: 30) | XP_010547517.1 | CDNVIDLLHATEEDAILRRDIYDRTPSFTWGKGRVTLLLGDSIHAMQPNMGQGGCMAIEDS |
| (SEQ ID NO: 31) | KFK28343.1 | CDNVLDLLHATEEEAILRRDIYDRSPSFTWGKGRVTLLGDSIHAMQPNMGQGGCMAIEDS |
| (SEQ ID NO: 32) | XP_010444704.1 | CDNVLDLLHATEEDAILRRDIYDRNPSFTWGKGRVTLLGDSTHAMQPNMGQGGCMAIEDS |
| (SEQ ID NO: 33) | XP_010484561.1 | CDNVLDLLHATEEDAILRRDIYDRNPSFTWGKGRVTLLGDSIHAMQPNMGQGGCMAIEDS |
| (SEQ ID NO: 34) | XP_006280131.1 | CDNVLDLLHATEEDAILRRDIYDRSPSFTWGKGRVTLLGDSIHAMQPNMGQGGCMAIEDS |
| (SEQ ID NO: 35) | NP_851285.1 | CDNVLDLLHATEEEAILRRDIYDRSPGGTWGKGRVTLLGDSIHAMQPNMGQGGCMAIEDS |
| (SEQ ID NO: 36) | XP_028650032.1 | CDNVLDLLHATEEDAILRRDIYDRSPSFTWGKGRVTLLGDSIHAMQPNMGQGGCMAIEDS |
| (SEQ ID NO: 37) | XP_018441511.1 | CDNVLDLLQATEEEAILRRDIYDKSPSFTWGKGRVTLLGDSIHAMQPNMGQGGCMAIEDS |
| (SEQ ID NO: 38) | CDY01444.1 | CDNVLDLLQATEEEAILRRDIYDRSPSFTWGKGRVTLLGDSIHAMQPNMGQGGCMAIEDS |
| (SEQ ID NO: 39) | XP_009103460.1 | CDNVLDLLHATEEEAILRRDIYDRTPSFTWGKGRVTLLGDSIHAMQPNMGQGGCMAIEDS |
| (SEQ ID NO: 40) | ACM68704.1 | CDNVLDLLHATEEEAILRRDIYDRTPSFNWGKGRVTLLGDSIHAMQPNMGQGGCMAIEDG |
| (SEQ ID NO: 41) | JAU06164.1 | CDNVLDLLHATEEDAILRRDIYDRTPIFTWGKGRVTLLGDSVHAMQPNMGQGGCMAIEDS |
| (SEQ ID NO: 42) | XP_006393901.1 | CDNVLDLIQATDEDSVLRRDIYDRTPTFTWGRGRVTLLGDSVHAMQPNMGQGGCMAIEDS |
| (SEQ ID NO: 43) | AAV85824.1 | CDNVLDLIATDEEAILRRDIYDRTPSLTWGKGRVTLLGDSIHAMQPNLGQGGCMAIEDS |
| (SEQ ID NO: 44) | KGN61963.1 | CDNVIDLLLATDEDSILRRDIYDREPIITWGKGRVTLLGDSVHAMQPNMGQGGCMAIEDS |
| (SEQ ID NO: 45) | NP_001268202.1 | CDNVLDLLHATDEDAILRRDIYDREPVFTWGKGRVTLLGDSIHAMQPNMGQGGCMAIEDS |
| (SEQ ID NO: 46) | CMP01999.1 | CDNVIDLLLATDEDAILRRDIYDRTPTLTWGRGRVTLLGDSVHAMQPNMGQGGCMAIEDG |
| (SEQ ID NO: 47) | XP_011043539.1 | |
| (SEQ ID NO: 48) | XP_002523587.1 | |
| (SEQ ID NO: 49) | XP_012079233.1 | |
| | | **  : :.:::.**:: :. * :*:*****.******* . |

(SEQ ID NO: 30) XP_010547517.1  YQLAWELEHAWRRSVETDKPIDIVSSLRSYEEARKLRVAIIHGMARMAAIMASTYKGYLG
(SEQ ID NO: 31) KFK28343.1       YQLASELEDAWKQSVDTNRPVDVVSSLKRYEESRRLRVAIIHGMARMAAIMASTYKAYLG
(SEQ ID NO: 32) XP_010444704.1   FQLALELDEAWKQSVETKTPVDVVSSLKRYEESRRLRVALIHGMARMAAIMASTYKAYLG
(SEQ ID NO: 33) XP_010484561.1   FQLALELEEAWKQSVKTKTPVDVVSSLKRYEESRRLRVAIIHGMARMAAIMASTYKAYLG
(SEQ ID NO: 34) XP_006280131.1   FQLALELEEAWKQSVETNTSVDVVSSLKRYEESRRLRVAIIHGMARMAAIMASTYKAYLG
(SEQ ID NO: 35) NP_851285.1      FQLALELEEAWKQSVETTTPVDVVSSLKRYEESRRLRVAIIHAMARMAAIMASTYKAYLG
(SEQ ID NO: 36) XP_002865032.1   FQLALELEEAWKQSVGTNTPVDVVSSLKRYEESRRLRVAIIHGMARMAAIMASTYKAYLG
(SEQ ID NO: 37) XP_018441511.1   FQLALEAAWKQSVETNTPVDVVSSLRRYEESRRLRCAIIHGMARMAAIMASTYKAYLG
(SEQ ID NO: 38) CDY01444.1       FQLGLELEQAWKQSVETNTPVDVVSSLRRYEESRRLRVAIIHGMARMAAIMASTYKAYLG
(SEQ ID NO: 39) XP_009103460.1   FQLGLELEQAWKQSVETNTPVDVVSSLRRYEESRRLRVAIIHGMARMAAIMASTYKAYLG
(SEQ ID NO: 40) ACM68704.1       FQLGLELEQAWKQSVETNTPVDVVSSLRRYEESRRLRVAIIHGMARMAAIMASTYKAYLG
(SEQ ID NO: 41) JAU06164.1       YQLAMELEGAWKQSVETNAPVDVVSSLKKYEESRRLRVAIIHGMARMAAIMASTYKAYLG
(SEQ ID NO: 42) XP_006393901.1   FQLALELEEAWERSVETNAPVDVVSSLRRYEESRRLRVAIIHGMARMAAIMASTYKAYLG
(SEQ ID NO: 43) AAV85824.1       YQLALELEEAWERSVETNAPVDVVSSLRRYEESRRLRVAIIHGMARMAAIMASTYKAYLG
(SEQ ID NO: 44) KGN61963.1       YQLALELDKAWNESVASGSPIDIVSSLKSYESSRRIRVAVIHGMARMAALMASTYKAYLG
(SEQ ID NO: 45) NP_001268202.1   YQLAMELDKAWEQSIKSGTPIDIVSSCLKSYEKARRIRVAVIHGMARMAAIMASTYKAYLG
(SEQ ID NO: 46) CMP01999.1       YQLALELDKAWKQSVESGTPIDVVSSLRSYESARRLRVAIIHGMARMAAIMASTYKAYLG
(SEQ ID NO: 47) XP_011043539.1   YQLASELERAWKQSIESGTPVDVLSSLRSYENARRLRVAIIHGMARMAAIMASTYKAYLG
(SEQ ID NO: 48) XP_002523587.1   YQLALELDKAWKQSIESGYPVDVVSSLKSYERTRRLRVAIIHGMARMAAIMASTYKAYLG
(SEQ ID NO: 49) XP_012079233.1   YQLALEIEKAWKQSIESGTPIDIVSSLKSYERARRLRVAIIHGMARMAAIMASTYKAYLG
                                  :*.  *:.   *:  :.:: *  * *** :.* : :* ***.*******

| | | |
|---|---|---|
| (SEQ ID NO: 30) | XP_010547517.1 | VGLGPLSFITMLRIPHPGTVGGRFFIDVAMPLMLNWVLGGNSSKLEGRLPCCRLSDKADD |
| (SEQ ID NO: 31) | KFK28343.1 | VGLGPLSFLTKFRVPHPGRVGGRFFIDIAMPLMLNWVLGGNSEKLEGRAPSCRLTDRADD |
| (SEQ ID NO: 32) | XP_010444704.1 | VGLGPLSFLTKFRVPHPGRVGGRFFIDIAMPLMLNWVLGGNSEKLEGRSPSCRLTDKADD |
| (SEQ ID NO: 33) | XP_010484561.1 | VGLGPLSFLTKFRVPHPGRVGGRFFIDIAMPMMLNWVLGGNSEKLEGRSPSCRLTDKADD |
| (SEQ ID NO: 34) | XP_006280131.1 | VGLGPLSFLTKFRVPHPGRVGGRFFIDIAMPMMLNWVLGGNSEKLEGRPPSCRLTDKADD |
| (SEQ ID NO: 35) | NP_851285.1 | VGLGPLSFLTKFRVPHPGRVGGRFFVDIAMPSMLDWVLGGNSEKLQGRPPSCRLTDKADD |
| (SEQ ID NO: 36) | XP_002865032.1 | VGLGPLSFLTKFRVPHPGRVGGRFFVDIAMPLMLDWVLGGNSEKLEGRPPSCRLTDKADD |
| (SEQ ID NO: 37) | XP_018441511.1 | VGLGPLSFLTKFRVPHPGRVGGRFFIDIAMPLMLNWVLGGNSEKLEGRPPSCRLTDKADD |
| (SEQ ID NO: 38) | CDY01444.1 | VGLGPLSFLTKFRVPHPGRVGGRFFIDIAMPLMLNWVLGGNSEKLEGRPPSCRLTDKADD |
| (SEQ ID NO: 39) | XP_009103460.1 | VGLGPLSFLTKFRVPHPGRVGGRFFIDIAMPLMLNWVLGGNSEKLEGRPPSCRLTDKADD |
| (SEQ ID NO: 40) | ACM68704.1 | VGLGPLSFLTKFRVPHPGRVGGRFFIDIAMPLMLNWVLGGNSEKLEGRSPSCRLTDKADD |
| (SEQ ID NO: 41) | JAU06164.1 | VGLGPLSFLTKFRVPHPGRVGGRFFIDIAMPLMLNWVLGGNSEKLEGRPPSCRLTDKADD |
| (SEQ ID NO: 42) | XP_006393901.1 | VGLGPLSFLTKFRVPHPGRVGGRFFIDIAMPLMLNWVLGXNSEKLEGRPPSCRLTDKADD |
| (SEQ ID NO: 43) | AAV85824.1 | VGLGPLSFLTQFRIPHPGTFGGRFFIDLAMPLMLNWVLGGNSSKLEGRPPSACRLSDKAND |
| (SEQ ID NO: 44) | KGN61963.1 | VGLGPLSFLTKLRIPHPGRVGGRFFIDIAMPLMLSWVLGGNSSKLEGRPPSCRLSDKAND |
| (SEQ ID NO: 45) | NP_001268202.1 | VGLGPLSFLTKYRIPHPGRVGGRFFIDIAMPLMLSWVLGGNSSKLEGRSLTCRLSDKASD |
| (SEQ ID NO: 46) | CMP01999.1 | VGLGPLSFLTKYRIPHPGRVGGRFFIDIAMPVMLNWVLGGNSSKLEGRSLSCRLSDKASD |
| (SEQ ID NO: 47) | XP_011043539.1 | VGLGPLSFLTKYRINFRIPHPGRVGGRFFIDIAMPVMLNWVLGGNSSKLEGRPLSCRLSDKASD |
| (SEQ ID NO: 48) | XP_002523587.1 | VGLGPLSFLTKYRIPHPGRVGGRFFIDIAMPVMLSWVLGGNSSKLEGRSQCCRLSDKASD |
| (SEQ ID NO: 49) | XP_012079233.1 | ::*::*:*:*****.:*:*.:*::.:.****:*:*:.***:* |

| | | |
|---|---|---|
| (SEQ ID NO: 30) | XP_010547517.1 | EIPSSQVSKVHARIIYKDGAFFVMDLIRSEYGTYITDNEGRRYRVTPNFPARFRPSDIIEL |
| (SEQ ID NO: 31) | KFK28343.1 | VIPSSQVSKMHARIIYKDGAFFVMDLIRSEHGTYVVDNEGGRYRATPNFPARFRPSDILEF |
| (SEQ ID NO: 32) | XP_010444704.1 | VIPSSQVSKMHARVIYKDGAFFLMDLIRSEHGTYVTDNEGRRYRATPNSPARFRTSDIIEF |
| (SEQ ID NO: 33) | XP_010484561.1 | VIPSSQVSKMHARVIYKDGAFFLMDLIRSEHGTYVTDNEGRRYRATPNSPARFRTSDIIEF |
| (SEQ ID NO: 34) | XP_006280131.1 | VIPSSQVSKMHARVIYKDGAFFLMDLGSEHGTFVTDNEGRRYRATPNFPGRFRPSDIIEF |
| (SEQ ID NO: 35) | NP_851285.1 | VIPSSQVSKMHARVIYKDGAFFLMDLIRSEHGTYVTDNEGRRYRATPNFPARFRSSDIIEF |
| (SEQ ID NO: 36) | XP_002865032.1 | VIPSSQVSKMHARVIYKDGVFFLMDLIRSEHGTYVTDNEGGKYRVTPNFPTRFRSSDIIEF |
| (SEQ ID NO: 37) | XP_018441511.1 | VIPSPQVSKMHARVIYKDGAFFLMDLIRSEHGTYLTDNEGGKYRVTPNFPARFRPSDIIEF |
| (SEQ ID NO: 38) | CDY01444.1 | VIPSPQVSKMHARVIYKDGAFFVMDLIRSEHGTYLTDNEGGKYRVTPNFPARFRPSDIIEF |
| (SEQ ID NO: 39) | XP_009103460.1 | VIPSPQVSKMHARVIYKDGAFFVMDLIRSEHGTYLTDNEGGKYRVTPNFPARFRPSDIIEF |
| (SEQ ID NO: 40) | ACM68704.1 | VIPSPQVSKMHARVTYKDGAFFLMDLIRSEHGTYVTDNEGRRYRASPNYPARFRPSDIIEF |
| (SEQ ID NO: 41) | JAU06164.1 | VIPSPQVSKMHARVTYKDGAFFLMDLIRSEHGTYVTDNEGRRYRVTPNFPARFRSSDIIEF |
| (SEQ ID NO: 42) | XP_006393901.1 | VIPAPQVSKMHARVTYKDGAFFLTDLIRSEHGTWLSDHEGRRYRAPPNFPVRFHQSDLIEF |
| (SEQ ID NO: 43) | AAV85824.1 | AIPLPQVSEKHARIYKDGAFFLTDLIRSEHGTWITDNVGRRQRVSPNFPTRFHPSEVIDF |
| (SEQ ID NO: 44) | KGN61963.1 | VIPSPKVSKMHARISCKDGAFYIKDLIRSEHGTYIINQEGKKSRVTPNVPTRIRPSDVIEF |
| (SEQ ID NO: 45) | NP_001268202.1 | VIPAPQVSKTHARITCKDGAFYLIDLIRSEHGTFITDIEGRRYRAPPNFPTLFHPSEAIEF |
| (SEQ ID NO: 46) | CMP01999.1 | VIPAPQVSKTHAQITYKDGGFYVIDLIRSEHGTFITDNDGRRSRVPPNFPTLFHPSEAIEF |
| (SEQ ID NO: 47) | XP_010435539.1 | VISSPQVSKMHARISYKDGGFYVIDLIRSEHGTYIISDADGRRYRVPQNSPTRFHPSDVIEF |
| (SEQ ID NO: 48) | XP_002523587.1 | VIPSPQVSEMHARISYKDGAFYVIDLIRSEHGTYISDADGRRYRVPQNSPTRFHPSDVIEF |
| (SEQ ID NO: 49) | XP_012079233.1 | |

FIG. 24B
(Continued)

| SEQ ID NO | Accession | Sequence |
|---|---|---|
| (SEQ ID NO: 30) | XP_010547517.1 | GSDKKAAFRVKVIRKTPKMTRRDDRESSSKLLQAA- |
| (SEQ ID NO: 31) | KFK28343.1 | GSDKKAAFKVKVIRKTPKSTKNESNG--KLLQAA- |
| (SEQ ID NO: 32) | XP_010444704.1 | GSDKKAAFRVKVIRTTPKSTRKNESND--KLLQ-AA |
| (SEQ ID NO: 33) | XP_010484561.1 | GSDKKAAFRVKVIRTTPKSTRKNESND KLLQ AA |
| (SEQ ID NO: 34) | XP_006280131.1 | GSDKKAAFRVKVIRKTPKATRKNESND--K-LLQAA |
| (SEQ ID NO: 35) | NP_851285.1 | GSDKKAAFRVKVIRKTPKSTRKNESNN--DKLLQTA |
| (SEQ ID NO: 36) | XP_002865032.1 | GSDKKAAFRVKVIRKTPKSTRKNESND---KLLQTA |
| (SEQ ID NO: 37) | XP_018441511.1 | GSDKKAAFRVKVIRTTPKLTRRDEKSD--GKLLQAA |
| (SEQ ID NO: 38) | CDY01444.1 | GSDKKAAFRVKVIRTTPKLTRRDEKSD---GKLLQAA |
| (SEQ ID NO: 39) | XP_009103460.1 | GSDKKAAFRVKVIRTTPKLTRRDEKSD--GKLLQAA |
| (SEQ ID NO: 40) | ACM68704.1 | GSDKKAAFRVKVIRTTPKSTSKN--ESN--GKLLQAA |
| (SEQ ID NO: 41) | JAU06164.1 | GSDKKAAFRVKVIRTTPKSTSKNKESN--GKLLQAA |
| (SEQ ID NO: 42) | XP_006393901.1 | GSDKKAAFRVKVIRTTPKSTSKNKESN--GKLLQAV |
| (SEQ ID NO: 43) | AAV85824.1 | GSDKKARFRVKVIRSSVENDREKVEMNS------- |
| (SEQ ID NO: 44) | KGN61963.1 | GSE-KASFRVKVKAIKSAPKIAEKEGSGVLQAA--- |
| (SEQ ID NO: 45) | NP_001268202.1 | GSDKKAAFRVKAIKSAPKIAEKEGSGVLQAA--- |
| (SEQ ID NO: 46) | CMP01999.1 | GSDKKVIFRVKVMRSPPKISEKKDEGQVLQSV---- |
| (SEQ ID NO: 47) | XP_011043539.1 | GSAGKAKFRVKVMKSPAKIKEKGGN-EILQSV---- |
| (SEQ ID NO: 48) | XP_002523587.1 | GSDEKAKFRVKVMKSPSRIKEKEGS-EILQSV---- |
| (SEQ ID NO: 49) | XP_012079233.1 | ** *. *:**.::  . |

FIG. 24B (Continued)

```
Violaxanthin de-epoxidase (VDE)
CLUSTAL O(1.2.4) multiple sequence alignment (SEQ ID NO: 50) XP_010043341.1   ---------------------------------MASMAAGSICLFRDESIGAASIAVTILANRSSHMAKLLCYRGKARATMW
(SEQ ID NO: 51) XP_010528777.1   ------------------------------------------------------------MAVAVQSFSSP-CYRD---TQFI
(SEQ ID NO: 52) XP_010475655.1   ------------------------------------------------------------MAVATHCFTSP-CHDR---IRFF
(SEQ ID NO: 53) XP_006307456.1   ------------------------------------------------------------MAVATHCFTSP-CHDR---IRFF
(SEQ ID NO: 54) NP_172331.1      ------------------------------------------------------------MAVATHCFTSP-CHDR---IRFF
(SEQ ID NO: 55) XP_002889702.1   ------------------------------------------------------------MAVATHCFTSP-CHGR---IRFF
(SEQ ID NO: 56) XP_013641072.1   ------------------------------------------------------------MSVSTHCFTSP-CHGR---IRFF
(SEQ ID NO: 57) XP_009148110.2   MSYPKGISSHPYISLFLFSLYLPP----LLPAELSVSSMSVSTHCFTSP-CHDR---TRFF
(SEQ ID NO: 58) JAU20005.1       LS--LSLSLSLSLLPAELSIFG----IASGRLATESMSVATHCFTSPTCHDR---IRFF
(SEQ ID NO: 59) XP_006417674.1   ------------------------------------------------------------MAVATYCFTSP-CHDR---IRFF
(SEQ ID NO: 60) AIZ75647.1       ---------------------MALAGRSIFLFSHNDSIG--NT------------C---------IR
(SEQ ID NO: 61) XP_009379699.1   ---------------------MAFAGRSVFLSHKESIG--NA------------C---------IR
(SEQ ID NO: 62) AMJ39491.1       ---------------------MALAPHST----------------------------H
(SEQ ID NO: 63) EOY10737.1       ---------------------MAQAARSLCFSHDKSVQ--VP------------C---------RT
(SEQ ID NO: 64) XP_017627747.1   ---------------------MAEAARLICFSHGKSVK--VP------------C---------RT
(SEQ ID NO: 65) XP_016673034.1   ---------------------MAEAARLICFSHGKSVK--VP------------C---------RT
(SEQ ID NO: 66) XP_002319136.2   ---------------------MALAANPFCLSQEQYIISSSS-----------V---------AK
(SEQ ID NO: 67) OAY41983.1       ---------------------MAISANSVCLSHEESIC--SS------------Y---------FR
(SEQ ID NO: 68) XP_012092715.1   ---------------------MALAANSIYLSHEESIS--SS------------Y---------IK
```

FIG. 24C

| | | |
|---|---|---|
| (SEQ ID NO: 50) | XP_010043341.1 | MGIKTTRRLAMK----------CSLESHCRSESSCSGFP---------------L-- |
| (SEQ ID NO: 51) | XP_010528777.1 | SGNRSNR--KLLRKRMVDSDTIVLVKICSGARGKIHCS------------------- |
| (SEQ ID NO: 52) | XP_010475655.1 | SSDDGIGRLGISRKRINGT---FLVKILPPIQNVDLRT------------------- |
| (SEQ ID NO: 53) | XP_006307456.1 | SSDDGIARLGISRKRINGT---FLVKILSPIQSADLRT------------------- |
| (SEQ ID NO: 54) | NP_172331.1 | SSDDGIGRLGITRKRINGT---FLLKILPPIQSADLRT------------------- |
| (SEQ ID NO: 55) | XP_002889702.1 | SSDD--GRLGITRKRINGT---FLLKILPPIQN------------------------ |
| (SEQ ID NO: 56) | XP_013641072.1 | SG--DDG-NKLLRKRIKGT---FLVKILPSSQNAYLRI------------------- |
| (SEQ ID NO: 57) | XP_009148110.2 | SG--DDG-NKLLRKRIKGT---FLVKILPSSQNAYLRV------------------- |
| (SEQ ID NO: 58) | JAU20005.1 | SRITSDD-GRLVRKRINGT---FLLKILPSSQNAHLRT------------------- |
| (SEQ ID NO: 59) | XP_006417674.1 | SGVTSFD-GRLLRKRINGT---FLVKILPPSQNADLRT------------------- |
| (SEQ ID NO: 60) | AIZ75647.1 | LGITSDE--GFQKRRMVGFHVVV--KFPSNRRKS-RYSQFIRSKRNFCVLGSKCSSLLSS |
| (SEQ ID NO: 61) | XP_009379699.1 | LGLKSDE--RLQKGRMVGFHVVV--KFSSQRRKS-RYCQFISAKRNFSGLGSKRSSLLSS |
| (SEQ ID NO: 62) | AMJ39491.1 | FSELTGR--REFLSRKVVHLHGMVLLRIQSDRKSR-YSKSINPYRNHIVSKLRCSDQLSE |
| (SEQ ID NO: 63) | EOY10737.1 | SGLTSNE--REHRRQIAHFHGIMLVKIQSGRKAR-YSQLNKSNPNYSASDLRCSNQLSR |
| (SEQ ID NO: 64) | XP_017627747.1 | SGFTRKE--REHRRLVAHFHGMLLKLQSSCRNSR-YSQLIKPNMNYSASKLRCSHQLSR |
| (SEQ ID NO: 65) | XP_016673034.1 | SGFTRKE--REHRRLVAHFHGMLLKLQSSCRNSR-YSQLIKPNMNYSASKLRCSHQFSR |
| (SEQ ID NO: 66) | XP_002319136.2 | SGLASDG--REHRRQRLHFHGAVLSQFWPNSRKLR-YIQSIRSHRHHYGGVIRCSNQLSD |
| (SEQ ID NO: 67) | OAY41983.1 | PGIASYE--RIHGRRGLNYQSIVVLNEWPNSRKSR-YVQLMRTHKNYHGIKLRCSHGFSG |
| (SEQ ID NO: 68) | XP_012092715.1 | SGI----E--REHGRKGLHFRSIVVLKILPNSRKSRRHVQLIRSYRNYCGLVLRCSHQFSG |

```
(SEQ ID NO: 50)  XP_010043341.1  -PRKEEVTSSRG-SRSGVPKVTE--SAREIFHLVREWSQRRVIQLAALAACTFLIIPSAD
(SEQ ID NO: 51)  XP_010528777.1  -LKARFSSPSSG-YKSGLSKGRPPFEALTLWNKLKEQSRQSLLKLVGILLACTFLIVPSVD
(SEQ ID NO: 52)  XP_010475655.1  -N-GRSSRPLSA-FRSGISKGVFDILSLPSKDELKELSTPLLLKLVGVFACAFLIVPSAE
(SEQ ID NO: 53)  XP_006307456.1  -S-GRSSRPLSA-FRSGFSKRVFDIVSLPSKNELKELSTPLLLKLVGVLACAFLIVPSAE
(SEQ ID NO: 54)  NP_172331.1     -TGGRSSRPLSA-FRSGFSKGIFDIVPLPSKNELKELTAPLLLKLVGVLACAFLIVPSAD
(SEQ ID NO: 55)  XP_002889702.1  -AGGRSSRPISA-FRSGFSKGIFDIVALPSKNELKELTTPLLLKLVFVLACAFLIVPSAD
(SEQ ID NO: 56)  XP_013641072.1  -TAKSSRPLS-G-FRSGISKGVFDIVALTSKNALKELTTPLMLKLVGVVACAFLIVPSAD
(SEQ ID NO: 57)  XP_009148110.2  -TAKSSRPLS-G-FRSGISKGVFDIVALTSKNALKELSTPLMLKLVGVVACAFLIVPSAD
(SEQ ID NO: 58)  JAU20005.1      -TLRSSRPLSAG-FRSGISKGVIDIVALTSRNALKELSTPLLLKLVGVLACAFLIVPSAD
(SEQ ID NO: 59)  XP_006417674.1  -TSRSSRPLS-G-FRSGTSKGVFDIVALTSRNALKELSTPMVLKLVGVLACAFLIVPSAD
(SEQ ID NO: 60)  AIZ75647.1      KTEEAFSKCSTR-TSEPEMKRVISFLLEEASSCIKEWSQLHFMKVAGLLACTFMIMPSAN
(SEQ ID NO: 61)  XP_009379699.1  RTEEAFSERSTK-TSEPEMGRAIDLMIEEVLSVIKEWSQLHFMKVAGLLCTFMVMPSAN
(SEQ ID NO: 62)  AMJ39491.1      GTHNISSTCSSNTRRKHEAKEGFEFVVPNLPNILRKWSQLQIMKVAGVLACALLVIPSAS
(SEQ ID NO: 63)  EOY10737.1      RKDRNFSSCSCNRR-RPKAEEAFAFLVPTISNVLKEWSQSKIVKVVGLLACAYLVIPSAS
(SEQ ID NO: 64)  XP_017627747.1  RKERKFSSSSNER-TPK------IPTISNLLEQWSQSTVKLVGLLACAYLVIPSAA
(SEQ ID NO: 65)  XP_016673034.1  RKERKFSSSSNER-TPKAEEVFSFQIPTISNLLEQWSQSTVKLVGLLACAYLVIPSAA
(SEQ ID NO: 66)  XP_002319136.2  WTKKFSSLCSSSRSMPKAIERLNFVVLSVTNALKERNNLECLKLAGILLCALLVIPSAD
(SEQ ID NO: 67)  OAY41983.1      WTKKFSSFCRTG-ANVTKAKEVLNFLMFSVSNNLKEKSHLQFLKVASILACVLLFIPSAD
(SEQ ID NO: 68)  XP_012092715.1  WTNKFPSFSSTA-ASINKAKEVLNFLMLSVSNNLKEKGQLQFLKVAGILACALLVIPSAD
                                                                     *.  ..:..   *   :..::
```

| | | |
|---|---|---|
| (SEQ ID NO: 50) | XP_010043341.1 | AVDALKTCACLLKECRIELAKCVANPSCAANVACLQTCNNRPDETECQ----IKCGDLFEN |
| (SEQ ID NO: 51) | XP_010528777.1 | AVDALKTCACLLKECRIELAKCISNPSCAANVACLQTCNNRPDETECQ----IKCGDLFEN |
| (SEQ ID NO: 52) | XP_010475655.1 | AVDALKTCACLLKGCRIELAKCISNPSCAANIACLQTCNNRPDETECQ----IKCGDLFEN |
| (SEQ ID NO: 53) | XP_006307456.1 | AVDALKTCACLLEGCRIELAKCIANPACAANVACLQTCNNRPDETECQ----IKCGDLFEN |
| (SEQ ID NO: 54) | NP_172331.1 | AVDALKTCACLLKGCRIELAKCIANPACAANVACLQTCNNRPDETECQ----IKCGDLFEN |
| (SEQ ID NO: 55) | XP_002889702.1 | AVDALKTCACLLKGCRIELAKCIANPACAANVACLQTCNNRPDETECQ----IKCGDLFEN |
| (SEQ ID NO: 56) | XP_013641072.1 | AVDALKTCACLLKGCRIELAKCIANPSCAANVACLQTCNNRPDETECQ----IKCGDLFEN |
| (SEQ ID NO: 57) | XP_009148110.2 | AVDALKTCACLLKGCRIELAKCIANPSCAANVACLQTCNNRPDETECQ----IKCGDLFEN |
| (SEQ ID NO: 58) | JAU20005.1 | AVDALKTCACLLKECRVELAKCIGNPSCAANIACLQTCNNRPDETECQ----IKCGDLFAN |
| (SEQ ID NO: 59) | XP_006417674.1 | AVDALKTCACLLKECRVELAKCIANPSCAANIACLQTCNNRPDETECQ----IKCFDLFEN |
| (SEQ ID NO: 60) | AIZ75647.1 | AADALKTCACLLKECRIELAKCIANPSCAANIACLQTCNDRPDETECQ----IKCGDLFEN |
| (SEQ ID NO: 61) | XP_009379699.1 | AVDALKTCACLLKECRIELAKCIANPSCAANIACLQTCNDRPDETECQ----IKCGDLFEN |
| (SEQ ID NO: 62) | AMJ39491.1 | AVDALKTCTCLLKECRIELAKCIANPSCAANVACLQTCNNRPDETECQ----IKCGDLFEN |
| (SEQ ID NO: 63) | EOY10737.1 | AVDALKTCTCLLKECRIELAKCIANPSCAANVACLQTCNDRPDETECQ----IKCGDLFEN |
| (SEQ ID NO: 64) | XP_017627747.1 | AVDALKTCTCLLKECRLELAKCIANPSCAANVACLQTCNDRPDETECQ----IKCGDLFEN |
| (SEQ ID NO: 65) | XP_016673034.1 | AVDALKTCTCLLKECRLELAKCIANPACAANVACLQTCNDRPDETECQ----IKCGDLFEN |
| (SEQ ID NO: 66) | XP_002319136.2 | AVDALKTCTCLLKECRLELAKCIANPACAANIACLQTCNNRPDETECQASSIKCGDLFEN |
| (SEQ ID NO: 67) | OAY41983.1 | AVDALKTCACLLKECRLELAKCIANPACAANIACLQTCNNRPDETECQ----IKCGDLFEN |
| (SEQ ID NO: 68) | XP_012092715.1 | AVDALKTCACLLKECRLELAKCIANPACAANIACLQTCNNRPDETECQ----IKCGDLFEN |
| | | *:******:::.:.**:*:*****    *****:* |

FIG. 24C
(Continued)

```
(SEQ ID NO: 50)  XP_010043341.1  SVVDEFNECAVSRKKCVPRKSDVGEFPVPDPAVLVKSFNMADFTGKWFISSGLNPTFDTF
(SEQ ID NO: 51)  XP_010528777.1  SVVDEFNECAVSRKKCVPRKSDLGEFPAPDPAVLVKSFNIGDFSGKWYISSGLNPTFDTF
(SEQ ID NO: 52)  XP_010475655.1  KVVDEFNECAVTRKKCVPRKSDLGEFPAPDPSVLVKRFNIGDFSGKWYISSGLNPTFDAF
(SEQ ID NO: 53)  XP_006307456.1  SVVDEFNECAVSRKKCVPRKSDLGEFPAPDPSVLVQNFNIGDFSGKWYITSGLNPTFDAF
(SEQ ID NO: 54)  NP_172331.1     SVVDEFNECAVSRKKCVPRKSDLGEFPAPDPSVLVQNFNISDFNGKWYITSGLNPTFDAF
(SEQ ID NO: 55)  XP_002889702.1  SVVDEFNECAVSRKKCVPRKSDLGEFPAPDPSVLVQNFNISDFNGKWYITSGLNPTFDAF
(SEQ ID NO: 56)  XP_013641072.1  SVVDEFNECAVSRKKCVPRKSDLGEFPAPDPSVLVKNFNINDFDGKWYITSGLNPTFDAF
(SEQ ID NO: 57)  XP_009148110.2  SVVDEFNECAVSRKKCVPRKSDLGEFPAPDPSVLVKNFNIQDFNGKWYITSGLNPTFDIF
(SEQ ID NO: 58)  JAU20005.1      SVVDEFNECAVSRKKCVPQKSDLGEFPVPDPSALVKNFNISDFNGKWYITSGLNPTFDTF
(SEQ ID NO: 59)  XP_006417674.1  KVVDEFNECAVSRKKCVPQKSDVGEFPIPDPAVLVKSFDIEKFNGKWFITSGLNPTFDVF
(SEQ ID NO: 60)  AIZ75647.1      SVVDEFNECAVSRKKCVPMKSDVGEFPIPDAAVLVKSFDMSKFNGKWFITSGLNPSFDTF
(SEQ ID NO: 61)  XP_009379699.1  SVVDVFNECAVSRKKCVPQKSDVGEFPVPSPAVLVKNFNIADFSGKWFISSGLNPTFDTF
(SEQ ID NO: 62)  AMJ39491.1      SVVDEFNECAVSRKKCVPQKSDIGEFPVPDPAVLVENFNIADFTGKWFISSGLNPTFDTF
(SEQ ID NO: 63)  EOY10737.1      SVVDEFNECAVSRKKCVPQKSDIGEFPVPDPAVLVENFNIADFTGKWFISSGLNPTFDTF
(SEQ ID NO: 64)  XP_017627747.1  SVVDEFNECAVSRKKCVPQKSDIGEFPVPDPAVLVENFNMADFSGKWFISSGLNPTFDTF
(SEQ ID NO: 65)  XP_016673034.1  SVVDEFNECAVSRKKCVPRKSDVGEFPVPDPAVLVKSFNIADFTGKWFISSGLNPTFDTF
(SEQ ID NO: 66)  XP_002319136.2  SVVDEFNECAVSRKKCVPRKSDVGEFPVPDPAVLVKSFNIADFSGKWFITSGLNPTFDTF
(SEQ ID NO: 67)  OAY41983.1      TVVDEFNECAVSRKKCVPKKSDVGEFPVPDPAVLVKSFNIITRGLNKWYITRGLNPTFDTF
(SEQ ID NO: 68)  XP_012092715.1  NVVDEFNECAVSRKKCVPKKSDVGEFPVPDPAVLVKSFNIADFSGKWFITSGLNPTFDTF
                                  .*** ************:* ***:** *** * **:***.: * . ** **:*****:*
```

```
(SEQ ID NO: 50) XP_010043341.1  DCQLHEFHTES-NKLMGNLTWRIRTPDSGFFTRTAVQRFVQDPEQPGILYNHDNEYLHYQ
(SEQ ID NO: 51) XP_010528777.1  DCQLHEFHTES-DKLVGNLSWRIRTPDGGFFTRSTVQKFVQDPNQPGILYNHDNEYLHYQ
(SEQ ID NO: 52) XP_010475655.1  DCQLHEFHTEGENKLVGNISWRIKTLDSGFFTRSAVQTFVQDPNQPGVLYNHDNEYLHYQ
(SEQ ID NO: 53) XP_006307456.1  DCQLHEFHTEGDNKLVGNISWRIKTLDSGFFTRSAVQKFVQDPNQPGVLYNHDNAYLHYQ
(SEQ ID NO: 54) NP_172331.1     DCQLHEFHTEGDNKLVGNISWRIKTLDSGFFTRSAVQKFVQDPNQPGVLYNHDNEYLHYQ
(SEQ ID NO: 55) XP_002889702.1  DCQVHEFHTEGDNKLVGNISWRIKTLDSGFFTRSAVQKFVQDPNQPAVFYNHDNEYLHYQ
(SEQ ID NO: 56) XP_013641072.1  DCQLHEFHTED-GKLVGNISWRIKTPDSGFFTRSTVQKFVQDPNQPAVFYNHDNEYLHYQ
(SEQ ID NO: 57) XP_009148110.2  DCQLHEFHTED-GKLVGNISWRIKTPDSGFFTRSTVQKFVQDPNQPAVLYNHDNEYLHYQ
(SEQ ID NO: 58) JAU20005.1      DCQLHEFHVQG-NKLVGNISWRIKTPDTGFFTRSAVQTFKQDPNQPAILYNHDNEYLHYQ
(SEQ ID NO: 59) XP_006417674.1  DCQRHEFHADG-DKLVGNLSWRIRTPDGGFFTRSAVQKFVQDPNQPGILYNHDNEYLHYQ
(SEQ ID NO: 60) AIZ75647.1      DCQLHEFHTES-SKLVGNLSWRIRTPDGGFFTRSAVQKFVQDPKQPGILYNHDNEYLHYQ
(SEQ ID NO: 61) XP_009379699.1  DCQLHEFHTES-SKLVGNLSWRIRTPDGGFFTRSTLQRFVQDPNYPGILYNHDNEYLHYQ
(SEQ ID NO: 62) AMJ39491.1      DCQLHEFHTEA-GKLVGNLSWRIGTPDGGFFTRSTLQRFVQDPNHPGILYNHDNEYLHYQ
(SEQ ID NO: 63) EOY10737.1      DCQLHEFHIEG-GKLVGNLSWRIRTPDGGFFTRSATQRFLQDPNHPGILYNHDNEYLHYQ
(SEQ ID NO: 64) XP_017627747.1  DCQLHEFHIEG-GKLVGNLSWRIRTPDGGFFTRSATQRFLQDPNHPGILYNHDNEYLHYQ
(SEQ ID NO: 65) XP_016673034.1  DCQLHEFHTES-NKLVGNLSWRIRTPDTGFFTRSAVQRFVQDPVHPGILYNHDNEYLHYQ
(SEQ ID NO: 66) XP_002319136.2  DCQLHEFHTES-NKLVGNISWRIRTPDGGFFTRSTVQRFVQDPMQPGILYNHDNEYLHYQ
(SEQ ID NO: 67) OAY41983.1      DCQLHDFHVES-NKLVGNLSWRIRTPDGGFFTRSTVQKFVQDPLQPGILYNHDNEYLHYQ
(SEQ ID NO: 68) XP_012092715.1  DCQLHDFHRES-NRLVGNLSWRIRTPDGGFFTRSTVQKFVQDPLQPGILYNHDNEYLHYQ
                                *** ** : .   :.*** ****:*** ****::::*:***: *.****:*:****
```

| SEQ ID NO | Accession | Sequence |
|---|---|---|
| 50 | XP_010043341.1 | DDWYILSSKTENKPDDYVFVYYRGRNDAWDGYGGAVVYTRSAVLPDSIVPELERAAKSVG |
| 51 | XP_010528777.1 | DDWYILSSKVENGPDDYVFVFVYYRGRNDAWDGYGGAVVYTRSAVLPNNIVPELERAAKSVG |
| 52 | XP_010475655.1 | DDWYILSSKIENKPEDYIFVYYRGRNDAWDGYGGAVVYTRSSVLPNSIVPELEKAAKSIG |
| 53 | XP_006307456.1 | DDWYILSSKIENKPEDYIFVYYRGRNDAWDGYGGAVVYTRSSVLPNSIVPELEKAAKSIG |
| 54 | NP_172331.1 | DDWYILSSKIENKPDDYIFVYYRGRNDAWDGYGGAVVYTRSSVLPNSIVPELEKAAKSIG |
| 55 | XP_002889702.1 | DDWYILSSKIENKPDDYIFVYYRGRNDAWDGYGGAVVYTRSSVLPNSIIPELEKAAKSIG |
| 56 | XP_013641072.1 | DDWYILSSKIENKPEDYIFVYYRGRNDAWDGYGGAVVYTRSASLPNTIVPELEKAAKSIG |
| 57 | XP_009148110.2 | DDWYILSSKIENKPEDYIFVYYRGRNDAWDGYGGAVVYTRSASLPNTIVPELEKAAKSIG |
| 58 | JAU20005.1 | DDWYILSSKIENKPEDYIFVYYRGRNDAWDGYGGAVVYTRSNVLPNSIVPELEKAAKSIG |
| 59 | XP_006417674.1 | DDQYILSSKVENKPDDYIFVYYRGRNDAWDGYGGAVIYTRSSVLPASIVPDLEKAAASVG |
| 60 | AIZ75647.1 | DDWYILSSKMENKPDDYIFVYYRGRNDAWDGYGGAVVYTRSSVLPASIVPDLEKAAASVG |
| 61 | XP_009379699.1 | DDWYILSSKIENTPEDYIFVYYRGRNDAWDGYGGAVVYTRSSVLPESIVPELERAAKCVG |
| 62 | AMJ39491.1 | DDWYILSSKIENKQDDYIFVYYQGRNDAWDGYGGAVVYTRSAVLPESIVPELEKAAKNVG |
| 63 | EOY10737.1 | DDWYIISSKIENKPDDYVFVYYRGRNDAWDGYGGAVVYTRSAVLPESIVPELKRAAQNVG |
| 64 | XP_017627747.1 | DDWYILSSKIENKPDDYVFVYYRGRNDAWDGYGGAVVYTRSAVLPETIVPELKRAAQNVG |
| 65 | XP_016673034.1 | DDWYILSSKIENKQDDYIFVYYQGRNDAWDGYGGAVVYTRSAVLPETIVPELKRAAQNVG |
| 66 | XP_002319136.2 | DDWYILSSKIENKQDDYIFVYYQGRNDAWDGYGGAVVYTRSAVLPESIVPELEKAAKSVG |
| 67 | OAY41983.1 | DDWYILSSKVENKSDDYIFVYYRGRNDAWDGYGGAVVYTRSSVLPESIAPELERAAKSVG |
| 68 | XP_012092715.1 | DDWYILSSKLENSENDYIFVYYRGRNDAWDGYFFAVVYTRSAVLPESIIPELETAAKKVG |
|   |   | *: :*:.* *:*****.:.*.*..*.*********:.*:.*.*:*.:*:* |

FIG. 24C
(Continued)

| | | |
|---|---|---|
| (SEQ ID NO: 50) | XP_010043341.1 | RDFKDFIRTDNTCGPEPPLVERIEKTVEEGEKTIVREVEQIED----EVQKVGKTEMTLF |
| (SEQ ID NO: 51) | XP_010528777.1 | RDFSKFIRTDNTCGPEPPLVERIEKTVEEGERTIVREVEQIEG----EVAKVGETEMTLL |
| (SEQ ID NO: 52) | XP_010475655.1 | RDFSTFIRTDNTCGPEPPLVERLEKTVEEGERIIVKDREEIEEVIKEVEKVGKTEMTLF |
| (SEQ ID NO: 53) | XP_006307456.1 | RDFSTFIRTDNTCGPEPPLVERLEKTVEEGERIIVKEVEEIEEEVEKEVEKVGKTEMTLF |
| (SEQ ID NO: 54) | NP_172331.1 | RDFSTFIRTDNTCGPEPALVERIEKTVEEGERIIVKEVEEIEEVEKEVEKVGRTEMTLF |
| (SEQ ID NO: 55) | XP_002889702.1 | RDFSTFIRTDNTCGPEPPLVERIEKTVEEGERIIVKEVEEIEEEVEKEVEKVGKTEMTLF |
| (SEQ ID NO: 56) | XP_013641072.1 | REFSTFIKTDNTCGPEPPLVERLEKTVEEGEKIIVKEVEEIEEVEKEVEKVGKTEMTLF |
| (SEQ ID NO: 57) | XP_009148110.2 | REFSTFIKTDNTCGPEPPLVERLEKTVEEGEKIIVKEVEEIEEEVEKEVEKVGKTEMTLF |
| (SEQ ID NO: 58) | JAU20005.1 | RDFNTFVRTDNTCGPEPPLVERFEKTVEEGEKMIEKEVEEIEEVEKEVEKVGKTEMTLF |
| (SEQ ID NO: 59) | XP_006417674.1 | RDFSTFVRTDNTCGPEPPLVERLEKTLEEGERNIEEVKQIEGEVE----KVEQTELTLL |
| (SEQ ID NO: 60) | AIZ75647.1 | RDFSKFIKTDNTCGPEPPLVERLEKTIEEGERTIIEEVKQIEGEVE----KVEQTELTLF |
| (SEQ ID NO: 61) | XP_009379699.1 | RDFNKFIKTDNTCGPEPPLVERLEKKVEEGETLIREVKEIEGEVE----KVGKTEMTLF |
| (SEQ ID NO: 62) | AMJ39491.1 | RDFNKFIRTDNTCGPEPPLVERLEKKVEEGEQTLIREVKEIEGEVE----KVGKTEMTLF |
| (SEQ ID NO: 63) | EOY10737.1 | RNFNKFIRTDNSCGPEPPLVERLEKKVEEGEQTLIREVGVEKGVEKVEKTEQTLF |
| (SEQ ID NO: 64) | XP_017627747.1 | RNFNKFIRTDNSCGPEPPLVERLEKKVEEGEQTLIREVGEVEKGVEKVEKTEQTLF |
| (SEQ ID NO: 65) | XP_016673034.1 | RDFSKFIRTDNTCGPEPPLVERLEKTIIKEVEEIIEQKVE----KAGKTELSLF |
| (SEQ ID NO: 66) | XP_002319136.2 | RDFSKFIRTDNTCGPEPPLVERLEKTVEEGEKSIIKEVQEIEGEVE----KVGKTEMTLF |
| (SEQ ID NO: 67) | OAY41983.1 | RDFNKFIITDNTCGPEPPLAERIEKTVEEGERTIIREVEEIEGNVE----KVGKTEMALF |
| (SEQ ID NO: 68) | XP_012092715.1 | *:*. *: .**:.**. . :: :: .: |

FIG. 24C
(Continued)

```
(SEQ ID NO: 50)  XP_010043341.1   QRLTEGFRELRQDEENFLRRLSQEEMEVLNELKMEATEVEKLFGRALPIRKLR
(SEQ ID NO: 51)  XP_010528777.1   QRLVEGFKELKQDEENFLQGLNKEEMELLSELKMEASEVEKLFGKALPIRKLR
(SEQ ID NO: 52)  XP_010475655.1   QRLAEGFNELRKDEENFMRELSKEEMEFLDEIKMEANEVEKLFGKALPIRKVR
(SEQ ID NO: 53)  XP_006307456.1   QRLAEGFNELKQDEENFVRELSKEEMEFLDEIKMEASEVEKLFGKALPIRKVR
(SEQ ID NO: 54)  NP_172331.1      QRLAEGFNELKQDEENFVRELSKEEMEFLDEIKMEASEVEKLFGKALPIRKVR
(SEQ ID NO: 55)  XP_002889702.1   QRLAEGFNELKQDEENFVREFSKEEMEFLDEIKMEASEIEKLFGKALPIRKVR
(SEQ ID NO: 56)  XP_013641072.1   QRLAEGFEELKQDEENFLRGLSKEEMELLDELKMEANEVEKLFGKALPIRKFR
(SEQ ID NO: 57)  XP_009148110.2   QRLAEGFEELKQDEENFLRGLSKEEMELLDELKMEANEVEKLFGKALPIRKFR
(SEQ ID NO: 58)  JAU20005.1       QRLAEGFNELKQDEENFLRGLSEEEMALLDELKMEAGEVEKLFGKALPIRKFR
(SEQ ID NO: 59)  XP_006417674.1   QRLAEGFNELKQDEENFLRGLSEEEMELLNELKMEASEVEKLFGKSLPIRKVR
(SEQ ID NO: 60)  AIZ75647.1       QKLAEGFNELKQDEENFLRGLSKEEMDILSELKMEAGEVEKLFGQTLPLRKLR
(SEQ ID NO: 61)  XP_009379699.1   QKLLEGFNVLKQDEENFLRGLSKEEMDLLSELKMEARENVEKLFGKTLPLRKLR
(SEQ ID NO: 62)  AMJ39491.1       QKLAEGFKELQKDEENFLEELSKEEMDVLSELKMEAREVEKLFGGALPLRKLR
(SEQ ID NO: 63)  EOY10737.1       QKLAEGFKELQQDEENFLRGLSKEEMGLLNELKMEASEVEKLFGEALPLRKLR
(SEQ ID NO: 64)  XP_017627747.1   QRLAEGFKELQQDEENFLRGLSKEEMELLNDLKMEASEVEKLFGEALPIRKLR
(SEQ ID NO: 65)  XP_016673034.1   QRLAEGFKELQQDEENFLRGLSKEEMELLNDLKMEASEVEKLFGEALPIRKLR
(SEQ ID NO: 66)  XP_002319136.2   QRLTEGFKEIQKDEENFLRELSKEETDLLNDLRMEAGEVEKLFGRALPIRKLR
(SEQ ID NO: 67)  OAY41983.1       QRLAEGFKELQQDEEILLRKLSKEEMELFNDLKMEASEVEKLFGGALPLRKLR
(SEQ ID NO: 68)  XP_012092715.1   QRLAEGFKELQQDEEFFVRELSKEEMDILNDLKMEAGEVEKLFGEALPLRKLR
                                  *::*  ***.   ***:     ::::.:*:* *: ..   ****.   ..:..
```

FIG. 24C (Continued)

TRANSGENIC PLANTS WITH INCREASED PHOTOSYNTHESIS EFFICIENCY AND GROWTH

CROSS REFERENCE TO RELATED APPLICATIONS

This application is the § 371 U.S. National Stage of International Application No. PCT/US2017/034840, filed May 26, 2017, which was published in English under PCT Article 21(2), which in turn claims the benefit of U.S. Provisional Application No. 62/342,248, filed May 27, 2016, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing, named Sequence_Listing.txt, which was created Nov. 24, 2018, and is 255 KB.

FIELD OF THE INVENTION

The present invention relates to a method of increasing plant photosynthetic efficiency and growth.

BACKGROUND

Light intensity in plant canopies is very dynamic and leaves routinely experience sharp fluctuations in levels of absorbed irradiance. Several photo-protective mechanisms are induced to protect the photosynthetic antenna complexes from over-excitation when light intensity is too high or increases too fast for photochemistry to utilize the absorbed energy. Excess excitation energy in the photosystem II (PSII) antenna complex is harmlessly dissipated as heat through an inducible protective process, which is observable and often named as non-photochemical quenching of chlorophyll fluorescence (NPQ; Miller et al. Plant Physiol. Vol 125, 1558-1566, 2000). Changes in NPQ can be fast but not instantaneous, and therefore lag behind fluctuations in absorbed irradiance. The rate of NPQ relaxation is considerably slower than the rate of induction, and this asymmetry is exacerbated by prolonged or repeated exposure to excessive light conditions. This relatively slow rate of recovery of PSII antennae from the quenched to the unquenched state may imply that photosynthetic quantum yield and associated $CO_2$ fixation are transiently limited by NPQ upon a change from high to low light intensity. When this hypothesis was tested in model simulations and integrated over a crop canopy, corresponding losses of $CO_2$ fixation were estimated to range between 7.5%-30% (Zhu et al. J. Exp. Bot. Vol 55, 1167-1175, 2004). Based on these computations, increasing the relaxation rate of NPQ suggests a possible strategy to improve photosynthetic efficiency, however experimental proof has so far been lacking.

While the exact NPQ quenching site and nature of the quenching mechanisms involved are still being elucidated, it is clear that for NPQ to occur, PSII-associated antennae need to undergo a conformational change to the quenched state, which can be induced by a number of different mechanisms with contrasting time constants. The predominant and universally present mechanism of NPQ in higher plants is so-called energy-dependent quenching (qE). Induction of qE requires low thylakoid lumen pH and is greatly aided by the presence of photosystem II subunit S (PsbS) and de-epoxidation of violaxanthin to antheraxanthin and zeaxanthin via the reversible xanthophyll pigment cycle.

Overexpression of PsbS strongly affects the amplitude of qE formation, and results in an increased rate of induction and relaxation of qE, but can compete with photosynthetic quantum yield under less stressful conditions. Thus, while the enhancement of qE via PsbS overexpression may offer increased photoprotection under high light or rapidly fluctuating conditions, the positive effects of PsbS overexpression alone on $CO_2$ fixation and plant growth, will depend greatly on the prevailing light environment. An alternative route of NPQ manipulation is to modify the reversible xanthophyll pigment cycle. A schematic representation of the pathway for the biosynthesis of carotenoids (carotenes and xanthophylls) from lycopene is shown in FIG. 17. Zeaxanthin accumulation is associated with several NPQ components (qE, qZ, and qI). The conversion of violaxanthin to zeaxanthin in excess light is catalyzed by the enzyme violaxanthin de-epoxidase (VDE). The conversion of zeaxanthin to violaxanthin is catalyzed by the enzyme zeaxanthin epoxidase (ZEP). *Arabidopsis* mutants with increased xanthophyll pigment pool size were shown to have slower rates of NPQ formation and relaxation while the amplitude of NPQ was unaffected. Interestingly, the rate of NPQ formation and relaxation in these mutants and the wild-type control plants appeared to be mainly controlled by the de-epoxidation state of the xanthophyll pigment pool. It was shown by Nilkens et al. Biochimica et Biophysica Acta 1797; 466-475 (2010) that in particular the kinetics of zeaxanthin epoxidation are strongly correlated with the rate of NPQ relaxation. Therefore, the rate of adjustment of xanthophyll cycle equilibrium also has control over the rate of NPQ formation and relaxation, and seems to be affected by the xanthophyll pool size relative to the rate of turn-over by violaxanthin de-epoxidase (VDE) and zeaxanthin epoxidase (ZEP).

It is yet to be determined whether NPQ can be manipulated to reduce transient competition with photosynthetic quantum yield at low light intensity, while maintaining photo-protection at high light intensity. Plants having improved quantum yield and $CO_2$ fixation under fluctuating light conditions could provide improved plant growth and crop yields.

BRIEF SUMMARY

One aspect of the present disclosure relates to a transgenic plant having one or more heterologous nucleotide sequences encoding PsbS, ZEP and/or VDE. In some embodiments, the nucleotide sequences are derived from a dicot plant. In some embodiments, the nucleotide sequences are derived from *Arabidopsis thaliana*. In some embodiments, the transgenic plant has one or more heterologous nucleotide sequences encoding PsbS, ZEP and VDE. In some embodiments, PsbS is encoded by the nucleotide sequence of SEQ ID NO: 1. In some embodiments, ZEP is encoded by the nucleotide sequence of SEQ ID NO: 2. In some embodiments. VDE is e encoded by the nucleotide sequence of SEQ ID NO: 3. In some embodiments, PsbS is encoded by a nucleotide sequence having at least 90% of sequence identity to SEQ ID NO: 1. In some embodiments, ZEP is encoded by a nucleotide sequence having at least 90% of sequence identity to SEQ ID NO: 2. In some embodiments, VDE is encoded by a nucleotide sequence having at least 90% of sequence identity to SEQ ID NO: 3. In some embodiments. PsbS is encoded by a nucleotide sequence having at least 70% of sequence identity to SEQ ID NO: 1. In some embodiments, ZEP is encoded by a nucleotide sequence having at least 70% of sequence identity to SEQ ID NO: 2. In some embodiments, VDE is encoded by a nucleotide sequence having at least 70% of sequence identity to SEQ ID NO: 3. In some embodiments, PsbS has the amino acid sequence of SEQ ID NO: 4. In some embodiments, ZEP has the amino acid sequence of SEQ ID NO:5. In some embodiments, VDE has the amino acid sequence of SEQ ID NO: 6. In some embodiments, PsbS has an amino acid sequence having at least 90% of sequence identity to SEQ ID NO: 4. In some embodiments. ZEP has an amino acid sequence having at least 90% of sequence identity to SEQ ID NO: 5. In some embodiments, VDE has an amino acid sequence having at least 90% of sequence identity to SEQ ID NO: 6. In some embodiments, PsbS has an amino acid sequence having at least 70% of sequence identity to SEQ ID NO: 4. In some embodiments, ZEP has an amino acid sequence having at least 70% of sequence identity to SEQ ID NO: 5. In some embodiments. VDE has an amino acid sequence having at least 70% of sequence identity to SEQ ID NO: 6. In some embodiments, PsbS further comprises a conserved domain of SEQ ID NO: 7. In some embodiments, ZEP further comprises a conserved domain of SEQ ID NO:8. In some embodiments, VDE further comprises a conserved domain of SEQ ID NO: 9. In some of the embodiments described above, the plant is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In some of the embodiments described above, the plant is switchgrass, *Miscanthus, Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop. In some embodiments, the plant is *Nicotiana tabacum*. In some embodiments, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some of the embodiments described above, the plant has increased growth under fluctuating light conditions as compared to a control plant under fluctuating light conditions. In some of the embodiments described above, the plant has increased photosynthetic efficiency under fluctuating light conditions as compared to a control plant under fluctuating light conditions. In some of the embodiments described above, the plant has improved photoprotection efficiency under fluctuating light conditions as compared to a control plant under fluctuating light conditions. In some of the embodiments described above, the plant has improved quantum yield and $CO_2$ fixation under fluctuating light conditions as compared to a control plant under fluctuating light conditions. In some of the embodiments described above, the plant is an elite line or elite strain. In some of the embodiments described above, the plant further comprises expression of at least one additional polypeptide that provides herbicide resistance, insect or pest resistance, disease resistance, modified fatty acid metabolism, and/or modified carbohydrate metabolism.

Another aspect of the present disclosure relates to an expression vector having one or more heterologous nucleotide sequences that encode PsbS, ZEP and/or VDE. In some embodiments, the vector contains a promoter of Rbcs1A, GAPA-1 or FBA2. In some embodiments, the Rbcs1A promoter drives expression of ZEP, a GAPA-1 promoter drives expression of PsbS, and an FBA2 promoter drives expression of VDE. In some embodiments, the vector is a T-DNA. In some embodiments, the vector has a nucleotide sequence encoding polypeptide that provides antibiotic resistance. In some embodiments, the vector has a left border (LB) and right border (RB) domain flanking the expression control sequences and the nucleotide sequence encoding the PsbS, ZEP and VDE polypeptides. In some embodiments, PsbS is encoded by the nucleotide sequence of SEQ ID NO: 1. In some embodiments, ZEP is encoded by the nucleotide sequence of SEQ ID NO: 2. In some embodiments. VDE is e encoded by the nucleotide sequence of SEQ ID NO: 3. In some embodiments, PsbS is encoded by a nucleotide sequence having at least 90% of sequence identity to SEQ ID NO: 1. In some embodiments, ZEP is encoded by a nucleotide sequence having at least 90% of sequence identity to SEQ ID NO: 2. In some embodiments. VDE is encoded by a nucleotide sequence having at least 90% of sequence identity to SEQ ID NO: 3. In some embodiments, PsbS is encoded by a nucleotide sequence having at least 70% of sequence identity to SEQ ID NO: 1. In some embodiments. ZEP is encoded by a nucleotide sequence having at least 70% of sequence identity to SEQ ID NO: 2. In some embodiments, VDE is encoded by a nucleotide sequence having at least 70% of sequence identity to SEQ ID NO: 3. In some embodiments, PsbS has the amino acid sequence of SEQ ID NO: 4. In some embodiments. ZEP has the amino acid sequence of SEQ ID NO:5. In some embodiments, VDE has the amino acid sequence of SEQ ID NO: 6. In some embodiments. PsbS has an amino acid sequence having at least 90% of sequence identity to SEQ ID NO: 4. In some embodiments, ZEP has an amino acid sequence having at least 90% of sequence identity to SEQ ID NO: 5. In some embodiments, VDE has an amino acid sequence having at least 90% of sequence identity to SEQ ID NO: 6. In some embodiments, PsbS has an amino acid sequence having at least 70% of sequence identity to SEQ ID NO: 4. In some embodiments. ZEP has an amino acid sequence having at least 70% of sequence identity to SEQ ID NO: 5. In some embodiments, VDE has an amino acid sequence having at least 70% of sequence identity to SEQ ID NO: 6. In some embodiments, PsbS further comprises a conserved domain of SEQ ID NO: 7. In some embodiments. ZEP further comprises a conserved domain of SEQ ID NO:8. In some embodiments. VDE further comprises a conserved domain of SEQ ID NO: 9. In some embodiments, the expression vector is in a bacterial cell. In some of the embodiments described above, the expression vector is in an *Agrobacterium* cell. In some of the embodiments described above, the expression vector is used to produce a transgenic plant. In some of the embodiments described above, the transgenic plant produces a seed. In some of the embodiments described above, the seed further produces a progeny plant.

Other aspects of the present disclosure relate to methods of increasing photosynthesis and growth in a plant, the methods including increasing expression in the plant of two or more polypeptides described herein. In one aspect, the present disclosure relates to a method for increasing growth in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing photosynthetic efficiency in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing photoprotection efficiency in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing quantum yield and $CO_2$ in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing the rate of relaxation of non-photochemical quenching (NPQ) in a plant, including increasing expression in the plant of at least two polypeptides from PsbS, ZEP and VDE, thereby producing a plant with increased expression of the two or more polypeptides as compared to a control plant. In some embodiments, expression is increased in PsbS and ZEP. In some embodiments, expression is increased in PsbS and VDE. In some embodiments, expression is increased in VDE and ZEP. In some embodiments, expression is increased in PsbS, ZEP and VDE. In some embodiments, expression of PsbS, ZEP and/or VDE is increased by expressing one or more heterologous nucleotide sequences encoding PsbS, ZEP and/or VDE. In some embodiments, expression of PsbS, ZEP and/or VDE is increased by modifying the promoter region of PsbS, ZEP and/or VDE. In some embodiments, promoter modification is achieved by a genome editing system. In some embodiments, the genome editing system is CRISPR.

Another aspect of the present disclosure relates to a method of selecting a plant for improved growth characteristics under fluctuating light conditions, including the steps of providing a population of plants; modifying the population of plants to increase the activity of any of PsbS, ZEP and VDE; detecting the level of non-photochemical quenching (NPQ) under fluctuating light conditions in a plant; comparing the level of NPQ under fluctuating light conditions in a plant with the control level of NPQ under fluctuating light conditions; and selecting a plant having increased rate of NPQ relaxation when the plant is transitioned from under high light intensity to low light intensity. In some embodiments, the control level of NPQ is the lowest level of NPQ in the population. In some embodiments, the control level of NPQ is the median level of NPQ in the population. In some embodiments, the control level of NPQ is the mean level of NPQ in the population. In some embodiments, the control level of NPQ is the level of NPQ in a control plant. In some embodiments, the plants are modified by inducing one or more mutations in PsbS, ZEP and/or VDE with a mutagen. In some embodiments, the mutagen is ethane methyl sulfonate (EMS). In some embodiments, the plants are modified by introducing heterologous PsbS, ZEP and/VDE using transgenic techniques. In some embodiments, the plants are modified by modifying the respective native promoters of PsbS, ZEP and/VDE using a genome editing system. In some embodiments, the genome editing system is CRISPR. Another aspect of the present disclosure relates to a method of screening for a nucleotide sequence polymorphism associated with improved growth characteristics under fluctuating light conditions, including the steps of providing a population of plants; obtaining the nucleotide sequences regulating and/or encoding any of PsbS, ZEP and VDE in the population of plants; obtaining one or more polymorphisms in the nucleotide sequences regulating and/or encoding any of PsbS, ZEP and VDE in the population of plants; detecting the rate of non-photochemical quenching (NPQ) relaxation upon transition from high light intensity to low light intensity in the population of plants; performing statistical analysis to determine association of the polymorphism with the rate of NPQ relaxation in the population of plants; and selecting the polymorphism having statistically significant association with the rate of NPQ relaxation. In some embodiments, the polymorphism is a single nucleotide polymorphism (SNP). In some embodiments, the polymorphism is located in the promoter of PsbS, ZEP and/or VDE. In some embodiments, the polymorphism is detected by sequence determination. In some embodiments, the polymorphism is detected by gel electrophoresis. In some embodiments, the polymorphism is further used to screen a population of plants to select a plant having improved growth characteristics under fluctuating light conditions. In some embodiments, the polymorphism is further used as a target for genome editing in PsbS, ZEP and/or VDE to improve growth characteristics in a plant under fluctuating light conditions. In some of the embodiments described above, the improved growth characteristic is improved growth, improved photosynthetic efficiency, improved photoprotection efficiency, improved quantum yield and/or improved CO2 fixation. In some of the embodiments described above, NPQ in a plant is detected by measuring chlorophyll fluorescence.

In some of the embodiments described above, the improved growth characteristic is improved growth. In some embodiments, the improved growth characteristic is improved photosynthetic efficiency. In some embodiments, the improved growth characteristic is improved photoprotection efficiency. In some embodiments, the improved growth characteristic is improved quantum yield and $CO_2$ fixation. In some embodiments, the improved growth characteristic is increased rate of relaxation of non-photochemical quenching (NPQ). In some embodiments, NPQ is detected using chlorophyll fluorescence imaging.

In some embodiments that may be combined with any of the preceding embodiments, PsbS is encoded by the nucleotide sequence of SEQ ID NO: 1. In some embodiments that may be combined with any of the preceding embodiments, ZEP is encoded by the nucleotide sequence of SEQ ID NO: 2. In some embodiments that may be combined with any of the preceding embodiments, VDE is e encoded by the nucleotide sequence of SEQ ID NO: 3. In some embodiments that may be combined with any of the preceding embodiments, PsbS is encoded by a nucleotide sequence having at least 90% of sequence identity to SEQ ID NO: 1. In some embodiments that may be combined with any of the preceding embodiments, ZEP is encoded by a nucleotide sequence having at least 90% of sequence identity to SEQ ID NO: 2. In some embodiments that may be combined with any of the preceding embodiments, VDE is encoded by a nucleotide sequence having at least 90% of sequence identity to SEQ ID NO: 3. In some embodiments that may be combined with any of the preceding embodiments. PsbS is encoded by a nucleotide sequence having at least 70% of sequence identity to SEQ ID NO: 1. In some embodiments that may be combined with any of the preceding embodiments, ZEP is encoded by a nucleotide sequence having at least 70% of sequence identity to SEQ ID NO: 2. In some embodiments that may be combined with any of the preceding embodiments, VDE is encoded by a nucleotide sequence having at least 70% of sequence identity to SEQ ID NO: 3. In some embodiments that may be combined with any of the preceding embodiments. PsbS has the amino acid sequence of SEQ ID NO: 4. In some embodiments that may be combined with any of the preceding embodiments, ZEP has the amino acid sequence of SEQ ID NO:5. In some embodiments that may be combined with any of the preceding embodiments, VDE has the amino acid sequence of SEQ ID NO: 6. In some embodiments that may be combined with any of the preceding embodiments, PsbS has an amino acid sequence having at least 90% of sequence identity to SEQ ID NO: 4. In some embodiments that may be combined with any of the preceding embodiments, ZEP has an amino acid sequence having at least 90% of sequence identity to SEQ ID NO: 5. In some embodiments that may be combined with any of the preceding embodiments, VDE has an amino acid sequence having at least 90% of sequence identity to SEQ ID NO: 6. In some embodiments that may be combined with any of the preceding embodiments, PsbS has an amino acid sequence having at least 70% of sequence identity to SEQ ID NO: 4. In some embodiments that may be combined with any of the preceding embodiments, ZEP has an amino acid sequence having at least 70% of sequence identity to SEQ ID NO: 5. In some embodiments that may be combined with any of the preceding embodiments, VDE has an amino acid sequence having at least 70% of sequence identity to SEQ ID NO: 6. In some embodiments that may be combined with any of the preceding embodiments, PsbS further comprises a conserved domain of SEQ ID NO: 7. In some embodiments that may be combined with any of the preceding embodiments, ZEP further comprises a conserved domain of SEQ ID NO:8. In some embodiments that may be combined with any of the preceding embodiments, VDE further comprises a conserved domain of SEQ ID NO: 9. In some embodiments that may be combined with any of the preceding embodiments, the plant is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In some embodiments that may be combined with any of the preceding embodiments, the plant is switchgrass, *Miscanthus*, *Medicago*, sweet *Sorghum*, grain *Sorghum*, sugarcane, energy cane, elephant grass, maize, wheat, barley, oats, rice, soybean, oil palm, safflower, sesame, tobacco, flax, cotton, sunflower, *Camelina*, *Brassica napus*, *Brassica carinata*, *Brassica juncea*, pearl millet, foxtail millet, other grain, rice, oilseed, a vegetable crop, a forage crop, an industrial crop, a woody crop or a biomass crops. In some embodiments that may be combined with any of the preceding embodiments, the plant is *Nicotiana tabacum*. In some embodiments that may be combined with any of the preceding embodiments, the plant is *Zea mays*. In some embodiments that may be combined with any of the preceding embodiments, the plant is *Oryza sativa*. In some embodiments that may be combined with any of the preceding embodiments, the plant is *Sorghum bicolor*. In some embodiments that may be combined with any of the preceding embodiments, the plant is *Glycine max*. In some embodiments that may be combined with any of the preceding embodiments, the plant is *Vigna unguiculata*. In some embodiments that may be combined with any of the preceding embodiments, the plant is *Populus* spp. In some embodiments that may be combined with any of the preceding embodiments, the plant is *Eucalyptus* spp. In some embodiments that may be combined with any of the preceding embodiments, the plant is *Manihot esculenta*. In some embodiments that may be combined with any of the preceding embodiments, the plant is *Hordeum vulgare*. In some embodiments that may be combined with any of the preceding embodiments, the plant is *Solanum tuberosum*. In some embodiments that may be combined with any of the preceding embodiments, the plant is *Saccharum* spp. In some embodiments that may be combined with any of the preceding embodiments, the plant is *Medicago sativa*.

In some embodiments that may be combined with any of the preceding embodiments, the transcript level of VDE in the plant is increased 3-fold as compared to a control plant. In some embodiments that may be combined with any of the preceding embodiments, the transcript level of PsbS in the plant is increased 3-fold as compared to a control plant. In some embodiments that may be combined with any of the preceding embodiments, the transcript level of ZEP in the plant is increased 8-fold as compared to a control plant. In some embodiments that may be combined with any of the preceding embodiments, the transcript level of VDE in the plant is increased 10-fold as compared to a control plant. In some embodiments that may be combined with any of the preceding embodiments, the transcript level of PsbS in the plant is increased 3-fold as compared to a control plant. In some embodiments that may be combined with any of the preceding embodiments, the transcript level of ZEP in the plant is increased 6-fold as compared to a control plant. In some embodiments that may be combined with any of the preceding embodiments, the transcript level of VDE in the plant is increased 4-fold as compared to a control plant. In some embodiments that may be combined with any of the preceding embodiments, the transcript level of PsbS in the plant is increased 1.2-fold as compared to a control plant. In some embodiments that may be combined with any of the preceding embodiments, the transcript level of ZEP in the plant is increased 7-fold as compared to a control plant. In some embodiments that may be combined with any of the preceding embodiments, the protein level of VDE in the plant is increased 16-fold as compared to a control plant. In some embodiments that may be combined with any of the preceding embodiments, the protein level of PsbS in the plant is increased 2-fold as compared to a control plant. In some embodiments that may be combined with any of the preceding embodiments, the protein level of ZEP in the plant is increased 80-fold as compared to a control plant. In some embodiments that may be combined with any of the preceding embodiments, the protein level of VDE in the plant is increased 30-fold as compared to a control plant. In some embodiments that may be combined with any of the preceding embodiments, the protein level of PsbS in the plant is increased 4-fold as compared to a control plant. In some embodiments that may be combined with any of the preceding embodiments, the protein level of ZEP in the plant is increased 74-fold as compared to a control plant. In some embodiments that may be combined with any of the preceding embodiments, the protein level of VDE in the plant is increased 47-fold as compared to a control plant. In some embodiments that may be combined with any of the preceding embodiments, the protein level of PsbS in the plant is increased 3-fold as compared to a control plant. In some embodiments that may be combined with any of the preceding embodiments, the protein level of ZEP in the plant is increased 75-fold as compared to a control plant. In some embodiments that may be combined with any of the preceding embodiments, the increase of transcript level in the plant as compared to a control plant between VDE, PsbS and ZEP has a ratio of 3:3:8, 10:3:6, or 4:1.2:7. In some embodiments that may be combined with any of the preceding embodiments, the increase of protein level in the plant as compared to a control plant between VDE, PsbS and ZEP has a ratio of 16:2:80, 30:4:74, or 47:3:75. In some embodiments that may be combined with any of the preceding embodiments, the increase of transcript level of VDE in the plant as compared to a control plant is in the range of 3-fold to 10-fold. In some embodiments that may be combined with any of the preceding embodiments, the increase of transcript level of PsbS in the plant as compared to a control plant is from about 1.2-fold to about 3-fold. In some embodiments that may be combined with any of the preceding embodiments, the increase of transcript level of ZEP in the plant as compared to a control plant is from about 6-fold to about 8-fold. In some embodiments that may be combined with any of the preceding embodiments, the increase of protein level of VDE in the plant as compared to a control plant is in the range of 16-fold to 47-fold. In some embodiments that may be combined with any of the preceding embodiments, the increase of protein level of PsbS in the plant as compared to a control plant is from about 2-fold to about 4-fold. In some embodiments that may be combined with any of the preceding embodiments, the increase of protein level of ZEP in the plant as compared to a control plant is from about 74-fold to about 80-fold.

BRIEF DESCRIPTION OF THE DRAWINGS

The features, objects and advantages other than those set forth above will become more readily apparent when consideration is given to the detailed description below. Such detailed description makes reference to the following drawings, wherein:

FIG. 16. Time constants of NPQ in the first induction/relaxation.

FIG. 24. Amino acid alignment of NPQ genes in representative plant species for (A) PsbS. (B) ZEP and (C) VDE.

Figure 1:
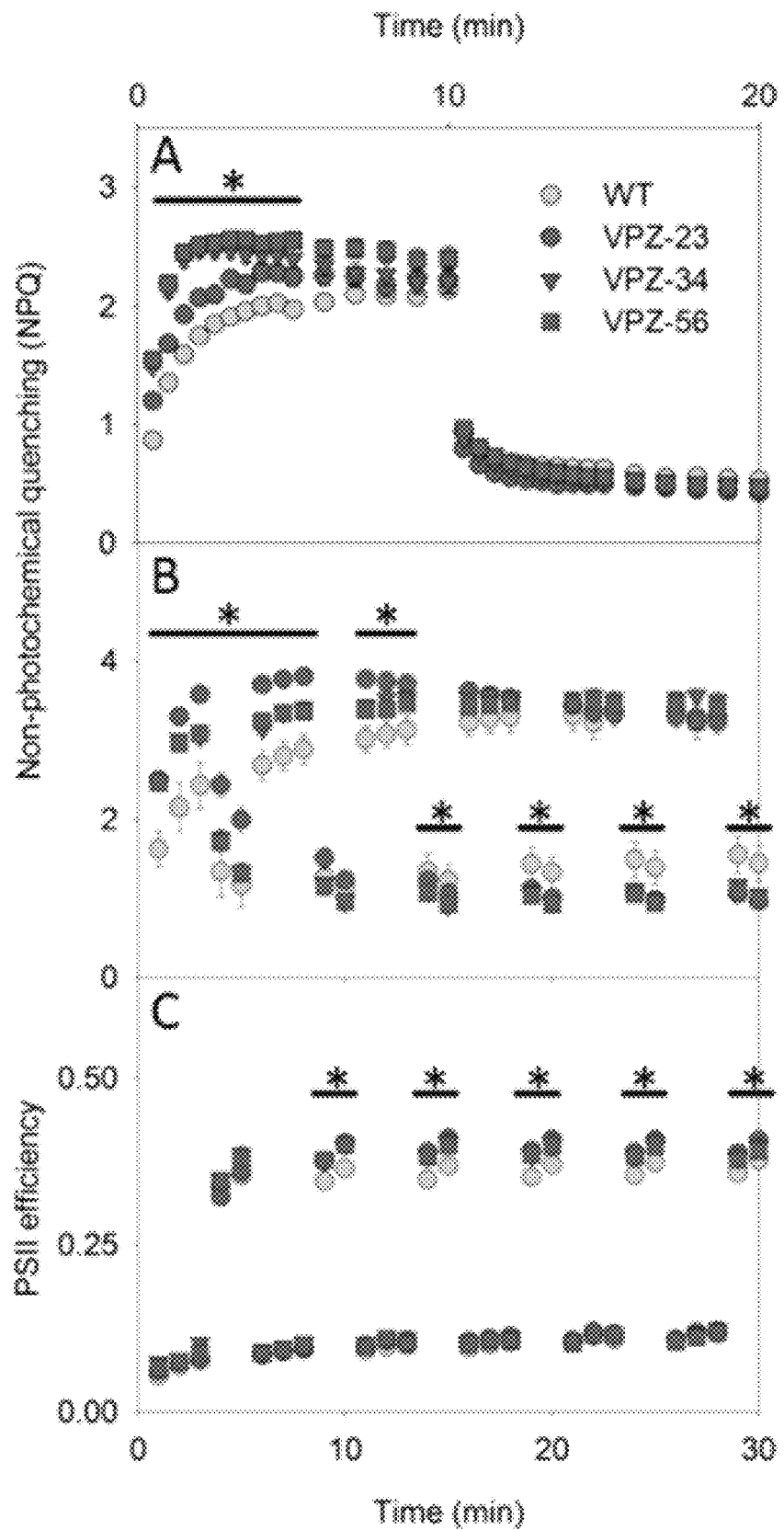
FIG. 1. (A) Non-photochemical quenching in young seedlings of wild-type and three (VDE-PsbS-ZEP) VPZ overexpressing lines during 10 min illumination with 1000 µmol $m^{-2}$ $s^{-1}$ PFD, followed by 10 min of dark relaxation. (B) Non-photochemical quenching and (C) PSII efficiency in young seedlings during repeated cycles of 3 min illumination with 2000 µmol $m^{-2}$ $s^{-1}$ PFD, followed by 2 min of 200 µmol $m^{-2}$ $s^{-1}$ PFD. Error bars indicate ±se (n=18), asterisks indicate significant differences between VPZ lines and wild-type ($\alpha$=0.05).

The patent or application file contains at least one drawing executed in color. Copies of this patent or patent application publication with color drawing(s) will be provided by the Office upon request and payment of the necessary fee.

DETAILED DESCRIPTION

The plants, vectors, and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the plants, vectors, and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Definitions

Unless otherwise noted, technical terms are used according to conventional usage. Definitions of common terms in molecular biology may be found in Lewin, Genes VII, 2001 (Oxford University Press), The Encyclopedia of Molecular Biology, Kendrew et al, eds., 1999 (Wiley-Interscience) and Molecular Biology and Biotechnology, a Comprehensive Desk Reference, Robert A. Meyers, ed., 1995 (VCH Publishers. Inc), Current Protocols In Molecular Biology, F. M. Ausubel et al., eds., 1987 (Green Publishing), Sambrook and Russell, Molecular Cloning: A Laboratory Manual, 3rd edition, 2001.

The terms "polynucleotide". "nucleotide", "nucleotide sequence", "nucleic acid". "gene," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" or "expression cassette" is a DNA sequence that controls and regulates the transcription and/or translation of another DNA sequence. The expression control sequence can comprise a heterologous or non-heterologous promoter.

As used herein. "operably linked" means incorporated into a genetic construct so that expression control sequences effectively control expression of a coding sequence of interest.

As used herein, "transformed" and "transfected" encompass the introduction of a nucleic acid (e.g., a vector) into a cell by a number of techniques known in the art.

"Plasmids" are designated by a lower case "p" preceded and/or followed by capital letters and/or numbers.

As used herein, the term "level of expression" refers to the measurable expression level of a given nucleic acid or polypeptide. The level of expression of a given nucleic acid or polypeptide is determined by methods well known in the art. The term "differentially expressed" or "differential expression" refers to an increase or decrease in the measurable expression level of a given a given nucleic acid or polypeptide. "Differentially expressed" or "differential expression" means a 1-fold, or more, up to and including 2-fold, 5-fold, 10-fold, 20-fold, 50-fold or more difference in the level of expression of a given nucleic acid or polypeptide in two samples used for comparison. A given nucleic acid or polypeptide is also said to be "differentially expressed" in two samples if one of the two samples contains no detectable expression of a given nucleic acid or polypeptide.

Polymorphism refers to variation in nucleotide sequences within a genome that may or may not have a functional consequence. These variants can be developed as genetic markers and used in all aspects of genetic investigation including the analysis of associating genetic differences with variation in traits of interest. As used herein, the term "polymorphism" includes, but is not limited to, single nucleotide polymorphism (SNP), insertion/deletion (InDel), simple sequence repeats (SSR), presence/absence variation (PAV), and copy number variation (CNV). Polymorphisms can be naturally occurring or artificially induced. The methods of inducing and detecting polymorphisms are well known in the art.

As used herein, the term "promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined. DNA fragments of some variation may have identical promoter activity. As is well-known in the art, promoters can be categorized according to their strength and/or the conditions under which they are active. e.g., constitutive promoters, strong promoters, weak promoters, inducible/repressible promoters, tissue-specific/developmentally regulated promoters, cell-cycle dependent promoters, etc.

As used herein, the term "genome editing" is a type of genetic engineering in which DNA is inserted, replaced, or removed from a genome using artificially engineered nucleases, or "molecular scissors." It is a useful tool to elucidate the function and effect of a gene in a sequence specific manner, and to make alterations within a genome that result in desirable phenotypic changes. Genome editing systems include, but are not limited to, meganucleases, zinc finger nucleases (ZFN), transcription activator-like effector-based nucleases (TALEN), and the clustered regularly interspaced short palindromic repeats (CRISPR).

The term "plant" refers to any of various photosynthetic, eukaryotic multi-cellular organisms of the kingdom Plantae, characteristically producing embryos, containing chloroplasts, having cellulose cell walls and lacking locomotion. As used herein, a "plant" includes any plant or part of a plant at any stage of development, including seeds, suspension cultures, plant cells, embryos, meristematic regions, callus tissue, leaves, roots, shoots, gametophytes, sporophytes, pollen, microspores, and progeny thereof. Also included are cuttings, and cell or tissue cultures. As used in conjunction with the present disclosure, plant tissue includes, for example, whole plants, plant cells, plant organs, e.g., leafs, stems, roots, meristems, plant seeds, protoplasts, callus, cell cultures, and any groups of plant cells organized into structural and/or functional units.

The term "plant" is used in its broadest sense. It includes, but is not limited to, any species of woody, ornamental or decorative, crop or cereal, fruit or vegetable plant, and algae (e.g., *Chlamydomonas reinhardii*). It also refers to a plurality of plant cells that is largely differentiated into a structure that is present at any stage of a plant's development. Such structures include, but are not limited to, a fruit, shoot, stem, leaf, flower petal, etc.

The term "control plant" or "wild type" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

The term "plant tissue" includes differentiated and undifferentiated tissues of plants including those present in roots, shoots, leaves, inflorescences, anthers, pollen, ovaries, seeds and tumors, as well as cells in culture (e.g., single cells, protoplasts, embryos, callus, etc.). Plant tissue may be in planta, in organ culture, tissue culture, or cell culture.

The term "plant part" as used herein refers to a plant structure, a plant organ, or a plant tissue.

A "non-naturally occurring plant" refers to a plant that does not occur in nature without human intervention. Non-naturally occurring plants include transgenic plants, plants created through genetic engineering and plants produced by non-transgenic means such as traditional or market assisted plant breeding.

The term "plant cell" refers to a structural and physiological unit of a plant, comprising a protoplast and a cell wall. The plant cell may be in the form of an isolated single cell or a cultured cell, or as a part of a higher organized unit such as, for example, a plant tissue, a plant organ, or a whole plant. The term "plant cell culture" refers to cultures of plant units such as, for example, protoplasts, cells and cell clusters in a liquid medium or on a solid medium, cells in plant tissues and organs, microspores and pollen, pollen tubes, anthers, ovules, embryo sacs, zygotes and embryos at various stages of development.

The term "plant material" refers to leaves, stems, roots, inflorescences and flowers or flower parts, fruits, pollen, anthers, egg cells, zygotes, seeds, cuttings, cell or tissue cultures, or any other part or product of a plant.

A "plant organ" refers to a distinct and visibly structured and differentiated part of a plant, such as a root, stem, leaf, flower bud, inflorescence, spikelet, floret, seed or embryo.

The term "crop plant", means in particular monocotyledons such as cereals (wheat, millet, *Sorghum*, rye, triticale, oats, barley, teff, spelt, buckwheat, fonio and *Quinoa*), rice, maize (corn), and/or sugar cane; or dicotyledon crops such as beet (such as sugar beet or fodder beet); fruits (such as pomes, stone fruits or soft fruits, for example apples, pears, plums, peaches, almonds, cherries, strawberries, raspberries or blackberries); leguminous plants (such as beans, lentils, peas or soybeans); oil plants (such as rape, mustard, poppy, olives, sunflowers, coconut, castor oil plants, cocoa beans or groundnuts); cucumber plants (such as marrows, cucumbers or melons); fiber plants (such as cotton, flax, hemp or jute); citrus fruit (such as oranges, lemons, grapefruit or mandarins); vegetables (such as spinach, lettuce, cabbages, carrots, tomatoes, potatoes, cucurbits or paprika); lauraceae (such as avocados, cinnamon or camphor); tobacco; nuts; coffee; tea; vines; hops; durian; bananas; natural rubber plants; and ornamentals (such as flowers, shrubs, broad-leaved trees or evergreens, for example conifers). This list does not represent any limitation.

The term "woody crop" or "woody plant" means a plant that produces wood as its structural tissue. Woody crops include trees, shrubs, or lianas. Examples of woody crops include, but are not limited to, thornless locust, hybrid chestnut, black walnut, Japanese maple, *Eucalyptus, Casuarina*, spruce, fir, pine (e.g. *Pinus radiata* and *Pinus caribaea*), and flowering dogwood.

The term "improved growth" or "increased growth" is used herein in its broadest sense. It includes any improvement or enhancement in the process of plant growth and development. Examples of improved growth include, but are not limited to, increased photosynthetic efficiency, increased biomass, increased yield, increased seed number, increased seed weight, increased stem height, increased leaf area, and increased plant dry weight.

By "quantum yield" it is meant the moles of $CO_2$ fixed per mole of quanta (photons) absorbed, or else the efficiency with which light is converted into fixed carbon. The quantum yield of photosynthesis is derived from measurements of light intensity and rate of photosynthesis. As such, the quantum yield is a measure of the efficiency with which absorbed light produces a particular effect. The amount of photosynthesis performed in a plant cell or plant can be indirectly detected by measuring the amount of starch produced by the transgenic plant or plant cell. The amount of photosynthesis in a plant cell culture or a plant can also be detected using a $CO_2$ detector (e.g., a decrease or consumption of $CO_2$ indicates an increased level of photosynthesis) or a $O_2$ detector (e.g., an increase in the levels of $O_2$ indicates an increased level of photosynthesis (see, e.g., the methods described in Silva et al., Aquatic Biology 7:127-141, 2009; and Bai et al., Biotechnol. Lett. 33:1675-1681, 2011). Photosynthesis can also be measured using radioactively labeled $CO_2$ (e.g., $14CO_2$ and $H_{14}CO_3$—) (see, e.g., the methods described in Silva et al., Aquatic Biology 7:127-141, 2009, and the references cited therein). Photosynthesis can also be measured by detecting the chlorophyll fluorescence (e.g., Silva et al., Aquatic Biology 7:127-141, 2009, and the references cited therein). Additional methods for detecting photosynthesis in a plant are described in Zhang et al., Mol. Biol. Rep. 38:4369-4379, 2011."

In the physical sciences, the term "relaxation" means the return of a perturbed system into equilibrium, usually from a high energy level to a low energy level. As used herein, the term "non-photochemical quenching relaxation" or "NPQ relaxation" refers to the process in which NPQ level decreases upon transition from high light intensity to low light intensity.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

Overview

Faced with a fast growing world population, further increases in food production are imperative for global political and societal stability, and as such, a two-fold increase of crop production has been projected necessary to meet this demand by 2050. A better understanding of physiological processes underlying important crop traits such as photosynthesis is hence key to ameliorating world's food security crisis. Photosynthesis is a process used by plants and green algae to convert light energy into chemical energy that can be later released to fuel the organisms' activities, during which atmospheric carbon dioxide ($CO_2$) is assimilated and oxygen is released. The ratio of the amount of $CO_2$ being fixed or assimilated over the amount of photon (quantum) absorbed, also known as quantum yield, is commonly used as a measure of the photosynthetic efficiency of a plant.

Although light is necessary for photosynthesis, damage can occur when leaves are exposed to high light intensity. To avoid this, plants have developed several photoprotective mechanisms. Non-photochemical quenching (NPQ) is one of those mechanisms, which allows excessive absorbed irradiance to be dissipated as heat. However, when a plant is transitioned from high to low light intensity, the quantum yield of photosynthesis is temporarily reduced, due to the fact that NPQ inhibits $CO_2$ fixation. In addition. NPQ turns on (induces) rapidly at high light intensity, but turns off (relaxes) more slowly upon a return to limiting irradiance. As a result, the photosynthetic efficiency and growth of plants under fluctuating light, a common occurrence under natural field conditions, are compromised.

The present disclosure provides a method to speed up the relaxation of NPQ after plants transition from high to low light intensity, thereby allowing a faster recovery of photosynthetic quantum yield of $CO_2$ fixation. This method includes increasing expression of one or more nucleotide sequences encoding photosystem II subunit S (PsbS), zeaxanthin epoxidase (ZEP), and violaxanthin de-epoxidase (VDE). Since this is achieved without reducing the amplitude of NPQ, normal photoprotection under high light intensity is not affected. Under fluctuating light conditions, where plants frequently undergo transitions from high to low light intensity, this method results in improved photoprotection efficiency and in turn photosynthetic efficiency and growth of plants.

The present disclosure further provides a method to genetically engineer plants for improved photosynthesis and growth. An expression vector comprising nucleotide sequences encoding PsbS, ZEP and VDE can be introduced into plants by currently available methods including, but not limited to, protoplast transformation, *Agrobacterium*-mediated transformation, electroporation, microprojectile bombardment. This method may be used to produce transgenic plants with improved photosynthesis and growth in plant species including, but not limited to, tobacco, wheat, maize, rice, soybean, *Sorghum, Cassava*, cowpea, poplar, and *Eucalyptus*.

It is well known in the art that mechanisms underlying NPQ response and the associated xanthophyll cycle are highly conserved across plants and green algae. See, e.g. Niyogi K K. Truong T B (2013). Evolution of flexible non-photochemical quenching mechanisms that regulate light harvesting in oxygenic photosynthesis. Curr Op Plant Biol 16: 307-314. Koziol A G, Borza T, Ishida K-I. Keeling P, Lee R W, Durnford D G (2007). Tracing the evolution of the light-harvesting antennae in chlorophyll a/b-containing organisms. Plant Physiol 143: 1802-1816, Engelken J. Brinkmann H. Adamska I (2010). Taxonomic distribution and origins of the extended LHC (light-harvesting complex) antenna protein superfamily. BMC Evol Biol 10: 233, Brooks M D, Jansson S, Niyogi K K (2014). PsbS-dependent non-photochemical quenching. In: Non-photochemical quenching and energy dissipation in plants, algae and cyanobacteria. Demmig-Adams B, Garab G, Adams W W III, Govindjee eds. (Dordrecht: Springer), pp. 297-314, Kasajima I, Ebana K, Yamamoto T, Takahara K, Yano M, Kawai-Yamada M, Uchimiya H (2011). Molecular distinction in genetic regulation of nonphotochemical quenching in rice. Proc Natl Acad Sci USA 108:13835-13840, Alboresi A, Gerotto C, Giacometti G M, Bassi R, Morosinotto T (2010). *Physcomitrella patens* mutants affected on heat dissipation clarify the evolution of photoprotection mechanisms upon land colonization. Proc Natl Acad Sci USA 107:11128-11133, and Goss R, Lepetit B (2015). Biodiversity of NPQ. Journal of Plant Physiology, 172, 13-32. Therefore, methods disclosed in the present invention can be applied to all plants and green algae.

Unless otherwise indicated, the disclosure encompasses all conventional techniques of plant transformation, plant breeding, microbiology, cell biology and recombinant DNA, which are within the skill of the art. See, e.g., Sambrook and Russell, Molecular Cloning: A Laboratory Manual, 3rd edition, 2001; Current Protocols in Molecular Biology, F. M. Ausubel et al. eds., 1987; Plant Breeding: Principles and Prospects, M. D. Hayward et al., 1993; Current Protocols in Protein Science, Coligan et al, eds., 1995, (John Wiley & Sons, Inc.); the series Methods in Enzymology (Academic Press. Inc.): PCR 2: A Practical Approach, M. J. MacPherson, B. D. Hames and G. R. Taylor eds., 1995.

In one aspect, a transgenic plant, or a portion of a plant, or a plant material, or a plant seed, or a plant cell is provided, comprising one or more heterologous nucleotide sequences encoding polypeptides selected from PsbS, ZEP and VDE operably linked to an expression control sequence. In one embodiment, the PsbS polypeptide is encoded by the nucleotide sequence of SEQ ID NO: 1, the ZEP polypeptide is encoded by the nucleotide sequence of SEQ ID NO:2, and the VDE polypeptide is encoded by the nucleotide sequence of SEQ ID NO: 3. In another embodiment, the transgenic plant comprises nucleotide sequences encoding PsbS, ZEP and VDE. The transgenic plant may comprise any combination of at least two of PsbS, ZEP and VDE, or comprise only one of PsbS, ZEP and VDE. The nucleotide sequences may have at least 60%, 65%, 70%, 75%, 80%, 85%, 90%, 95%, or 99% sequence identity to SEQ ID NO: 1, SEQ ID NO:2, and/or SEQ ID NO:3. In another embodiment, the PsbS polypeptide has the amino acid sequence of SEQ ID NO: 4, the ZEP polypeptide has the amino acid sequence of SEQ ID NO:5, and the VDE polypeptide has the amino acid sequence of SEQ ID NO: 6. The polypeptides may be at least 60%, 65%, 70%, 75%, 80%, 85%, 90%, 95%, or 99% amino acid sequence identity to SEQ ID NO: 4. SEQ ID NO:5, or SEQ ID NO:6. Homologues of *Arabidopsis* PsbS, Zep and VDE nucleotides and the polypeptides encoded by the nucleotide sequences exist in most species of plants, and the plants listed below, and may be used in place of the *Arabidopsis* genes.

Enzymes having similar activity to PsbS, ZEP and VDE, or those having conserved domains could alternatively be used, including, but not limited to, homologues in switchgrass, *Miscanthus, Medicago*, sweet *Sorghum*, grain *Sorghum*, sugarcane, energy cane, elephant grass, maize, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, vegetable, forage, industrial, woody and biomass crops. PsbS has a conserved Chloroa_b-binding domain (SEQ ID NO: 7), ZEP comprises a NADB_Rossman and FHA superfamily domain (SEQ ID NO:8), and VDE has a Lipocalin domain (SEQ ID NO:9). Homologues having these domains could also be used.

In another embodiment, the transgenic plant, or a portion of a plant, or a plant material, or a plant seed, or a plant cell is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In another embodiment, the plant is selected from switchgrass, *Miscanthus, Medicago*, sweet *Sorghum*, grain *Sorghum*, sugarcane, energy cane, elephant grass, maize, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, vegetable, forage, industrial, woody and biomass crops. In a further embodiment, the transgenic plant is *Nicotiana tabacum*. In another embodiment, the plant has improved quantum yield and/or $CO_2$ fixation under fluctuating light conditions, and/or improved growth. A balance of level of gene expression can play a role in plant improvements. In one embodiment, VDE and ZEP polypeptides are expressed at relatively similar levels.

In another embodiment, the transgenic plant, or a portion of a plant, or a plant material, or a plant seed, or a plant cell has additional characteristics, for example, herbicide resistance, insect or pest resistance, disease resistance, modified fatty acid metabolism, and/or modified carbohydrate metabolism.

Figure 9:
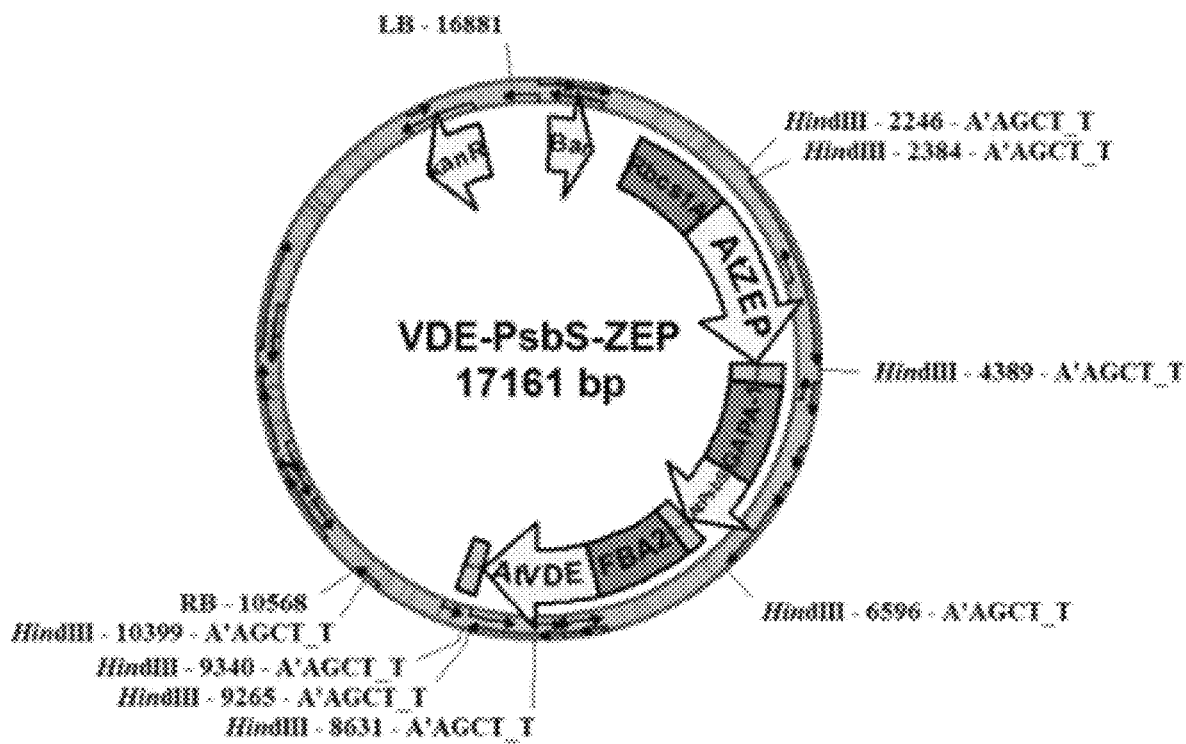
FIG. 9. Plasmid map of VDE-PsbS-ZEP construct.
Figure 10:
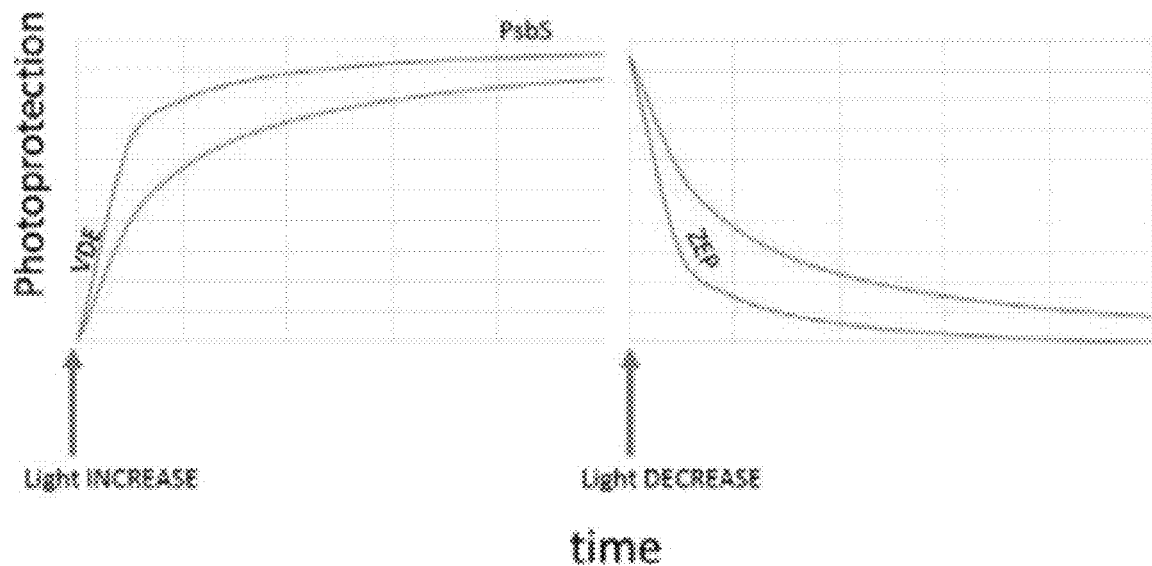
FIG. 10. The intended goal to increase speed in which photoprotection responds to changes in light intensity and the role VDE, PsbS and ZEP play in this process. Blue lines represent transgenic plants compared to orange lines (wild type).
Figure 11:
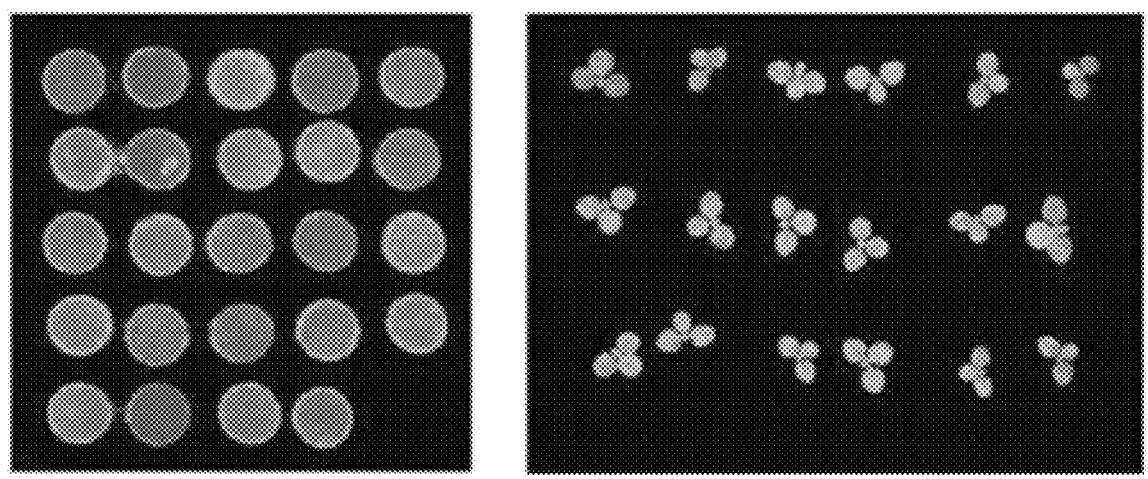
FIG. 11. Fast high throughput screening of phenotypes. Chlorophyll fluorescence of leaf discs (left) and chlorophyll fluorescence of young seedlings (right).

In another aspect, an expression vector is provided, the expression vector comprising at least one expression control sequence operably linked to at least one nucleotide sequence encoding one or more polypeptides selected from PsbS, ZEP and VDE. In one embodiment, the vector comprises at least one expression control sequence comprising a promoter capable of driving expression of the nucleotide sequence encoding one or more polypeptides selected from PsbS, ZEP and VDE, in a plant, a portion of a plant, or a plant material, or a plant seed, or a plant cell. In another embodiment, the promoter is selected from Rbcs1A, GAPA-1 and FBA2. In a further embodiment, the vector comprises an Rbcs1A promoter drives expression of ZEP, a GAPA-1 promoter drives expression of PsbS, and an FBA2 promoter drives expression of VDE. In another embodiment, the vector is a T-DNA. In another embodiment, the vector comprises a vector as shown in FIG. 9. In another embodiment, the vector can express the nucleotide sequence encoding the PsbS, ZEP and VDE polypeptides in a plant, a portion of a plant, or a plant material, or a plant seed, or a plant cell of a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In another embodiment, the plant is selected from switchgrass, *Miscanthus*, *Medicago*, sweet *Sorghum*, grain *Sorghum*, sugarcane, energy cane, elephant grass, maize, wheat, barley, oats, rice, soybean, oil palm, safflower, sesame, tobacco, flax, cotton, sunflower, *Camelina*, *Brassica napus*, *Brassica carinata*, *Brassica juncea*, pearl millet, foxtail millet, other grain, rice, oilseed, vegetable, forage, industrial, woody and biomass crops.

In another aspect, a transgenic plant, or a portion of a plant, or a plant material, or a plant seed is provided, comprising a recombinant vector as described herein.

In another aspect, methods of increasing biomass production and/or carbon fixation and/or growth in a plant, or a portion of a plant, or a plant material, or a plant seed, or a plant cell are provided, the method comprising introducing into the genome of the plant, plant tissue, plant seed, or plant cell one or more nucleotide sequences encoding polypeptides selected from PsbS, ZEP and VDE operably linked to one or more expression control sequences. It was found that incorporation of polypeptides encoded by the nucleotides SEQ ID NO: 1, SEQ ID NO: 2, and SEQ ID NO: 3 increased quantum yield, $CO_2$ fixation under fluctuating light conditions, and improved plant growth. In one embodiment, the method comprises a recombinant vector as described herein.

Transgenic Plants of the Disclosure

In one aspect, provided herein is a transgenic plant having one or more heterologous nucleotide sequences encoding one or more polypeptides PsbS, ZEP, or VDE. In some embodiments, the transgenic plant has one or more heterologous nucleotide sequences encoding PsbS. In some embodiments, the transgenic plant has one or more heterologous nucleotide sequences encoding ZEP. In some embodiments, the transgenic plant has one or more heterologous nucleotide sequences encoding VDE. In some embodiments, the transgenic plant has one or more heterologous nucleotide sequences encoding PsbS and ZEP. In some embodiments, the transgenic plant has one or more heterologous nucleotide sequences encoding PsbS and VDE. In some embodiments, the transgenic plant has one or more heterologous nucleotide sequences encoding ZEP and VDE. In some embodiments, the transgenic plant has one or more heterologous nucleotide sequences encoding PsbS, ZEP and VDE.

In some of the embodiments described above, the one or more heterologous nucleotide sequences are derived from a dicot. In some embodiments, the one or more heterologous nucleotide sequences are derived from a monocot. In some embodiments, the one or more heterologous nucleotide sequences are derived from *Arabidopsis thaliana*. In some embodiments, the one or more heterologous nucleotide sequences are derived from *Zea mays*. In some embodiments, the one or more heterologous nucleotide sequences are derived from *Oryza sativa*. In some embodiments, the one or more heterologous nucleotide sequences are derived from *Sorghum bicolor*. In some embodiments, the one or more heterologous nucleotide sequences are derived from *Glycine max*. In some embodiments, the one or more heterologous nucleotide sequences are derived from *Vigna unguiculata*. In some embodiments, the one or more heterologous nucleotide sequences are derived from *Populus* spp. In some embodiments, the one or more heterologous nucleotide sequences are derived from *Eucalyptus* spp. In some embodiments, the one or more heterologous nucleotide sequences are derived from *Manihot esculenta*. In some embodiments, the one or more heterologous nucleotide sequences are derived from *Hordeum vulgare*. In some embodiments, the one or more heterologous nucleotide sequences are derived from *Solanum tuberosum*. In some embodiments, the one or more heterologous nucleotide sequences are derived from *Saccharum* spp. In some embodiments, the one or more heterologous nucleotide sequences are derived from *Medicago sativa*. In some embodiments, the one or more heterologous nucleotide sequences are derived from switchgrass, *Miscanthus*, *Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina*, *Brassica napus*, *Brassica carinata*, *Brassica juncea*, pearl millet, foxtail millet, other grain, rice, oilseed, a vegetable crop, a forage crop, an industrial crop, a woody crop or a biomass crop.

In some of the embodiments described above, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant.

Photoprotection mechanism has a high degree of conservation among higher plants. The degree of conservation, or homology, can be analyzed through comparing sequences of nucleotides or amino acids of genes of interest. As used herein "sequence identity" refers to the percentage of residues that are identical in the same positions in the sequences being analyzed. Methods of alignment of sequences for comparison are well known to one of skill in the art, including, but not limited to, manual alignment and computer assisted sequence alignment and analysis. This latter approach is a preferred approach in the present disclosure, due to the increased throughput afforded by computer assisted methods. The determination of percent sequence identity between any two sequences can be accomplished using a mathematical algorithm. Examples of such mathematical algorithms are the algorithm of Myers and Miller. CABIOS 4:11-17 (1988); the local homology algorithm of Smith et al., Adv. Appl. Math. 2:482 (1981); the homology alignment algorithm of Needleman and Wunsch, J. Mol. Biol. 48:443-453 (1970); the search-for-similarity-method of Pearson and Lipman. Proc. Natl. Acad. Sci. 85:2444-2448 (1988); the algorithm of Karlin and Altschul. Proc. Natl. Acad. Sci. USA 87:2264-2268 (1990), modified as in Karlin and Altschul. Proc. Natl. Acad. Sci. USA 90:5873-5877 (1993). Computer implementations of these mathematical algorithms can be utilized for comparison of sequences to determine sequence identity and/or similarity. Such implementations include, for example: CLUSTAL in the PC/Gene program (available from Intelligenetics, Mountain View, Calif.); the AlignX program, version 10.3.0 (Invitrogen, Carlsbad, Calif.) and GAP, BESTFIT, BLAST, FASTA, and TFASTA in the Wisconsin Genetics Software Package. Version 8 (available from Genetics Computer Group (GCG), 575 Science Drive, Madison, Wis., USA). Alignments using these programs can be performed using the default parameters. The CLUSTAL program is well described by Higgins et al. Gene 73:237-244 (1988); Higgins et al. CABIOS 5:151-153 (1989); Corpet et al., Nucleic Acids Res. 16:10881-90 (1988); Huang et al. CABIOS 8:155-65 (1992); and Pearson et al., Meth. Mol. Biol. 24:307-331 (1994). The BLAST programs of Altschul et al. J. Mol. Biol. 215:403-410 (1990) are based on the algorithm of Karlin and Altschul (1990) supra.

In some of the embodiments described above. PsbS is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 1. In some embodiments, ZEP is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 2. In some embodiments, VDE is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 3. In some embodiments. PsbS has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 4. In some embodiments, ZEP has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 5. In some embodiments, VDE has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the transgenic plant contains an expression vector, wherein the expression vector contains one or more nucleotide sequences described herein. In some embodiments, the transgenic plant produces a seed containing an expression vector that has one or more heterologous nucleotide sequences encoding any of PsbS, ZEP or VDE. In some embodiments, the seed that is derived from the transgenic plant further produces a progeny plant.

In some of the embodiments described above, the transgenic plant has increased growth under fluctuating light conditions as compared to a control plant under fluctuating light conditions. In some embodiments, the transgenic plant has increased photosynthetic efficiency under fluctuating light conditions as compared to a control plant under fluctuating light conditions. In some embodiments, the transgenic plant has improved photoprotection efficiency under fluctuating light conditions as compared to a control plant under fluctuating light conditions. In some embodiments, the transgenic plant has improved quantum yield and $CO_2$ fixation under fluctuating light conditions as compared to a control plant under fluctuating light conditions. In some embodiments, the transgenic plant is an elite line or elite strain. In some embodiments, the transgenic plant further includes expression of at least one additional polypeptide that provides herbicide resistance, insect or pest resistance, disease resistance, modified fatty acid metabolism, and/or modified carbohydrate metabolism.

In some of the embodiments described above, the transcript level of VDE in the plant is increased 3-fold as compared to a control plant. In some of the embodiments described above, the transcript level of PsbS in the plant is increased 3-fold as compared to a control plant. In some of the embodiments described above, the transcript level of ZEP in the plant is increased 8-fold as compared to a control plant. In some of the embodiments described above, the transcript level of VDE in the plant is increased 10-fold as compared to a control plant. In some of the embodiments described above, the transcript level of PsbS in the plant is increased 3-fold as compared to a control plant. In some of the embodiments described above, the transcript level of ZEP in the plant is increased 6-fold as compared to a control plant. In some of the embodiments described above, the transcript level of VDE in the plant is increased 4-fold as compared to a control plant. In some of the embodiments described above, the transcript level of PsbS in the plant is increased 1.2-fold as compared to a control plant. In some of the embodiments described above, the transcript level of ZEP in the plant is increased 7-fold as compared to a control plant. In some of the embodiments described above, the protein level of VDE in the plant is increased 16-fold as compared to a control plant. In some of the embodiments described above, the protein level of PsbS in the plant is increased 2-fold as compared to a control plant. In some of the embodiments described above, the protein level of ZEP in the plant is increased 80-fold as compared to a control plant. In some of the embodiments described above, the protein level of VDE in the plant is increased 30-fold as compared to a control plant. In some of the embodiments described above, the protein level of PsbS in the plant is increased 4-fold as compared to a control plant. In some of the embodiments described above, the protein level of ZEP in the plant is increased 74-fold as compared to a control plant. In some of the embodiments described above, the protein level of VDE in the plant is increased 47-fold as compared to a control plant. In some of the embodiments described above, the protein level of PsbS in the plant is increased 3-fold as compared to a control plant. In some of the embodiments described above, the protein level of ZEP in the plant is increased 75-fold as compared to a control plant. In some of the embodiments described above, the increase of transcript level in the plant as compared to a control plant between VDE, PsbS and ZEP has a ratio of 3:3:8, 10:3:6, or 4:1.2:7. In some of the embodiments described above, the increase of protein level in the plant as compared to a control plant between VDE, PsbS and ZEP has a ratio of 16:2:80, 30:4:74, or 47:3:75. In some of the embodiments described above, the increase of transcript level of VDE in the plant as compared to a control plant is in the range of 3-fold to 10-fold. In some of the embodiments described above, the increase of transcript level of PsbS in the plant as compared to a control plant is from about 1.2-fold to about 3-fold. In some of the embodiments described above, the increase of transcript level of ZEP in the plant as compared to a control plant is from about 6-fold to about 8-fold. In some of the embodiments described above, the increase of protein level of VDE in the plant as compared to a control plant is in the range of 16-fold to 47-fold. In some of the embodiments described above, the increase of protein level of PsbS in the plant as compared to a control plant is from about 2-fold to about 4-fold. In some of the embodiments described above, the increase of protein level of ZEP in the plant as compared to a control plant is from about 74-fold to about 80-fold.

Expression Vectors of the Disclosure

In another aspect, the present disclosure relates to an expression vector having one or more nucleotide sequences encoding any of PsbS, ZEP, and VDE. In some embodiments, the expression vector has one or more nucleotide sequences encoding PsbS. In some embodiments, the expression vector has one or more nucleotide sequences encoding ZEP. In some embodiments, the expression vector has one or more nucleotide sequences encoding VDE. In some embodiments, the expression vector has one or more nucleotide sequences encoding PsbS and ZEP. In some embodiments, the expression vector has one or more nucleotide sequences encoding PsbS and VDE. In some embodiments, the expression vector has one or more nucleotide sequences encoding ZEP and VDE. In some embodiments, the expression vector has one or more nucleotide sequences encoding PsbS, ZEP and VDE.

In some of the embodiments described above, PsbS is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 1. In some embodiments, ZEP is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 2. In some embodiments, VDE is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 3. In some embodiments, PsbS has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 4. In some embodiments, ZEP has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 5. In some embodiments, VDE has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the vector includes one or more expression control sequences having a promoter capable of driving expression of the nucleotide sequence of PsbS, ZEP, or VDE, in a plant. In some embodiments, the promoter is an inducible promoter. In some embodiments, the promoter is a constitutive promoter. In some embodiments, the promoter is a weak promoter. In some embodiments, the promoter is a tissue-specific promoter. In some embodiments, the promoter is a seed- and/or embryo-specific promoter. In some embodiments, the promoter is a leaf-specific promoter. In some embodiments, the promoter is a temporal-specific promoter. In some embodiments, the promoter is an anther- and/or pollen-specific promoter. In some embodiments, the promoter is a floral-specific promoter. In some embodiments, a combination of promoters is used in the expression vector.

In some of the embodiments described above, the promoter is Rbcs1A. GAPA-1, or FBA2. In some embodiments, the Rbcs1A promoter drives expression of ZEP, a GAPA-1 promoter drives expression of PsbS, and an FBA2 promoter drives expression of VDE. In some embodiments, the vector is a T-DNA. In some embodiments, the expression vector further includes a nucleotide sequence encoding polypeptide that provides antibiotic resistance. In some embodiments, the expression vector further includes a left border (LB) and right border (RB) domain flanking the expression control sequences and the nucleotide sequence encoding the PsbS, ZEP and VDE polypeptides. In some embodiments, the expression vector is in a bacterial cell. In some embodiments, the expression vector is in an *Agrobacterium* cell.

Methods of the Disclosure

In certain other aspects, the present disclosure relates to methods of increasing photosynthesis and growth in a plant, including increasing expression in the plant of one or more polypeptides described herein.

In some embodiments, the increased expression is achieved by introducing to a plant one or more heterologous nucleotide sequences encoding any of PsbS, ZEP and VDE. In some embodiments, the increased expression is achieved by modifying expression of the endogenous nucleotide sequences encoding any of PsbS, ZEP and VDE. In some embodiments, the increased expression is achieved by modifying the promoter of the endogenous nucleotide sequences encoding any of PsbS, ZEP and VDE. In some embodiments, the increased expression is achieved by modifying transcription factors that regulate the transcription efficiency of any of PsbS, ZEP and VDE. In some embodiments, the increased expression is achieved by increasing the stability of the mRNA of any of PsbS, ZEP and VDE. In some embodiments, the increased expression is achieved by optimizing codon usage of any of PsbS, ZEP and VDE in a target plant. In some embodiments, the increased expression is achieved by altering epigenetics in a plant. In some embodiments, the increased expression is achieved by altering DNA methylation in a plant. In some embodiments, the increased expression is achieved by altering histone modification in a plant. In some embodiments, the increased expression is achieved by altering small RNAs (sRNA) in a plant. In some embodiments, the increased expression is achieved by increasing the translation efficiency of any of PsbS, ZEP and VDE. In some embodiments, genome-editing techniques including, but not limited to, ZFN, TALEN and CRISPR are used to modify the nucleotide sequences regulating the expression of any of PsbS, ZEP and VDE.

In some embodiments, the transcript level of VDE in the plant is increased 3-fold as compared to a control plant. In some embodiments, the transcript level of PsbS in the plant is increased 3-fold as compared to a control plant. In some embodiments, the transcript level of ZEP in the plant is increased 8-fold as compared to a control plant. In some embodiments, the transcript level of VDE in the plant is increased 10-fold as compared to a control plant. In some embodiments, the transcript level of PsbS in the plant is increased 3-fold as compared to a control plant. In some embodiments, the transcript level of ZEP in the plant is increased 6-fold as compared to a control plant. In some embodiments, the transcript level of VDE in the plant is increased 4-fold as compared to a control plant. In some embodiments, the transcript level of PsbS in the plant is increased 1.2-fold as compared to a control plant. In some embodiments, the transcript level of ZEP in the plant is increased 7-fold as compared to a control plant. In some embodiments, the protein level of VDE in the plant is increased 16-fold as compared to a control plant. In some embodiments, the protein level of PsbS in the plant is increased 2-fold as compared to a control plant. In some embodiments, the protein level of ZEP in the plant is increased 80-fold as compared to a control plant. In some embodiments, the protein level of VDE in the plant is increased 30-fold as compared to a control plant. In some embodiments, the protein level of PsbS in the plant is increased 4-fold as compared to a control plant. In some embodiments, the protein level of ZEP in the plant is increased 74-fold as compared to a control plant. In some embodiments, the protein level of VDE in the plant is increased 47-fold as compared to a control plant. In some embodiments, the protein level of PsbS in the plant is increased 3-fold as compared to a control plant. In some embodiments, the protein level of ZEP in the plant is increased 75-fold as compared to a control plant. In some embodiments, the increase of transcript level in the plant as compared to a control plant between VDE, PsbS and ZEP has a ratio of 3:3:8, 10:3:6, or 4:1.2:7. In some embodiments, the increase of protein level in the plant as compared to a control plant between VDE, PsbS and ZEP has a ratio of 16:2:80, 30:4:74, or 47:3:75. In some embodiments, the increase of transcript level of VDE in the plant as compared to a control plant is in the range of 3-fold to 10-fold. In some embodiments, the increase of transcript level of PsbS in the plant as compared to a control plant is from about 1.2-fold to about 3-fold. In some embodiments, the increase of transcript level of ZEP in the plant as compared to a control plant is from about 6-fold to about 8-fold. In some embodiments, the increase of protein level of VDE in the plant as compared to a control plant is in the range of 16-fold to 47-fold. In some embodiments, the increase of protein level of PsbS in the plant as compared to a control plant is from about 2-fold to about 4-fold. In some embodiments, the increase of protein level of ZEP in the plant as compared to a control plant is from about 74-fold to about 80-fold.

Methods for Increasing Growth Under Fluctuating Light Conditions

In one aspect, provided herein is a method for increasing growth in a plant under fluctuating light conditions, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments. VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass. *Miscanthus, Medicago,* sweet *Sorghum,* grain *Sorghum,* sugarcane, energy cane, elephant grass, maize, *Cassava,* cowpea, wheat, barley, oats, rice, soybean, oil palm, safflower, sesame, tobacco, flax, cotton, sunflower, *Camelina, Brassica napus, Brassica carinata, Brassica juncea,* pearl millet, foxtail millet, other grain, rice, oilseed, a vegetable crop, a forage crop, an industrial crop, a woody crop or a biomass crop.

Methods for Increasing Photosynthetic Efficiency Under Fluctuating Light Conditions In another aspect, provided herein is a method for increasing photosynthetic efficiency in a plant under fluctuating light conditions, including increasing expression in the plant of any of PsbS, ZEP, or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above. PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments. VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments. PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago,* sweet *Sorghum,* grain *Sorghum,* sugarcane, energy cane, elephant grass, maize, *Cassava,* cowpea, wheat, barley, oats, rice, soybean, oil palm, safflower, sesame, tobacco, flax, cotton, sunflower, *Camelina, Brassica napus, Brassica carinata, Brassica juncea,* pearl millet, foxtail millet, other grain, rice, oilseed, a vegetable crop, a forage crop, an industrial crop, a woody crop or a biomass crop.

Methods for Increasing Photoprotection Efficiency Under Fluctuating Light Conditions In another aspect, provided herein is a method for increasing photoprotection efficiency in a plant under fluctuating light conditions, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above. PsbS has an amino acid sequence at least about 65%, 70%, 75%, 80%, 85%, 90%, 91%, 92%, 93%, 94%, 95%, 96%, 97%, 98%. 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments. ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass. *Miscanthus*, *Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina*, *Brassica napus*, *Brassica carinata*, *Brassica juncea*, pearl millet, foxtail millet, other grain, rice, oilseed, a vegetable crop, a forage crop, an industrial crop, a woody crop or a biomass crop.

Methods for Increasing Quantum Yield and $CO_2$ Fixation Under Fluctuating Light Conditions In another aspect, provided herein is a method for increasing quantum yield and $CO_2$ fixation in a plant under fluctuating light conditions, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments. VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass. *Miscanthus, Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Increasing the Rate of Relaxation of Non-Photochemical Quenching (NPQ) Under Fluctuating Light Conditions In another aspect, provided herein is a method for increasing the rate of relaxation of non-photochemical quenching (NPQ) in a plant, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above. PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments. VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments. PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Selecting a Plant for Improved Growth Characteristics Under Fluctuating Light Conditions In another aspect, provided herein are methods of selecting a plant for improved growth characteristics under fluctuating light conditions, including the steps of providing a population of plants; modifying the population of plants to increase the activity of any of PsbS, ZEP and VDE; detecting the level of non-photochemical quenching (NPQ) under fluctuating light conditions in a plant; comparing the level of NPQ under fluctuating light conditions in a plant with the control level of NPQ under fluctuating light conditions; and selecting a plant having increased rate of NPQ relaxation when the plant is transitioned from under high light intensity to low light intensity. In some embodiments, the control level of NPQ is the lowest level of NPQ in the population. In some embodiments, the control level of NPQ is the median level of NPQ in the population. In some embodiments, the control level of NPQ is the mean level of NPQ in the population. In some embodiments, the control level of NPQ is the level of NPQ in a control plant. In some embodiments, the population includes plants expressing heterologous sequences of PsbS, ZEP and/or VDE or in which the genome has been edited in order to increase expression of PsbS, ZEP, and/or VDE. In some embodiments, the genome editing technique is ZFN. In some embodiments, the genome editing technique is TALEN. In some embodiments, the genome editing technique is CRISPR. In some embodiments, the promoter of PsbS is modified. In some embodiments, the promoter of ZEP is modified. In some embodiments, the promoter of VDE is modified. In some embodiments, the population includes plants that have been treated to induce mutations in PsbS, ZEP and/or VDE. In some embodiments, the mutagen is EMS.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above. PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments. PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Screening for a Polymorphism Associated with Improved Growth Characteristics Under Fluctuating Light Conditions In another aspect, provided herein are methods of screening for a nucleotide sequence polymorphism associated with improved growth characteristics under fluctuating light conditions, including the steps of providing a population of plants; obtaining the nucleotide sequences regulating and/or encoding any of PsbS, ZEP and VDE in the population of plants; obtaining one or more polymorphisms in the nucleotide sequences regulating and/or encoding any of PsbS, ZEP and VDE in the population of plants; detecting the rate of non-photochemical quenching (NPQ) relaxation upon transition from high light intensity to low light intensity in the population of plants; performing statistical analysis to determine association of the polymorphism with the rate of NPQ relaxation in the population of plants; and selecting the polymorphism having statistically significant association with the rate of NPQ relaxation. In some embodiments, the population is a collection of germplasm. In some embodiments, the population includes plants expressing heterologous sequences of PsbS, ZEP and/or VDE or in which the genome has been edited in order to increase expression of PsbS, ZEP, and/or VDE. In some embodiments, the population includes plants that have not been treated to induce mutations. In some embodiments, the population includes plants that have been treated to induce mutations in PsbS, ZEP and/or VDE. In some embodiments, the polymorphism is a single nucleotide polymorphism (SNP). In some embodiments, the polymorphism is an insertion/deletion (InDel). In some embodiments, the polymorphism is a simple sequence repeat (SSR). In some embodiments, the polymorphism is a presence/absence variation (PAV). In some embodiments, the polymorphism is a copy number variation (CNV). In some embodiments, the polymorphism is located in the promoter of PsbS. In some embodiments, the polymorphism is located in the promoter of ZEP. In some embodiments, the polymorphism is located in the promoter of VDE. In some embodiments, the polymorphism is detected by Sanger sequencing. In some embodiments, the polymorphism is detected by next-generation-sequencing. In some embodiments, the polymorphism is detected by agarose gel electrophoresis. In some embodiments, the polymorphism is detected by polyacrylamide gel electrophoresis. In some embodiments, the polymorphism is further used to screen a population different from the one from which the polymorphism is identified. In some embodiments, the polymorphism is further used as a target for genome editing in order to improve growth characteristics of a plant.

In some of the embodiments described above, the improved growth characteristic is improved growth. In some embodiments, the improved growth characteristic is improved photosynthetic efficiency. In some embodiments, the improved growth characteristic is improved photoprotection efficiency. In some embodiments, the improved growth characteristic is improved quantum yield and $CO_2$ fixation. In some embodiments, the improved growth characteristic is increased rate of relaxation of non-photochemical quenching (NPQ). In some embodiments, NPQ is detected using chlorophyll fluorescence imaging.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments. VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass. *Miscanthus, Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

General Methods for Practice of the Embodiments Described Herein

Transformation of Plants with Nucleotide Sequences of Interest

Transgenic plants can be produced using conventional techniques to express any nucleotide sequence of interest in plants or plant cells (Methods in Molecular Biology, 2005, vol. 286, Transgenic Plants: Methods and Protocols, Pena L., ed., Humana Press, Inc. Totowa, NT). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole plants. Detailed description of transformation techniques are within the knowledge of those skilled in the art.

Genetic Constructs for Transformation

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Several plant transformation vector options are available, including those described in Gene Transfer to Plants, 1995, Potrykus et al, eds., Springer-Verlag Berlin Heidelberg N.Y., Transgenic Plants: A Production System for Industrial and Pharmaceutical Proteins, 1996, Owen et al. eds., John Wiley & Sons Ltd. England, and Methods in Plant Molecular Biology: A Laboratory Course Manual, 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts. In one embodiment the vector comprises at least one expression control sequence comprising a promoter capable of driving expression of the nucleotide sequence encoding one or more polypeptides selected from PsbS, ZEP and VDE, in a plant, a portion of a plant, or a plant material, or a plant seed, or a plant cell. In another embodiment, the promoter is selected from Rbcs1A, GAPA-1 and FBA2. In another embodiment, the Rbcs1A promoter drives expression of ZEP, a GAPA-1 promoter drives expression of PsbS, and an FBA2 promoter drives expression of VDE. In another embodiment, the vector is a T-DNA. In another embodiment, the vector is as shown in FIG. 9. Particular promoters and vectors that work in one plant type may not work in another, as known by one of skill in the art. Methods of making transgenic plants are well known in the art, as described herein.

T-DNA

Methods for introducing transgenes into plants by an *Agrobacterium*-mediated transformation method generally involve a T-DNA (transfer DNA) that incorporates the genetic elements of at least one transgene and transfers those genetic elements into the genome of a plant. The transgene (s) are typically constructed in a DNA plasmid vector and are usually flanked by an *Agrobacterium* Ti plasmid right border DNA region (RB) and a left border DNA region (LB). During the process of *Agrobacterium*-mediated transformation, the DNA plasmid is nicked by an endonuclease, VirD2, at the right and left border regions. A single strand of DNA from between the nicks, called the T-strand, is transferred from the *Agrobacterium* cell to the plant cell. The sequence corresponding to the T-DNA region is inserted into the plant genome.

Integration of the T-DNA into the plant genome generally begins at the RB and continues to the end of the T-DNA, at the LB. However, endonucleases sometimes do not nick equally at both borders. When this happens, the T-DNA that is inserted into the plant genome often contains some or all of the plasmid vector DNA. This phenomenon is referred to as "read-through." A desired approach is often that only the transgene(s) located between the right and left border regions (the T-DNA) is transferred into the plant genome without any of the adjacent plasmid vector DNA (the vector backbone). Vector backbone DNA contains various plasmid maintenance elements, including, for example, origin of replications, bacterial selectable marker genes, and other DNA fragments that are not required to express the desired trait(s) in plants.

Engineered minichromosomes can also be used to express one or more genes in plant cells. Cloned telomeric repeats introduced into cells may truncate the distal portion of a chromosome by the formation of a new telomere at the integration site. Using this method, a vector for gene transfer can be prepared by trimming off the arms of a natural plant chromosome and adding an insertion site for large inserts (Yu et al., 2006, Proc. Natl. Acad. Sci. USA 103: 17331-17336; Yu et al., 2007, Proc. Natl. Acad. Sci. USA 104: 8924-8929).

An alternative approach to chromosome engineering in plants involves in vivo assembly of autonomous plant minichromosomes (Carlson et al., 2007, PLoS Genet. 3: 1965-74). Plant cells can be transformed with centromeric sequences and screened for plants that have assembled autonomous chromosomes de novo. Useful constructs combine a selectable marker gene with genomic DNA fragments containing centromeric satellite and retroelement sequences and/or other repeats.

Another approach useful to the described invention is Engineered Trait Loci ("ETL") technology (U.S. Pat. No. 6,077,697; US 2006/0143732). This system targets DNA to a heterochromatic region of plant chromosomes, such as the pericentric heterochromatin, in the short arm of acrocentric chromosomes. Targeting sequences may include ribosomal DNA (rDNA) or lambda phage DNA. The pericentric rDNA region supports stable insertion, low recombination, and high levels of gene expression. This technology is also useful for stacking of multiple traits in a plant (US 2006/0246586).

Zinc-finger nucleases (ZFN), TALEN and CRISPR-Cas9 are also useful for practicing the invention in that they allow double strand DNA cleavage at specific sites in plant chromosomes such that targeted gene insertion or deletion can be performed (Shukla et al., 2009, Nature 459: 437-441; Townsend et al, 2009, Nature 459: 442-445, WO 2015089427 A1).

Tissue Culture-Based Methods for Nuclear Transformation

Transformation protocols, as well as protocols for introducing nucleotide sequences into plants may vary depending on the type of plant or plant cell. i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques. See, for example, McCormick et al., 1986, Plant Cell Rep. 5: 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

In Planta Transformation Methods

Procedures for in planta transformation are not complex. Tissue culture manipulations and possible somaclonal variations are avoided and only a short time is required to obtain transgenic plants. However, the frequency of transformants in the progeny of such inoculated plants is relatively low and variable. At present, there are very few species that can be routinely transformed in the absence of a tissue culture-based regeneration system. Stable *Arabidopsis* transformants can be obtained by several in planta methods including vacuum infiltration (Clough & Bent, 1998, The Plant J. 16: 735-743), transformation of germinating seeds (Feldmann & Marks, 1987, Mol. Gen. Genet. 208: 1-9), floral dip (Clough and Bent, 1998, Plant J. 16: 735-743), and floral spray (Chung et al., 2000, Transgenic Res. 9: 471-476). Other plants that have successfully been transformed by in planta methods include rapeseed and radish (vacuum infiltration. Ian and Hong, 2001. Transgenic Res., 10: 363-371; Desfeux et al., 2000, Plant Physiol. 123: 895-904), *Medicago truncatula* (vacuum infiltration. Trieu et al., 2000, Plant J. 22: 531-541), camelina (floral dip, WO/2009/117555 to Nguyen et al.), and wheat (floral dip, Zale et al., 2009, Plant Cell Rep. 28: 903-913). In planta methods have also been used for transformation of germ cells in maize (pollen, Wang et al. 2001, Acta Botanica Sin., 43, 275-279; Zhang et al, 2005, Euphytica, 144, 11-22; pistils, Chumakov et al. 2006, Russian J. Genetics, 42, 893-897; Mamontova et al. 2010, Russian J. Genetics, 46, 501-504) and *Sorghum* (pollen, Wang et al. 2007, Biotechnol. Appl. Biochem., 48, 79-83)

Reporter Genes and Selectable Marker Genes

Reporter genes and/or selectable marker genes may be included in an expression control sequence (expression cassette) as described in US Patent Applications 20100229256 and 20120060413, incorporated by reference herein. An expression cassette including a promoter sequence operably linked to a heterologous nucleotide sequence of interest can be used to transform any plant by any of the methods described above. Useful selectable marker genes and methods of selection transgenic lines for a range of different crop species are described in the examples herein.

Nucleotide Sequence Expression in Plants

Plant promoters can be selected to control the expression of the nucleotide sequence in different plant tissues or organelles for all of which methods are known to those skilled in the art (Gasser & Fraley, 1989, Science 244: 1293-1299).

The choice of promoter(s) that can be used depends upon several factors, including, but not limited to, efficiency, selectability, inducibility, desired expression level, and/or preferential cell or tissue expression. It is a routine matter for one of skill in the art to modulate the expression of a nucleotide sequence by appropriately selecting and positioning promoters and other regulatory regions relative to that sequence. Examples of promoters that can be used are known in the art. Promoters that can be used include those present in plant genomes, as well as promoters from other sources. Some suitable promoters initiate transcription only, or predominantly, in certain cell types. Methods for identifying and characterizing promoter regions in plant genomic DNA include, for example, those described in Jordano, et al., *Plant Cell* 1:855-866, 1989; Bustos, et al., *Plant Cell* 1:839-854, 1989; Green, et al., *EMBO J.* 7:4035-4044, 1988; Meier et al., *Plant Cell* 3:309-316, 1991; and Zhang et al., *Plant Physiology* 110: 1069-1079, 1996.

Additional examples of promoters that can be used include ribulose-1,5-bisphosphate carboxylase (RbcS) promoters, such as the RbcS promoter from Eastern larch (*Larix laricina*), the pine cab6 promoter (Yamamoto et al., *Plant Cell Physiol.* 35:773-778, 1994), the Cab-1 gene promoter from wheat (Fejes et al., *Plant Mol. Biol.* 15:921-932, 1990), the CAB-1 promoter from spinach (Lubberstedt et al., *Plant Physiol.* 104:997-1006, 1994), the cab1R promoter from rice (Luan et al., *Plant Cell* 4:971-981, 1992), the GAPA-1 promoters from maize, the FBA2 promoter from *Saccharomyces cerevisiae*, the pyruvate orthophosphate dikinase (PPDK) promoter from maize (Matsuoka et al., *Proc. Natl. Acad Sci. U.S.A.* 90:9586-9590, 1993), the tobacco Lhcb1*2 promoter (Cerdan et al., *Plant Mol. Biol.* 33:245-255, 1997), the *Arabidopsis thaliana* SUC2 sucrose-$H^+$ symporter promoter (Truernit et al., *Planta* 196:564-570, 1995), and thylakoid membrane protein promoters from spinach (psaD, psaF, psaE, PC, FNR, atpC, atpD, cab, and rbcS). Additional exemplary promoters that can be used to drive gene transcription in stems, leafs, and green tissue are described in U.S. Patent Application Publication No. 2007/0006346, herein incorporated by reference in its entirety. Additional promoters that result in preferential expression in plant green tissues include those from genes such as *Arabidopsis thaliana* ribulose-1,5-bisphosphate carboxylase (Rubisco) small subunit (Fischhoff et al., *Plant Mol. Biol.* 20:81-93, 1992), aldolase and pyruvate orthophosphate dikinase (PPDK) (Taniguchi et al., *Plant Cell Physiol.* 41(1):42-48, 2000).

Inducible Promoters

Chemical-regulated promoters can be used to modulate the expression of a nucleotide sequence in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize ln 2-2 promoter, which is activated by benzenesulfonamide herbicide safeners, the maize GST promoter, which is activated by hydrophobic electrophlic compounds that are used as pre-emergent herbicides, and the tobacco PR-1 promoter which is activated by salicylic acid. Other chemical-regulated promoters include steroid-responsive promoters [see, for example, the glucocorticoid-inducible promoter (Schena et al, 1991, Proc. Natl. Acad. Sci. USA 88: 10421-10425; McNellis et al., 1998, Plant 14:247-257) and tetracycline-inducible and tetracycline-repressible promoters (see, for example, Gatz et al., 1991, Mol. Gen. Genet. 227: 229-237; U.S. Pat. Nos. 5,814,618 and 5,789,156, herein incorporated by reference in their entirety). A three-component osmotically inducible expression system suitable for plant metabolic engineering has recently been reported (Feng et al, 2011, PLoS ONE 6: 1-9).

Constitutive Promoters

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, Nature 313: 810-812), rice actin (McElroy et al., 1990, Plant Cell 2: 163-171), ubiquitin (Christensen et al., 1989, Plant Mol. Biol. 12: 619-632; Christensen et al, 1992, Plant Mol. Biol. 18: 675-689), pEMU (Last et al, 1991, Theor. Appl. Genet. 81: 581-588), MAS (Velten et al., 1984, EMBO J. 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

Weak Promoters

Where low level expression is desired, weak promoters may be used. Generally, the term "weak promoter" is intended to describe a promoter that drives expression of a nucleotide sequence at a low level. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050).

Tissue Specific Promoters

"Tissue-preferred" promoters can be used to target gene expression within a particular tissue. Compared to chemically inducible systems, developmentally and spatially regulated stimuli are less dependent on penetration of external factors into plant sells. Tissue-preferred promoters include those described by Van Ex et al., 2009, Plant Cell Rep. 28: 1509-1520; Yamamoto et al. 1997, Plant J. 12: 255-265; Kawamata et al., 1997, Plant Cell Physiol. 38: 792-803; Hansen et al., 1997, Mol. Gen. Genet. 254: 337-343; Russell et al., 199), Transgenic Res. 6: 157-168; Rinehart et al., 1996, Plant Physiol. 1 12: 1331-1341; Van Camp et al., 1996, Plant Physiol. 112: 525-535; Canevascini et al., 1996, Plant Physiol. 1 12: 513-524; Yamamoto et al., 1994, Plant Cell Physiol. 35: 773-778; Lam, 1994, Results Probl. Cell Differ. 20: 181-196, Orozco et al., 1993, Plant Mol. Biol. 23: 1 129-1 138; Matsuoka et al., 1993, Proc. Natl. Acad. Sci. USA 90: 9586-9590, and Guevara-Garcia et al. 1993, Plant J. 4: 495-505. Such promoters can be modified, if necessary, for weak expression.

Seed/Embryo Specific Promoters

"Seed-preferred" promoters include both "seed-specific" promoters (those promoters active during seed development such as promoters of seed storage proteins) as well as "seed-germinating" promoters (those promoters active during seed germination). See Thompson et al., 1989, BioEssays 10: 108-1 13, herein incorporated by reference. Such seed-preferred promoters include, but are not limited to, Ciml (cytokinin-induced message), cZI9B1 (maize 19 kDa zein), milps (myo-inositol-1-phosphate synthase), and celA (cellulose synthase). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1. The stage specific developmental promoter of the late embryogenesis abundant protein gene LEA has successfully been used to drive a recombination system for excision-mediated expression of a lethal gene at late embryogenesis stages in the seed terminator technology (U.S. Pat. No. 5,723,765 to Oliver et al.).

Leaf Specific Promoters

Leaf-specific promoters are known in the art. See, for example WO/2011/041499 and U.S. Patent No 2011/0179511 A1 to Thilmony et al.; Yamamoto et al., 1997, Plant J. 12: 255-265; Kwon et al., 1994, Plant Physiol. 105: 357-367; Yamamoto et al. 1994, Plant Cell Physiol. 35: 773-778; Gotor et al, 1993, Plant J. 3: 509-518; Orozco et al., 1993, Plant Mol. Biol. 23: 1 129-1 138, and Matsuoka et al, 1993, Proc. Natl. Acad. Sci. USA 90: 9586-9590.

Temporal Specific Promoters

Also contemplated are temporal promoters that can be utilized during the developmental time frame, for example, switched on after plant reaches maturity in leaf to enhance carbon flow.

Anther/Pollen Specific Promoters

Numerous genes specifically expressed in anthers and/or pollen have been identified and their functions in pollen development and fertility have been characterized. The specificity of these genes has been found to be regulated mainly by their promoters at the transcription level (Ariizumi et al., 2002, Plant Cell Rep. 21: 90-96 and references therein). A large number of anther- and/or pollen-specific promoters and their key ds-elements from different plant species have been isolated and functionally analyzed.

Floral Specific Promoters

Floral-preferred promoters include, but are not limited to, CHS (Liu et al., 201 1, Plant Cell Rep. 30: 2187-2194), OsMADS45 (Bai et al., 2008, Transgenic Res. 17: 1035-1043), PSC (Liu et al. 2008, Plant Cell Rep. 27: 995-1004), LEAFY, AGAMOUS, and API (Van Ex et al., 2009, Plant Cell Rep. 28: 1509-1520), API (Verweire et al, 2007, Plant Physiol. 145: 1220-1231), PtAGIP (Yang et al. 2011, Plant Mol. Biol. Rep. 29: 162-170), Lem1 (Somleva & Blechl, 2005, Cereal Res. Comm. 33: 665-671; Skadsen et al. 2002, Plant Mol. Biol. 45: 545-555), Lem2 (Abebe et al., 2005, Plant Biotechnol. J. 4: 35-44), AGL6 and AGL13 (Schauer et al., 2009, Plant J. 59: 987-1000).

Combinations of Promoters

Certain embodiments use transgenic plants or plant cells having multi-gene expression constructs harboring more than one promoter. The promoters can be the same or different.

Any of the described promoters can be used to control the expression of one or more of the nucleotide sequences of the invention, their homologues and/or orthologues as well as any other genes of interest in a defined spatiotemporal manner.

Maize Promoters

Transgenic DNA constructs used for transforming plant cells will comprise the heterologous nucleotides which one desires to introduced into and a promoter to express the heterologous nucleotides in the host maize cells. As is well known in the art such constructs can further include elements such as regulatory elements, 3' untranslated regions (such as polyadenylation sites), transit or signal peptides and marker genes elements as desired. 1. Regulatory Elements A number of promoters that are active in plant cells have been described in the literature both constitutive and tissue specific promoters and inducible promoters. See the background section of U.S. Pat. No. 6,437,217 for a description of a wide variety of promoters that are functional in plants. Such promoters include the nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (e35S), the light-inducible promoter from the small subunit of ribulose bisphosphate carboxylase (ssRUBISCO, a very abundant plant polypeptide). For instance, see U.S. Pat. No. 6,437,217 which discloses a maize RS81 promoter. U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter and U.S. Pat. No. 6,177,611 which discloses constitutive maize promoters, all of which are incorporated herein by reference.

Requirements for Construction of Plant Expression Cassettes

Nucleotide sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described herein. The following is a description of various components of typical expression cassettes.

Transcriptional Terminators

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

Sequences for the Enhancement or Regulation of Expression

Numerous sequences have been found to enhance gene expression from within the transcriptional unit and these sequences can be used in conjunction with the genes to increase their expression in transgenic plants. For example, various intron sequences such as introns of the maize Adh1 gene have been shown to enhance expression, particularly in monocotyledonous cells. In addition, a number of non-translated leader sequences derived from viruses are also known to enhance expression, and these are particularly effective in dicotyledonous cells.

Coding Sequence Optimization

The coding sequence of the selected gene may be genetically engineered by altering the coding sequence for optimal expression in the crop species of interest. Methods for modifying coding sequences to achieve optimal expression in a particular crop species are well known (Perlak et al, 1991, Proc. Natl. Acad. Sci. USA 88: 3324 and Koziel et al., 1993, Biotechnology 11: 194-200).

Construction of Plant Transformation Vectors

Numerous vectors available for plant transformation are known to those of ordinary skill in the plant transformation arts. The genes pertinent to this disclosure can be used in conjunction with any such vectors. The choice of vector depends upon the selected transformation technique and the target species.

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof. (See, for example, U.S. Pat. No. 5,639,949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. (See, for example, U.S. Pat. No. 5,639,949).

Transformation and Selection of Cultures and Plants

Plant cultures can be transformed and selected using one or more of the methods described above which are well known to those skilled in the art.

Manipulation of Endogenous Promoters

Zinc-finger nucleases (ZFN), TALEN, and CRISPR-Cas9 are also useful for practicing the invention in that they allow double strand DNA cleavage at specific sites in plant chromosomes such that targeted gene insertion or deletion can be performed (Shukla et al., 2009, Nature 459: 437-441; Townsend et al, 2009, Nature 459: 442-445). This approach may be particularly useful for the present invention to modify the promoter of endogenous genes to modify expression of genes homologous to PsbS, ZEP and VDE, which are present in the genome of the plant of interest. In this case the ZFN, TALEN or CRISPR/Cas9 can be used to change the sequences regulating the expression of the TF of interest to increase the expression or alter the timing of expression beyond that found in a non-engineered or wild type plant.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1. Transgenic *Nicotiana tabacum*

*Nicotiana tabacum* plants were transformed with a T-DNA cassette containing three *Arabidopsis thaliana* genes. *Arabidopsis* ZEP was overexpressed to increase the rate of xanthophyll epoxidation and corresponding NPQ relaxation, together with *Arabidopsis* PsbS overexpression to stimulate the amplitude of qE formation and *Arabidopsis* VDE to maintain critical levels of zeaxanthin for ROS scavenging. The resulting transgenic plants are shown to have modified NPQ kinetics leading to higher quantum yield and $CO_2$ fixation without loss of photo-protective efficiency under fluctuating light intensity and increased growth in two independent greenhouse experiments. These results confirm that photosynthetic efficiency is transiently limited by NPQ under fluctuating light intensity and provide the first proof of principle for improvement of photosynthetic efficiency and crop yield via changes in NPQ kinetics.

Example 2. NPQ and PSII Operating Efficiency in Young Seedlings

Transient NPQ was determined from chlorophyll fluorescence imaging on $T_1$ progeny of 20 independent transformation events with the vde-psbs-zep (VPZ) construct during 10 minutes of illumination with 1000 μmol quanta $m^{-2}$ $s^{-1}$, followed by 10 minutes of dark relaxation. Since the aim was to maintain similar non-photochemical quenching capacity, lines with maximum levels of NPQ similar to WT were selected for further investigation. This yielded eight lines from which two lines harboring a single T-DNA copy (VPZ-34 and 56) and one line with two T-DNA insertions (VPZ-23) were included in the present work. All results are reported for homozygous $T_2$ progeny. NPQ kinetic behavior showed substantial differences between the three VPZ lines and WT (FIG. 1A). NPQ in the VPZ lines rapidly increased, reaching the maximum NPQ level between two to four minutes, after which the level of NPQ stabilized (VPZ-23) or even slightly decreased (VPZ-34 and VPZ-56). In contrast, NPQ in the WT control continued to increase for seven minutes, after which the maximum level was retained for the remaining three minutes. As a result of these contrasting induction patterns, NPQ was significantly higher in all three transgenic lines during the initial five minutes of induction, but not in the final five minutes (FIG. 1A). After turning the lights off, NPQ relaxation was very rapid and very similar in both WT and VPZ lines.

Repetitive cycles of light intensity between 2000 (3 min) and 200 (2 min) μmol $m^{-2}$ $s^{-1}$ resulted in even more pronounced differences in NPQ between the VPZ lines and WT (FIG. 1B). NPQ in the VPZ lines increased rapidly during the high light phase of the first two cycles, reaching maximum levels during the second minute of the second cycle. In contrast. NPQ increased more slowly in the WT seedlings, only reaching maximum levels in the third minute of the fourth cycle. Interestingly, NPQ during the low light phase of the cycles showed the opposite pattern. In the first cycle, NPQ levels during the low light phase were higher in the VPZ lines, however NPQ levels in the second cycle were equal between the VPZ lines and WT, and were significantly lower in the VPZ lines in the final three cycles.

Photosystem II (PSII) operating efficiency, estimated in conjunction with NPQ, showed no differences between VPZ lines and WT in the first cycle (FIG. 1C). However, during the five following cycles, VPZ lines showed superior PSII operating efficiency during the low light phase of the cycles, whereas no differences were found during the high light phase. This pattern was established in the second cycle, and repeated throughout the remainder of the experiment.

Example 3. Transcription and Protein Expression

Figure 2:
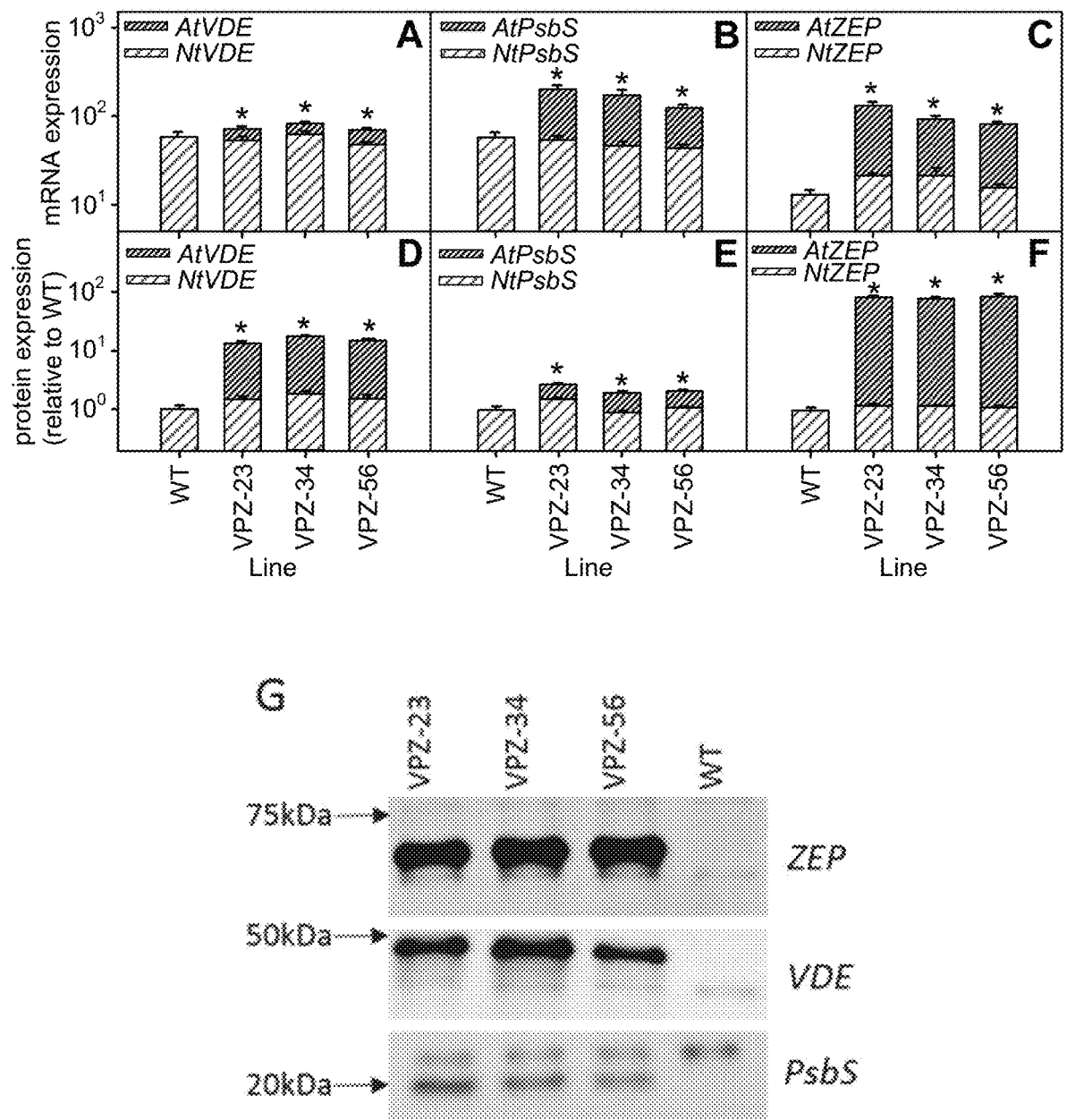
FIG. 2. mRNA and protein expression of native (Nt) and transgenic (At) violaxanthin de-epoxidase (VDE), photosystem II subunit S (PsbS) and zeaxanthin epoxidase (ZEP). (A-C) mRNA levels relative to actin and tubulin, (D-F) protein levels relative to wild-type, determined from densitometry on western blots, error bars indicate ±se (n=5) asterisks indicate significant differences between VPZ lines and wild-type ($\alpha$=0.05), (G) Example of western blots for VDE, PsbS and ZEP.

All three VPZ-lines showed significant increases in combined transgenic (At) and native (Nt) transcript levels of VDE (3-fold), PsbS (3-fold) and ZEP (8-fold) relative to wild-type (FIGS. 2A, B and C). For PsbS the increase in transcript levels translated into approximately 2-fold higher PsbS protein level (FIG. 2E), as exemplified in two approximately equal density bands around 22 kDa (FIG. 2G, VPZ lanes), representing the native and transgenic protein. However, for VDE and ZEP the increase in transcript levels was amplified in the protein levels (FIG. 2G, labelled bands around 73 kDa for ZEP and 45 kDa for VDE), showing substantial increases of VDE (FIG. 2D) and ZEP (FIG. 2F) protein relative to WT (16 and 80-fold, respectively). Interaction between transgenic and native transcript and protein levels appeared to be negligible, since transcript and protein levels of the native proteins were similar in the VPZ lines and WT.

Figure 7:
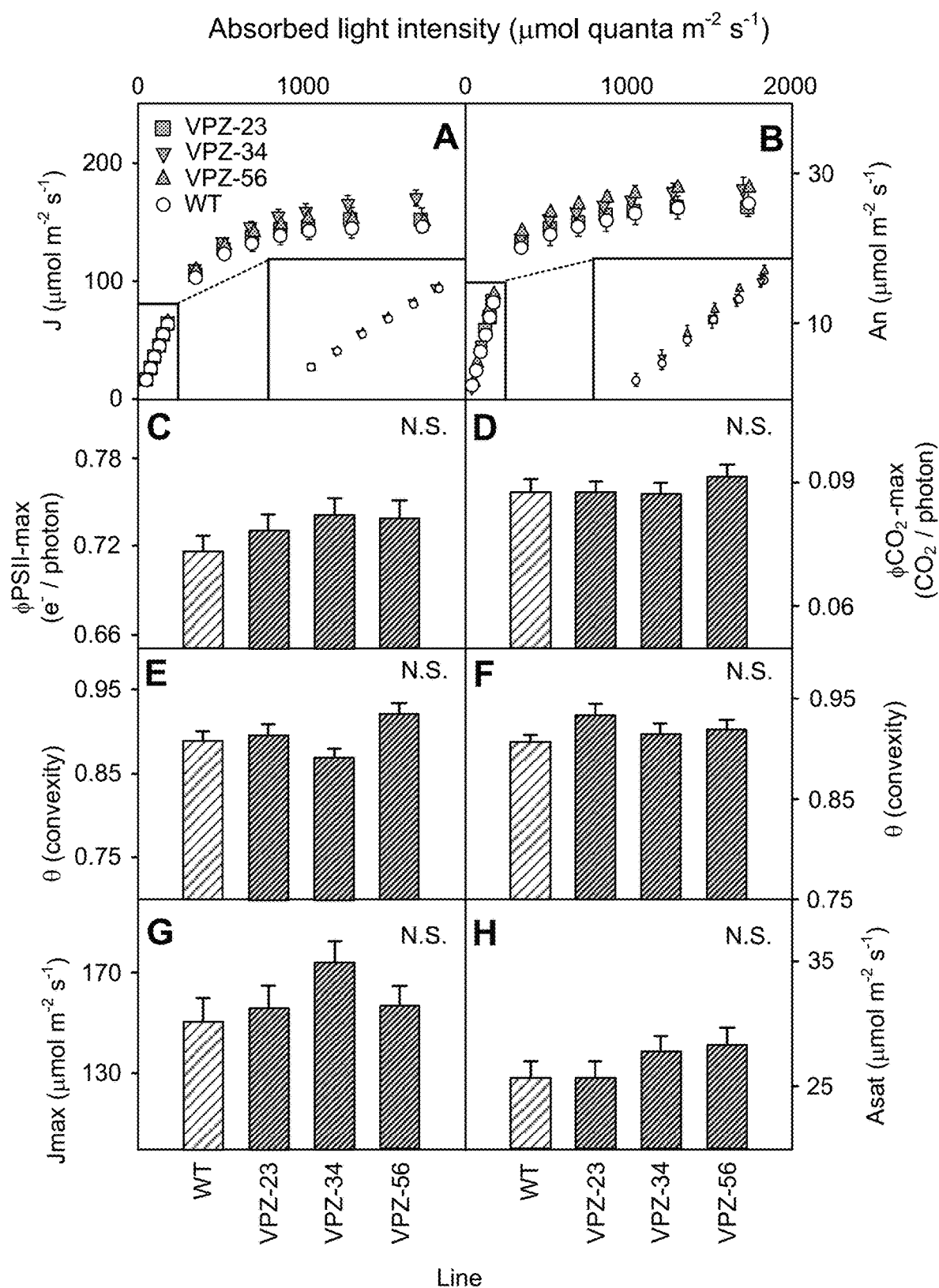
FIG. 7. Linear electron transport and net assimilation rate as a function of light intensity. Light intensity was varied from high to low PFD with 4 min of 2000 µmol $m^{-2}$ $s^{-1}$ PFD before each light intensity change. (A-B) Linear electron transport (J) and net assimilation rate (An) and corresponding parameter fits for initial slope (C-D), convexity (E-F) and asymptote (G-H). Error bars indicate ±se (n=6).
Figure 8:
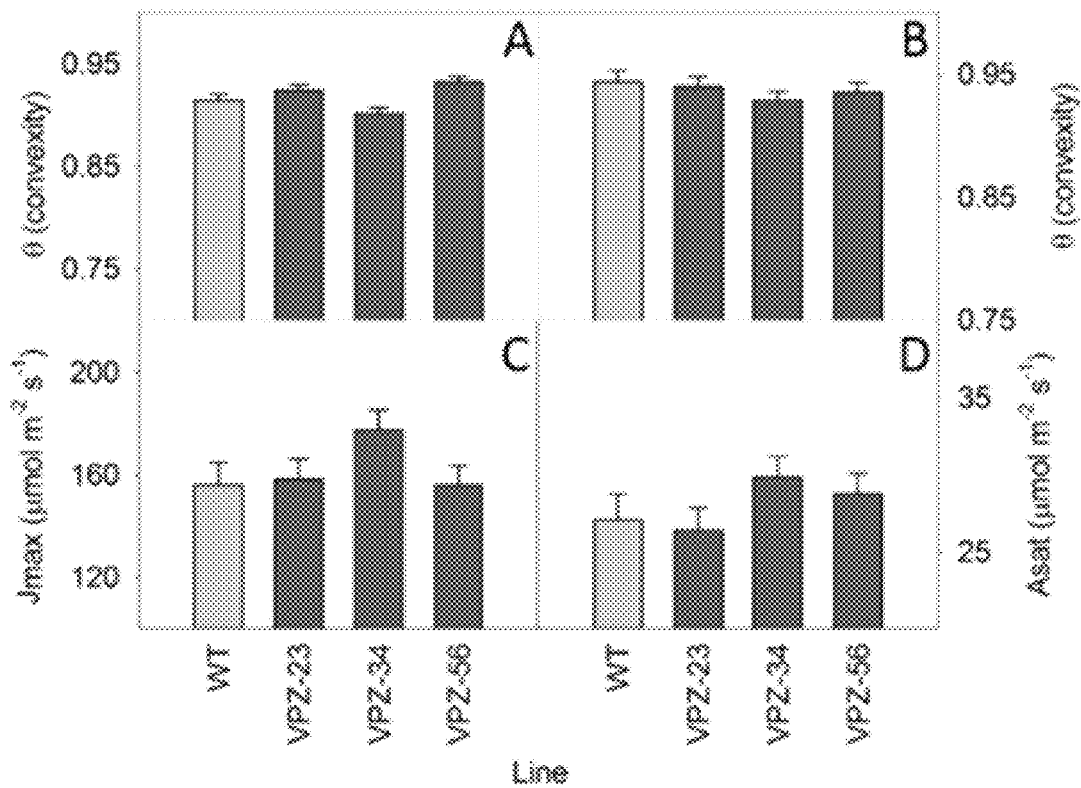
FIG. 8. Convexity (A-B) and asymptote (C-D) parameter fits to linear electron transport (J) and net assimilation rate (An) as a function of light intensity. Light intensity was varied from high to low PFD with 4 min of 2000 µmol $m^{-2}$ $s^{-1}$ PFD before each light intensity change. Error bars indicate ±se (n=6).

Example 4. Kinetics of NPQ in Young Seedlings Following Repeated Changes in Light Intensity To compare the kinetics of dynamic NPQ adjustment, time constants of a double exponential model were fitted to time-series of NPQ in young seedlings as a function of repeated changes in light intensity between 2000 and 200 µmol m$^{-2}$ s$^{-1}$ (Table 1). During the first 2000/200 cycle no consistent differences between WT and VPZ overexpression lines were observed. The time constant of NPQ induction varied between 49.3±1.9 (VPZ-34) to 91.8±6.2 (VPZ-56), and time constants of readjustment from 2000 to 200 µmol m$^{-2}$ s$^{-1}$ were also similar across WT and the three VPZ lines, averaging 10.2 s for $\tau_1$ and 669.9 s for $\tau_2$. During the second 2000/200 cycle, the effect of VPZ expression on NPQ kinetics became more apparent. The fast phase of NPQ increase in the WT was approximately 2.3 times faster than in the VPZ lines, with $\tau_1$ of 5.5 s in WT versus average $\tau_1$ of 12.6 s in the VPZ lines (Table 1). The second adjustment of NPQ to 200 µmol m$^{-2}$ s$^{-1}$ showed a pronounced difference in the slow component of NPQ decline. Estimated $T_2$ in the VPZ lines, was found to be 1.9 times faster than WT (464.3 versus 886.4 s). Thus, repeated light intensity changes resulted in faster build-up and slower relaxation of NPQ in the WT, but the time constants in the VPZ lines were relatively unaffected. This same trend continued in the final 3 min at 2000 µmol m$^{-2}$ s$^{-1}$ followed by 10 min of darkness. The fast phase of NPQ increase in the WT seedlings was approximately 2.4 times faster than the VPZ lines ($\tau_1$ of 4.3 versus 10.3 s) but final relaxation of NPQ during 10 min of darkness was 1.4 ($\tau_1$) and 3.5 times ($\tau_2$) faster in the VPZ lines relative to WT. In addition, $\tau_1$ and $\tau_2$ determined for recovery of PSII operating efficiency were 2.1 and 4.1 times faster in the VPZ lines, compared to WT.

port and net assimilation rate as a function of absorbed light intensity did not show significant differences between WT and VPZ lines (FIG. 7). Additionally, fitted parameter values $V_{cmax}$, J, TPU, and Rd derived from $CO_2$ response curves were also similar between WT and the VPZ lines (Table 2.)

TABLE 2

Parameter fits derived from $CO_2$ response curves. Maximal carboxylation capacity (Vcmax), maximal rate of linear electron transport (Jmax), mitochondrial respiration rate not associated with photorespiration ($R_d$) and maximal rate of triose phosphate utilization (TPU). Values ± se, n = 10, no significant differences between wild-type and VPZ lines were found.

| | WT | VPZ-23 | VPZ-34 | VPZ-56 |
|---|---|---|---|---|
| Vcmax (µmol m$^{-2}$ s$^{-1}$) | 112.3 ± 4.5 | 108.2 ± 2.7 | 104.7 ± 3.7 | 121.8 ± 6.1 |
| Jmax (µmol m$^{-2}$ s$^{-1}$) | 146.0 ± 5.7 | 136.2 ± 3.4 | 137.8 ± 4.2 | 149.0 ± 3.8 |
| TPU (µmol m$^{-2}$ s$^{-1}$) | 11.1 ± 0.4 | 10.1 ± 0.3 | 10.5 ± 0.3 | 10.9 ± 0.3 |
| $R_d$ (µmol m$^{-2}$ s$^{-1}$) | 2.1 ± 0.3 | 1.8 ± 0.3 | 2.2 ± 0.2 | 2.3 ± 0.3 |

Figure 3:
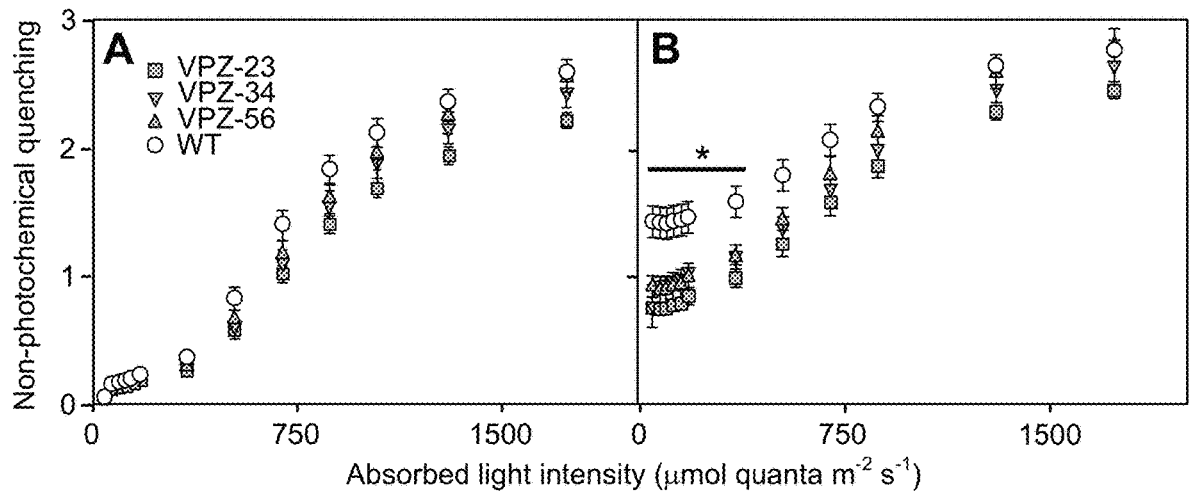
FIG. 3. Non-photochemical quenching during gas exchange as a function of absorbed light intensity in fully-expanded leaves of wild-type and VPZ-overexpressing lines. Light intensity was either increased from low to high PFD, while waiting for steady state at each step (A), or varied from high to low PFD with 4 min of 2000 µmol $m^{-2}$ $s^{-1}$ before each light intensity change (B). Error bars indicate ±se (n=6), asterisks indicate significant differences between VPZ lines and wild-type ($\alpha$=0.05).

Example 6. NPQ, Electron Transport and $CO_2$ Fixation Under Fluctuating Light To evaluate the dynamic effect of VPZ overexpression on the shape of the light response curve, light intensity was varied in 4 min steps from high to low PFD with intermittent steps of 4 min of 2000 µmol m$^{-2}$ s$^{-1}$ before each light transition. NPQ in the VPZ lines was similar to WT at high light intensity, but significantly lower than WT at low light intensity (FIG. 3B). The resulting response curves of linear

TABLE 1

Time constants of NPQ adjustment to repeated changes in light intensity (value ± se). Asterisks indicate significant differences between VPZ lines and wild-type (α = 0.05).

| Experiment phase (HL = 2000, LL = 200 µmol m$^{-2}$ s$^{-1}$, D = dark) | Time constant (s) | WT | VPZ-23 | VPZ-34 | VPZ-56 |
|---|---|---|---|---|---|
| 1$^{st}$ HL | $\tau_1^a$ | 82.7 ± 3.2 | *63.4 ± 2.8 | *49.3 ± 1.9 | 91.8 ± 6.2 |
| 1$^{st}$ LL | $\tau_1$ | 10.4 ± 2.9 | 5.6 ± 1.9 | 14.6 ± 5.4 | n.d.$^b$ |
| | $\tau_2$ | 564.9 ± 48.1 | *1175.3 ± 130.8 | 511.5 ± 39.7 | 428.0 ± 20.9 |
| 2$^{nd}$ HL | $\tau_1$ | 5.5 ± 0.4 | 13.5 ± 3.5 | 11.3 ± 2.8 | *12.9 ± 3.2 |
| | $\tau_2$ | 115.3 ± 24.4 | 127.5 ± 150.1 | 111.2 ± 71.2 | 389.3 ± 1586.8 |
| 2$^{nd}$ LL | $\tau_1$ | 9.2 ± 0.6 | 7.7 ± 1.2 | 9.9 ± 1.4 | 9.9 ± 1.1 |
| | $\tau_2$ | 886.4 ± 101.9 | *470.1 ± 45.0 | *461.5 ± 60.3 | *461.4 ± 64.6 |
| 3$^{rd}$ HL | $\tau_1$ | 4.3 ± 0.3 | *10.1 ± 1.2 | *10.2 ± 1.4 | *10.6 ± 2.6 |
| | $\tau_2$ | 37.2 ± 4.8 | 55.4 ± 33.4 | 53.8 ± 28.2 | 35.5 ± 9.9 |
| D | $\tau_1$ | 21.4 ± 1.2 | *13.3 ± 1.3 | 19.4 ± 1.4 | *13.2 ± 1.0 |
| | $\tau_2$ | 2641.1 ± 821.2 | 792.6 ± 131.7 | *692.6 ± 77.9 | *774.9 ± 94.5 |
| D (PSII efficiency) | $\tau_1$ | 29.2 ± 2.0 | *20.6 ± 2.4 | *14.2 ± 1.0 | *7.7 ± 0.6 |
| | $\tau_2$ | 357.9 ± 480.0 | 106.3 ± 29.5 | 85.6 ± 5.8 | 68.3 ± 3.7 |

$^a$Data in 1$^{st}$ HL phase didn't constrain two time constants, so the model was reduced to a single exponential function and only one time constant was fitted.
$^b$Data resolution was not sufficient to properly constrain fast phase, only slow phase was fitted.

Example 5. NPQ, Linear Electron Transport and $CO_2$ Uptake in Steady State

Figure 4:
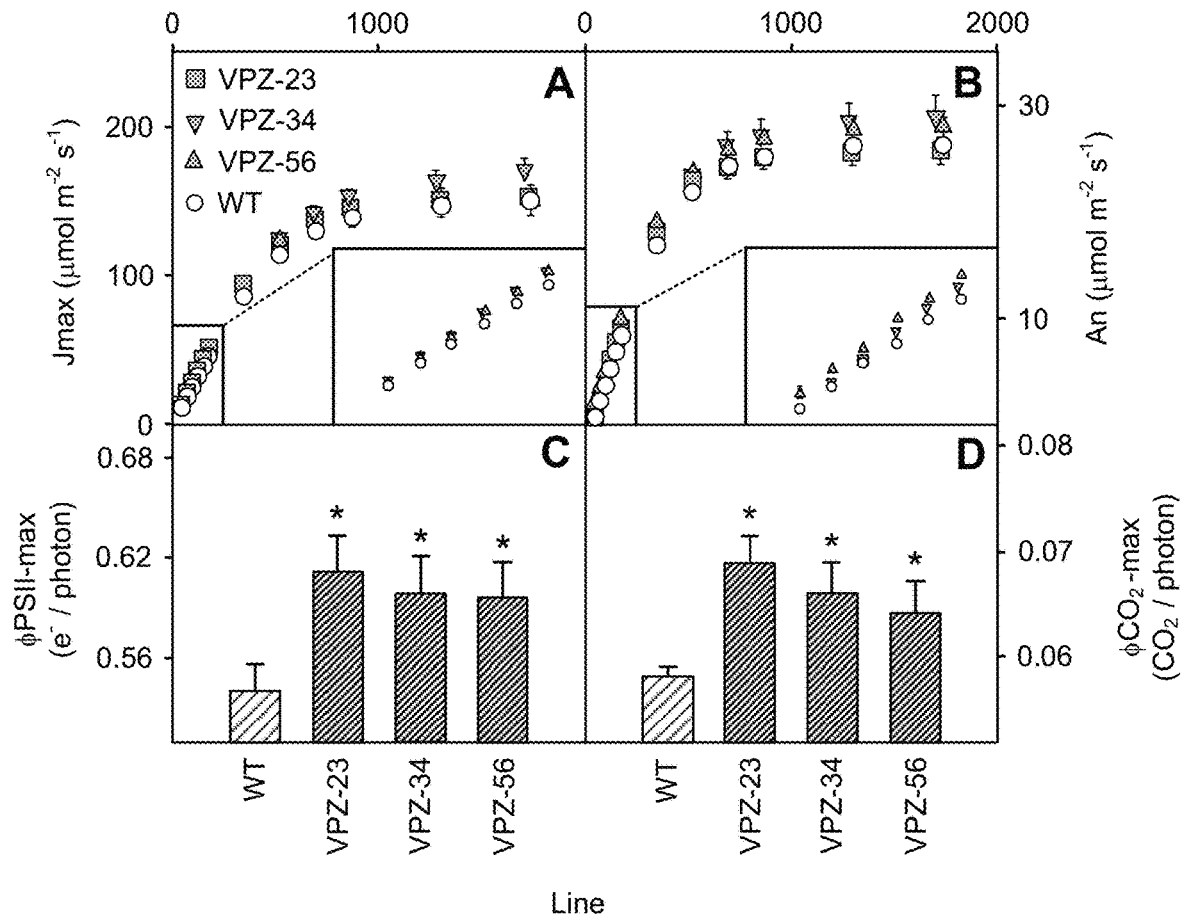
FIG. 4. (A-B) Linear electron transport (J) and net assimilation rate (An) as a function of light intensity and corresponding parameter fits for initial slope (C-D). Light intensity was varied from high to low PFD with 4 min of 2000 µmol $m^{-2}$ $s^{-1}$ PFD before each light intensity change. Error bars indicate ±se (n=6), asterisks indicate significant differences between VPZ lines and wild-type ($\alpha$=0.05).

To measure steady state gas exchange and chlorophyll fluorescence in fully expanded leaves, light intensity was varied from low to high intensity, taking great care to allow gas exchange and fluorescence to fully stabilize at each intensity. NPQ was very similar between WT and VPZ lines, especially at light intensity below 400 µmol m$^{-2}$ s$^{-1}$ (FIG. 3A). Corresponding response curves of linear electron transelectron transport rate and net assimilation rate were distinctly different between WT and VPZ lines (FIGS. 4A and B). Fitted convexity and asymptote parameters were similar between WT and VPZ lines (FIG. 8A-D), but initial slopes were distinctly different (FIGS. 4C and D). Fluctuating intensity reduced ΦPSIImax to 0.541±0.012 in the WT plants (FIG. 4C), but VPZ lines maintained a less reduced ΦPSII$_{max}$ of 0.612±0.021 (VPZ-23), 0.599±0.023 (VPZ-34) and 0.595±0.023 (VPZ-56). Similarly Φ$CO_2$-max was reduced to 0.058±0.001 in the WT plants (FIG. 4D), whereas ΦCO$_2$-max values in the VPZ lines were much less impacted by intermittent high light intensity, yielding 0.069±0.003 for VPZ-23, 0.066+0.003 for VPZ-34 and 0.064±0.003 for VPZ-56. Thus, under these fluctuating conditions, average ΦPSII-max and CO$_2$-max of the VPZ lines were 11.3% and 14.0% higher than WT.

Figure 5:
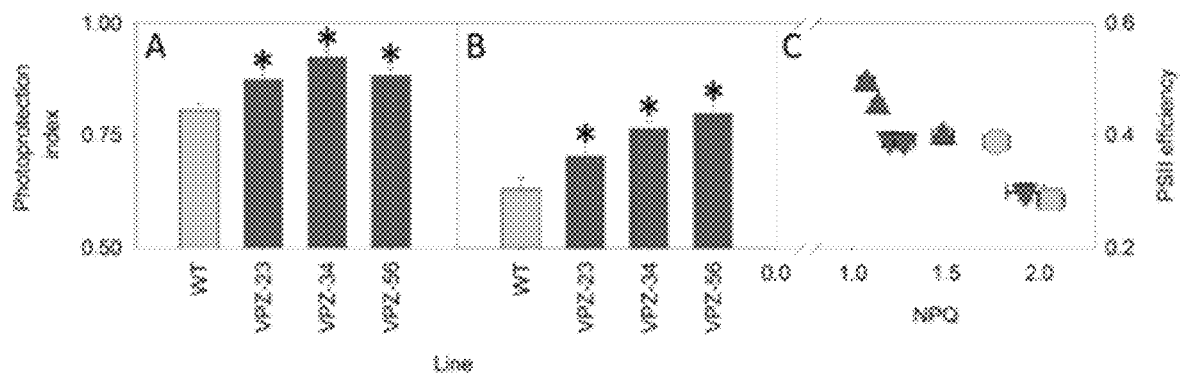
FIG. 5. Photo-protection index after exposure of (A) one hour or (B) two hours to 2000 µmol $m^{-2}$ $s^{-1}$ PFD ($\lambda_{max}$=470 nm) in seedlings of VPZ overexpression lines and wild-type. Index values less than one indicate occurrence of photo-inhibition. (C) PSII efficiency plotted against residual NPQ in young seedlings after exposure to one hour (Upward pointing triangles—VPZ, Circle—WT) or two hours (Downward pointing triangles—VPZ, Square—WT) of 2000 µmol $m^{-2}$ $s^{-1}$ and 10 min of subsequent dark relaxation. Error bars indicate ±se (n=18), asterisks indicate significant differences between VPZ lines and wild-type ($\alpha$=0.05).
Figure 6:
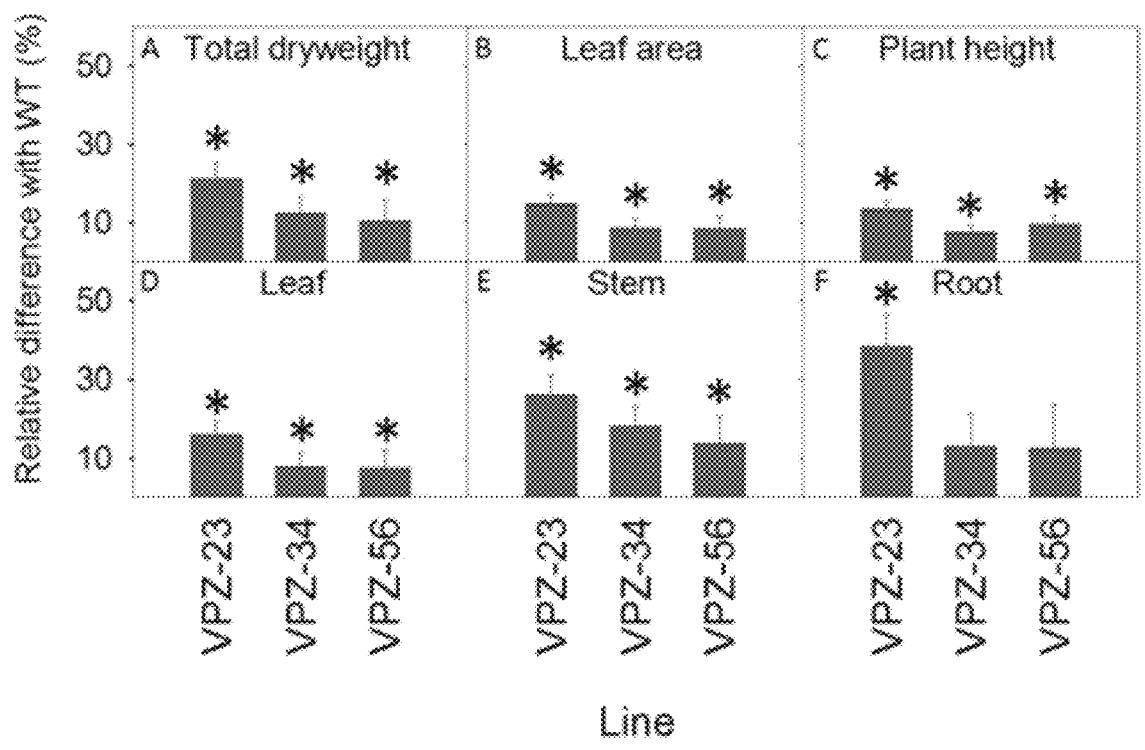
FIG. 6. Final plant size and weight in greenhouse experiments relative to WT. (A) Total dry-weight per plant. (B) leaf area per plant, (C) Plant height. (D) Leaf dry-weight per plant, (E) Stem dry-weight per plant. (F) Root dry-weight per plant. Error bars indicate ±se (n=20 and n=19 for experiment 1 and 2), asterisks indicate significant differences between VPZ lines and wild-type ($\alpha$=0.05).

Example 7. Xanthophyll Cycle De-Epoxidation as a Function of Different Light Treatments To evaluate the effects of VPZ overexpression on the xanthophyll cycle, leaves were subjected to four different light treatments (Table 3). The combined pool size of violaxanthin, antheraxanthin, and zeaxanthin was similar between WT and VPZ lines. The xanthophyll pigment pool was completely epoxidated in dark-adapted leaves and no differences between WT and VPZ were observed. Exposure to PFD of 400 µmol m$^{-2}$ s$^{-1}$ resulted in almost no change in the xanthophyll composition and DES remained close to zero, but illumination with PFD of 2000 µmol m$^{-2}$ s$^{-1}$ led to considerable build-up of antheraxanthin and mainly zeaxanthin. VPZ lines retained significantly more violaxanthin and accumulated less zeaxanthin and antheraxanthin compared to WT, which led to xanthophyll DES in the VPZ lines to be almost two times lower than WT (25.5% versus 46.2%). The fluctuating light treatment showed the same trend as high light exposure, with even less xanthophyll de-epoxidation in the VPZ lines, relative to WT (17.8% versus 52.5%).

lines (FIG. 5A). Photo-protective efficiency after two hours (FIG. 5B) was considerably less than after one hour, but VPZ seedlings were again found to be less photo-inhibited than WT. Residual NPQ after ten minutes of dark recovery tended to be lower in the VPZ seedlings (FIG. 5C). As a result of lower residual NPQ and higher photo-protection index, PSII efficiency in the VPZ seedlings also tended to be higher after 10 min of dark recovery (FIG. 5C).

Example 9. Plant Growth Under Greenhouse Conditions

To investigate if the aforementioned differences in photosynthetic efficiency would affect growth, biomass accumulation was evaluated in two greenhouse experiments. Temperature was similar between both experiments and varied between 21 and 25° C. Peak light intensity exceeded 2000 µmol m$^{-2}$ s$^{-1}$ in the first experiment and 1600 µmol m$^{-2}$ s$^{-1}$ in the second experiment and daily light integrals averaged 21.3 and 19.3 mol m$^{-2}$ d$^{-1}$ in the first and second experiment, respectively. However, in the final week of the second experiment peak light intensity and daily light integral were decreasing substantially to 1037 µmol m$^{-2}$ s$^{-1}$ and 8.9 mol m$^{-2}$ d$^{-1}$, due to seasonal decline in light intensity. As a result, average plant dry weight was substantially higher in the first experiment, 35.6 g versus 22.5 g respectively. Across both trials, plants from VPZ lines exhibited increased stem height (FIG. 5B) and leaf area (FIG. 5C), relative to WT. Additionally, total dry weight per plant was between 10 to 21% higher in VPZ lines (FIG. 5A), mainly due to substantial increases in stem dry weight (14 to 26%, FIG. 5D) as well as increases in leaf (7.5 to 16%, FIG. 5E) and root (12.5 to 38.3%) dry weight.

TABLE 3

Xanthophyll cycle pigment concentrations and de-epoxidation state (DES) in fully expanded leaves in either dark-adapted state or after exposure to constant 400 or 2000 µmol m$^{-2}$ s$^{-1}$ PFD or 3 cycles of 3 min 2000/3 min 200 µmol m$^{-2}$ s$^{-1}$ PFD. Pigment concentration (value ± se, n = 3-5) has been normalized per unit leaf area (g m$^{-2}$). DES (%) = (Zea + 0.5Ant)/(Zea + Ant + Viola), n.d. = not detected. Asterisks indicate significant differences between VPZ lines and wild-type (α = 0.05).

| Light treatment | Pigment (g m$^{-2}$) | WT | VPZ-23 | VPZ-34 | VPZ-56 |
|---|---|---|---|---|---|
| Dark-adapted | Vio | 7.72 ± 0.37 | 6.64 ± 0.45 | 6.94 ± 0.64 | 6.70 ± 0.40 |
| | Ant | 0.01 ± 0.00 | 0.00 ± 0.00 | 0.00 ± 0.00 | 0.01 ± 0.00 |
| | Zea | n.d. | n.d. | n.d. | n.d. |
| | DES | 0.0 | 0.0 | 0.0 | 0.0 |
| Constant at 400 µmol m$^{-2}$ s$^{-1}$ PFD | Vio | 6.68 ± 0.62 | 7.29 ± 0.47 | 7.05 ± 0.48 | 7.07 ± 0.31 |
| | Ant | 0.03 ± 0.01 | 0.01 ± 0.00 | 0.02 ± 0.01 | 0.01 ± 0.00 |
| | Zea | 0.20 ± 0.10 | 0.00 ± 0.00 | 0.05 ± 0.05 | 0.00 ± 0.00 |
| | DES | 2.9 ± 1.4 | 0.1 ± 0.0 | 0.7 ± 0.6 | 0.1 ± 0.0 |
| Constant at 2000 µmol m$^{-2}$ s$^{-1}$ PFD | Vio | 4.47 ± 0.41 | 5.09 ± 0.52 | 3.63 ± 0.59 | 5.02 ± 0.09 |
| | Ant | 0.07 ± 0.00 | 0.08 ± 0.01 | 0.06 ± 0.01 | 0.09 ± 0.01 |
| | Zea | 3.81 ± 3.81 | *1.48 ± 0.48 | *1.23 ± 0.24 | *1.94 ± 0.49 |
| | DES | 46.2 ± 2.8 | *22.9 ± 7.5 | *26.2 ± 5.3 | *27.4 ± 5.1 |
| Fluctuating between 2000 and 200 µmol m$^{-2}$ s$^{-1}$ PFD | Vio | 4.20 ± 0.16 | *7.11 ± 0.57 | *5.72 ± 0.15 | *6.14 ± 0.34 |
| | Ant | 0.16 ± 0.02 | *0.08 ± 0.01 | 0.13 ± 0.03 | *0.08 ± 0.01 |
| | Zea | 4.70 ± 0.36 | *0.88 ± 0.08 | *2.29 ± 0.85 | *1.20 ± 0.21 |
| | DES | 52.5 ± 5.5 | *11.4 ± 0.9 | *25.5 ± 17.3 | *16.4 ± 4.2 |

Example 8. Efficiency of Photo-Protection by Non-Photochemical Quenching

Figure 12:
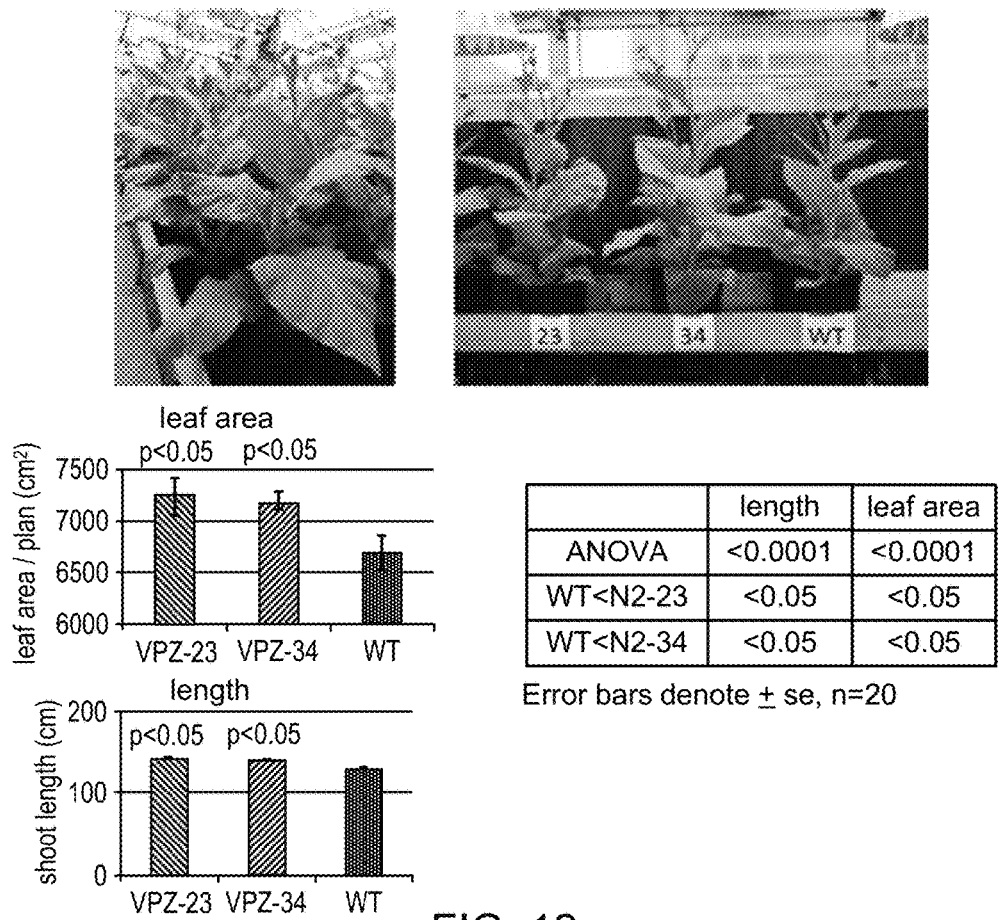
FIG. 12. Growth experiment comparing VPZ-23 and VPZ-34 transgenic to wild type plants.
Figure 13:
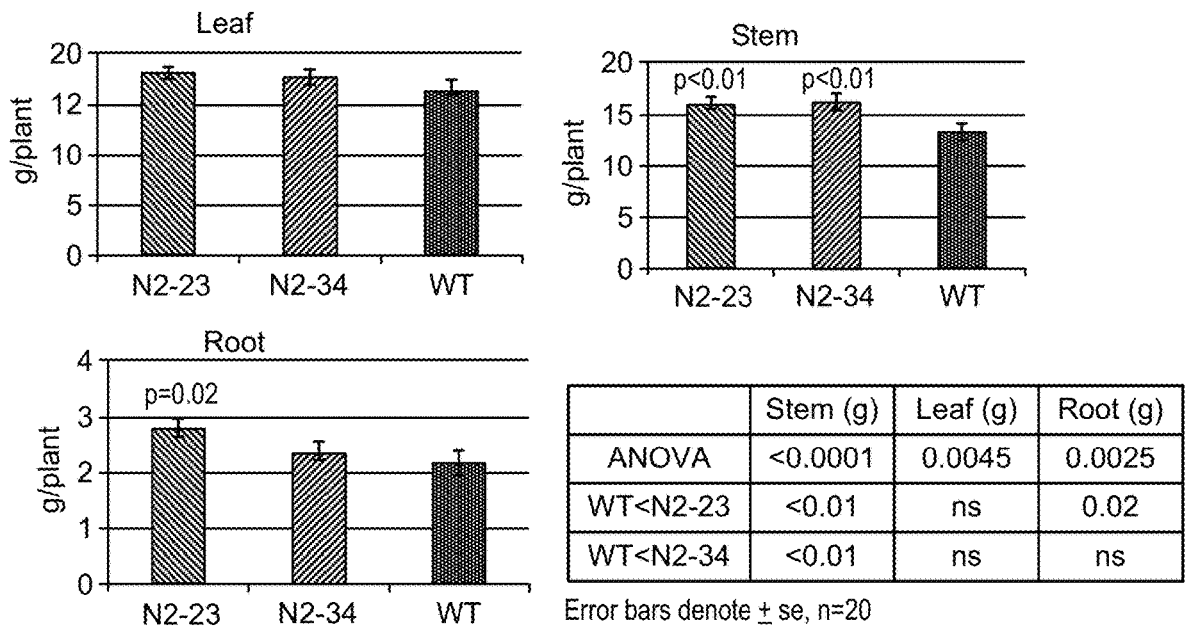
FIG. 13. Greenhouse experiment showing significantly increased growth in all lines.
Figure 14:
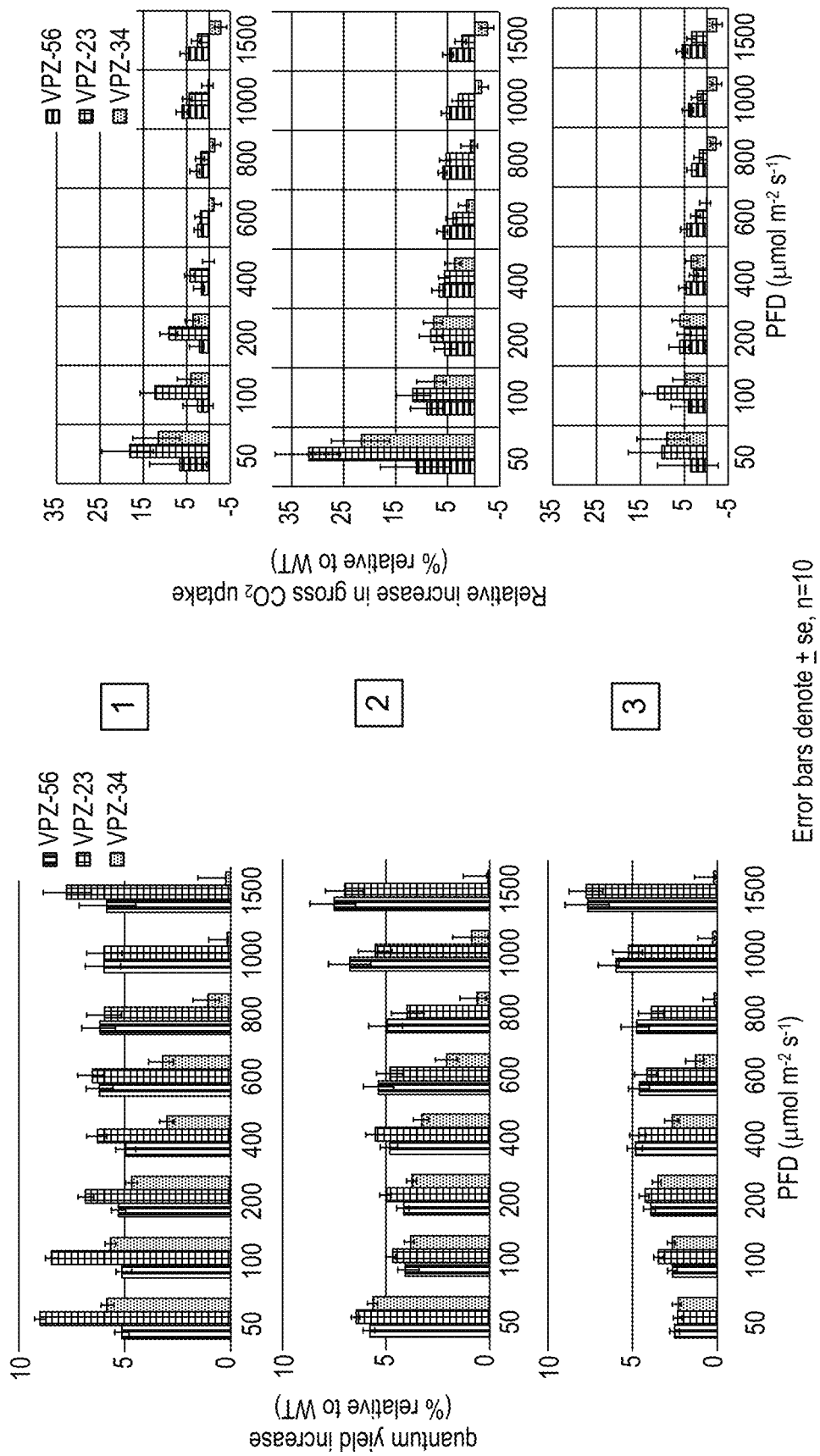
FIG. 14. Results of quantum yield and $CO_2$ fixation at various light intensities, after prior exposure of the leaf to 2000 µmol $m^{-2}$ $s^{-1}$ PFD.
Figure 15:
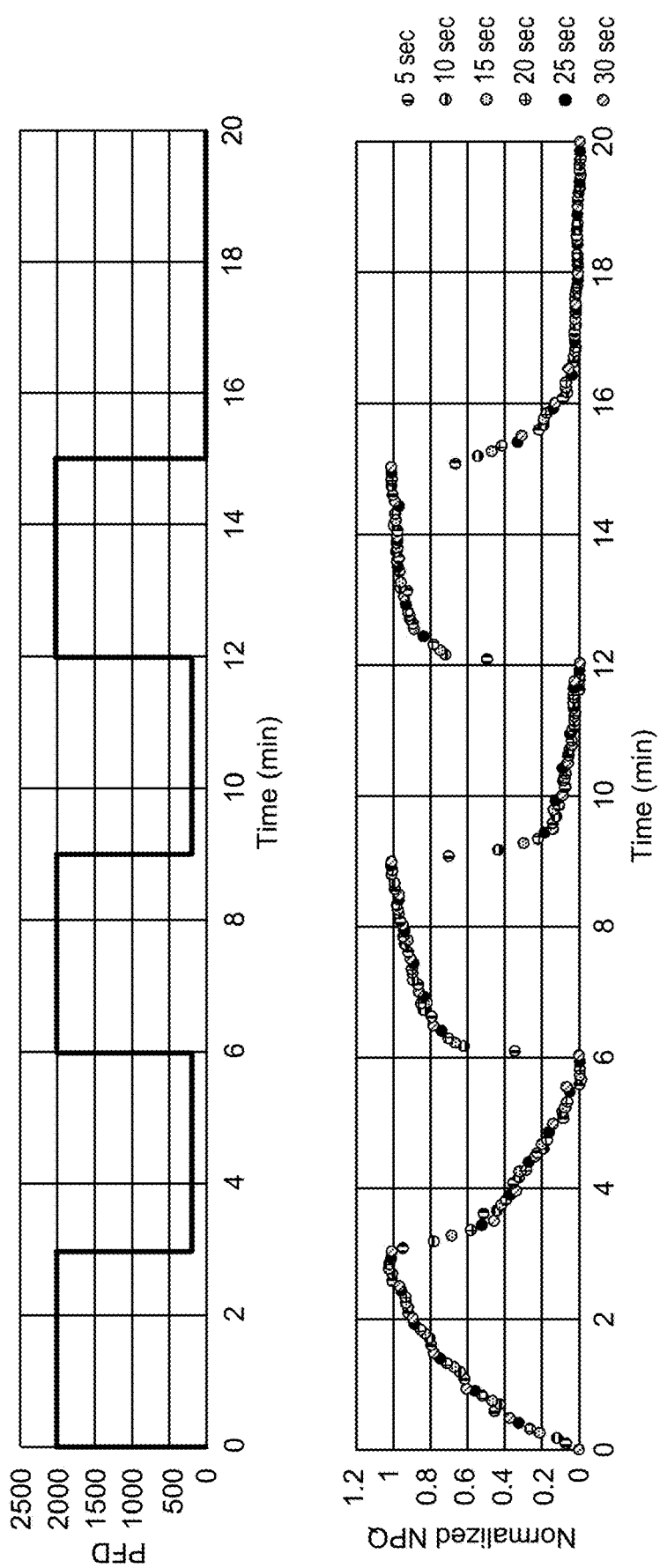
FIG. 15. NPQ kinetics under fluctuating light.
Figure 17:
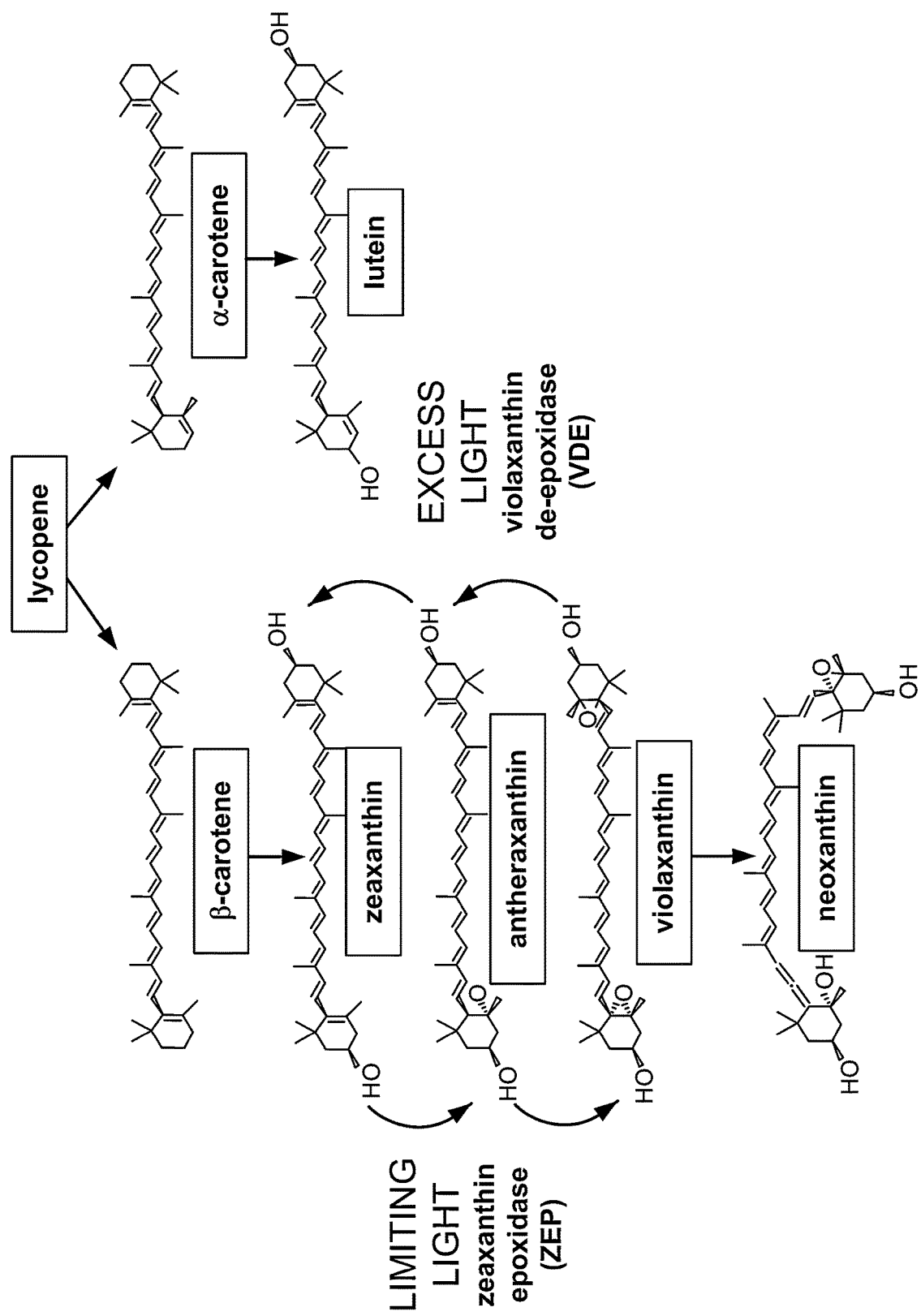
FIG. 17. NPQ components (qE, qZ, and qI) association with conversion of violaxanthin to zeaxanthin.

To evaluate the photo-protective efficiency in the VPZ lines relative to WT, seedlings were exposed to 2000 µmol m$^{-2}$ s$^{-1}$ of blue light for one and two hours. The contrasting effects of photoinhibition and NPQ on Fo' after the high light treatment were used to calculate a photo-protection index (FIG. 5), in which a value of 1 equals complete protection from photo-inhibitory damage. One hour of high light exposure resulted in significant induction of photo-inhibition, which was slightly higher in WT seedlings than in the VPZ Example 10. Additional Data FIGS. 12 and 13 leaf, stem and root size, and growth, increase in transgenic plant lines N2-23 and N2-34 compared to wild type. FIG. 14 shows increased NPQ kinetics, quantum yield and CO$_2$ fixation in transgenic lines VPZ-56, VPZ-23 and VPZ-34. These results show an increase in quantum yield and $CO_2$ fixation at various light intensities, after prior exposure of the leaf to 2000 µmol m$^{-2}$ s$^{-1}$ PFD. 1, 2 and 3 show the progression of this increase in time after exposure.

FIG. 16 shows that the time constants of NPQ in the first induction/relaxation are similar, but subsequent light cycles lead to slower build up (independent of amplitude, these are time constants) and faster relaxation of NPQ in transgenic plants, and faster recovery of quantum yield in dark relaxation. These comparative results are entirely consistent with reduced build up of zeaxanthin in the transgenic lines. Levels of NPQ in VPZ lines at high light are similar or higher than WT. Levels of qE in VPZ lines estimated by dA532 nm are higher than WT, most likely associated with PsbS overexpression. Repeated high light exposure shows higher time constants of NPQ increase, and lower time constants of NPQ relaxation in VPZ lines. VPZ lines show 5-10% improved quantum yield at low PFD during rapid switches in PFD, due to faster rate of NPQ relaxation.

Combined overexpression of VDE, ZEP and PsbS leads to modified kinetics of build-up and relaxation of NPQ in seedlings and fully grown plants, higher quantum yield under fluctuating light conditions in seedlings and fully grown plants, no significant differences in steady state gas exchange in fully grown plants, higher gross assimilation rate under fluctuating conditions in fully grown plants, and approximately 10% increase in growth in greenhouse.

Example 11. Materials and Methods

Transformation

*N. tabacum* cv. 'Petite Havana' was transformed using the *Agrobacterium*-mediated leaf disc protocol according to Clemente. *Agrobacterium* Protocols (ed Wang K.). pp. 143-154. Humana Press Inc., Totowa. The binary plasmid contained coding sequences of three genes from *A. thaliana*: violaxanthin de-epoxidase (AtVDE), AtPsbS and zeaxanthin epoxidase (AtZEP) as well as the bar gene encoding resistance for bialaphos (Thompson et. al. Journal of Agricultural and Food Chemistry 35, 361-365, 1987). 20 independent $T_0$ transformants were generated and T-DNA copy number was determined using digital droplet PCR (ddPCR) analysis of genomic DNA according to Glowacka et al Plant Cell and Environment doi: 10.1111/pce.12693, 2015. Two lines with a single copy (VPZ-34 and 56) and one line with two copies (VPZ-23) of the T-DNA were used to generate $T_1$ progeny in which homozygous plants were identified by ddPCR according to Glowacka et al and self-pollinated to obtain homozygous T2 offspring for further analysis.

Propagation of Plant Material $T_2$ seeds of VPZ lines and WT seeds from the same harvest date were germinated on growing medium (LC1 Sunshine mix, Sun Gro Horticulture, Agawam, Mass., USA) in a controlled environment walk-in growing chamber (Environmental Growth Chambers. Chagrin Falls, Ohio, USA) with 12 h day (23° C.)/12 h night (18° C.) cycle under 150 µmol quanta m$^{-2}$ s$^{-1}$. Five days after germination, seedlings were transplanted to 8×12 potting trays (812 series, Hummert International, Earth City, Mo., USA) for chlorophyll fluorescence imaging or 9×4 potting trays (3600 series, Hummert International) and grown until two true leaves had emerged. Seedlings to be used in gas exchange and biomass analyses were moved to the greenhouse after the first transplant.

Transcription and Protein Expression

Five leaf discs (total 2.9 cm2) were sampled from the youngest fully expanded leaves from five plants per line, from the position of the leaf where gas exchange was also performed. Protein and mRNA were extracted from the same leaf sample (NucleoSpin RNA/Protein kit. REF740933, Macherey-Nagel). Extracted mRNA was treated by DNase (Turbo DNA-free kit; AM 1907, Thermo Fisher Scientific, Waltham, Mass., USA) and transcribed to cDNA using Superscript III First-Strand Synthesis System for RT-PCR (18080-051; Thermo Fisher Scientific). RT-qPCR was used to quantify expression levels of the transgenes AtZEP, AtPsbS and AtVDE, and the native genes NtZEP, NtPsbS and NtVDE relative to NtActin and NtTubulin (primer sequences provided supplemental materials).

After quantification of total protein concentration (protein quantification assay ref740967.50. Macherey-Nagel), 4 µg protein was separated by SDS-PAGE electrophoresis, blotted to membrane (Immobilon-P, IPVH00010, Millipore, USA) using semi-dry blotting (Trans-Blot SD, Bio-Rad) and immuno-labelled with primary antibodies raised against AtPsbS (AS09533, Agrisera, Vannias, Sweden), AtZEP (AS08289, Agrisera) and AtVDE (AS153091, Agrisera) followed by incubation with secondary antibodies (Promega W401B). Chemiluminescence was detected using a scanner (ImageQuant LAS-4010, Fuji,) and densitometry was performed using ImageJ (version 1.47 v, National Institute of Health, USA) to estimate protein concentrations Wild-type protein concentrations were used for normalization.

NPQ and PSII Operating Efficiency in Young Seedlings

Non-photochemical quenching (NPQ) was determined in 18 seedlings simultaneously, using a chlorophyll fluorescence imager (CF Imager, Technologica, Colchester, UK). Seedlings were first dark adapted for 20 minutes after which the dark-adapted minimal fluorescence (Fo) and maximal fluorescence (Fm) were imaged using a 800 ms pulse of saturating light intensity (6000 µmol quanta m$^{-2}$ s$^{-1}$, λmax=470 nm). Subsequently, seedlings were subjected to either 10 minutes of 1000 µmol quanta m$^{-2}$ s$^{-1}$ followed by 10 minutes of darkness or six cycles of three minutes 2000 µmol quanta m$^{-2}$ s$^{-1}$ followed by two minutes of 200 µmol quanta m$^{-2}$ s$^{-1}$. Saturating flashes were provided at regular intervals to image variable fluorescence (F') and the maximum fluorescence under illuminated conditions (Fm'). Average NPQ per seedling was then calculated from these measurements according to Eq. 1, assuming the Stern-Volmer quenching model:

$$NPQ=Fm/Fm'-1 \qquad \text{Eq. 1}$$

Maximal or operating PSII efficiency were estimated from the fluorescence measurements according to equation 2 and 3, following Genty et al. *Biochimica et Biophysica Acta* 990, 87-921989, 1989.

$$\text{Maximal PSII efficiency}=(Fm-Fo)/Fm \qquad \text{Eq. 2}$$

$$\text{PSII operating efficiency}=(Fm'-F')/Fm' \qquad \text{Eq. 3}$$

Time Constants of NPQ Adjustment to Changes in Light Intensity

Seedlings were dark-adapted and chlorophyll fluorescence was determined using a chlorophyll fluorescence imager as described above. Maximal fluorescence was measured every 30 seconds while light intensity was changed every 3 min from 2000 to 200, 2000, 200, 2000 and finally 0 µmol quanta m$^{-2}$ s$^{-1}$. The final relaxation in darkness lasted 10 minutes. Six sets of 18 seedlings of three VPZ transformed lines and wild-type were measured accordingly, whereby a 5 second frameshift was created between fluorescence measurements and light intensity changes between each set. NPQ was computed according to Eq. 1, normalized against the highest value within each set after which all six sets were compiled as a function of time to generate time-series of normalized NPQ with a resolution of 5 seconds. Time constants in a double exponential function for induction or relaxation of NPQ were fitted to the compiled time-series after each change in light intensity. For the final recovery in darkness, time constants were also fitted for PSII operating efficiency (estimated using equation 3).

Photo-Protection Efficiency

Seedlings were dark-adapted for 20 min after which dark-adapted maximal PSII efficiency (Fv/Fm) was determined using the chlorophyll fluorescence imager as described above. Subsequently, seedlings were exposed to 2000 µmol quanta m$^{-2}$ s$^{-1}$ for a duration of 60 min or 120 min. After the exposure, seedlings were allowed to recover in darkness for 10 min to allow relaxation of qE, after which minimal fluorescence (Fo') and maximal fluorescence (Fm') without full dark-adaptation were measured. The measurement of Fo' was compared to a derived value which considers exclusively the effect of NPQ on Fo' (Oxborough and Baker, *Photosynthesis Research* 54: 135-142, 1997). The difference between PSII efficiency using either measured or derived Fo' was then used to determine the efficiency of photo-protection.

Gas Exchange and Linear Electron Transport in Fully Expanded Leaves

For gas exchange analyses, seedlings were transplanted from trays to 3.8 L pots (400 C, Hummert International) filled with growing medium (LC1 Sunshine mix, supplemented with 10 g granulated fertilizer per pot (Osmocote Plus 15/9/12. The Scotts Company LLC, Marysville, Ohio, USA). Pots were randomized and spaced 30 cm apart on greenhouse tables. Plants were watered and plant positions were changed randomly every two days, until the fifth leaf was fully expanded. Gas exchange measurements were performed using an open gas exchange system (LI6400XT, LI-COR, Lincoln, Nebr., USA) equipped with a 2 cm2 leaf chamber fluorometer. All gas exchange measurements were corrected for diffusive leaks between cuvette and surrounding atmosphere, using dark measurements at various $CO_2$ concentrations according to Gong et al. *Plant, Cell and Environment* 38, 2417-24322015).

To determine the light dose response curves of net assimilation rate and linear electron transport in fully expanded leaves, gas exchange and pulse amplitude modulated chlorophyll fluorescence were measured at a range of light intensities. All chlorophyll fluorescence measurements were performed using the multiphase flash routine (Loriaux et al. 2013). Youngest fully expanded leaves (n=6) were clamped in the cuvette with block temperature set at 25° C. and [$CO_2$] in the airstream controlled at 1500 ppm. After 30 min of dark adaptation, minimal fluorescence (Fo) and maximal fluorescence (Fm) were determined. Subsequently, light intensity was varied in two different ways. The first experiment consisted of slowly increasing the light intensity from 0 to 50, 80, 110, 140, 170, 200, 400, 600, 800, 1000, 1200, 1500 and 2000 µmol m$^{-2}$ s$^{-1}$, trying to keep induction of NPQ at each light intensity to an absolute minimum. When steady state was reached, gas exchange parameters were logged and baseline fluorescence (F') and light-adapted maximal fluorescence (Fm') were measured to estimate NPQ (Eq. 1) and PSII operating efficiency (Eq. 3). In the second experiment leaves were allowed to reach steady state gas exchange at 2000 µmol m$^{-2}$ s$^{-1}$. Subsequently, light intensity was changed from 2000 to 1500, 1000, 800, 600, 400, 200, 170, 140, 110, 80 and 50, each step lasted 4 minutes and was preceded by 4 minutes of 2000 µmol m$^{-2}$ s$^{-1}$. At each light intensity, F' and Fm' and gas exchange parameters were determined after 60 s, 140 s and 220 s. Average values of these three measurements were used for subsequent analysis to reconstruct light response curves with intermittent high PFD.

Leaf absorptance of incident irradiance was measured on the same spot used for gas exchange analysis, using an integrating sphere (LI1800, LI-COR, USA) connected to a spectrometer (USB-2000, Ocean Optics Inc, Dunedin, Fla., USA). Rates of linear electron transport (J) were determined for both experiments according to:

$$J = \text{Leaf absorptance} * \text{PSII operating efficiency} * PFD * 0.5 \quad \text{Eq. 4}$$

Light intensity dose response curves for linear electron transport and gas exchange from both experiments were adjusted to constant leaf temperature according to equations in Sharkey et al. (2007) and fitted to a descriptive non-rectangular hyperbola model (Von Caemmerer, Biochemical models of leaf photosynthesis. Collingwood, Australia: CSIRO Publishing 2000), yielding estimates for initial slope, convexity and asymptote.

To analyze the $CO_2$ dose response curve of net assimilation rate, leaves were clamped in the cuvette with block temperature controlled at 25° C. and light intensity set to 2000 µmol m$^{-2}$ s$^{-1}$. $CO_2$ concentration in the airstream was controlled at 400, 300, 200, 100, 75, 400, 400, 500, 600, 700, 800, 1200 and 1600 ppm and gas exchange parameters were logged when steady state was reached. The model for leaf photosynthesis by Farquhar et al. Planta 149, 78-90.1980 assuming infinite mesophyll conductance, with temperature corrections according to Sharkey et al. Plant Cell Environ. 30, 1035-1040, 2007 was fitted to derive the maximal carboxylation rate (Vcmax), electron transport rate at 2000 µmol m$^{-2}$ s$^{-1}$ (J), triose phosphate utilization rate (TPU) and mitochondrial respiration rate not associated with photorespiration (Rd).

Xanthophyll Cycle Pigment Concentrations

Leaves were clamped in the leaf cuvette of an open gas exchange system and dark-adapted as described above. Subsequently. $CO_2$ and $H_2O$ exchange were either allowed to reach steady state at 0, 400 and 2000 µmol m$^{-2}$ s$^{-1}$ or subjected to a series of changes in light intensity (three cycles of 3 min 2000/3 min 200 µmol m$^{-2}$ s$^{-1}$), immediately after which leaf discs (0.58 cm2) were sampled from the enclosed leaf spot, snap-frozen in liquid nitrogen and stored at −80° C. until extraction. Pigment analysis took place at the Horn Point Laboratory (University of Maryland Center for Environmental Science, Cambridge, Md., USA). Frozen samples were macerated in 90% acetone using an ultrasonic probe and the crude extract was filtered (0.45 µm). Pigments were separated by HPLC using a Zorbax Eclipse XDB-C8 column (963967-906, Agilent Technologies. Santa Clara, Calif., USA) and quantified according to the protocol by Van Heukelem and Thomas (2001).

Growth and Final Biomass Accumulation

To evaluate the effects of VPZ overexpression on growth, two independent greenhouse experiments were performed from May 25-Jun. 29, 2015 (using WT, VPZ-23 and VPZ-34) and from Oct. 9-Nov. 13, 2015 (using WT, VPZ-23, VPZ-34 and VPZ-56). Seedlings were propagated as specified above (paragraph plant propagation) and transplanted from trays to 14.5 L pots (2000 C, Hummert International) filled with growing medium (LC1 Sunshine mix, Sun Gro Horticulture) supplemented with 30 g slow release granulated fertilizer per pot (Osmocote Plus 15/9/12, The Scotts Company LLC). Pots were randomized and placed on greenhouse tables with 30 cm spacing. Plants were watered and plant positions were changed randomly every two days. Light intensity at leaf level was logged with a quantum sensor (LI-190R, LI-COR, USA) at the center of the greenhouse table, which was mounted on a tripod and adjusted daily to maintain a position of 10 cm above the youngest leaves. Air temperature, relative humidity and [$CO_2$] were measured approximately 1 m above the plant canopy, using a combined temperature and humidity sensor (HMP60-L, Vaisala Oyj, Helsinki, Finland) and an infrared gas analyzer (SBA-5, PPsystems, Amesbury, Mass., USA). All climate data was logged every 30 min using a datalogger (CR1000, Campbell Scientific Inc, Logan, Utah, USA). Temperature in the greenhouse was generally kept between 28° C. (day) and 18° C. (night), using a combination of ventilation, evaporative cooling and gas heaters. Light intensity varied with incoming irradiance, with midday peaks reaching approximately 1800 µmol $m^{-2}$ $s^{-1}$ in the first experiment and 1000-1500 µmol $m^{-2}$ $s^{-1}$ in the second experiment. [$CO_2$] was not controlled and varied between 360 ppm (day) and 430 ppm (night). After the first flower had opened, stem length and the number of leaves per plant were determined and total leaf area per plant was measured with a conveyor-belt scanner (LI-3100C Area Meter, LI-COR, USA). Plants were subsequently separated into leaf, stem and root fractions and dried to constant weight at 70° C.

Statistical Analysis

All statistical analyses were performed using SAS (version 9.3, SAS Institute Inc., Cary, N.C., USA). Data was tested for homogeneity of variance using Brown-Forsythe's test and normality using Shapiro-Wilk's test. One-way analysis of variance was applied to fitted gas exchange parameters, transcription levels and protein expression. Datasets of chlorophyll fluorescence imaging of NPQ in young seedlings were analyzed by two-way (photo-protection), or repeated measures one-way (10 min on/off) or two-way (high/low light) analysis of variance. Analysis of the two replicated greenhouse trials was performed using a mixed model with two fully randomized blocks. In all cases, significant effects in ANOVA were followed by Dunnett's multiple comparison test of line means against WT control ($\alpha$=0.05). Fitted time constants of NPQ induction and relaxation were compared based on 95% confidence intervals.

Example 12. Transgenic Maize (Prophetic)

This invention can also provide for a maize line with improved photosynthesis and growth as compared to a phenotype in parental units of said maize line. The maize line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic maize having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of maize transformation protocol is described herein.

Initiate *Agrobacterium* Culture

1. Streak AGL carrying a simple binary vector (e.g., pZY102) from −80° C. stock on ABC agar plates with appropriate antibiotics (for the vector and strain illustrated here, 100 mg/liter spectinomycin and 30 mg/liter rifampin), preparing a dilution series in order to obtain single colonies. Incubate the plates in the dark for 3 days at 28° C.

2. Select a single colony and streak it on YEP agar plates containing appropriate antibiotics (for the vector and strain illustrated here, 100 mg/liter spectinomycin and 30 mg/liter rifampin). Incubate the plates in the dark for 3 days at 20° C.

3. Add 5 ml of sterile PHI-A (inoculation medium) to a 15-ml conical centrifuge tube.

4. Transfer two full loops of AGL1 from the YEP plate to the tube prepared in step 3. After 2 to 3 min, shake the tube to thoroughly suspend bacterial cells.

5. Remove 1 ml of this suspension and place it in a spectrophotometer cuvette to check the optical density at 550 nm (OD550). Adjust the cell suspension to an OD550 of 0.35 (0.5×109 cfu/ml) at room temperature (e.g., 24° C.) by either adding more *Agrobacterium* cells or diluting the culture with more PHI-A.

6. Shake the culture in a shaker at 100 rpm for 4 to 5 hr at room temperature (e.g., 24° C.).

7. Aliquot 1 ml of the suspension into 2-ml sterile microcentrifuge tube.

Embryo Isolation, Inoculation, and Co-Cultivation

8. Remove the husks and silk from ears which were harvested 10 to 13 days post-pollination (with embryo size of 1.5 mm; see Support Protocol). Insert a pair of forceps into one end of the ear.

9. Completely submerge the fresh Hi-II ears in a solution containing 0.5 liters of 30% commercial bleach with a few drops of Tween 20 (in a sterile 1-liter wide-mouth bottle) for 20 min.

10. Wash ears three times with sterile water (making sure ears are completely submerged in the water each time), and let the ear stand upright on a sterile 150×15-mm petri dish.

11. Remove top half of the kernels from each ear with a sterile #11 razor blade.

12. Isolate 1.5-mm immature embryos from the sterile ear with a sterile microspatula and transfer 50 to 100 embryos per 1.7- to 2.0-ml microcentrifuge tube. Wash the embryos with 1 ml PHI-A solution three times to remove debris and starch.

13. Immediately afterwards, add 1 ml of the *Agrobacterium* suspension to the tube containing the immature embryos, allow the tube to stand 5 min in the sterile hood, then pour the entire contents including all of the embryos onto PHI-B (co-cultivation medium) agar plate.

14. Draw off *Agrobacterium* suspension using a pipet with a fine tip, then spread the embryos evenly across the plate and place embryos with scutellum face up and flat side face down on the medium.

15. Seal the plate with parafilm and incubate in the dark at 20° C. for 3 days.

Resting

16. Transfer the embryos with a spatula to a plate of PHI-C (resting medium). Avoid damaging the embryos.

17. Seal the plate with parafilm and incubate in the dark at 28° C. for 7 days.

Selection

18. Transfer embryos with spatula or forceps to a plate of PHI-D1 (selection medium I). Place 25 embryos per plate and seal the plate. Incubate the embryos in the dark at 28° C. for the first 2-week selection.

19. Transfer calli with forceps from the PHI-D1 plate to a plate of PHI-D2 (selection medium II). Subculture the calli every 2 weeks onto fresh PHI-D2 medium for a total of 2 months using the incubation conditions in step 18.

20. Bulk up the herbicide-resistant calli by growing them on fresh PHI-D2 medium for another 2 weeks under the same conditions as in steps 18 and 19, until the diameter of the calli is about 1.0 cm.

Maturation and Regeneration

21. Using forceps, transfer each entire callus mass containing opaque embryos onto PHI-E (maturation medium) in 20×100 mm petri plates (wrapped with 3 M porous tape) and place culture plates in the dark at 28° C. for two 2 to 3 weeks to allow somatic embryos to mature.

22. Transfer ivory-white calli onto PHI-F (regeneration medium) and incubate at 25° C. under 16-hr photoperiod until shoots and roots develop.

23. Transfer each small plantlet to a 25×150-mm tube containing PHI-F (regeneration medium), and grow at 25° C. under 16-hr photoperiod for 2 to 3 weeks.

24. Transfer the plants to small plastic pots with soil mixture, e.g., Promix BX soil, in a light incubator or culture room at 24° C. with an 18 hr/light, 6 hr/dark cycle.

Example 13. Transgenic *Sorghum* (Prophetic)

This invention can also provide for a *Sorghum* line with improved photosynthesis and growth as compared to a phenotype in parental units of said *Sorghum* line. The *Sorghum* line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic *Sorghum* having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

Examples of *Sorghum* transformation protocol are described in Guo et al., Methods Mol Biol 1223, 181-188, 2015, as well as Howe et al., Plant Cell Rep 25(8): 784-791, 2006.

Example 14. Transgenic Soybean (Prophetic)

This invention can also provide for a soybean line with improved photosynthesis and growth as compared to a phenotype in parental units of said soybean line. The soybean line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic soybean having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of soybean transformation protocol is described herein.

Cotyledonary explants are prepared from the 5-day-old soybean seedlings by making a horizontal slice through the hypocotyl region, approximately 3-5 mm below the cotyledon. A subsequent vertical slice is made between the cotyledons, and the embryonic axis is removed. This manipulation generates 2 cotyledonary node explants. Approximately 7-12 vertical slices are made on the adaxial surface of the ex-plant about the area encompassing 3 mm above the cotyledon/hypocotyl junction and 1 mm below the cotyledon/hypocotyl junction. Explant manipulations are conducted with a No. 15 scalpel blade.

Explants are immersed in the *Agrobacterium* inoculum for 30 min and then co-cultured on 100×15 mm Petri plates containing the *Agrobacterium* resuspension medium solidified with 0.5% purified agar (BBL Cat #11853). The co-cultivation plates are overlaid with a piece of Whatman #1 filter paper (Mullins et al., 1990; Janssen and Gardner, 1993; Zhang et al., 1997). The explants (5 per plate) are cultured adaxial side down on the co-cultivation plates, that are overlaid with filter paper, for 3 days at 24° C., under an 18/6 hour light regime with an approximate light intensity of 80 µmol s-1 m-2 (F17T8/750 cool white bulbs, Litetronics). The co-cultivation plates are wrapped with Parafilm.

Following the co-cultivation period explants are briefly washed in B5 medium supplemented with 1.67 mg 1-1 BAP, 3% sucrose, 500 mg 1-1 ticarcillin and 100 mg 1-1 cefotaxime. The medium is buffered with 3 mM MES. pH 5.6. Growth regulator, vitamins and antibiotics are filter sterilized post autoclaving. Following the washing step, explants are cultured (5 per plate) in 100×20 mm Petri plates, adaxial side up with the hypocotyl imbedded in the medium, containing the washing medium solidified with 0.8% purified agar (BBL Cat #11853) amended with either 3.3 or 5.0 mg 1-1 glufosinate (AgrEvo USA). This medium is referred to as shoot initiation medium (SI). Plates are wrapped with 3M pressure sensitive tape (Scotch™, 3M, USA) and cultured under the environmental conditions used during the seed germination step.

After 2 weeks of culture, the hypocotyl region is excised from each of the explants, and the remaining explant, cotyledon with differentiating node, is subsequently subcultured onto fresh SI medium. Following an additional 2 weeks of culture on SI medium, the cotyledons are removed from the differentiating node. The differentiating node is sub-cultured to shoot elongation medium (SE) composed of Murashige and Skoog (MS) (1962) basal salts, B5 vitamins, 1 mg 1-1 zeatin-riboside, 0.5 mg 1-1 GA3 and 0.1 mg 1-1 IAA, 50 mg 1-1 glutamine, 50 mg 1-1 asparagine, 3% sucrose and 3 mM MES, pH 5.6. The SE medium is amended with either 1.7 or 2.0 mg 1-1 glufosinate. The explants are sub-cultured biweekly to fresh SI medium until shoots reached a length greater than 3 cm. The elongated shoots are rooted on Murashige and Skoog salts with B5 vitamins, 1% sucrose, 0.5 mg 1-1 NAA without further selection in either Magenta boxes or Sundae cups (Industrial Soap Company, St. Louis Mo.).

Example 15. Transgenic Rice (Prophetic)

This invention can also provide for a rice line with improved photosynthesis and growth as compared to a phenotype in parental units of said rice line. The rice line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic rice having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of rice transformation protocol is described herein.

Infection and Co-Cultivation

Transfer the callus into sterile tea strainer and incubate the tea strainer in the *Agrobacterium* suspension by very gently and intermittently shaking the strainer for 15 min, then blot dry strainer on top of stacked Whatmann 1 sterile filter paper in a sterile Petri dish to remove excess bacteria. Transfer the callus onto sterile filter paper placed on top of MSG4K medium, and culture in the dark at 25° C. for 48 h.

Resting and Bialaphos (Basta) Selection

Transfer the co-cultivated callus to a sterile 50 ml tube and wash them with sterile water for 5 times and once with liquid co-cultivation medium containing timentin 200 mg/1. Blot the callus dry in sterile Whatman filter paper and transfer them to MSG2K "rest" medium containing plates. Culture the callus plates in the dark at 25° C. for 7 days. Transfer the callus to MSG2K bialaphos selection medium. Culture the plates in the dark at 25° C. for 3 weeks. Repeat the process for additional 5 weeks subculturing into fresh medium in every 3 weeks.

Callus Desiccation, Shoot Regeneration and Rooting

After 8 weeks in selection medium with 3-4 rounds of selection, transfer the callus to sterile Petri dishes stacked with 2 layers of sterile Whatman #1 filter paper in sterile hood. Wrap it with 3M surgical tapes and leave in the hood as such undisturbed in dark for 24 h. The plates need to wrapped in aluminum foil to ensure the darkness for the callus. This partial desiccation of callus step is absolutely necessary to induce shoots in shoot regeneration medium. After 48 h, transfer the callus to MSG75K shoot regeneration medium and incubate in dark for 3 weeks. Transfer the proliferating callus with somatic embryos to same medium and incubate under low light, approximately 20 to 30 µE m-2 s$^{-1}$ with 12 h/8 h dark cycle. Shoots will start appearing after 10 days in light and most of callus will become green. Continue to culture the green callus along embryos in MSG75K shoot regeneration medium under same light regime until satisfied amount of shoots were obtained. Meanwhile, when shoots reaches above 5 cm in length dissect them in the base and transfer to Greiner Bio-One plant culture containers (#968161-82051-508-container with lid, 330 ml sterile, 68 Dia.×110 H mm) with MSG100K rooting medium.

Example 16. Transgenic Wheat (Prophetic)

This invention can also provide for a wheat line with improved photosynthesis and growth as compared to a phenotype in parental units of said wheat line. The wheat line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic wheat having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of wheat transformation protocol is described in Medvecká E, Harwxood W A. Wheat (*Triticum aestivum* L.) Transformation Using Mature Embryos. *Agrobacterium* Protocols: Volume 1, 2015:199-209.

Example 17. Transgenic Cowpea

Figure 27:
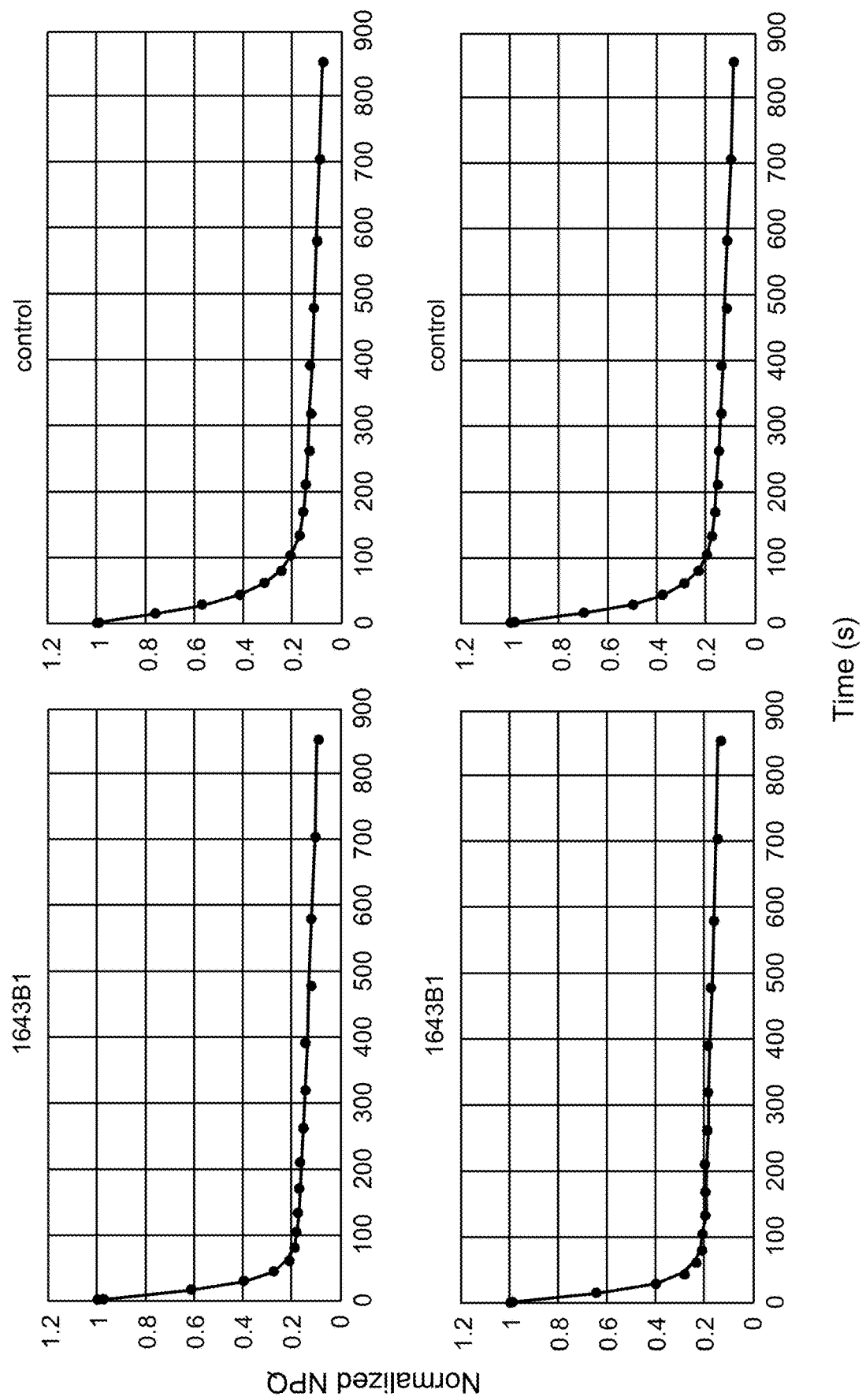
FIG. 27. NPQ relaxation kinetics in transgenic cowpea 1643B1. X-axis is time in seconds. Y-axis is normalized NPQ.
Figure 28:
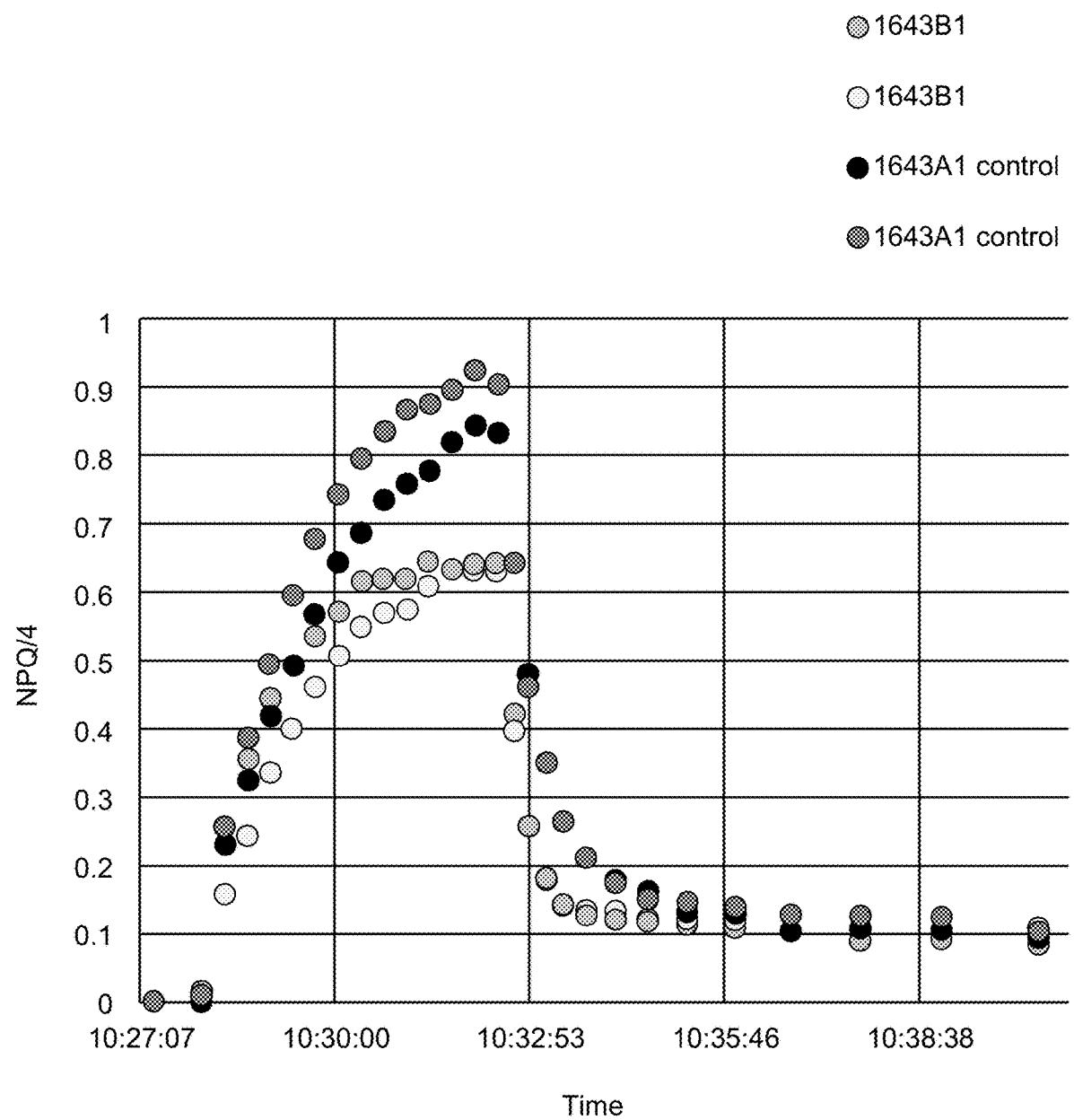
FIG. 28. NPQ induction and relaxation kinetics in transgenic cowpea 1643B1. X-axis is time. Y-axis is NPQ divided by 4.
Figure 29:
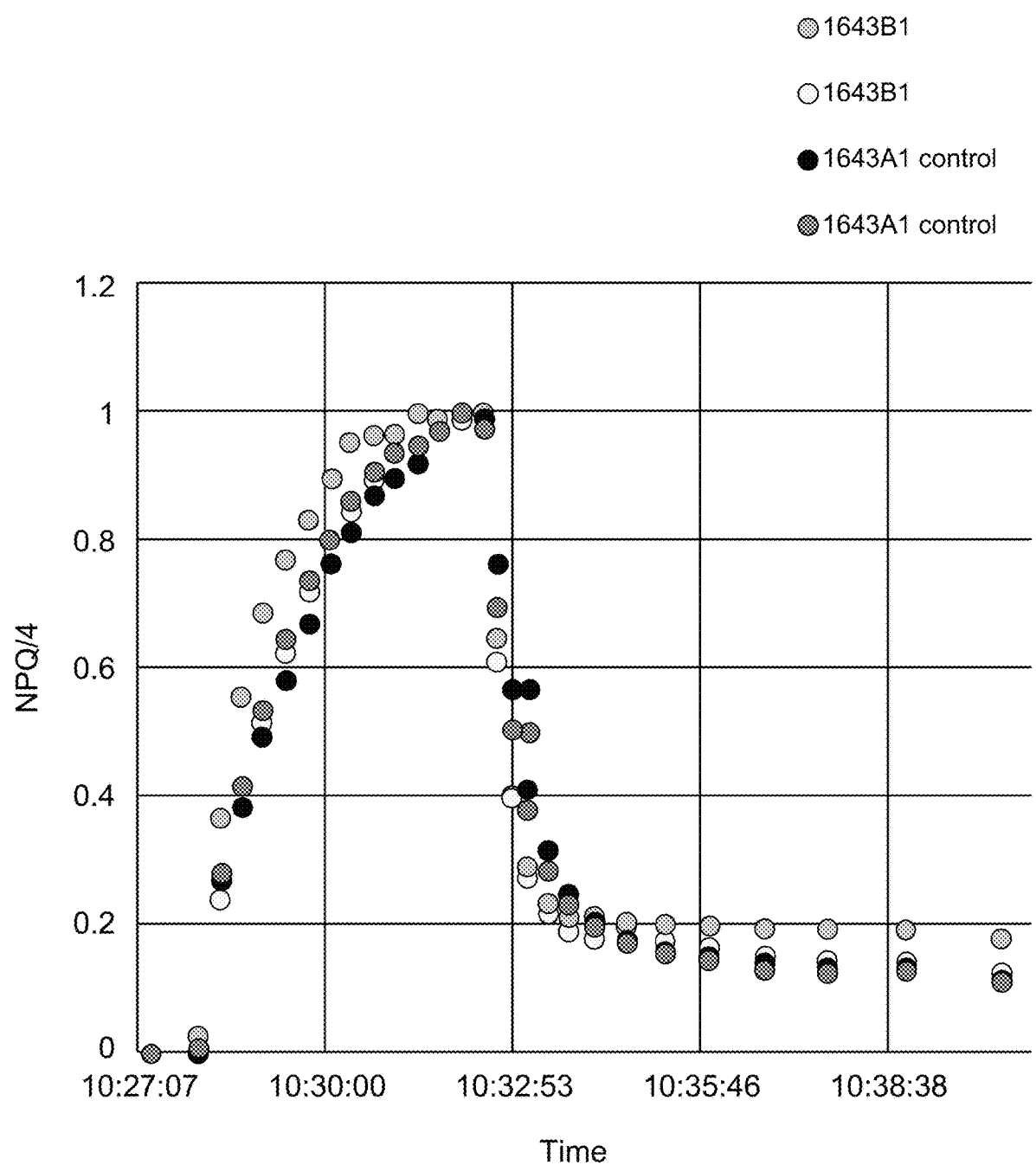
FIG. 29. Normalized NPQ induction and relaxation kinetics under fluctuating light in transgenic cowpea 1643B1. X-axis is time. Y-axis is NPQ divided by 4. Data is normalized to the highest NPQ within each set.
Figure 30:
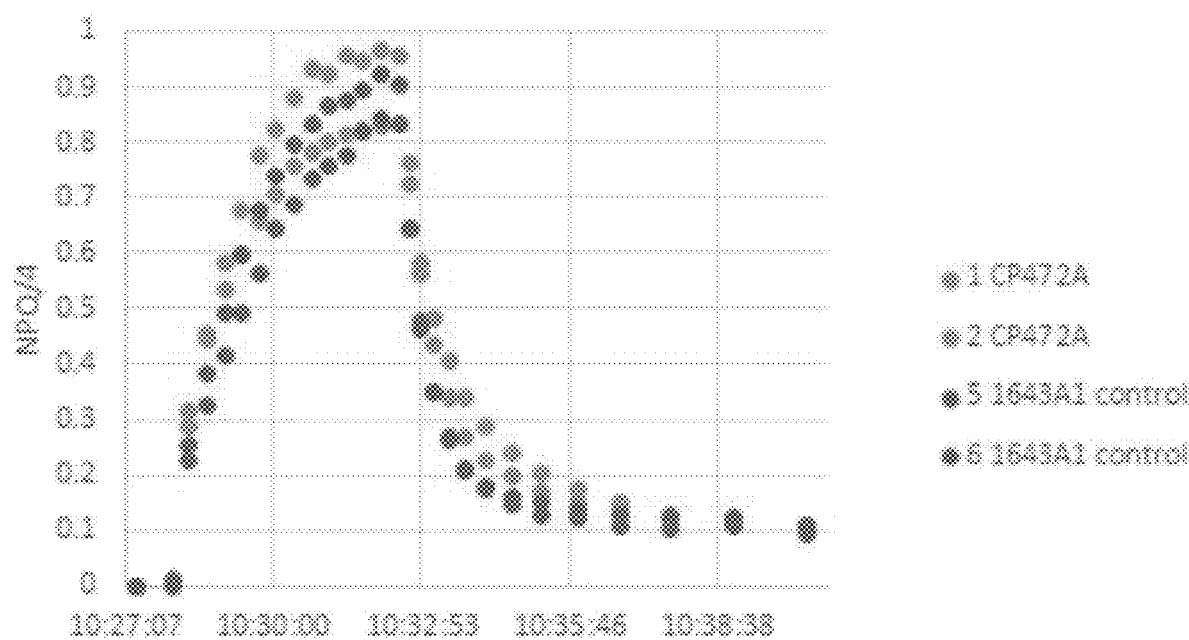
FIG. 30. NPQ induction and relaxation kinetics in transgenic cowpea CP472A. X-axis is time. Y-axis is NPQ divided by 4.

Cowpea plants were transformed with a T-DNA construct containing nucleotide sequences encoding PsbS, ZEP and VDE, following the transformation protocol as described in Higgins et al., Innovative research along the cowpea value chain. Ibadan, Nigeria: International Institute of Tropical Agriculture, pp. 133-139, 2013. To compare the kinetics of dynamic NPQ adjustment, a double exponential model was fitted to dark relaxation of NPQ in $T_0$ transgenic cowpea after exposure to fluctuating light. As shown in Table 4, the qE relaxation ($\tau 1$) was noticeably faster in the transformant line 164381A as compared to the control, with measurements of 20.5 s and 19.7 s versus 35.9 s and 29.7 s. The qZ phase of NPQ relaxation ($\tau 2$) was slower in the transformant line 1643B1 as compared to the control, likely caused by the limitation that the measurements were taken on $T_0$ transgenic plants. As is known in the art, transgenic plants from $T_1$ or $T_2$ generations are usually preferred over $T_0$ for phenotypic measurements. One reason is that in $T_0$ transgenic plants, stress from the transformation and tissue culture processes can interfere with normal plant physiology and affect phenotypic measurements. Another reason is that molecular characterization of a transgene cannot be complete until in the $T_1$ or $T_2$ generation and transgenic characteristics such as copy number and insertion location in the genome can have significant effects on the transgene expression. As shown in FIG. 27, FIG. 28 and FIG. 29, NPQ relaxed faster in the transformant line 1643B1 than in the control plant. As shown in FIG. 30. NPQ relaxed slower in the transformant line CP472A (orange dots) than in the control plant (blue dots), which is likely caused by the limitation that measurements were taken on $T_0$ transgenic plants as discussed above.

TABLE 4

Time constants of NPQ relaxation in transgenic cowpea.

|  | 1643B1 | | Control | |
| --- | --- | --- | --- | --- |
|  | Measurement 1 | Measurement 2 | Measurement 1 | Measurement 2 |
| Time constant $\tau 1$ (s) | 20.5 | 19.7 | 35.9 | 29.7 |
| Time constant $\tau 2$ (s) | 1220.8 | 2272.0 | 1099.2 | 1043.0 |

Example 18. Transgenic Cassava (Prophetic)

This invention can also provide for a *Cassava* line with improved photosynthesis and growth as compared to a phenotype in parental units of said *Cassava* line. The *Cassava* line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic *Cassava* having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of *Cassava* transformation protocol is described in Chetty et al., New Biotechnology 30.2: 136-143, 2013.

Example 19. Transgenic Poplar (Prophetic)

This invention can also provide for a poplar line with improved photosynthesis and growth as compared to a phenotype in parental units of said poplar line. The poplar line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic poplar having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of poplar transformation protocol is described in Movahedi et al., International Journal of Molecular Science 15.6: 10780-10793, 2014.

Example 20. Transgenic *Eucalyptus* (Prophetic)

This invention can also provide for a *Eucalyptus* line with improved photosynthesis and growth as compared to a phenotype in parental units of said *Eucalyptus* line. The *Eucalyptus* line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic *Eucalyptus* having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect of the method a large population is screened by employing at least one heterologous nucleotide sequences encoding polypeptides selected from PsbS, ZEP and VDE. Other preferred aspects of the method employ nucleotide constructs where the heterologous DNA is operably linked to a selected promoter, e.g. the 5' end of a promoter region. The DNA construct may be introduced into a random location in the genome or into a preselected site in the genome.

An example of *Eucalyptus* transformation protocol is described in Diwakar et al., Plant Tissue Culture: Propagation, Conservation and Crop Improvement, 219-244, 2016.

Example 21. Sequence Identity Analysis of NPQ Genes

To identify amino acid sequences that are homologous to the *Arabidopsis* PsbS, ZEP and VDE. BLAST protein searches was performed with the BLASTX program. Percentage of sequence similarity by BLAST is presented in Table 4 for PsbS, Table 5 for ZEP, and Table 6 for VDE, where top 100 hits of sequences ordered by descending percentage of sequence identity to the *Arabidopsis* homologue are listed.

Figure 24B:
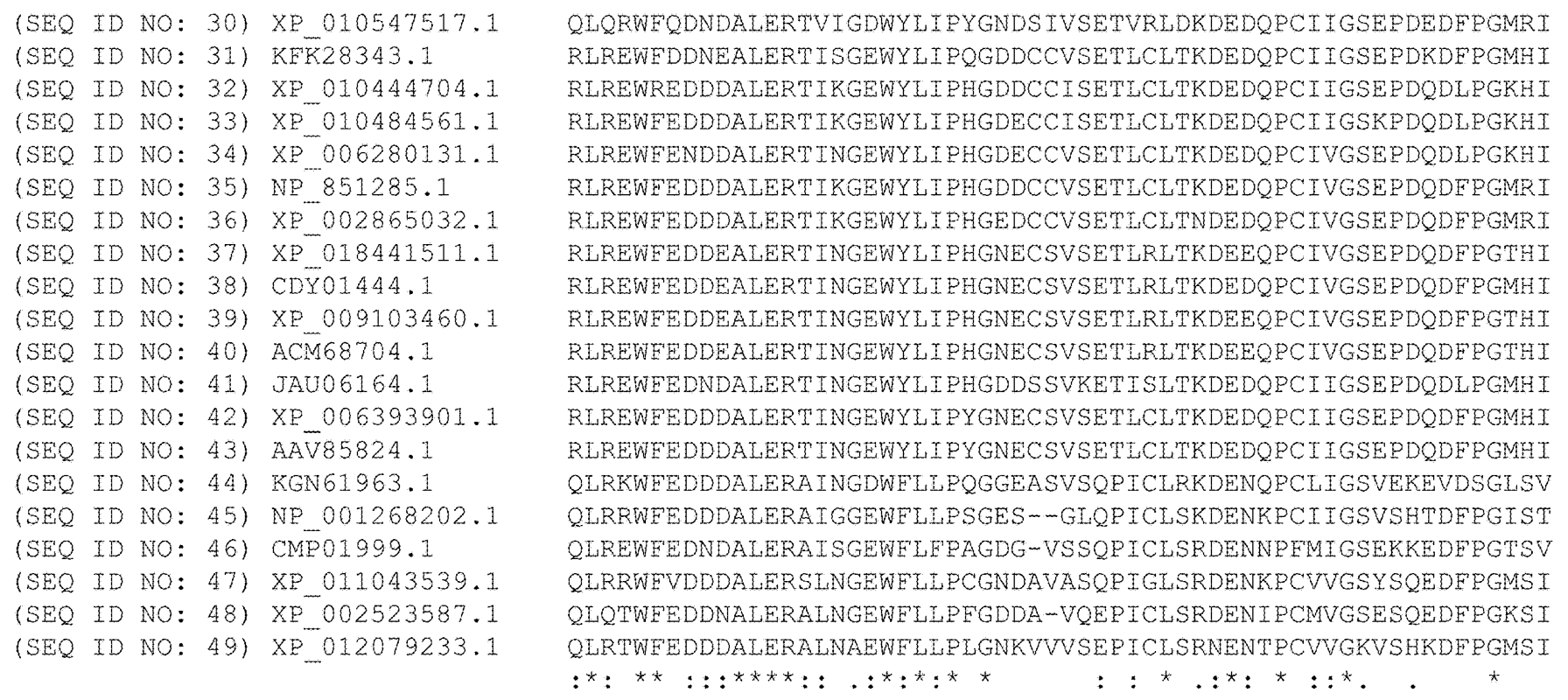

To compare the sequence identity and/or similarity of the amino acid sequences that are homologous to the *Arabidopsis* PsbS, ZEP and VDE, alignment of sequences was performed with the CLUSTAL OMEGA program. FIG. 24 illustrates the amino acid sequence similarity through CLUSTAL O for (A) PsbS, (B) ZEP and (C) VDE, respectively.

TABLE 5

Percentage of sequence identity for PsbS.

| Description | Query cover | E value | Identity | Accession |
|---|---|---|---|---|
| Chlorophyll A-B binding family protein [*Arabidopsis thaliana*] | 100% | 0 | 100% | NP_175092.1 |
| unknown protein [*Arabidopsis thaliana*] | 100% | 0 | 99% | AAK95290.1 |
| hypothetical protein ARALYDRAFT_891398 [*Arabidopsis lyrata* subsp. *lyrata*] | 100% | 0 | 98% | XP_002891292.1 |
| PREDICTED: photosystem II 22 kDa protein, chloroplastic-like [*Camelina sativa*] | 100% | 2.00E−178 | 97% | XP_010500150.1 |
| PREDICTED: photosystem II 22 kDa protein, chloroplastic isoform X1 [*Camelina sativa*] | 100% | 3.00E−178 | 97% | XP_010479050.1 |
| PREDICTED: photosystem II 22 kDa protein, chloroplastic-like [*Camelina sativa*] | 100% | 2.00E−177 | 97% | XP_010461444.1 |
| hypothetical protein CARUB_v10010031mg [*Capsella rubella*] | 100% | 8.00E−176 | 96% | XP_006304103.1 |
| Photosystem II 22 kDa protein, chloroplastic [*Noccaea caerulescens*] | 100% | 3.00E−156 | 95% | JAU12851.1 |
| PREDICTED: photosystem II 22 kDa protein, chloroplastic [*Raphanus sativus*] | 100% | 8.00E−151 | 95% | XP_018447609.1 |
| PREDICTED: photosystem II 22 kDa protein, chloroplastic [*Brassica rapa*] | 100% | 1.00E−149 | 95% | XP_009107479.1 |
| hypothetical protein EUTSA_v10011718mg [*Eutrema salsugineum*] | 99% | 3.00E−148 | 94% | XP_006393723.1 |
| PREDICTED: photosystem II 22 kDa protein, chloroplastic-like [*Brassica napus*] | 100% | 4.00E−148 | 95% | XP_013681211.1 |
| PREDICTED: photosystem II 22 kDa protein, chloroplastic [*Raphanus sativus*] | 100% | 5.00E−148 | 95% | XP_018467982.1 |
| PREDICTED: photosystem II 22 kDa protein, chloroplastic [*Brassica oleracea* var. *oleracea*] | 100% | 6.00E−148 | 95% | XP_013592876.1 |
| PREDICTED: photosystem II 22 kDa protein, chloroplastic-like [*Brassica oleracea* var. *oleracea*] | 100% | 3.00E−147 | 94% | XP_013599587.1 |
| PREDICTED: photosystem II 22 kDa protein, chloroplastic [*Brassica rapa*] | 99% | 4.00E−147 | 95% | XP_009123055.1 |
| PREDICTED: photosystem II 22 kDa protein, chloroplastic [*Cucumis melo*] | 99% | 6.00E−125 | 78% | XP_008466710.1 |
| Chlorophyll A-B binding family protein [*Arabidopsis thaliana*] | 96% | 1.00E−124 | 100% | NP_973971.1 |
| PREDICTED: photosystem II 22 kDa protein, chloroplastic [*Cucumis sativus*] | 99% | 3.00E−122 | 76% | XP_004150442.1 |
| PREDICTED: photosystem II 22 kDa protein, chloroplastic [*Phoenix dactylifera*] | 97% | 2.00E−121 | 77% | XP_008783427.1 |
| Photosystem II protein, chloroplastic [*Anthurium amnicola*] | 99% | 5.00E−121 | 76% | JAT63827.1 |

TABLE 5-continued

Percentage of sequence identity for PsbS.

| Description | Query cover | E value | Identity | Accession |
|---|---|---|---|---|
| PREDICTED: photosystem II 22 kDa protein, chloroplastic isoform X1 [*Beta vulgaris* subsp. *vulgaris*] | 99% | 2.00E−120 | 77% | XP_010692414.1 |
| hypothetical protein TSUD_300570 [*Trifolium subterraneum*] | 99% | 1.00E−119 | 71% | GAU40978.1 |
| Chloroa_b-bind domain-containing protein [*Cephalotus follicularis*] | 100% | 3.00E−119 | 74% | GAV71974.1 |
| PsbS [*Pisum sativum*] | 99% | 5.00E−119 | 71% | AKG94171.1 |
| PREDICTED: photosystem II 22 kDa protein, chloroplastic [*Elaeis guineensis*] | 88% | 5.00E−119 | 84% | XP_010911871.1 |
| PREDICTED: photosystem II 22 kDa protein, chloroplastic [*Camelina sativa*] | 96% | 2.00E−118 | 96% | XP_010479049.1 |
| PREDICTED: photosystem II 22 kDa protein, chloroplastic [*Vitis vinifera*] | 99% | 3.00E−118 | 76% | XP_002285857.1 |
| PREDICTED: photosystem II 22 kDa protein, chloroplastic [*Tarenaya hassleriana*] | 99% | 2.00E−117 | 82% | XP_010544817.1 |
| RecName: Full = Photosystem II 22 kDa protein, chloroplastic; AltName: Full = CP22; Flags: Precursor | 82% | 2.00E−116 | 88% | Q02060.1 |
| PREDICTED: photosystem II 22 kDa protein, chloroplastic-like [*Gossypium raimondii*] | 99% | 7.00E−116 | 78% | XP_012447533.1 |
| PREDICTED: photosystem II 22 kDa protein, chloroplastic-like [*Gossypium hirsutum*] | 99% | 7.00E−116 | 78% | XP_016708802.1 |
| PREDICTED: photosystem II 22 kDa protein, chloroplastic-like [*Gossypium arboreum*] | 99% | 3.00E−115 | 78% | XP_017604982.1 |
| PREDICTED: photosystem II 22 kDa protein, chloroplastic-like [*Gossypium hirsutum*] | 99% | 5.00E−115 | 78% | XP_016687044.1 |
| Photosystem II 22 kDa, chloroplastic [*Gossypium arboreum*] | 99% | 5.00E−115 | 78% | KHG12586.1 |
| PREDICTED: photosystem II 22 kDa protein, chloroplastic [*Amborella trichopoda*] | 99% | 1.00E−114 | 73% | XP_006847012.1 |
| Chain A, Crystal Structure Of The Photoprotective Protein Psbs From Spinach | 80% | 1.00E−114 | 88% | 4RI2_A |
| hypothetical protein PRUPE_ppa009763mg [*Prunus persica*] | 100% | 2.00E−114 | 73% | XP_007222356.1 |
| PREDICTED: photosystem II 22 kDa protein, chloroplastic-like [*Lupinus angustifolius*] | 93% | 3.00E−114 | 77% | XP_019415222.1 |
| light-harvesting complex I chlorophyll A/B-binding protein [*Medicago truncatula*] | 99% | 3.00E−114 | 73% | XP_003602031.1 |
| unknown [*Lotus japonicus*] | 99% | 4.00E−114 | 75% | AFK43146.1 |
| PREDICTED: photosystem II 22 kDa protein, chloroplastic [*Ricinus communis*] | 99% | 6.00E−114 | 75% | XP_002513761.1 |
| PREDICTED: photosystem II 22 kDa protein, chloroplastic [*Fragaria vesca* subsp. *vesca*] | 99% | 8.00E−114 | 73% | XP_004290871.1 |
| PREDICTED: photosystem II 22 kDa protein, chloroplastic [*Prunus mume*] | 100% | 1.00E−113 | 73% | XP_008219642.1 |
| Chlorophyll A-B binding protein [*Corchorus capsularis*] | 99% | 2.00E−113 | 73% | OMO59479.1 |
| Chlorophyll A-B binding protein [*Corchorus olitorius*] | 99% | 8.00E−113 | 73% | OMP06543.1 |
| PREDICTED: photosystem II 22 kDa protein, chloroplastic [*Theobroma cacao*] | 99% | 2.00E−112 | 76% | XP_007019073.2 |
| PREDICTED: photosystem II 22 kDa protein, chloroplastic-like [*Malus domestica*] | 100% | 2.00E−112 | 74% | XP_008375547.1 |
| photosystem II 22 kDa protein [*Pyrus × bretschneideri*] | 100% | 7.00E−112 | 73% | AHM26637.1 |
| Photosystem II 22 kDa family protein [*Populus trichocarpa*] | 99% | 3.00E−111 | 74% | XP_002300987.1 |
| hypothetical protein L484_004387 [*Morus notabilis*] | 100% | 8.00E−111 | 72% | XP_010106359.1 |
| PREDICTED: photosystem II 22 kDa protein, chloroplastic [*Oryza sativa Japonica* Group] | 99% | 1.00E−110 | 73% | XP_015621169.1 |
| PREDICTED: photosystem II 22 kDa protein, chloroplastic [*Nelumbo nucifera*] | 100% | 2.00E−110 | 75% | XP_010242794.1 |
| PREDICTED: photosystem II 22 kDa protein, chloroplastic [*Daucus carota* subsp. *sativus*] | 99% | 3.00E−110 | 76% | XP_017247379.1 |
| PREDICTED: photosystem II 22 kDa protein, chloroplastic [*Populus euphratica*] | 99% | 3.00E−110 | 74% | XP_011027529.1 |
| PREDICTED: photosystem II 22 kDa protein, chloroplastic-like [*Malus domestica*] | 79% | 3.00E−110 | 87% | XP_008352659.1 |
| PREDICTED: photosystem II 22 kDa protein, chloroplastic-like [*Gossypium arboreum*] | 100% | 5.00E−110 | 75% | XP_017613374.1 |
| PREDICTED: photosystem II 22 kDa protein, chloroplastic [*Cicer arietinum*] | 99% | 2.00E−109 | 70% | XP_004502468.1 |
| hypothetical protein B456_009G245800 [*Gossypium raimondii*] | 99% | 4.00E−109 | 76% | KJB59229.1 |
| unknown [*Picea sitchensis*] | 80% | 6.00E−109 | 83% | ABK20973.1 |
| PREDICTED: photosystem II 22 kDa protein, chloroplastic [*Jatropha curcas*] | 99% | 1.00E−108 | 76% | XP_012078240.1 |
| photosystem II 22 kDa protein, chloroplastic [*Dorcoceras hygrometricum*] | 99% | 4.00E−108 | 74% | KZV16554.1 |
| PREDICTED: photosystem II 22 kDa protein, chloroplastic [*Malus domestica*] | 100% | 5.00E−108 | 74% | XP_008378474.1 |
| chloroplast photosystem II subunit [*Sedum alfredii*] | 74% | 7.00E−108 | 88% | AEK26371.1 |
| predicted protein [*Hordeum vulgare* subsp. *vulgare*] | 99% | 2.00E−107 | 70% | BAJ90394.1 |

TABLE 5-continued

Percentage of sequence identity for PsbS.

| Description | Query cover | E value | Identity | Accession |
|---|---|---|---|---|
| PREDICTED: photosystem II 22 kDa protein, chloroplastic [*Juglans regia*] | 98% | 2.00E−107 | 74% | XP_018817122.1 |
| unknown [*Medicago truncatula*] | 95% | 2.00E−107 | 73% | ACJ84782.1 |
| putative photosystem II protein [*Gossypioides kirkii*] | 99% | 3.00E−107 | 76% | ACD56611.1 |
| Photosystem II, 22 kDa Protein [*Plantago major*] | 99% | 3.00E−107 | 72% | CAJ38395.1 |
| PREDICTED: photosystem II 22 kDa protein, chloroplastic [*Pyrus × bretschneideri*] | 100% | 6.00E−107 | 72% | XP_018501271.1 |
| PREDICTED: photosystem II 22 kDa protein, chloroplastic-like [*Musa acuminata* subsp. *malaccensis*] | 99% | 9.00E−107 | 75% | XP_009399195.1 |
| Photosystem II 22 kDa protein, chloroplastic [*Glycine soja*] | 100% | 4.00E−106 | 71% | KHN09207.1 |
| hypothetical protein CICLE_v10002099mg [*Citrus clementina*] | 99% | 2.00E−105 | 72% | XP_006434195.1 |
| putative photosystem II protein [*Gossypium hirsutum*] | 100% | 2.00E−105 | 75% | ABO41853.1 |
| PREDICTED: photosystem II 22 kDa protein, chloroplastic [*Arachis ipaensis*] | 99% | 3.00E−105 | 72% | XP_016163508.1 |
| PREDICTED: photosystem II 22 kDa protein, chloroplastic [*Citrus sinensis*] | 99% | 4.00E−105 | 72% | XP_006472781.1 |
| photosystem II 22 kDa protein, chloroplastic [*Cajanus cajan*] | 98% | 5.00E−105 | 70% | XP_020228501.1 |
| Chlorophyll A-B binding family protein [*Theobroma cacao*] | 99% | 2.00E−104 | 74% | EOY16298.1 |
| PREDICTED: photosystem II 22 kDa protein, chloroplastic [*Glycine max*] | 100% | 3.00E−104 | 69% | XP_003523444.1 |
| PREDICTED: photosystem II 22 kDa protein, chloroplastic [*Eucalyptus grandis*] | 100% | 3.00E−104 | 73% | XP_010065001.1 |
| unnamed protein product [*Coffea canephora*] | 98% | 5.00E−104 | 71% | CDP10910.1 |
| unknown [*Picea sitchensis*] | 80% | 6.00E−104 | 80% | ABK25763.1 |
| photosystem II 22 kDa protein, chloroplastic-like [*Glycine max*] | 100% | 1.00E−103 | 70% | NP_001276237.1 |
| PREDICTED: photosystem II 22 kDa protein, chloroplastic [*Ziziphus jujuba*] | 100% | 2.00E−103 | 71% | XP_015885664.1 |
| PREDICTED: photosystem II 22 kDa protein, chloroplastic [*Sesamum indicum*] | 99% | 3.00E−103 | 73% | XP_011074844.1 |
| PREDICTED: photosystem II 22 kDa protein, chloroplastic-like [*Gossypium raimondii*] | 90% | 4.00E−103 | 82% | XP_012467939.1 |
| unknown [*Glycine max*] | 100% | 5.00E−103 | 69% | ACU23291.1 |
| PREDICTED: photosystem II 22 kDa protein, chloroplastic [*Oryza sativa* Japonica Group] | 86% | 7.00E−103 | 80% | XP_015633953.1 |
| PREDICTED: photosystem II 22 kDa protein, chloroplastic-like [*Oryza brachyantha*] | 83% | 8.00E−103 | 80% | XP_006653075.1 |
| PREDICTED: photosystem II 22 kDa protein, chloroplastic-like [*Gossypium hirsutum*] | 90% | 8.00E−103 | 82% | XP_016727785.1 |
| PREDICTED: photosystem II 22 kDa protein, chloroplastic-like [*Gossypium hirsutum*] | 90% | 1.00E−102 | 82% | XP_016732479.1 |
| B0518A01.1 [*Oryza sativa* Indica Group] | 100% | 1.00E−102 | 72% | CAH68096.1 |
| PsbS protein [*Phyllostachys edulis*] | 74% | 1.00E−102 | 86% | ACU33835.1 |
| PREDICTED: photosystem II 22 kDa protein, chloroplastic [*Nicotiana tomentosiformis*] | 99% | 1.00E−102 | 72% | XP_009623344.1 |
| PREDICTED: photosystem II 22 kDa protein, chloroplastic [*Oryza brachyantha*] | 74% | 2.00E−102 | 86% | XP_006645083.2 |
| OSJNBa0039K24.28 [*Oryza sativa* Japonica Group] | 86% | 2.00E−102 | 80% | CAE01809.2 |
| chloroplast photosystem II 22 kDa component [*Nicotiana benthamiana*] | 99% | 3.00E−102 | 71% | ABC59515.1 |
| PREDICTED: photosystem II 22 kDa protein, chloroplastic [*Nicotiana sylvestris*] | 99% | 3.00E−102 | 71% | XP_009771859.1 |
| Photosystem II subunit S [*Zostera marina*] | 99% | 5.00E−102 | 70% | KMZ60119.1 |
| hypothetical protein M569_10990 [*Genlisea aurea*] | 80% | 1.00E−101 | 84% | EPS63793.1 |

TABLE 6

Percentage of sequence identity for ZEP.

| Description | Query cover | E value | Identity | Accession |
|---|---|---|---|---|
| zeaxanthin epoxidase (ZEP) (ABA1) [*Arabidopsis thaliana*] | 100% | 0 | 100% | NP_851285.1 |
| AtABA1 [*Arabidopsis thaliana*] | 100% | 0 | 99% | BAB11935.1 |
| zeaxanthin epoxidase [*Arabidopsis thaliana*] | 100% | 0 | 99% | AAF82390.1 |
| zeaxanthin epoxidase [*Arabidopsis thaliana*] | 100% | 0 | 99% | AAG17703.1 |
| hypothetical protein CARUB_v10026026mg [*Capsella rubella*] | 100% | 0 | 93% | XP_006280131.1 |
| PREDICTED: zeaxanthin epoxidase, chloroplastic [*Camelina sativa*] | 100% | 0 | 94% | XP_010444704.1 |
| hypothetical protein ARALYDRAFT_496897 [*Arabidopsis lyrata* subsp. *lyrata*] | 100% | 0 | 95% | XP_002865032.1 |

TABLE 6-continued

Percentage of sequence identity for ZEP.

| Description | Query cover | E value | Identity | Accession |
|---|---|---|---|---|
| PREDICTED: zeaxanthin epoxidase, chloroplastic [*Camelina sativa*] | 100% | 0 | 93% | XP_010484561.1 |
| hypothetical protein EUTSA_v10003769mg [*Eutrema salsugineum*] | 99% | 0 | 91% | XP_006393901.1 |
| zeaxanthin epoxidase [*Eutrema halophilum*] | 99% | 0 | 91% | AAV85824.1 |
| hypothetical protein EUTSA_v10003769mg [*Eutrema salsugineum*] | 99% | 0 | 91% | XP_006393902.1 |
| hypothetical protein AALP_AA8G503900 [*Arabis alpina*] | 100% | 0 | 90% | KFK28343.1 |
| Zeaxanthin epoxidase, chloroplastic [*Noccaea caerulescens*] | 100% | 0 | 90% | JAU06164.1 |
| Zeaxanthin epoxidase, chloroplastic [*Noccaea caerulescens*] | 100% | 0 | 90% | JAU34415.1 |
| Zeaxanthin epoxidase, chloroplastic [*Noccaea caerulescens*] | 100% | 0 | 90% | JAU86000.1 |
| BnaA07g12170D [*Brassica napus*] | 99% | 0 | 90% | CDY01444.1 |
| zeaxanthin epoxidase, chloroplastic [*Brassica napus*] | 99% | 0 | 90% | NP_001302817.1 |
| PREDICTED: zeaxanthin epoxidase, chloroplastic [*Brassica rapa*] | 99% | 0 | 90% | XP_009103460.1 |
| zeaxanthin epoxidase [*Brassica rapa* subsp. *pekinensis*] | 99% | 0 | 90% | ACM68704.1 |
| PREDICTED: zeaxanthin epoxidase, chloroplastic [*Raphanus sativus*] | 99% | 0 | 89% | XP_018441511.1 |
| zeaxanthin epoxidase [*Brassica napus*] | 100% | 0 | 90% | ADC29517.1 |
| PREDICTED: zeaxanthin epoxidase, chloroplastic-like isoform X2 [*Brassica napus*] | 100% | 0 | 89% | XP_013686243.1 |
| PREDICTED: zeaxanthin epoxidase, chloroplastic isoform X2 [*Brassica oleracea* var. *oleracea*] | 100% | 0 | 89% | XP_013597987.1 |
| PREDICTED: zeaxanthin epoxidase, chloroplastic-like isoform X1 [*Brassica napus*] | 100% | 0 | 89% | XP_013686242.1 |
| PREDICTED: zeaxanthin epoxidase, chloroplastic isoform X1 [*Brassica oleracea* var. *oleracea*] | 100% | 0 | 89% | XP_013597986.1 |
| zeaxanthin epoxidase (ZEP) (ABA1) [*Arabidopsis thaliana*] | 91% | 0 | 96% | NP_201504.2 |
| PREDICTED: zeaxanthin epoxidase, chloroplastic [*Brassica oleracea* var. *oleracea*] | 100% | 0 | 85% | XP_013613157.1 |
| PREDICTED: zeaxanthin epoxidase, chloroplastic-like isoform X3 [*Raphanus sativus*] | 100% | 0 | 86% | XP_018457364.1 |
| BnaC09g07550D [*Brassica napus*] | 100% | 0 | 85% | CDX81344.1 |
| PREDICTED: zeaxanthin epoxidase, chloroplastic-like [*Brassica rapa*] | 100% | 0 | 84% | XP_009112352.1 |
| BnaA09g07610D [*Brassica napus*] | 100% | 0 | 84% | CDY18634.1 |
| PREDICTED: zeaxanthin epoxidase, chloroplastic-like isoform X4 [*Raphanus sativus*] | 95% | 0 | 86% | XP_018457365.1 |
| PREDICTED: zeaxanthin epoxidase, chloroplastic-like isoform X1 [*Raphanus sativus*] | 95% | 0 | 86% | XP_018457362.1 |
| PREDICTED: zeaxanthin epoxidase, chloroplastic-like isoform X2 [*Raphanus sativus*] | 95% | 0 | 86% | XP_018457363.1 |
| PREDICTED: zeaxanthin epoxidase, chloroplastic-like [*Tarenaya hassleriana*] | 100% | 0 | 80% | XP_010547517.1 |
| PREDICTED: zeaxanthin epoxidase, chloroplastic [*Tarenaya hassleriana*] | 100% | 0 | 79% | XP_010558547.1 |
| PREDICTED: zeaxanthin epoxidase, chloroplastic isoform X3 [*Brassica oleracea* var. *oleracea*] | 86% | 0 | 90% | XP_013597988.1 |
| zeaxanthin epoxidase precursor [*Arabidopsis thaliana*] | 74% | 0 | 100% | AAL91193.1 |
| PREDICTED: zeaxanthin epoxidase, chloroplastic [*Ricinus communis*] | 99% | 0 | 72% | XP_002523587.1 |
| PREDICTED: zeaxanthin epoxidase, chloroplastic [*Jatropha curcas*] | 99% | 0 | 72% | XP_012079233.1 |
| hypothetical protein COLO4_11419 [*Corchorus olitorius*] | 92% | 0 | 75% | OMP01999.1 |
| zeaxanthin epoxidase [*Vitis vinifera*] | 99% | 0 | 71% | NP_001268202.1 |
| PREDICTED: zeaxanthin epoxidase, chloroplastic-like [*Populus euphratica*] | 95% | 0 | 73% | XP_011043539.1 |
| unnamed protein product [*Vitis vinifera*] | 99% | 0 | 71% | CBI21425.3 |
| zeaxanthin epoxidase [*Vitis vinifera*] | 99% | 0 | 71% | AAR11195.1 |
| hypothetical protein JCGZ_12396 [*Jatropha curcas*] | 92% | 0 | 74% | KDP31935.1 |
| hypothetical protein Csa_2G277050 [*Cucumis sativus*] | 98% | 0 | 70% | KGN61963.1 |
| hypothetical protein CCACVL1_26372 [*Corchorus capsularis*] | 92% | 0 | 75% | OMO56663.1 |
| RecName: Full = Zeaxanthin epoxidase, chloroplastic; AltName: Full = PA-ZE; Flags: Precursor | 98% | 0 | 72% | O81360.1 |
| PREDICTED: zeaxanthin epoxidase, chloroplastic-like [*Vigna radiate* var. *radiata*] | 100% | 0 | 70% | XP_014509031.1 |
| zeaxanthin epoxidase, chloroplastic [*Cucumis sativus*] | 98% | 0 | 70% | NP_001292713.1 |
| PREDICTED: zeaxanthin epoxidase, chloroplastic [*Juglans regia*] | 97% | 0 | 73% | XP_018844974.1 |
| zeaxanthin epoxidase family protein [*Populus tomentosa*] | 94% | 0 | 73% | APR63737.1 |
| hypothetical protein PRUPE_ppa002248mg [*Prunus persica*] | 98% | 0 | 72% | XP_007204247.1 |
| hypothetical protein PRUPE_7G133100 [*Prunus persica*] | 98% | 0 | 72% | ONH96498.1 |
| FHA domain-containing protein/FAD_binding_3 domain-containing protein [*Cephalotus follicularis*] | 99% | 0 | 70% | GAV73676.1 |
| zeaxanthin epoxidase 1 [*Bixa orellana*] | 97% | 0 | 73% | AMJ39488.1 |

TABLE 6-continued

Percentage of sequence identity for ZEP.

| Description | Query cover | E value | Identity | Accession |
|---|---|---|---|---|
| PREDICTED: zeaxanthin epoxidase, chloroplastic isoform X2 [*Theobroma cacao*] | 96% | 0 | 73% | XP_007047261.2 |
| zeaxanthin epoxidase [*Camellia sinensis*] | 98% | 0 | 71% | AJB84624.1 |
| Zeaxanthin epoxidase (ZEP) (ABA1) isoform 2 [*Theobroma cacao*] | 96% | 0 | 73% | EOX91418.1 |
| zeaxanthin epoxidase, chloroplastic [*Cucumis melo*] | 98% | 0 | 70% | NP_001315402.1 |
| PREDICTED: zeaxanthin epoxidase, chloroplastic-like [*Vigna angularis*] | 97% | 0 | 71% | XP_0317411486.1 |
| zeaxanthin epoxidase family protein [*Populus trichocarpa*] | 93% | 0 | 71% | XP_002307265.1 |
| PREDICTED: zeaxanthin epoxidase, chloroplastic [*Eucalyptus grandis*] | 98% | 0 | 70% | XP_010028248.1 |
| zeaxanthin epoxidase, chloroplastic-like isoform X1 [*Cajanus cajan*] | 98% | 0 | 71% | XP_020238178.1 |
| PREDICTED: zeaxanthin epoxidase, chloroplastic [*Prunus mume*] | 98% | 0 | 72% | XP_008241462.1 |
| hypothetical protein PHAVU_003G243800g [*Phaseolus vulgaris*] | 98% | 0 | 71% | XP_007155924.1 |
| Zeaxanthin epoxidase (ZEP) (ABA1) isoform 3 [*Theobroma cacao*] | 96% | 0 | 72% | EOX91419.1 |
| PREDICTED: zeaxanthin epoxidase, chloroplastic isoform X1 [*Theobroma cacao*] | 96% | 0 | 72% | XP_007047260.2 |
| PREDICTED: zeaxanthin epoxidase, chloroplastic [*Ziziphus jujuba*] | 100% | 0 | 70% | XP_015890147.1 |
| PREDICTED: zeaxanthin epoxidase, chloroplastic-like [*Populus euphratica*] | 90% | 0 | 75% | XP_011005864.1 |
| Zeaxanthin epoxidase (ZEP) (ABA1) isoform 1 [*Theobroma cacao*] | 96% | 0 | 72% | EOX91417.1 |
| PREDICTED: zeaxanthin epoxidase, chloroplastic-like [*Arachis duranensis*] | 98% | 0 | 70% | XP_015955494.1 |
| hypothetical protein MANES_13G124100 [*Manihot esculents*] | 98% | 0 | 72% | OAY33781.1 |
| zeaxanthin epoxidase [*Citrus unshiu*] | 99% | 0 | 70% | BAB78733.1 |
| zeaxanthin epoxidase [*Citrus unshiu*] | 99% | 0 | 70% | BAI79257.1 |
| hypothetical protein GLYMA_11G055700 [*Glycine max*] | 99% | 0 | 70% | KRH28470.1 |
| PREDICTED: zeaxanthin epoxidase, chloroplastic [*Citrus sinensis*] | 99% | 0 | 70% | XP_006466600.1 |
| hypothetical protein CISIN_1g005770mg [*Citrus sinensis*] | 99% | 0 | 69% | KDO79210.1 |
| PREDICTED: zeaxanthin epoxidase, chloroplastic-like [*Citrus sinensis*] | 99% | 0 | 69% | XP_006494451.1 |
| hypothetical protein CICLE_v10025089mg [*Citrus Clementina*] | 99% | 0 | 69% | XP_006425899.1 |
| zeaxanthin epoxidase, chloroplastic-like [*Glycine max*] | 97% | 0 | 71% | NP_001241348.1 |
| Zeaxanthin epoxidase, chloroplastic [*Glycine soja*] | 98% | 0 | 70% | KHN26473.1 |
| PREDICTED: zeaxanthin epoxidase, chloroplastic-like [*Pyrus × bretschneideri*] | 97% | 0 | 71% | XP_009343160.1 |
| PREDICTED: zeaxanthin epoxidase, chloroplastic-like [*Malus domestics*] | 100% | 0 | 69% | XP_008340140.1 |
| zeaxanthin epoxidase [*Citrullus lanatus*] | 98% | 0 | 69% | ADI56522.1 |
| PREDICTED: zeaxanthin epoxidase, chloroplastic [*Arachis ipaensis*] | 98% | 0 | 69% | XP_016185162.1 |
| zeaxanthin epoxidase [*Malus domestica*] | 98% | 0 | 69% | AHA61555.1 |
| PREDICTED: zeaxanthin epoxidase, chloroplastic [*Nicotiana sylvestris*] | 98% | 0 | 70% | XP_009767383.1 |
| zeaxanthin epoxidase [*Chrysanthemum × morifolium*] | 91% | 0 | 74% | BAE79556.1 |
| PREDICTED: zeaxanthin epoxidase, chloroplastic-like [*Cicer arietinum*] | 98% | 0 | 70% | XP_004511928.1 |
| PREDICTED: zeaxanthin epoxidase, chloroplastic-like [*Pyrus × bretschneideri*] | 98% | 0 | 70% | XP_018505293.1 |
| RecName: Full = Zeaxanthin epoxidase, chloroplastic; Flags: Precursor | 98% | 0 | 71% | Q40412.1 |
| zeaxanthin epoxidase [*Chrysanthemum boreale*] | 91% | 0 | 74% | AGU91434.1 |
| zeaxanthin epoxidase 1 isoform [*Bixa orellana*] | 93% | 0 | 74% | AMJ39489.1 |
| PREDICTED: zeaxanthin epoxidase, chloroplastic [*Nicotiana tabacum*] | 98% | 0 | 70% | XP_016476042.1 |
| PREDICTED: zeaxanthin epoxidase, chloroplastic [*Pyrus × bretschneideri*] | 98% | 0 | 70% | XP_009345968.1 |
| PREDICTED: zeaxanthin epoxidase, chloroplastic [*Beta vulgaris* subsp. *vulgaris*] | 99% | 0 | 67% | XP_010666612.1 |
| hypothetical protein CISIN_1g005770mg [*Citrus sinensis*] | 99% | 0 | 68% | KDO79209.1 |
| PREDICTED: zeaxanthin epoxidase, chloroplastic isoform X1 [*Nelumbo nucifera*] | 98% | 0 | 69% | XP_010269709.1 |

TABLE 7

Percentage of sequence identity for VDE.

| Description | Query cover | E value | Identity | Accession |
|---|---|---|---|---|
| non-photochemical quenching 1 [*Arabidopsis thaliana*] | 100% | 0 | 100% | NP_172331.1 |
| non-photochemical quenching 1 [*Arabidopsis lyrata* subsp. *lyrata*] | 100% | 0 | 96% | XP_002889702.1 |
| hypothetical protein CARUB_v10009082mg [*Capsella rubella*] | 100% | 0 | 95% | XP_006307456.1 |
| PREDICTED: violaxanthin de-epoxidase, chloroplastic [*Camelina sativa*] | 100% | 0 | 93% | XP_010475655.1 |
| PREDICTED: violaxanthin de-epoxidase, chloroplastic [*Camelina sativa*] | 100% | 0 | 94% | XP_010458094.1 |
| PREDICTED: violaxanthin de-epoxidase, chloroplastic [*Camelina sativa*] | 100% | 0 | 94% | XP_010488996.1 |
| PREDICTED: violaxanthin de-epoxidase, chloroplastic [*Brassica napus*] | 100% | 0 | 88% | XP_013641072.1 |
| PREDICTED: violaxanthin de-epoxidase, chloroplastic [*Brassica rapa*] | 100% | 0 | 87% | XP_009148110.2 |
| BnaA06g04940D [*Brassica napus*] | 100% | 0 | 87% | CDX93554.1 |
| Violaxanthin de-epoxidase, chloroplastic [*Noccaea caerulescens*] | 100% | 0 | 87% | JAU20005.1 |
| Violaxanthin de-epoxidase, chloroplastic [*Noccaea caerulescens*] | 100% | 0 | 87% | JAU75731.1 |
| Violaxanthin de-epoxidase, chloroplastic [*Noccaea caerulescens*] | 100% | 0 | 87% | JAU51142.1 |
| violaxanthin de-epoxidase, chloroplastic-like [*Brassica napus*] | 100% | 0 | 87% | NP_001302836.1 |
| BnaC05g06200D [*Brassica napus*] | 100% | 0 | 87% | CDX95051.1 |
| hypothetical protein EUTSA_v10007587mg [*Eutrema salsugineum*] | 100% | 0 | 88% | XP_006417674.1 |
| Violaxanthin de-epoxidase, chloroplastic [*Noccaea caerulescens*] | 100% | 0 | 87% | JAU77894.1 |
| PREDICTED: violaxanthin de-epoxidase, chloroplastic [*Tarenaya hassleriana*] | 100% | 0 | 74% | XP_010528777.1 |
| NPQ1 [*Arabidopsis thaliana*] | 72% | 0 | 100% | OAP18415.1 |
| PREDICTED: violaxanthin de-epoxidase, chloroplastic [*Eucalyptus grandis*] | 88% | 0 | 76% | XP_010043341.1 |
| PREDICTED: violaxanthin de-epoxidase, chloroplastic isoform X2 [*Gossypium arboreum*] | 89% | 0 | 74% | XP_017627747.1 |
| hypothetical protein MANES_09G144600 [*Manihot esculenta*] | 91% | 0 | 73% | OAY41983.1 |
| Non-photochemical quenching 1 isoform 1 [*Theobroma cacao*] | 91% | 0 | 73% | EOY10737.1 |
| PREDICTED: violaxanthin de-epoxidase, chloroplastic isoform X1 [*Gossypium arboreum*] | 82% | 0 | 79% | XP_017627745.1 |
| PREDICTED: violaxanthin de-epoxidase, chloroplastic-like [*Gossypium hirsutum*] | 82% | 0 | 79% | XP_016673034.1 |
| PREDICTED: violaxanthin de-epoxidase, chloroplastic [*Theobroma cacao*] | 91% | 0 | 72% | XP_007030235.2 |
| hypothetical protein POPTR_0013s05000g [*Populus trichocarpa*] | 83% | 0 | 78% | XP_002319136.2 |
| PREDICTED: violaxanthin de-epoxidase, chloroplastic isoform X3 [*Gossypium arboreum*] | 83% | 0 | 78% | XP_017627748.1 |
| PREDICTED: violaxanthin de-epoxidase, chloroplastic [*Jatropha curcas*] | 84% | 0 | 78% | XP_012092715.1 |
| chloroplast violaxanthin de-epoxidase [*Prunus humilis*] | 81% | 0 | 79% | AIZ75647.1 |
| PREDICTED: violaxanthin de-epoxidase, chloroplastic isoform X1 [*Pyrus × bretschneideri*] | 81% | 0 | 79% | XP_009379699.1 |
| PREDICTED: violaxanthin de-epoxidase, chloroplastic isoform X2 [*Pyrus × bretschneideri*] | 81% | 0 | 79% | XP_009379700.1 |
| violaxanthin de-epoxidase 1 [*Bixa orellana*] | 94% | 0 | 68% | AMJ39491.1 |
| hypothetical protein PRUPE_ppa005029mg [*Prunus persica*] | 81% | 0 | 79% | XP_007207430.1 |
| PREDICTED: violaxanthin de-epoxidase, chloroplastic [*Vitis vinifera*] | 82% | 0 | 78% | XP_002267152.1 |
| PREDICTED: violaxanthin de-epoxidase, chloroplastic [*Prunus mume*] | 81% | 0 | 79% | XP_016651828.1 |
| hypothetical protein CICLE_v10019925mg [*Citrus Clementina*] | 82% | 0 | 77% | XP_006443345.1 |
| hypothetical protein PRUPE_6G356100 [*Prunus persica*] | 81% | 0 | 79% | ONI05101.1 |
| hypothetical protein PRUPE_6G356100 [*Prunus persica*] | 81% | 0 | 79% | ONI05102.1 |
| unnamed protein product [*Vitis vinifera*] | 82% | 0 | 78% | CBI28686.3 |
| hypothetical protein CISIN_1g011550mg [*Citrus sinensis*] | 82% | 0 | 77% | KDO45543.1 |
| PREDICTED: violaxanthin de-epoxidase, chloroplastic [*Malus domestica*] | 81% | 0 | 79% | XP_008388766.1 |
| violaxanthin de-epoxidase [*Citrus sinensis*] | 84% | 0 | 74% | NP_001275810.1 |
| violaxanthin de-epoxidase 1 [*Vitis vinifera*] | 82% | 0 | 78% | AFP28802.1 |
| PREDICTED: violaxanthin de-epoxidase, chloroplastic isoform X2 [*Gossypium raimondii*] | 89% | 0 | 75% | XP_012492660.1 |
| hypothetical protein B456_007G268500 [*Gossypium raimondii*] | 89% | 0 | 75% | KJB44721.1 |
| PREDICTED: LOW QUALITY PROTEIN: violaxanthin de-epoxidase, chloroplastic-like [*Malus domestica*] | 81% | 0 | 78% | XP_008350656.1 |
| PREDICTED: violaxanthin de-epoxidase, chloroplastic [*Populus euphratica*] | 100% | 0 | 67% | XP_011034433.1 |

TABLE 7-continued

Percentage of sequence identity for VDE.

| Description | Query cover | E value | Identity | Accession |
|---|---|---|---|---|
| VDE domain-containing protein [*Cephalotus follicularis*] | 81% | 0 | 82% | GAV86158.1 |
| PREDICTED: violaxanthin de-epoxidase, chloroplastic isoform X1 [*Gossypium raimondii*] | 82% | 0 | 79% | XP_012492659.1 |
| PREDICTED: violaxanthin de-epoxidase, chloroplastic isoform X3 [*Gossypium raimondii*] | 82% | 0 | 79% | XP_012492661.1 |
| PREDICTED: violaxanthin de-epoxidase, chloroplastic [*Fragaria vesca* subsp. *vesca*] | 84% | 0 | 73% | XP_004302125.1 |
| PREDICTED: violaxanthin de-epoxidase, chloroplastic [*Ziziphus jujuba*] | 90% | 0 | 76% | XP_015901670.1 |
| violaxanthin de-epoxidase [*Fragaria × ananassa*] | 84% | 0 | 72% | AFR11775.2 |
| hypothetical protein B456_007G268500 [*Gossypium raimondii*] | 82% | 0 | 79% | KJB44724.1 |
| Violaxanthin de-epoxidase, chloroplastic [*Gossypium arboreum*] | 89% | 0 | 72% | KHG25773.1 |
| RecName: Full = Violaxanthin de-epoxidase, chloroplastic; Flags: Precursor | 82% | 0 | 75% | Q9SM43.2 |
| PREDICTED: violaxanthin de-epoxidase, chloroplastic [*Phoenix dactylifera*] | 82% | 0 | 75% | XP_008810272.1 |
| Violaxanthin de-epoxidase [*Corchorus capsularis*] | 83% | 0 | 78% | OMO84679.1 |
| violaxanthin de-epoxidase [*Coffea arabica*] | 79% | 0 | 82% | ABB70816.1 |
| PREDICTED: violaxanthin de-epoxidase, chloroplastic isoform X2 [*Elaeis guineensis*] | 82% | 0 | 75% | XP_010913044.1 |
| PREDICTED: violaxanthin de-epoxidase, chloroplastic isoform X1 [*Elaeis guineensis*] | 82% | 0 | 75% | XP_010913041.1 |
| Violaxanthin de-epoxidase [*Morus notabilis*] | 85% | 0 | 72% | XP_010109315.1 |
| PREDICTED: violaxanthin de-epoxidase, chloroplastic [*Ricinus communis*] | 83% | 0 | 78% | XP_002525473.1 |
| violaxanthin de-epoxidase [*Coffea canephora*] | 79% | 0 | 82% | ABB70514.1 |
| PREDICTED: violaxanthin de-epoxidase, chloroplastic isoform X1 [*Nelumbo nucifera*] | 82% | 0 | 78% | XP_010247237.1 |
| PREDICTED: violaxanthin de-epoxidase, chloroplastic isoform X2 [*Nelumbo nucifera*] | 82% | 0 | 78% | XP_010247238.1 |
| violaxanthin de-epoxidase [*Camellia sinensis*] | 84% | 0 | 77% | AJB84625.1 |
| PREDICTED: violaxanthin de-epoxidase, chloroplastic [*Juglans regia*] | 84% | 0 | 76% | XP_018826961.1 |
| PREDICTED: violaxanthin de-epoxidase, chloroplastic [*Oryza brachyantha*] | 81% | 0 | 76% | XP_006652202.2 |
| violaxanthin deepoxidase [*Chrysanthemum × morifolium*] | 83% | 0 | 78% | BAE79554.1 |
| violaxanthin de-epoxidase [*Medicago truncatula*] | 79% | 0 | 79% | XP_003626506.2 |
| RecName: Full = Violaxanthin de-epoxidase, chloroplastic; Rags: Precursor | 79% | 0 | 81% | Q40251.1 |
| violaxanthin deepoxidase [*Chrysanthemum boreale*] | 83% | 0 | 79% | AGU91436.1 |
| violaxanthin de-epoxidase [*Camellia sinensis*] | 84% | 0 | 77% | AAL67858.2 |
| violaxanthin de-epoxidase [*Citrus limon*] | 81% | 0 | 75% | BAO18773.1 |
| violaxanthin de-epoxidase, chloroplastic [*Ananas comosus*] | 83% | 0 | 76% | XP_020111643.1 |
| violaxanthin de-epoxidase [*Citrus sinensis*] | 81% | 0 | 75% | BAO18772.1 |
| PREDICTED: violaxanthin de-epoxidase, chloroplastic-like isoform X5 [*Glycine max*] | 81% | 0 | 78% | XP_006576259.1 |
| PREDICTED; violaxanthin de-epoxidase, chloroplastic [*Amborella trichopoda*] | 79% | 0 | 79% | XP_006830529.1 |
| PREDICTED: violaxanthin de-epoxidase, chloroplastic [*Setaria italica*] | 81% | 0 | 77% | XP_004975369.1 |
| PREDICTED: violaxanthin de-epoxidase, chloroplastic-like [*Camelina sativa*] | 65% | 0 | 96% | XP_010462602.2 |
| violaxanthin de-epoxidase [*Citrus unshiu*] | 81% | 0 | 74% | BAN91498.1 |
| violaxanthin de-epoxidase, chloroplastic isoform X2 [*Cajanus cajan*] | 97% | 0 | 68% | XP_020213947.1 |
| PREDICTED: violaxanthin de-epoxidase, chloroplastic [*Oryza sativa Japonica* Group] | 82% | 0 | 75% | XP_015636342.1 |
| violaxanthin de-epoxidase, chloroplastic isoform X1 [*Cajanus cajan*] | 97% | 0 | 68% | XP_020213942.1 |
| PREDICTED: violaxanthin de-epoxidase, chloroplastic-like isoform X3 [*Glycine max*] | 81% | 0 | 78% | XP_014628869.1 |
| PREDICTED: violaxanthin de-epoxidase, chloroplastic-like isoform X1 [*Glycine max*] | 81% | 0 | 78% | XP_014628868.1 |
| Violaxanthin de-epoxidase, chloroplastic [*Glycine soja*] | 81% | 0 | 78% | KHN35342.1 |
| PREDICTED: violaxanthin de-epoxidase, chloroplastic [*Beta vulgaris* subsp. *vulgaris*] | 84% | 0 | 75% | XP_010674199.1 |
| PREDICTED: violaxanthin de-epoxidase, chloroplastic-like isoform X2 [*Glycine max*] | 81% | 0 | 78% | XP_006576257.1 |
| violaxanthin de-epoxidase, chloroplastic-like precursor [*Glycine max*] | 81% | 0 | 78% | NP_001241404.1 |
| PREDICTED: violaxanthin de-epoxidase, chloroplastic isoform X1 [*Cicer arietinum*] | 81% | 0 | 79% | XP_004494767.1 |
| violaxanthin de-epoxidase precursor [*Oryza sativa Japonica* Group] | 82% | 0 | 75% | AAL09678.1 |

TABLE 7-continued

Percentage of sequence identity for VDE.

| Description | Query cover | E value | Identity | Accession |
|---|---|---|---|---|
| OSJNBb0089B03.4 [*Oryza sativa Japonica* Group] | 82% | 0 | 75% | CAE03990.1 |
| violaxanthin de-epoxidase precursor [*Oryza sativa* Indica Group] | 81% | 0 | 76% | AAF97601.3 |
| PREDICTED: violaxanthin de-epoxidase, chloroplastic isoform X2 [*Cicer arietinum*] | 81% | 0 | 79% | XP_004494768.1 |
| hypothetical protein TSUD_347010 [*Trifolium subterraneum*] | 81% | 0 | 78% | GAU13597.1 |
| hypothetical protein LR48_Vigan10g159600 [*Vigna angularis*] | 79% | 0 | 79% | KOM55704.1 |
| violaxanthin de-epoxidase, chloroplastic-like [*Glycine max*] | 81% | 0 | 77% | NP_001240949.1 |
| PREDICTED: violaxanthin de-epoxidase, chloroplastic [*Vigna angularis*] | 79% | 0 | 78% | XP_017437597.1 |

Example 22. Greenhouse NPQ Expression Experiment

Figure 25:
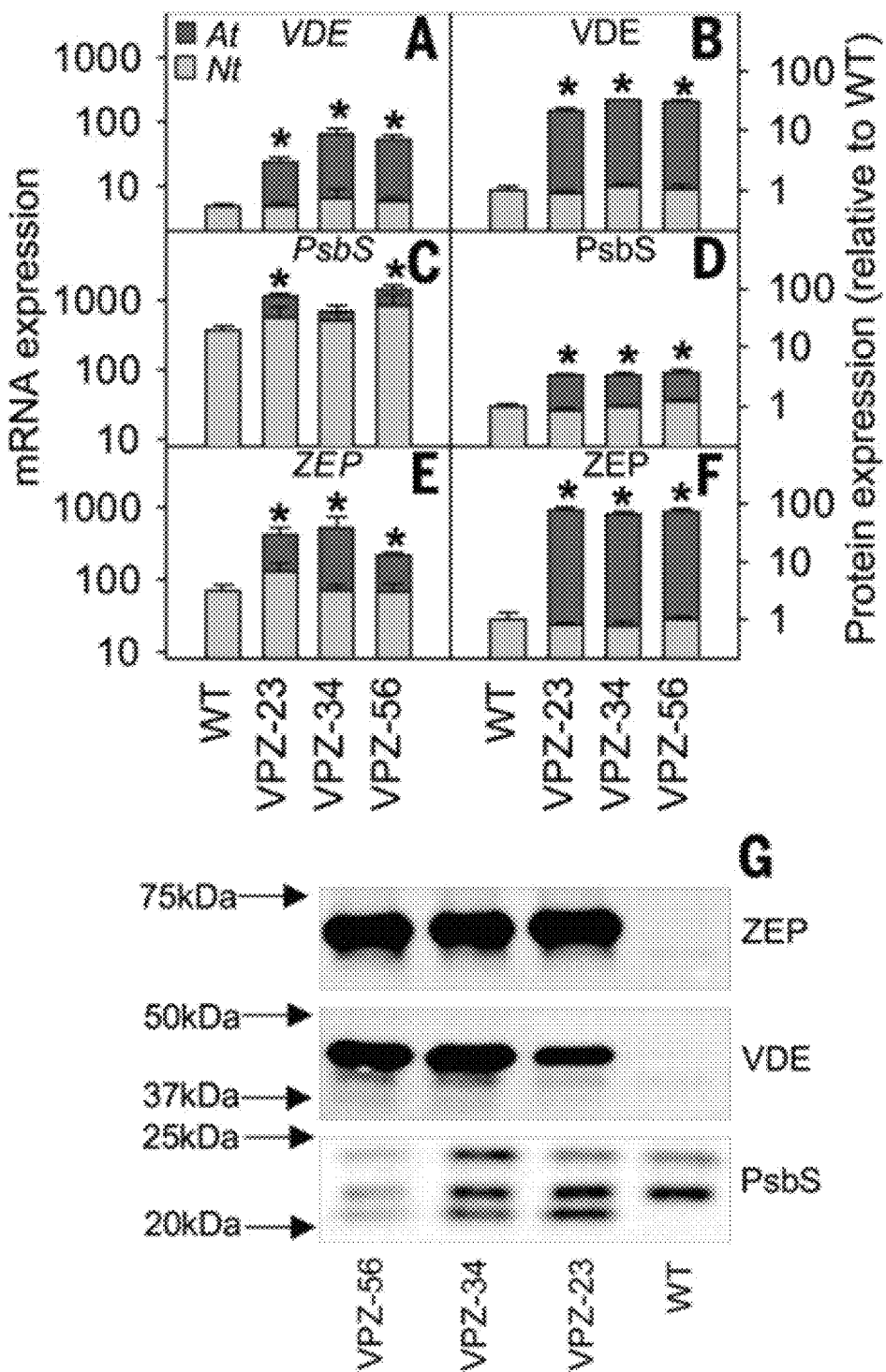
FIG. 25. Levels of mRNA and protein of VDE, PsbS, and ZEP in leaves of transgenic tobacco plants grown under greenhouse conditions. (A, C, and E) mRNA levels relative to actin and tubulin. (B, D, and F) Protein levels relative to wild type (WT), determined from densitometry on immunoblots. Error bars indicate standard error of measurement (SEM) (n=5 biological replicates), and asterisks indicate significant differences between VPZ lines and WT ($\alpha$=0.05). (G) Representative immunoblots for VDE, PsbS, and ZEP.

*Nicotiana tabacum* was transformed with the coding sequences of *Arabidopsis* VDE, ZEP, and PsbS under the control of different promoters for expression in leaves. Two transformants with a single transfer DNA (T-DNA) integration (VPZ-34 and -56) and one transformant with two T-DNA insertions (VPZ-23) were selected based on a seedling NPQ screen and self-pollinated to obtain homozygous $T_2$ progeny for further investigation. These plants were then grown in a greenhouse. Levels of mRNA and protein of VDE, PsbS, and ZEP were measured (FIG. 25).

All three VPZ lines showed increases in total (transgenic plus native) transcript levels of VDE (10-fold), PsbS (threefold), and ZEP (sixfold) relative to those of WT (A, C, and E). For PsbS, the increase in transcript levels translated into an approximately fourfold-higher PsbS protein level (D), as exemplified in bands at 21 kDa (AtPsbS) and 24 kDa (NtPsbS) (G). For VDE and ZEP, the increase in transcript levels corresponded to 30-fold for VDE (45 kDa) (B and G) and 74-fold for ZEP (73 kDa) (F and G) increases over WT protein levels.

Example 23. Field NPQ Expression Experiment

Figure 26:
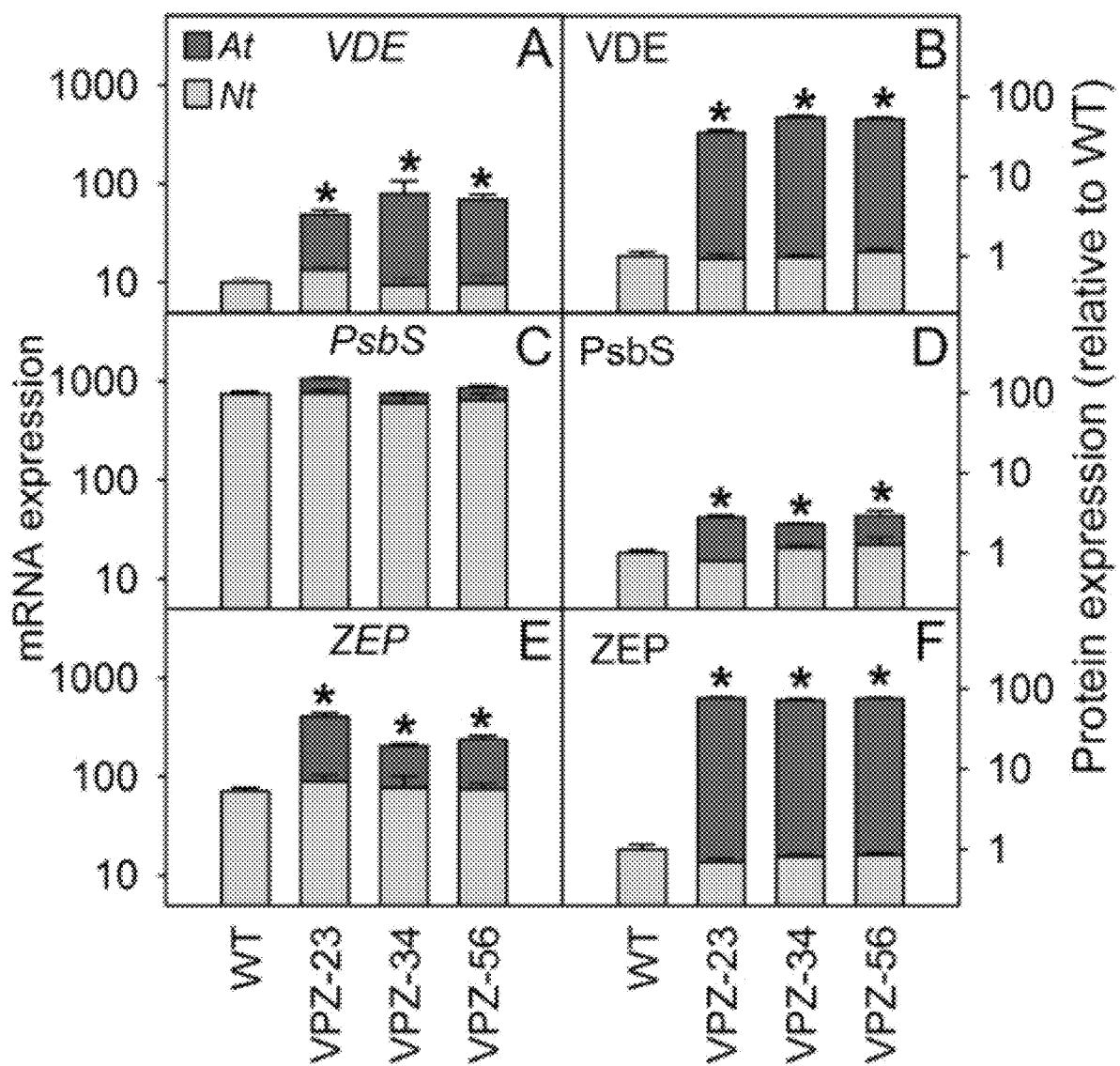
FIG. 26. Levels of mRNA and protein of VDE, PsbS, and ZEP in leaves of transgenic tobacco plants grown under field conditions. (A, C, E) mRNA levels relative to actin and tubulin. (B, D, F) Protein levels relative to wild type (WT), determined from densitometry on immunoblots. Error bars indicate SEM (n=4), and asterisk indicates significant differences between VPZ lines and WT ($\alpha$=0.05).

*Nicotiana tabacum* was transformed with the coding sequences of *Arabidopsis* VDE, ZEP, and PsbS under the control of different promoters for expression in leaves. Two transformants with a single transfer DNA (T-DNA) integration (VPZ-34 and -56) and one transformant with two T-DNA insertions (VPZ-23) were selected based on a seedling NPQ screen and self-pollinated to obtain homozygous $T_2$ progeny for further investigation. These plants were then grown in a field. Levels of mRNA and protein of VDE, PsbS, and ZEP were measured (FIG. 26).

All three VPZ lines showed increases in total (transgenic plus native) transcript levels of VDE (4-fold), PsbS (1.2-fold), and ZEP (7-fold) relative to those of WT. All three VPZ lines also showed increases in total (transgenic plus native) protein levels of VDE (47-fold), PsbS (3-fold), and ZEP (75-fold) relative to those of the WT.

Example 24. Transgenic Rice Experiment

Figure 31:
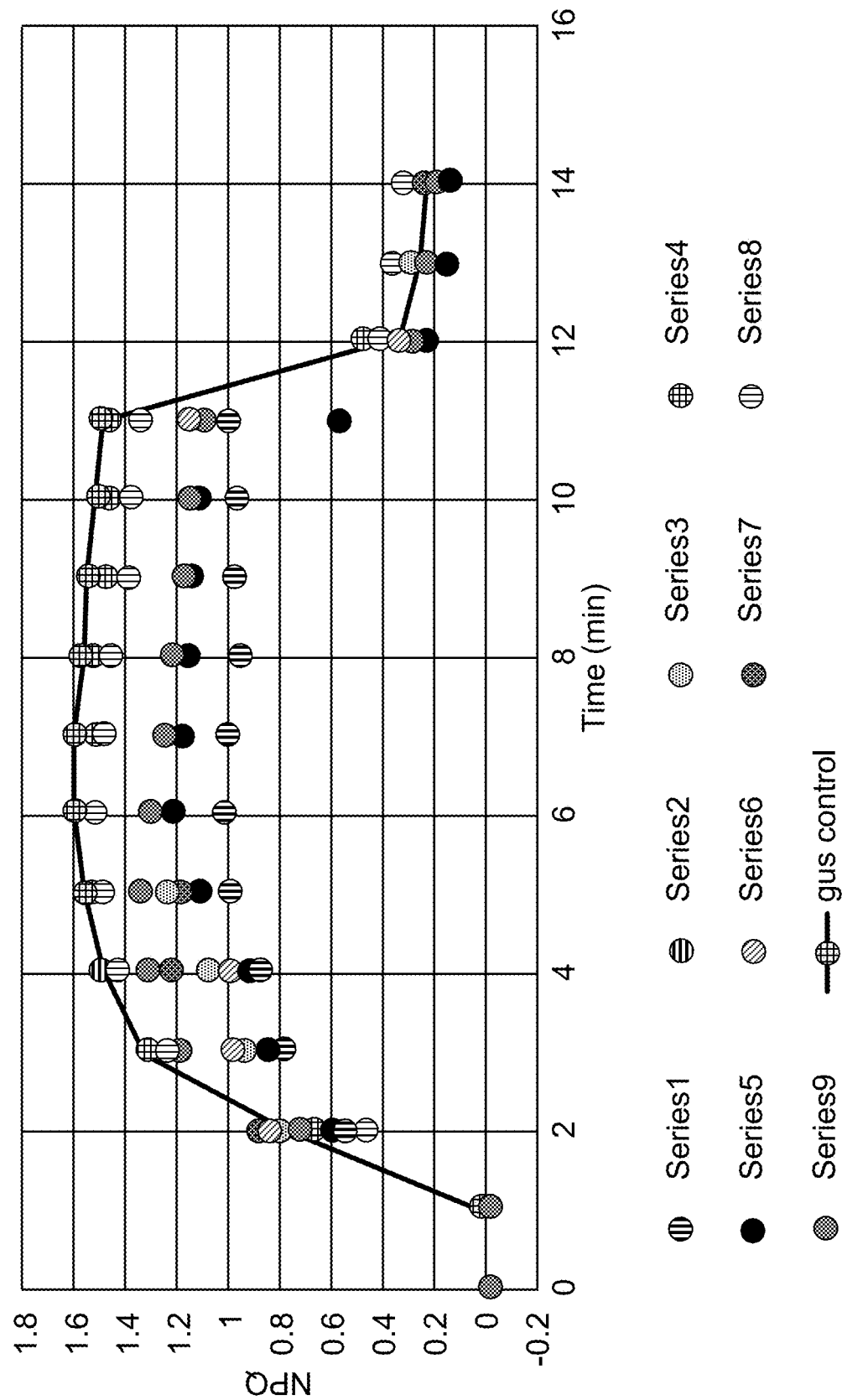
FIG. 31. NPQ induction and relaxation kinetics in nine transgenic rice lines.
Figure 32:
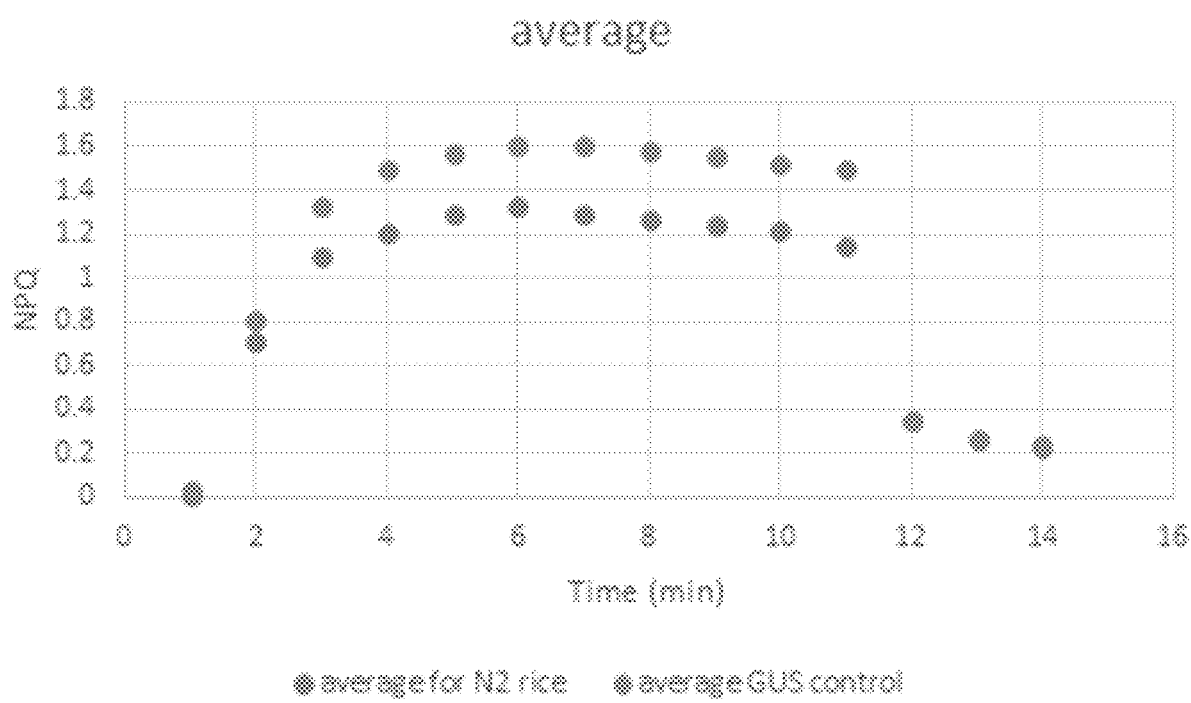
FIG. 32. Average NPQ induction and relaxation kinetics in transgenic rice.

Rice plants were transformed with a T-DNA construct containing nucleotide sequences encoding PsbS, ZEP and VDE, following the transformation protocol described in Example 15. The same expression construct used in the transgenic tobacco experiment was used in this experiment. Leaves of nine independent $T_0$ transformants and two GUS controls were dark adapted. Subsequently, NPQ was measured during 10 min of 1000 µmol m-2 s-1 light followed by 3 min of darkness. FIG. 31 shows the NPQ of the nine rice transformants (dots) and the control (line) over the course of 10 min of 1000 µmol m-2 s-1 light followed by 3 min of darkness. FIG. 32 shows the average of NPQ of the nine rice transformants (blue dot) and the control (orange dot) over the course of 10 min of 1000 µmol m-2 s-1 light followed by 3 min of darkness.

As shown in FIG. 31 and FIG. 32, NPQ amplitudes of these nine transformants were lower than the control during the 10 min of 1000 µmol m-2 s-1 light. This result is consistent with increased expression of ZEP in these transformants, which prevents zeaxanthin formation and thus reduces NPQ amplitude. An alternative explanation is that PsbS overexpression interferes with expression of native PsbS and thus reduces the NPQ amplitude. Results also showed that there was no significant difference in NPQ between the transformants and the control during the 3-min relaxation in the dark, due to the possible lack of zeaxanthin built up in this experiment.

The lack of change in NPQ kinetics in these transgenic rice plants is most plausibly ascribed to a limitation of the experimental design: in this experiment, the rice plants were transformed with an expression cassette constructed for tobacco transformation, which contains promoters designed for optimal gene expression in dicot plants. It is known in the art that dicot promoters do not work well in monocot plants. Therefore, expression of PsbS, ZEP and VDE in these transgenic rice plants was likely not optimally increased to the level that would be conducive to increase of NPQ relaxation rate.

Example 25. Additional Experiments

Figure 18:
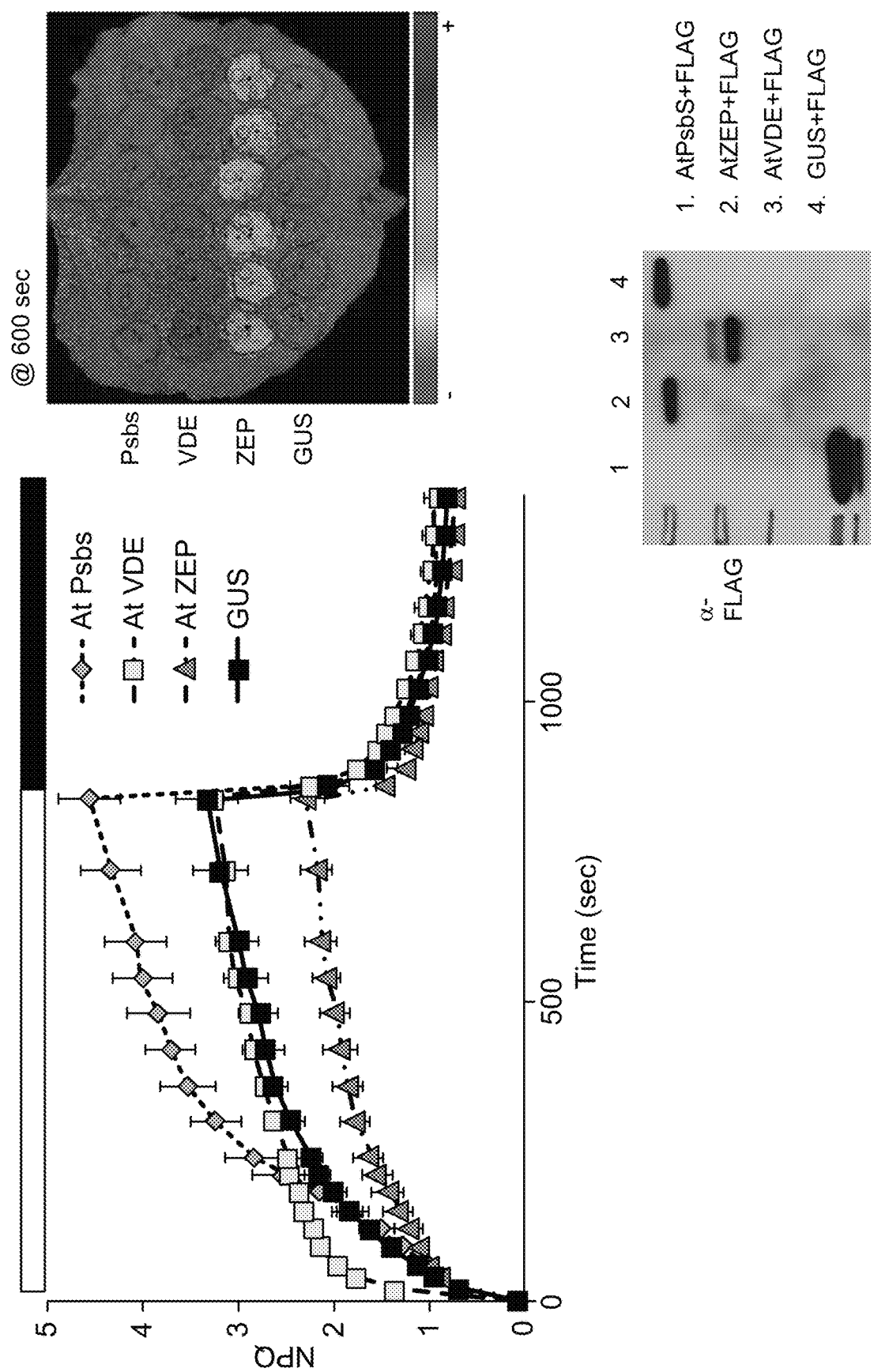
FIG. 18. Transient overexpression of NPQ-related genes in *Nicotiana benthamiana*. The upper left panel shows NPQ measurements on leaf spots overexpressing FLAG-tagged PsbS, VDE. ZEP, and GUS as a negative control, during 13 min illumination at 600 μmol photons m-2 s-1 (white bar), followed by 10 min of dark (black bar). Error bars represent standard deviation (n=6). The upper right panel shows the false-color image of NPQ of a leaf expressing PSBS, VDE, ZEP and GUS 10 min after high light exposure. Rainbow bar indicates relative amount of NPQ. The lower panel shows the immunoblot analysis of tissue collected from the leaf in the upper right panel and probed with anti-FLAG.

Transient overexpression of NPQ-related genes was conducted in *Nicotiana benthamiana*. Measurements of NPQ were taken on leaf spots overexpressing FLAG-tagged PsbS, VDE. ZEP, and GUS as a negative control, during 13 min illumination at 600 µmol photons m-2 s-1, followed by 10 min of dark. As shown in FIG. 18, results showed that overexpression of PsbS increased NPQ capacity relative to the GUS control. Overexpression of VDE sped up NPQ induction. Overexpression of ZEP sped up NPQ relaxation but negatively impacted NPQ induction and capacity.

Figure 19:
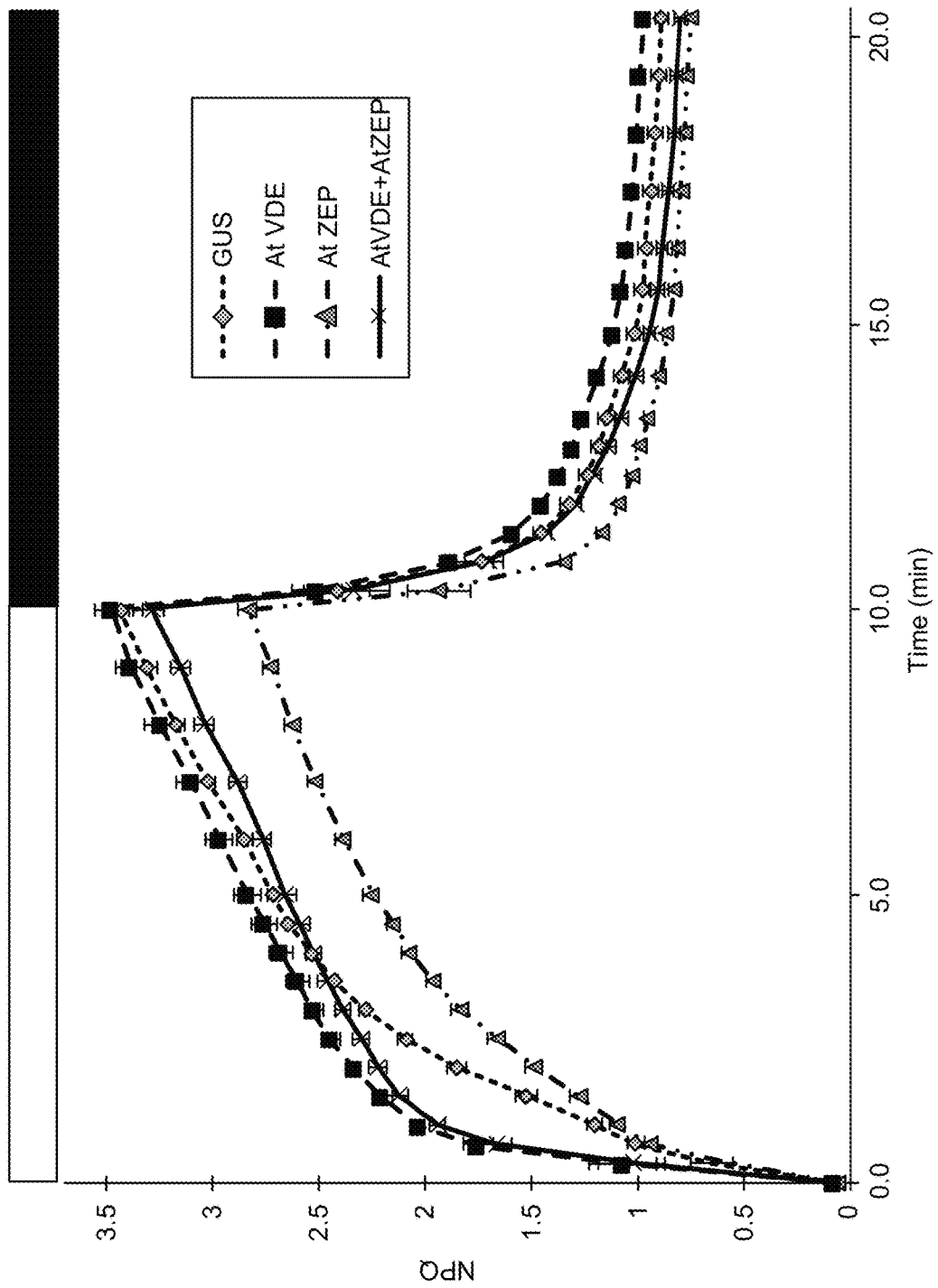
FIG. 19. Transient co-overexpression of VDE and ZEP in *Nicotiana benthamiana* speeds up NPQ induction and relaxation. Error bars represent standard error (n=4).

Transient co-overexpression of VDE and ZEP was conducted in *Nicotiana benthamiana*. Results showed an increased rate of NPQ induction and relaxation as seen in FIG. 19. Co-overexpression of VDE was shown necessary to balance overexpression of ZEP and prevent negative impact of ZEP overexpression on NPQ induction and capacity.

Figure 20:
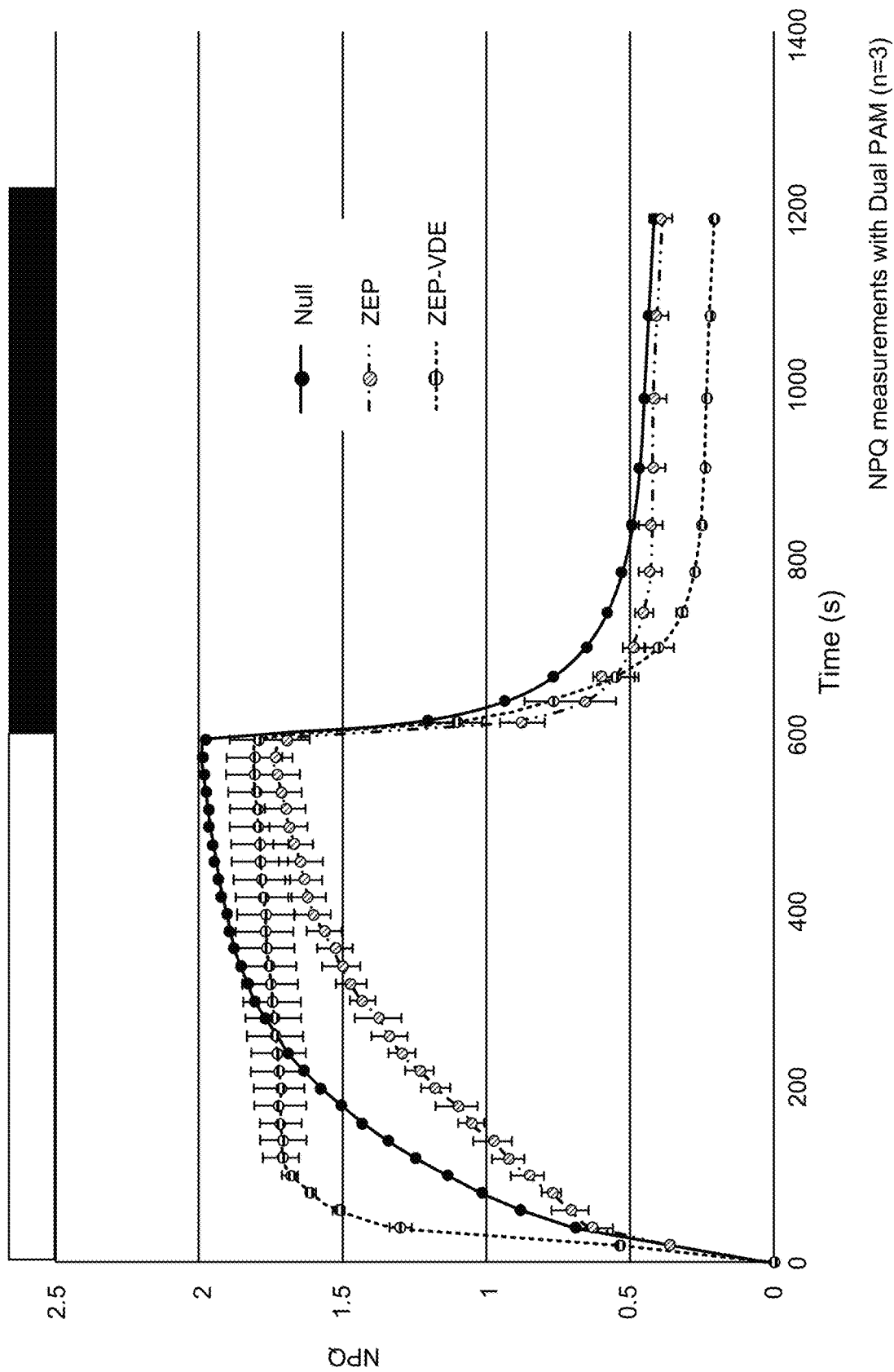
FIG. 20. NPQ kinetics of transgenic $T_1$ progeny. NPQ measurements with DUAL PAM were taken on the youngest fully developed leaf of $T_1$ adult plants for three different lines: one wild-type segregant (Null), one overexpressing ZEP (ZEP) and one overexpressing ZEP and VDE (ZEP-VDE), during 10 min illumination at 600 μmol photons m-2 s-1 (white bar), followed by 10 min of dark (black bar). Each curve corresponds to the average NPQ measurement of three different plants; error bars indicate standard error (n=3).

FIG. 20 shows the NPQ kinetics of stable transgenic $T_1$ plants of Nicotiana tabacum cv. Petite Havana. NPQ measurements with DUAL PAM were taken on the youngest fully developed leaf of $T_1$ adult plants for three different lines: one wild-type segregant (Null), one overexpressing ZEP (ZEP) and one overexpressing ZEP and VDE (ZEP-VDE), during 10 min illumination at 600 µmol photons m-2 s-1, followed by 10 min of dark. Results showed that the ZEP-VDE line showed faster NPQ induction and relaxation.

Figure 21:
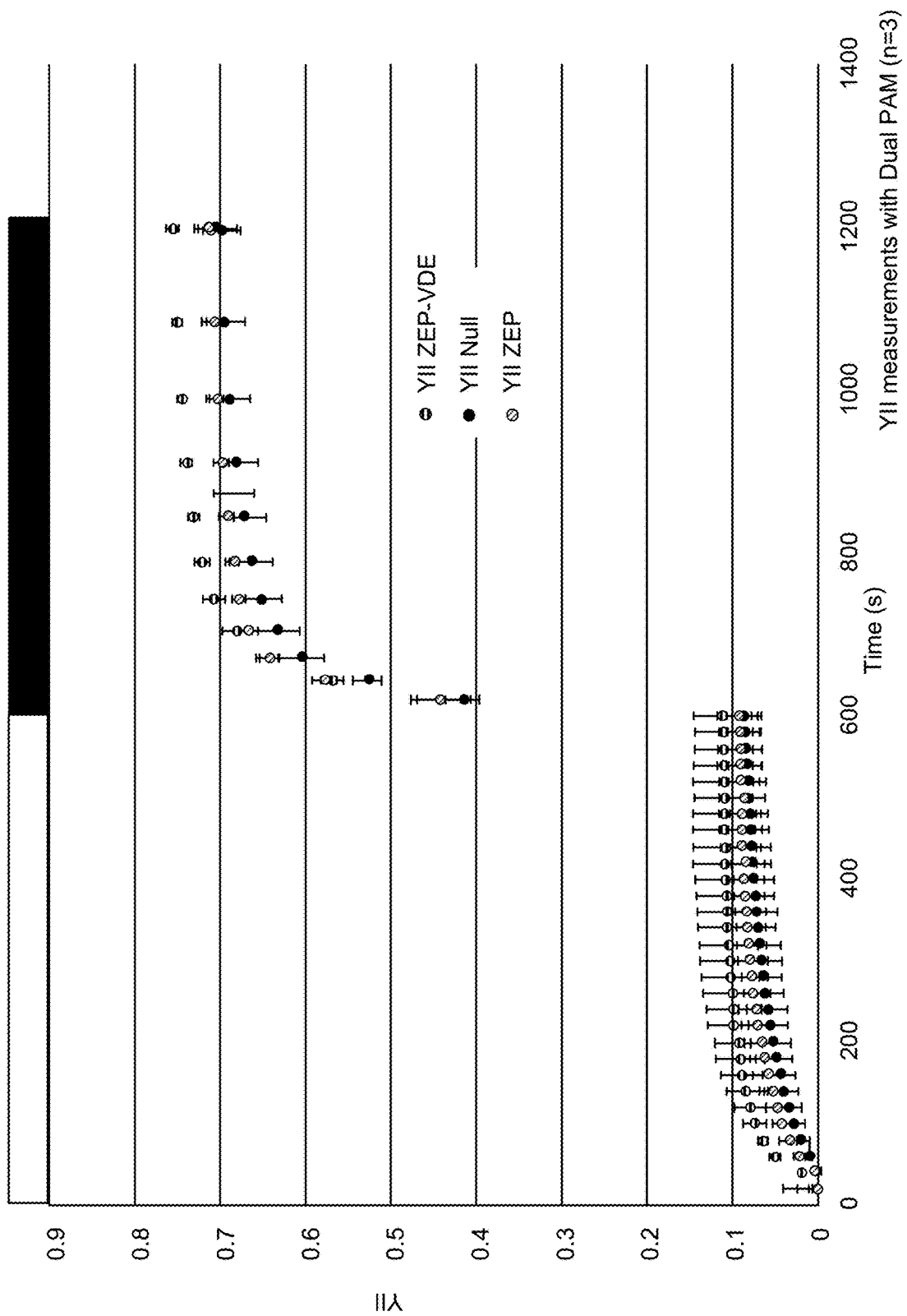
FIG. 21. Photosystem II quantum yield (YII) of stable transgenic $T_1$ plants of *Nicotiana tabacum* cv. Petite Havana.

FIG. 21 shows the photosystem II quantum yield (YII) of stable transgenic $T_1$ plants of Nicotiana tabacum cv. Petite Havana. Measurements of YII performed simultaneously with NPQ measurements described in FIG. 20, were taken on the same plants and in the same conditions. During the dark recovery period, YII was higher for the line overexpressing ZEP-VDE compared to the one overexpressing ZEP or the Null.

Figure 22:
FIG. 22. Growth experiment in the greenhouse. Four sets of plants are shown in the figure, one per transgenic line. Each set contains 36 plants.
Figure 23:
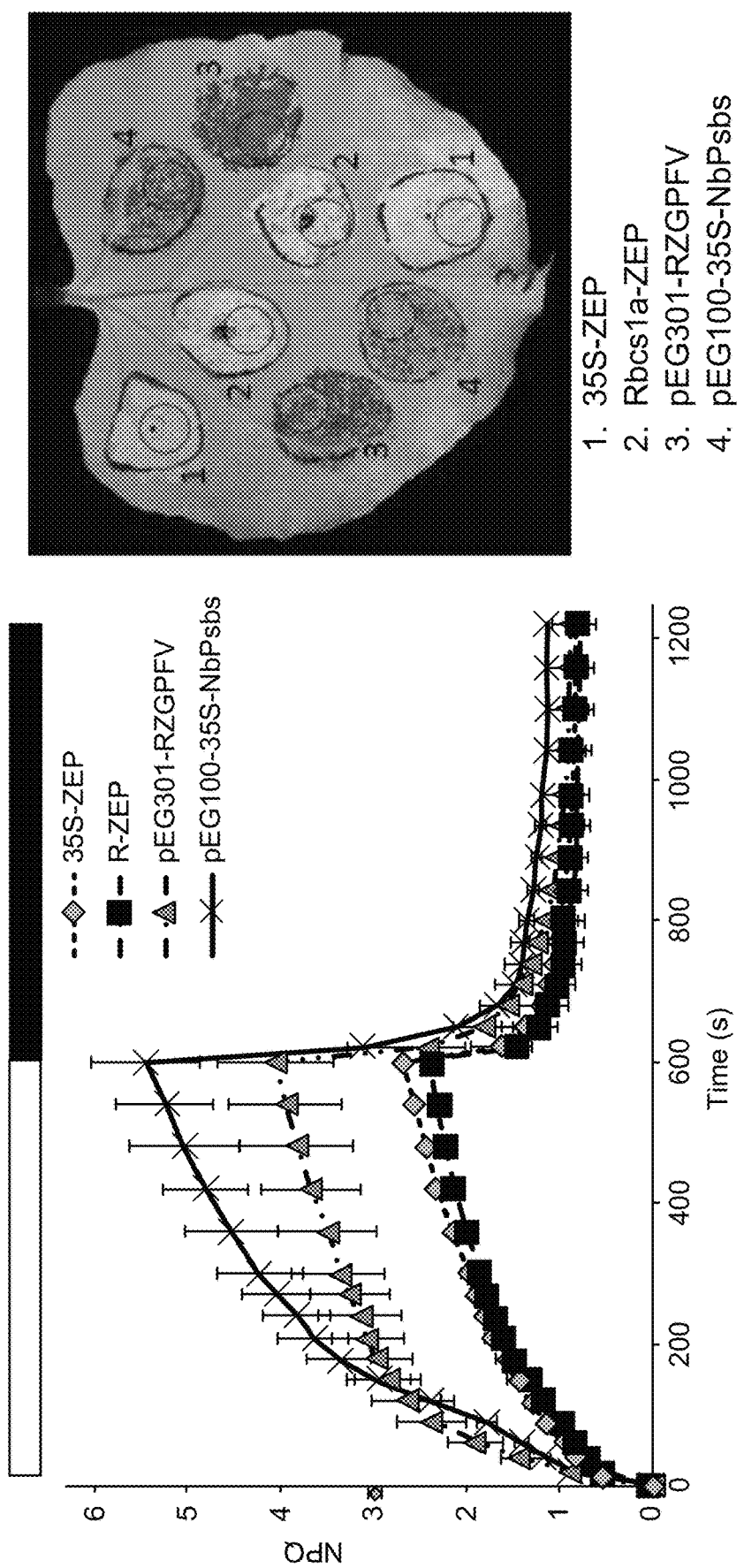
FIG. 23. Transient overexpression of NbPsbS and Rbcs1aAtZEP+Gapa1AtPsbS+Fba2AtVDE constructs in *N. benthamiana*.

FIG. 22 shows the growth experiment in the greenhouse. Results demonstrated the increased size and biomass of stable transgenic $T_1$ plants of Nicotiana tabacum cv. Petite Havana that overexpress ZEP and VDE (ZEP-VDE), compared to wild type (Null). Lines overexpressing PsbS (PsbS) or ZEP and PSBS (ZEP-PsbS) showed a similar biomass to wild type. Four sets of plants are shown in the figure, one per transgenic line. Each set contains 36 plants. The aboveground biomass for each set was determined by the total wet weight and total dry weight of the harvest of the 36 plants, after 19 days of growth. The data represent the results of a single experiment.

The invention claimed is:

1. A genetically modified higher plant (tracheophyte) comprising transfected nucleotide sequences encoding photosystem II subunit S (PsbS), zeaxanthin epoxidase (ZEP), and violaxanthin de-epoxidase (VDE), operably linked to at least one expression control sequence, wherein the transcript levels of PsbS, ZEP and VDE are all increased as compared to a control plant lacking the transfected nucleotide sequences grown under the same conditions and the plant has improved growth under fluctuating light conditions as compared to the control plant grown under the same fluctuating light conditions.

2. The genetically modified plant of claim 1, wherein the transfected nucleotide sequences are derived from a dicot or wherein the transfected nucleotide sequences are derived from *Arabidopsis thaliana*.

3. The genetically modified plant of claim 1, wherein the transcript levels of all three of VDE, PsbS, and ZEP are increased as compared to a control plant lacking the transfected nucleotide sequences grown under the same conditions.

4. The genetically modified plant of claim 1, wherein:
PsbS is encoded by the nucleotide sequence of SEQ ID NO: 1, ZEP is encoded by the nucleotide sequence of SEQ ID NO:2, and VDE is encoded by the nucleotide sequence of SEQ ID NO: 3;
PsbS is encoded by a nucleotide sequence having at least 90% identity to SEQ ID NO: 1, ZEP is encoded by a nucleotide sequence having at least 90% identity to SEQ ID NO:2, and VDE is encoded by a nucleotide sequence having at least 90% identity to SEQ ID NO: 3;

PsbS is encoded by a nucleotide sequence having at least 70% identity to SEQ ID NO: 1, ZEP is encoded by the nucleotide sequence having at least 70% identity to SEQ ID NO:2, and VDE is encoded by the nucleotide sequence having at least 70% identity to SEQ ID NO:3;

PsbS has the amino acid sequence of SEQ ID NO: 4, ZEP has the amino acid sequence of SEQ ID NO:5, and VDE has the amino acid sequence of SEQ ID NO: 6;

PsbS has an amino acid sequence at least 90% identical to SEQ ID NO: 4, ZEP has an amino acid sequence at least 90% identical to SEQ ID NO:5, and VDE has an amino acid sequence at least 90% identical to SEQ ID NO: 6;

PsbS has an amino acid sequence at least 70% identical to SEQ ID NO: 4, ZEP has an amino acid sequence at least 70% identical to SEQ ID NO:5, and VDE has an amino acid sequence at least 70% identical to SEQ ID NO: 6; and/or PsbS comprises a conserved domain of SEQ ID NO: 7, ZEP comprises a conserved domain of SEQ ID NO:8, and VDE comprises a conserved domain of SEQ ID NO: 9.

5. The genetically modified plant of claim 1, wherein the plant is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant, tobacco (*Nicotiana tabacum*), corn (*Zea mays*), rice (*Oryza sativa*), sorghum (*Sorghum bicolor*), soybean (*Glycine max*), cowpea (*Vigna unguiculata*), poplar (*Populus* spp), eucalyptus (*Eucalyptus* spp), cassava (*Manihot esculenta*), barley (*Hordeum vulgare*), potato (*Solanum tuberosum*), sugarcane (*Saccharum* spp), alfalfa (*Medicago sativa*), or wherein the plant is selected from the group consisting of switchgrass, *Miscanthus*, *Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina*, *Brassica napus*, *Brassica carinata*, *Brassica juncea*, pearl millet, foxtail millet, other grain, rice, oilseed, a vegetable crop, a forage crop, an industrial crop, a woody crop and a biomass crop.

6. The genetically modified plant of claim 1, wherein:
the plant has increased photosynthetic efficiency under fluctuating light conditions as compared to the control plant grown under the same fluctuating light conditions;
the plant has improved photoprotection efficiency under fluctuating light conditions as compared to the control plant grown under the same fluctuating light conditions;
the plant has an increased rate of relaxation of non-photochemical quenching (NPQ) under fluctuating light conditions as compared to the control plant grown under the same fluctuating light conditions; and/or
the plant has improved quantum yield and CO2 fixation under fluctuating light conditions as compared to the control plant grown under the same fluctuating light conditions.

7. The genetically modified plant of claim 1, wherein the plant further comprises expression of at least one additional polypeptide that provides herbicide resistance, insect or pest resistance, disease resistance, modified fatty acid metabolism, and/or modified carbohydrate metabolism.

8. An expression vector comprising one or more nucleotide sequences encoding a higher plant (tracheophyte) PsbS, ZEP and VDE, operably linked to at least one expression control sequence, wherein the at least one expression control sequence provides that the transcript levels of PsbS, ZEP and VDE are all increased under the same conditions when the expression vector is transfected into a plant as compared to a control plant lacking the transfected nucleotide sequences grown under the same conditions and the plant has improved growth under fluctuating light conditions as compared to the control plant grown under the same fluctuating light conditions after selection for a transfected plant with increased transcript levels of PsbS, ZEP and VDE, with improved growth, with increased yield, with increased photosynthetic efficiency under fluctuating light conditions, with improved photoprotection efficiency under fluctuating light conditions, with an increased rate of relaxation of non-photochemical quenching (NPQ) under fluctuating light conditions, and/or with improved quantum yield and CO2 fixation under fluctuating light conditions, in each as compared to the control plant grown under the same conditions.

9. The expression vector of claim 8, wherein the at least one expression control sequence comprises a promoter selected from the group consisting of a Rbcs1A promoter, a GAPA-1 promoter, and a FBA2 promoter.

10. The expression vector of claim 8, wherein:
PsbS is encoded by the nucleotide sequence of SEQ ID NO: 1, ZEP is encoded by the nucleotide sequence of SEQ ID NO:2, and VDE is encoded by the nucleotide sequence of SEQ ID NO: 3;

PsbS is encoded by a nucleotide sequence having at least 90% identity to SEQ ID NO: 1, ZEP is encoded by a nucleotide sequence having at least 90% identity to SEQ ID NO:2, and VDE is encoded by a nucleotide sequence having at least 90% identity to SEQ ID NO: 3;

PsbS is encoded by a nucleotide sequence having at least 70% identity to SEQ ID NO: 1, ZEP is encoded by a nucleotide sequence having at least 70% identity to SEQ ID NO:2, and VDE is encoded by a nucleotide sequence having at least 70% identity to SEQ ID NO: 3;

PsbS has the amino acid sequence of SEQ ID NO: 4, ZEP has the amino acid sequence of SEQ ID NO:5, and VDE has the amino acid sequence of SEQ ID NO: 6;

PsbS has an amino acid sequence at least 90% identical to SEQ ID NO: 4, ZEP has an amino acid sequence at least 90% identical to SEQ ID NO:5, and VDE has an amino acid sequence at least 90% identical to SEQ ID NO: 6;

PsbS has an amino acid sequence at least 70% identical to SEQ ID NO: 4, ZEP has an amino acid sequence at least 70% identical to SEQ ID NO:5, and VDE has an amino acid sequence at least 70% identical to SEQ ID NO: 6; and/or PsbS comprises a conserved domain of SEQ ID NO: 7, ZEP comprises a conserved domain of SEQ ID NO:8, and VDE comprises a conserved domain of SEQ ID NO: 9.

11. A bacterial cell or an *Agrobacterium* cell comprising the expression vector of claim 8.

12. A genetically modified plant or a seed comprising the expression vector of claim 8.

13. A progeny plant from the seed of claim 12.

14. A method for increasing growth, increasing photosynthetic efficiency, improving photoprotection efficiency, or improving quantum yield and CO$_2$ fixation in a genetically modified higher plant (tracheophyte), said method comprising cultivating the plant under fluctuating light conditions, wherein all three of a PsbS, a ZEP, and a VDE polypeptide have increased expression as compared to expression of the PsbS, the ZEP, and the VDE polypeptide in a control plant without the genetic modifications grown under the same conditions, and wherein the expression of the PsbS polypeptide is increased by expressing a transfected nucleotide sequence encoding the PsbS polypeptide in the genetically modified plant and/or by a genetic modification in a promoter of a nucleotide sequence encoding the PsbS polypeptide, wherein the expression of the VDE polypeptide is increased by expressing a transfected nucleotide sequence encoding the VDE polypeptide in the genetically modified plant and/or by a genetic modification in a promoter of a nucleotide sequence encoding the VDE polypeptide, and wherein the expression of the ZEP polypeptide is increased by expressing a transfected nucleotide sequence encoding the ZEP polypeptide in the genetically modified plant and/or by a genetic modification in a promoter of a nucleotide sequence encoding the ZEP polypeptide.

15. A method of increasing the rate of relaxation of non-photochemical quenching (NPQ) in a genetically modified higher plant (tracheophyte), said method comprising cultivating the plant under fluctuating light conditions, wherein all three of a PsbS, a ZEP, and a VDE polypeptide have increased expression as compared to expression of the PsbS, the ZEP, and the VDE polypeptide in a control plant without the genetic modifications grown under the same conditions, and wherein the expression of the PsbS polypeptide is increased by expressing a transfected nucleotide sequence encoding the PsbS polypeptide in the genetically modified plant and/or by a genetic modification in a promoter of a nucleotide sequence encoding the PsbS polypeptide, wherein the expression of the VDE polypeptide is increased by expressing a transfected nucleotide sequence encoding the VDE polypeptide in the genetically modified plant and/or by a genetic modification in a promoter of a nucleotide sequence encoding the VDE polypeptide, and wherein the expression of the ZEP polypeptide is increased by expressing a transfected nucleotide sequence encoding the ZEP polypeptide in the genetically modified plant and/or by a genetic modification in a promoter of a nucleotide sequence encoding the ZEP polypeptide.

16. The method of claim 14, wherein promoter genetic modification is achieved by a genome editing system.

17. The method of claim 14, wherein:
PsbS is encoded by the nucleotide sequence of SEQ ID NO: 1, ZEP is encoded by the nucleotide sequence of SEQ ID NO:2, and VDE is encoded by the nucleotide sequence of SEQ ID NO: 3;
PsbS is encoded by a nucleotide sequence having at least 90% identity to SEQ ID NO: 1, ZEP is encoded by a nucleotide sequence having at least 90% identity to SEQ ID NO:2, and VDE is encoded by a nucleotide sequence having at least 90% identity to SEQ ID NO: 3;
PsbS is encoded by a nucleotide sequence having at least 70% identity to SEQ ID NO: 1, ZEP is encoded by a nucleotide sequence having at least 70% identity to SEQ ID NO:2, and VDE is encoded by a nucleotide sequence having at least 70% identity to SEQ ID NO: 3;
PsbS has the amino acid sequence of SEQ ID NO: 4, ZEP has the amino acid sequence of SEQ ID NO:5, and VDE has the amino acid sequence of SEQ ID NO: 6;
PsbS has an amino acid sequence at least 90% identical to SEQ ID NO: 4, ZEP has an amino acid sequence at least 90% identical to SEQ ID NO:5, and VDE has an amino acid sequence at least 90% identical to SEQ ID NO: 6;
PsbS has an amino acid sequence at least 70% identical to SEQ ID NO: 4, ZEP has an amino acid sequence at least 70% identical to SEQ ID NO:5, and VDE has an amino acid sequence at least 70% identical to SEQ ID NO: 6; or
PsbS comprises a conserved domain of SEQ ID NO: 7, ZEP comprises a conserved domain of SEQ ID NO:8, and VDE comprises a conserved domain of SEQ ID NO: 9.

18. The method of claim 14, wherein the plant is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant, tobacco (*Nicotiana tabacum*), corn (*Zea mays*), rice (*Oryza sativa*), sorghum (*Sorghum bicolor*), soybean (*Glycine max*), cowpea (*Vigna unguiculata*), poplar (*Populus* spp), eucalyptus (*Eucalyptus* spp), cassava (*Manihot esculenta*), barley (*Hordeum vulgare*), potato (*Solanum tuberosum*), sugarcane (*Saccharum* spp), alfalfa (*Medicago sativa*), or the plant is selected from the group consisting of switchgrass, *Miscanthus, Medicago*, sweet *Sorghum*, grain *Sorghum*, sugarcane, energy cane, elephant grass, maize, *Cassava*, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop and a biomass crop.

19. The genetically modified plant of claim 1, wherein:
the transcript level of VDE is increased 3-fold as compared to the control plant, wherein the transcript level of PsbS is increased 3-fold as compared to the control plant, and wherein the transcript level of ZEP is increased 8-fold as compared to the control plant;
the transcript level of VDE is increased 10-fold as compared to the control plant, wherein the transcript level of PsbS is increased 3-fold as compared to the control plant, and wherein the transcript level of ZEP is increased 6-fold as compared to the control plant;
the transcript level of VDE is increased 4-fold as compared to the control plant, wherein the transcript level of PsbS is increased 1.2-fold as compared to the control plant, and wherein the transcript level of ZEP is increased 7-fold as compared to the control plant;
the protein level of VDE is increased 16-fold as compared to the control plant, wherein the protein level of PsbS is increased 2-fold as compared to the control plant, and wherein the protein level of ZEP is increased 80-fold as compared to the control plant;
the protein level of VDE is increased 30-fold as compared to the control plant, wherein the protein level of PsbS is increased 4-fold as compared to the control plant, and wherein the protein level of ZEP is increased 74-fold as compared to the control plant;
the protein level of VDE is increased 47-fold as compared to the control plant, wherein the protein level of PsbS is increased 3-fold as compared to the control plant, and wherein the protein level of ZEP is increased 75-fold as compared to the control plant;

the increase of transcript level as compared to the control plant between VDE, PsbS and ZEP has a ratio selected from the group consisting of 3:3:8, 10:3:6, and 4:1.2:7;

the increase of protein level as compared to the control plant between VDE, PsbS and ZEP has a ratio selected from the group consisting of 16:2:80, 30:4:74, and 47:3:75;

the increase of transcript level of VDE as compared to the control plant is from about 3-fold to about 10-fold, wherein the increase of transcript level of PsbS as compared to the control plant is from about 1.2-fold to about 3-fold, and wherein the increase of transcript level of ZEP as compared to the control plant is from about 6-fold to about 8-fold; or the increase of protein level of VDE as compared to the control plant is in from about 16-fold to about 47-fold, wherein the increase of protein level of PsbS as compared to the control plant is from about 2-fold to about 4-fold, and wherein the increase of protein level of ZEP as compared to the control plant is from about 74-fold to about 80-fold.

20. The method of claim 14, wherein:

increasing expression comprises increasing the transcript level of VDE in the plant 3-fold as compared to the control plant, wherein increasing expression comprises increasing the transcript level of PsbS in the plant 3-fold as compared to the control plant, and wherein increasing expression comprises increasing the transcript level of ZEP in the plant 8-fold as compared to the control plant;

increasing expression comprises increasing the transcript level of VDE in the plant 10-fold as compared to the control plant, wherein increasing expression comprises increasing the transcript level of PsbS in the plant 3-fold as compared to the control plant, and wherein increasing expression comprises increasing the transcript level of ZEP in the plant 6-fold as compared to the control plant;

increasing expression comprises increasing the transcript level of VDE in the plant 4-fold as compared to the control plant, wherein increasing expression comprises increasing the transcript level of PsbS in the plant 1.2-fold as compared to the control plant, and wherein increasing expression comprises increasing the transcript level of ZEP in the plant 7-fold as compared to the control plant;

increasing expression comprises increasing the protein level of VDE in the plant 16-fold as compared to the control plant, wherein increasing expression comprises increasing the protein level of PsbS in the plant 2-fold as compared to the control plant, and wherein increasing expression comprises increasing the protein level of ZEP in the plant 80-fold as compared to the control plant;

increasing expression comprises increasing the protein level of VDE in the plant 30-fold as compared to the control plant, wherein increasing expression comprises increasing the protein level of PsbS in the plant 4-fold as compared to the control plant, and wherein increasing expression comprises increasing the protein level of ZEP in the plant 74-fold as compared to the control plant;

increasing expression comprises increasing the protein level of VDE in the plant 47-fold as compared to the control plant, wherein increasing expression comprises increasing the protein level of PsbS in the plant 3-fold as compared to the control plant, and wherein increasing expression comprises increasing the protein level of ZEP in the plant 75-fold as compared to the control plant;

increasing expression comprises increasing the transcript level in the plant as compared to the control plant of VDE, PsbS and ZEP in a ratio selected from the group consisting of 3:3:8, 10:3:6, and 4:1.2:7;

increasing expression comprises increasing the protein level in the plant as compared to the control plant of VDE, PsbS and ZEP in a ratio selected from the group consisting of 16:2:80, 30:4:74, and 47:3:75;

increasing expression comprises increasing the transcript level of VDE in the plant as compared to the control plant from about 3-fold to about 10-fold, wherein increasing expression comprises increasing the transcript level of PsbS in the plant as compared to the control plant from about 1.2-fold to about 3-fold, and wherein increasing expression comprises increasing the transcript level of ZEP in the plant as compared to the control plant from about 6-fold to about 8-fold; or increasing expression comprises increasing the protein level of VDE in the plant as compared to the control plant from about 16-fold to about 47-fold, wherein increasing expression comprises increasing the protein level of PsbS in the plant as compared to the control plant from about 2-fold to about 4-fold, and wherein increasing expression comprises increasing the protein level of ZEP in the plant as compared to the control plant from about 74-fold to about 80-fold.

21. The expression vector of claim 9, wherein the Rbcs1A promoter drives expression of ZEP, the GAPA-1 promoter drives expression of PsbS, and the FBA2 promoter drives expression of VDE.

22. The expression vector of claim 8, wherein the plant has an increased rate of relaxation of non-photochemical quenching (NPQ) under fluctuating light conditions as compared to the control plant grown under the same fluctuating light conditions.

* * * * *

```
                      SEQUENCE LISTING

<160> NUMBER OF SEQ ID NOS: 68

<210> SEQ ID NO 1
<211> LENGTH: 1059
<212> TYPE: DNA
<213> ORGANISM: Arabidopsis thaliana

<400> SEQUENCE: 1
atcttttaat ctcttcactt ccacaacaca acacaaaaca catcactgat ccttctctca        60
tcctcagaaa gaatggctca aaccatgctg cttacttcag gcgtcaccgc cggccatttt       120
ttgaggaaca agagcccttt ggctcagccc aaagttcacc atctcttcct ctctggaaac       180
tctccggttg cactaccatc taggagacaa tcattcgttc ctctcgctct cttcaaaccc       240
aaaaccaaag ctgctcctaa aaaggttgag aagccgaaga gcaaggttga ggatggcatc       300
tttggaacgt ctggtgggat tggtttcaca aaggcgaatg agctattcgt tggtcgtgtt       360
gctatgatcg gtttcgctgc atcgttgctt ggtgaggcgt tgacgggaaa agggatatta       420
gctcagctga atctggagac agggataccg atttacgaag cagagccatt gcttctcttc       480
ttcatcttgt tcactctgtt gggagccatt ggagctctcg gagacagagg aaaattcgtc       540
gacgatcctc ccaccgggct cgagaaagcc gtcattcctc ccggcaaaaa cgtccgatct       600
gccctcggtc tcaaagaaca aggtccattg tttgggttca cgaaggcgaa cgagttattc       660
gtaggaagat tggcacagtt gggaatagca tttttcactga taggagagat tattaccggg       720
aaaggagcat tagctcaact caacattgag accggtatac caattcaaga tatcgaacca       780
cttgtcctct taaacgttgc tttcttcttc ttcgctgcca ttaatcctgg taatggaaaa       840
ttcatcaccg atgatggtga agaaagctaa attatcatgt acttaaattt agtagagagt       900
gtgtgacctt ctcttcatgt tgagacaaaa ggaaatggac agcttaaatt gttgtaatac       960
ttatatcctt ttgtttttaa cttggaattt tctgattata tatagtttta ttacacctaa      1020
gtgactaggt gattgatatc atctagcatc tcttaacag                             1059

<210> SEQ ID NO 2
<211> LENGTH: 2385
<212> TYPE: DNA
<213> ORGANISM: Arabidopsis thaliana

<400> SEQUENCE: 2
atttgcctcc ttcttcttca aaccaatttc ttcttcttct tctctcaggt ttgagtctga        60
ggcatcacaa cagataaagt cttgaacttt gatcaagaat tctaaacgga gttttgctc       120
```

```
ttctcgtcgg tgaaagaaaa atcgagatgg gttcaactcc gttttgctac tctatcaatc    180
catctccatc aaagcttgat ttcacgagga cccatgtgtt tagtcctgtt tctaaacagt    240
tttacttaga tttatcatcg ttttccggaa acccggagg agtatctggg tttaggagcc     300
gtcgagcttt gctcggagta aaggcggcga cggcgttagt tgagaaggag gagaagagag    360
aggcggtgac ggagaagaag aagaaatcga gggttttagt tgccggaggt ggaatcggag    420
gattggtgtt tgctttagcg gctaagaaga aaggattcga tgtgttagtg tttgagaaag    480
atttgagtgc tataagagga gaaggaaaat acagaggccc gattcaaata cagagcaacg    540
ctttagctgc tttggaagct attgatattg aagttgctga acaagttatg gaagctgggt    600
gtatcactgg tgatcggatt aacggtctcg ttgatggtat ctctggtact tggtatgtaa    660
agtttgatac tttcactcct gcggcgtcac ggggacttcc tgtgactaga gtaattagta    720
gaatgactct gcagcagatt ctagcacgtg cggttggaga agatgtgatt agaaacgaga    780
gtaatgttgt tgattttgaa gattctggag ataaggttac tgtggtactc gagaatggtc    840
aacgctatga aggtgatctg cttgtgggtg cagatggcat ttggtctaag gtgagaaata    900
atttgtttgg ccgtagtgaa gctacttatt caggctacac ttgttacacg gggattgcag    960
attttatacc agcggatatc gagtctgttg gctaccgggt tttcttggga cacaaacagt   1020
actttgtttc ttcggatgtt ggtggtggaa aaatgcaatg gtatgcattt cacgaggaac   1080
cagctggtgg ggctgatgct ccaaatggta tgaagaaaag gttgtttgaa atatttgacg   1140
gttggtgcga caatgtactc gacttgttgc atgcgactga ggaggaagcc attctgagaa   1200
gagatattta tgatagaagt cctggtttta cttggggtaa agggcgtgtt acgctgctcg   1260
gggattctat ccatgcgatg cagccaaata tgggtcaagg tggatgcatg gccattgagg   1320
atagttttca actagcattg gagcttgatg aagcatggaa acagagtgtt gaaacgacta   1380
cacctgttga tgttgtttcc tctttgaaaa gatatgagga atctagaaga ctgagagtcg   1440
ctattatcca tgcaatggcg aggatggctg caattatggc ttccacttac aaagcatact   1500
taggtgttgg gcttggtcct ctgtctttct tgacaaagtt tagagtacca catccaggaa   1560
gagttggtgg tagattcttc gttgacattg ctatgccatc gatgcttgac tgggtccttg   1620
gaggtaacag tgaaaaactc caaggaaggc cacctagttg cagactcact gacaaagccg   1680
atgaccggct tcgagagtgg tttgaagatg acgatgctct tgaacgtact ataaagggag   1740
aatggtatct aattccacac ggcgacgatt gttgcgtttc ggaaacatta tgtctaacca   1800
aagatgaaga tcaaccttgc atcgtcggaa gcgaaccaga tcaagatttt cctggaatgc   1860
gcattgtgat cccttcgtct caggtttcga agatgcatgc tcgtgtgatt tacaaagacg   1920
gagctttctt cttgatggat cttcgaagcg aacacggaac ctatgtgacc gataacgaag   1980
gaagaagata tagagcaaca ccgaattttc ccgcgcggtt tagatcgtcc gacatcatcg   2040
agtttggttc agataagaag gcggcgttta gggtgaaagt aatcaggaaa actccgaaat   2100
cgacgaggaa gaatgagagt aacaacgata aattacttca gacagcttga aataagtaaa   2160
ccgatggtga aattaagtaa ttttaatcgg tttggcagat aatttgagta gtaattttct   2220
caaaagaaaa aaaatctgct ttcagctatt ccttgcatga caatgtatat ataggtctga   2280
aacaaaatat aaattataca agacattaat cttcatttct tcaacttcca ggcaacaata   2340
atctaatttt gattactaaa aggtaattat attatcaaat tgttt             2385
```

<210> SEQ ID NO 3
<211> LENGTH: 1776

```
<212> TYPE: DNA
<213> ORGANISM: Arabidopsis thaliana

<400> SEQUENCE: 3
gagatatttg ggtggagaaa acaaccgcct aggacaaaaa aaaattgtgg gtagaggagg      60
aggaggaggc tttgttcaca caccacacga cggaacattc tcttccgagt cttatccaaa     120
gcaaaatcat attttgctta aatatcttct tctccggctc tgtctctgtc tctcttcttc     180
ccgcggagct ttcagttttt gtttggtatt gcttggtgtg gggaagatta gatagtgtga     240
agaatggcag tagctacaca ttgtttcact tcaccttgtc atgaccgtat tcgattttc      300
tcaagtgatg atggtattgg taggcttggc attacaagaa agaggatcaa tggcactttc     360
ttgctcaaga ttttacctcc aatccaaagt gctgatctca gaacaactgg tgggagatcc     420
tcacgtcctt tatctgcatt caggtcagga ttctctaagg ggatatttga cattgtgcca     480
ttaccatcaa agaatgagct gaaagagctg accgctccgc tgttgctaaa actcgtgggt     540
gttttagctt gcgcgttcct tattgttcca tctgcagatg cagttgatgc acttaaaact     600
tgtgcatgct tattgaaggg atgcaggata gaactcgcaa agtgcattgc caaccctgcc     660
tgtgcagcca atgtcgcgtg ccttcagacc tgcaataacc gtccagatga accgagtgc      720
cagattaaat gtggggatct gtttgagaac agtgttgttg atgagttcaa cgagtgtgct     780
gtgtcgagaa aaagtgtgt tcctagaaaa tctgatctcg gagaatttcc tgccccagac      840
ccttctgttc ttgtacagaa cttcaacatc tcggacttta acgggaagtg gtacattaca     900
agtggcttga atccaaacctt tgatgccttc gactgccagc tgcatgagtt ccacacagaa     960
ggtgacaaca agcttgttgg aaacatctct tggagaataa agaccctaga cagtggattc    1020
tttactaggt cagccgtaca aaaattcgtg caagatccta accaacctgg tgttctctac    1080
aatcatgaca acgagtacct tcactatcaa gatgactggt atatcctgtc atcaaagata    1140
gagaataaac ctgaagacta tatttgta tactaccgtg ggcgaaacga tgcttgggat     1200
ggatatggtg gtgcagttgt atacacgaga agttctgtat acccaatag cattataca      1260
gaactcgaaa aagcagcaaa aagcataggc agagacttca gcacattcat tagaacggat    1320
aacacatgtg gtcctgaacc tgcgctcgtg gagagaattg agaagacagt ggaagaaggt    1380
gaaaggataa tcgtaaaaga ggttgaagag atagaagaag aggtagagaa ggaagtggag    1440
aaggtcggta ggactgagat gaccttgttc cagagattgg ctgaaggatt taatgaactg    1500
aagcaagacg aggagaattt cgtgagagag ttaagtaaag aagagatgga gtttttggat    1560
gagatcaaaa tggaagcaag tgaggttgaa aaattgtttg ggaaagcttt gccaatcagg    1620
aaggtcaggt agaaacaaga accaccattg ttgtacaaac tatattatac atactgtgtt    1680
cggttcatat aaagtaatat ttttgtacac agtcatcatc attccataac aattggatac    1740
agaaaacaca aggattaaac atcctttgag cgaaac                               1776

<210> SEQ ID NO 4
<211> LENGTH: 265
<212> TYPE: PRT
<213> ORGANISM: Arabidopsis thaliana

<400> SEQUENCE: 4

Met Ala Gln Thr Met Leu Leu Thr Ser Gly Val Thr Ala Gly His Phe
1               5                   10                  15

Leu Arg Asn Lys Ser Pro Leu Ala Gln Pro Lys Val His His Leu Phe
            20                  25                  30
```

```
Leu Ser Gly Asn Ser Pro Val Ala Leu Pro Ser Arg Arg Gln Ser Phe
         35                  40                  45

Val Pro Leu Ala Leu Phe Lys Pro Lys Thr Lys Ala Ala Pro Lys Lys
 50                  55                  60

Val Glu Lys Pro Lys Ser Lys Val Glu Asp Gly Ile Phe Gly Thr Ser
 65                  70                  75                  80

Gly Gly Ile Gly Phe Thr Lys Ala Asn Glu Leu Phe Val Gly Arg Val
                 85                  90                  95

Ala Met Ile Gly Phe Ala Ala Ser Leu Leu Gly Glu Ala Leu Thr Gly
             100                 105                 110

Lys Gly Ile Leu Ala Gln Leu Asn Leu Glu Thr Gly Ile Pro Ile Tyr
             115                 120                 125

Glu Ala Glu Pro Leu Leu Leu Phe Phe Ile Leu Phe Thr Leu Leu Gly
130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Asn Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Ile Pro Ile Gln Asp Ile Glu Pro Leu Val Leu Leu
225                 230                 235                 240

Asn Val Ala Phe Phe Phe Phe Ala Ala Ile Asn Pro Gly Asn Gly Lys
                245                 250                 255

Phe Ile Thr Asp Asp Gly Glu Glu Ser
            260                 265

<210> SEQ ID NO 5
<211> LENGTH: 667
<212> TYPE: PRT
<213> ORGANISM: Arabidopsis thaliana

<400> SEQUENCE: 5

Met Gly Ser Thr Pro Phe Cys Tyr Ser Ile Asn Pro Ser Pro Ser Lys
 1               5                  10                  15

Leu Asp Phe Thr Arg Thr His Val Phe Ser Pro Val Ser Lys Gln Phe
             20                  25                  30

Tyr Leu Asp Leu Ser Ser Phe Ser Gly Lys Pro Gly Gly Val Ser Gly
             35                  40                  45

Phe Arg Ser Arg Arg Ala Leu Leu Gly Val Lys Ala Ala Thr Ala Leu
 50                  55                  60

Val Glu Lys Glu Lys Arg Glu Ala Val Thr Glu Lys Lys Lys Lys
 65                  70                  75                  80

Ser Arg Val Leu Val Ala Gly Gly Ile Gly Gly Leu Val Phe Ala
                 85                  90                  95

Leu Ala Ala Lys Lys Lys Gly Phe Asp Val Leu Val Phe Glu Lys Asp
             100                 105                 110

Leu Ser Ala Ile Arg Gly Glu Gly Lys Tyr Arg Gly Pro Ile Gln Ile
             115                 120                 125

Gln Ser Asn Ala Leu Ala Ala Leu Glu Ala Ile Asp Ile Glu Val Ala
130                 135                 140
```

```
Glu Gln Val Met Glu Ala Gly Cys Ile Thr Gly Asp Arg Ile Asn Gly
145                 150                 155                 160

Leu Val Asp Gly Ile Ser Gly Thr Trp Tyr Val Lys Phe Asp Thr Phe
                165                 170                 175

Thr Pro Ala Ala Ser Arg Gly Leu Pro Val Thr Arg Val Ile Ser Arg
            180                 185                 190

Met Thr Leu Gln Gln Ile Leu Ala Arg Ala Val Gly Glu Asp Val Ile
        195                 200                 205

Arg Asn Glu Ser Asn Val Val Asp Phe Glu Asp Ser Gly Asp Lys Val
    210                 215                 220

Thr Val Val Leu Glu Asn Gly Gln Arg Tyr Glu Gly Asp Leu Leu Val
225                 230                 235                 240

Gly Ala Asp Gly Ile Trp Ser Lys Val Arg Asn Asn Leu Phe Gly Arg
                245                 250                 255

Ser Glu Ala Thr Tyr Ser Gly Tyr Thr Cys Tyr Thr Gly Ile Ala Asp
            260                 265                 270

Phe Ile Pro Ala Asp Ile Glu Ser Val Gly Tyr Arg Val Phe Leu Gly
        275                 280                 285

His Lys Gln Tyr Phe Val Ser Ser Asp Val Gly Gly Lys Met Gln
    290                 295                 300

Trp Tyr Ala Phe His Glu Glu Pro Ala Gly Gly Ala Asp Ala Pro Asn
305                 310                 315                 320

Gly Met Lys Lys Arg Leu Phe Glu Ile Phe Asp Gly Trp Cys Asp Asn
                325                 330                 335

Val Leu Asp Leu Leu His Ala Thr Glu Glu Ala Ile Leu Arg Arg
            340                 345                 350

Asp Ile Tyr Asp Arg Ser Pro Gly Phe Thr Trp Gly Lys Gly Arg Val
        355                 360                 365

Thr Leu Leu Gly Asp Ser Ile His Ala Met Gln Pro Asn Met Gly Gln
    370                 375                 380

Gly Gly Cys Met Ala Ile Glu Asp Ser Phe Gln Leu Ala Leu Glu Leu
385                 390                 395                 400

Asp Glu Ala Trp Lys Gln Ser Val Glu Thr Thr Thr Pro Val Asp Val
                405                 410                 415

Val Ser Ser Leu Lys Arg Tyr Glu Glu Ser Arg Arg Leu Arg Val Ala
            420                 425                 430

Ile Ile His Ala Met Ala Arg Met Ala Ala Ile Met Ala Ser Thr Tyr
        435                 440                 445

Lys Ala Tyr Leu Gly Val Gly Leu Gly Pro Leu Ser Phe Leu Thr Lys
    450                 455                 460

Phe Arg Val Pro His Pro Gly Arg Val Gly Gly Arg Phe Phe Val Asp
465                 470                 475                 480

Ile Ala Met Pro Ser Met Leu Asp Trp Val Leu Gly Gly Asn Ser Glu
                485                 490                 495

Lys Leu Gln Gly Arg Pro Ser Cys Arg Leu Thr Asp Lys Ala Asp
            500                 505                 510

Asp Arg Leu Arg Glu Trp Phe Glu Asp Asp Ala Leu Glu Arg Thr
        515                 520                 525

Ile Lys Gly Glu Trp Tyr Leu Ile Pro His Gly Asp Asp Cys Cys Val
    530                 535                 540

Ser Glu Thr Leu Cys Leu Thr Lys Asp Glu Asp Gln Pro Cys Ile Val
545                 550                 555                 560
```

```
Gly Ser Glu Pro Asp Gln Asp Phe Pro Gly Met Arg Ile Val Ile Pro
                565                 570                 575

Ser Ser Gln Val Ser Lys Met His Ala Arg Val Ile Tyr Lys Asp Gly
            580                 585                 590

Ala Phe Phe Leu Met Asp Leu Arg Ser Glu His Gly Thr Tyr Val Thr
            595                 600                 605

Asp Asn Glu Gly Arg Arg Tyr Arg Ala Thr Pro Asn Phe Pro Ala Arg
        610                 615                 620

Phe Arg Ser Ser Asp Ile Ile Glu Phe Gly Ser Asp Lys Lys Ala Ala
625                 630                 635                 640

Phe Arg Val Lys Val Ile Arg Lys Thr Pro Lys Ser Thr Arg Lys Asn
            645                 650                 655

Glu Ser Asn Asn Asp Lys Leu Leu Gln Thr Ala
            660                 665

<210> SEQ ID NO 6
<211> LENGTH: 462
<212> TYPE: PRT
<213> ORGANISM: Arabidopsis thaliana

<400> SEQUENCE: 6

Met Ala Val Ala Thr His Cys Phe Thr Ser Pro Cys His Asp Arg Ile
1               5                   10                  15

Arg Phe Phe Ser Ser Asp Asp Gly Ile Gly Arg Leu Gly Ile Thr Arg
            20                  25                  30

Lys Arg Ile Asn Gly Thr Phe Leu Leu Lys Ile Leu Pro Pro Ile Gln
        35                  40                  45

Ser Ala Asp Leu Arg Thr Thr Gly Gly Arg Ser Ser Arg Pro Leu Ser
50                  55                  60

Ala Phe Arg Ser Gly Phe Ser Lys Gly Ile Phe Asp Ile Val Pro Leu
65                  70                  75                  80

Pro Ser Lys Asn Glu Leu Lys Glu Leu Thr Ala Pro Leu Leu Leu Lys
                85                  90                  95

Leu Val Gly Val Leu Ala Cys Ala Phe Leu Ile Val Pro Ser Ala Asp
            100                 105                 110

Ala Val Asp Ala Leu Lys Thr Cys Ala Cys Leu Leu Lys Gly Cys Arg
        115                 120                 125

Ile Glu Leu Ala Lys Cys Ile Ala Asn Pro Ala Cys Ala Ala Asn Val
130                 135                 140

Ala Cys Leu Gln Thr Cys Asn Asn Arg Pro Asp Glu Thr Glu Cys Gln
145                 150                 155                 160

Ile Lys Cys Gly Asp Leu Phe Glu Asn Ser Val Val Asp Glu Phe Asn
                165                 170                 175

Glu Cys Ala Val Ser Arg Lys Lys Cys Val Pro Arg Lys Ser Asp Leu
            180                 185                 190

Gly Glu Phe Pro Ala Pro Asp Pro Ser Val Leu Val Gln Asn Phe Asn
        195                 200                 205

Ile Ser Asp Phe Asn Gly Lys Trp Tyr Ile Thr Ser Gly Leu Asn Pro
210                 215                 220

Thr Phe Asp Ala Phe Asp Cys Gln Leu His Glu Phe His Thr Glu Gly
225                 230                 235                 240

Asp Asn Lys Leu Val Gly Asn Ile Ser Trp Arg Ile Lys Thr Leu Asp
                245                 250                 255

Ser Gly Phe Phe Thr Arg Ser Ala Val Gln Lys Phe Val Gln Asp Pro
            260                 265                 270
```

```
Asn Gln Pro Gly Val Leu Tyr Asn His Asp Asn Glu Tyr Leu His Tyr
            275                 280                 285

Gln Asp Asp Trp Tyr Ile Leu Ser Ser Lys Ile Glu Asn Lys Pro Glu
        290                 295                 300

Asp Tyr Ile Phe Val Tyr Tyr Arg Gly Arg Asn Asp Ala Trp Asp Gly
305                 310                 315                 320

Tyr Gly Gly Ala Val Val Tyr Thr Arg Ser Ser Val Leu Pro Asn Ser
                325                 330                 335

Ile Ile Pro Glu Leu Glu Lys Ala Ala Lys Ser Ile Gly Arg Asp Phe
            340                 345                 350

Ser Thr Phe Ile Arg Thr Asp Asn Thr Cys Gly Pro Glu Pro Ala Leu
        355                 360                 365

Val Glu Arg Ile Glu Lys Thr Val Glu Glu Gly Glu Arg Ile Ile Val
370                 375                 380

Lys Glu Val Glu Glu Ile Glu Glu Val Glu Lys Glu Val Glu Lys
385                 390                 395                 400

Val Gly Arg Thr Glu Met Thr Leu Phe Gln Arg Leu Ala Glu Gly Phe
                405                 410                 415

Asn Glu Leu Lys Gln Asp Glu Glu Asn Phe Val Arg Glu Leu Ser Lys
            420                 425                 430

Glu Glu Met Glu Phe Leu Asp Glu Ile Lys Met Glu Ala Ser Glu Val
        435                 440                 445

Glu Lys Leu Phe Gly Lys Ala Leu Pro Ile Arg Lys Val Arg
450                 455                 460

<210> SEQ ID NO 7
<211> LENGTH: 46
<212> TYPE: PRT
<213> ORGANISM: Arabidopsis thaliana

<400> SEQUENCE: 7

Gln Leu Asn Leu Glu Thr Gly Ile Pro Ile Tyr Glu Ala Glu Pro Leu
1               5                   10                  15

Leu Leu Phe Phe Ile Leu Phe Thr Leu Leu Gly Ala Ile Gly Ala Leu
            20                  25                  30

Gly Asp Arg Gly Glu Ala Glu Pro Leu Leu Leu Phe Phe Ile
        35                  40                  45

<210> SEQ ID NO 8
<211> LENGTH: 49
<212> TYPE: PRT
<213> ORGANISM: Arabidopsis thaliana

<400> SEQUENCE: 8

Ile Gly Gly Leu Val Phe Ala Leu Ala Ala Lys Arg Lys Gly Phe Glu
1               5                   10                  15

Val Leu Val Phe Glu Lys Asp Leu Ser Ala Val Arg Gly Glu Gly Gln
            20                  25                  30

Tyr Arg Gly Pro Ile Gln Ile Gln Ser Asn Ala Leu Ala Ala Leu Glu
        35                  40                  45

Ala

<210> SEQ ID NO 9
<211> LENGTH: 56
<212> TYPE: PRT
<213> ORGANISM: Arabidopsis thaliana
```

```
<400> SEQUENCE: 9

Cys Ala Ala Asn Ile Ala Cys Leu Gln Thr Cys Asn Asn Arg Pro Asp
1               5                   10                  15

Glu Thr Glu Cys Gln Ile Lys Cys Gly Asp Leu Phe Glu Asn Asn Val
            20                  25                  30

Val Asp Glu Phe Asn Glu Cys Ala Val Ser Arg Lys Lys Cys Val Cys
        35                  40                  45

Ala Val Ser Arg Lys Lys Cys Val
        50                  55

<210> SEQ ID NO 10
<211> LENGTH: 272
<212> TYPE: PRT
<213> ORGANISM: Cucumis melo

<400> SEQUENCE: 10

Met Ala Ala Gln Thr Met Leu Leu Thr Ser Gly Val Cys Val Gly His
1               5                   10                  15

Gly Val Cys Leu Lys Arg Glu Leu Ser Leu Arg Pro Asn Asn Asn Gln
            20                  25                  30

Phe Thr Arg Leu Phe Phe Asn Pro Leu Pro Asn His Ser Val Ser Leu
        35                  40                  45

Pro Ala Arg Gly Phe Thr Pro Leu Ala Val Phe Lys Ser Arg Thr Lys
    50                  55                  60

Ala Pro Pro Lys Lys Val Glu Lys Pro Lys Gln Lys Val Glu Asp Gly
65                  70                  75                  80

Ile Phe Gly Thr Ser Gly Gly Ile Gly Phe Thr Lys Gln Asn Glu Leu
                85                  90                  95

Phe Val Gly Arg Val Ala Met Ile Gly Phe Ala Ala Ser Leu Leu Gly
            100                 105                 110

Glu Ala Ile Thr Gly Lys Gly Ile Leu Ala Gln Leu Asn Leu Glu Thr
        115                 120                 125

Gly Ile Pro Ile Tyr Glu Ala Glu Pro Leu Leu Leu Phe Phe Ile Leu
    130                 135                 140

Phe Thr Leu Leu Gly Ala Ile Gly Ala Leu Gly Asp Arg Gly Lys Phe
145                 150                 155                 160

Ile Asp Asp Pro Glu Pro Ala Thr Gly Leu Glu Arg Ala Val Ile Pro
                165                 170                 175

Pro Gly Lys Ser Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
        195                 200                 205

Gln Leu Gly Phe Ala Phe Ser Leu Ile Gly Ile Ile Thr Gly Lys
    210                 215                 220

Gly Ala Leu Ala Gln Leu Asn Ile Glu Thr Gly Val Pro Ile Asn Glu
225                 230                 235                 240

Ile Glu Pro Leu Val Leu Leu Asn Val Val Phe Phe Ile Ala Ala
                245                 250                 255

Val Asn Pro Gly Thr Gly Lys Phe Val Thr Asp Glu Glu Asp Asp Glu
            260                 265                 270

<210> SEQ ID NO 11
<211> LENGTH: 272
<212> TYPE: PRT
<213> ORGANISM: Cucumis sativus
```

<400> SEQUENCE: 11

```
Met Ala Ala Gln Thr Met Leu Leu Thr Ser Gly Val Cys Val Gly His
1               5                   10                  15

Gly Val Cys Leu Lys Arg Glu Leu Ser Leu Arg Pro Asn Tyr Thr Gln
            20                  25                  30

Phe Thr Arg Leu Phe Phe Asn Pro Leu Pro Ser His Ser Val Ser Leu
        35                  40                  45

Pro Pro Arg Gly Phe Thr Thr Leu Ala Val Phe Lys Ser Arg Thr Lys
    50                  55                  60

Ala Pro Pro Lys Lys Val Glu Lys Pro Lys Gln Lys Val Glu Asp Gly
65                  70                  75                  80

Ile Phe Gly Thr Ser Gly Gly Ile Gly Phe Thr Lys Gln Asn Glu Leu
                85                  90                  95

Phe Val Gly Arg Val Ala Met Ile Gly Phe Ala Ala Ser Ile Leu Gly
            100                 105                 110

Glu Ala Ile Thr Gly Lys Gly Ile Leu Ala Gln Leu Asn Leu Glu Thr
        115                 120                 125

Gly Ile Pro Ile Tyr Glu Ala Glu Pro Leu Leu Leu Phe Phe Ile Leu
    130                 135                 140

Phe Thr Leu Leu Gly Ala Ile Gly Ala Leu Gly Asp Arg Gly Lys Phe
145                 150                 155                 160

Ile Asp Asp Pro Glu Pro Ala Thr Gly Leu Glu Arg Ala Val Ile Pro
                165                 170                 175

Pro Gly Lys Ser Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
        195                 200                 205

Gln Leu Gly Phe Ala Phe Ser Leu Ile Gly Glu Ile Ile Thr Gly Lys
    210                 215                 220

Gly Ala Leu Ala Gln Leu Asn Ile Glu Thr Gly Val Pro Ile Asn Glu
225                 230                 235                 240

Ile Glu Pro Leu Val Leu Leu Asn Val Val Phe Phe Ile Ala Ala
                245                 250                 255

Val Asn Pro Gly Thr Gly Lys Phe Val Thr Asp Glu Glu Asp Asp Glu
            260                 265                 270
```

<210> SEQ ID NO 12
<211> LENGTH: 267
<212> TYPE: PRT
<213> ORGANISM: Eutrema salsugineum

<400> SEQUENCE: 12

```
Met Ala Gln Thr Met Met Leu Thr Ser Gly Val Ser Ala Asn Gln Phe
1               5                   10                  15

Leu Arg Asn Lys Asn Pro Leu Ala Gln Pro Lys Val His His Leu Phe
            20                  25                  30

Leu Ser Gly Asn Ser Pro Val Val Ile Pro Ser Arg Arg Gln Ser Leu
        35                  40                  45

Val Pro Leu Ala Leu Phe Lys Pro Lys Thr Lys Ala Ala Pro Lys Lys
    50                  55                  60

Val Glu Lys Val Lys Pro Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95
```

```
Ala Met Ile Gly Phe Ala Ala Ser Leu Leu Gly Glu Ala Val Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
    130                 135                 140

Ala Ile Gly Ala Leu Gly Asp Arg Gly Lys Phe Val Asp Asp Pro Pro
145                 150                 155                 160

Thr Pro Thr Gly Leu Glu Lys Ala Val Ile Ala Pro Gly Lys Asn Val
                165                 170                 175

Arg Ser Ala Leu Gly Leu Lys Glu Gln Gly Pro Leu Phe Gly Phe Thr
            180                 185                 190

Lys Ala Asn Glu Leu Phe Val Gly Arg Leu Ala Gln Leu Gly Ile Ala
        195                 200                 205

Phe Ser Leu Ile Gly Glu Ile Ile Thr Gly Lys Gly Ala Leu Ala Gln
    210                 215                 220

Leu Asn Ile Glu Thr Gly Ile Pro Ile Gln Asp Ile Glu Pro Leu Val
225                 230                 235                 240

Leu Leu Asn Val Ala Phe Phe Phe Ala Ala Ile Asn Pro Gly Asn
                245                 250                 255

Gly Lys Phe Ile Thr Asp Asp Gly Glu Asp Met
            260                 265

<210> SEQ ID NO 13
<211> LENGTH: 265
<212> TYPE: PRT
<213> ORGANISM: Arabidopsis thaliana

<400> SEQUENCE: 13

Met Ala Gln Thr Met Leu Leu Thr Ser Gly Val Thr Ala Gly His Phe
1               5                   10                  15

Leu Arg Asn Lys Ser Pro Leu Ala Gln Pro Lys Val His His Leu Phe
            20                  25                  30

Leu Ser Gly Asn Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys
    50                  55                  60

Val Glu Lys Pro Lys Ser Lys Val Glu Asp Gly Ile Phe Gly Thr Ser
65                  70                  75                  80

Gly Gly Ile Gly Phe Thr Lys Ala Asn Glu Leu Phe Val Gly Arg Val
            85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
    130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Asn Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205
```

```
Leu Ile Gly Glu Ile Ile Thr Gly Lys Gly Ala Leu Ala Gln Leu Asn
210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
                260                 265

<210> SEQ ID NO 14
<211> LENGTH: 265
<212> TYPE: PRT
<213> ORGANISM: Arabidopsis lyrata

<400> SEQUENCE: 14

Met Ala Gln Thr Met Leu Leu Thr Ser Gly Val Ser Ala Gly Gln Phe
1               5                   10                  15

Leu Arg Asn Lys Ser Pro Leu Ala Gln Pro Lys Val His His Leu Phe
                20                  25                  30

Leu Ser Gly Asn Ser Pro Val Val Leu Pro Ser Arg Arg Gln Ser Phe
            35                  40                  45

Val Pro Leu Ala Leu Phe Lys Pro Lys Thr Lys Ala Ala Pro Lys Lys
50                  55                  60

Val Glu Lys Pro Lys Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Ala Leu Thr Gly
                100                 105                 110

Lys Gly Ile Leu Ala Gln Leu Asn Leu Glu Thr Gly Ile Pro Ile Tyr
                115                 120                 125

Glu Ala Glu Pro Leu Leu Leu Phe Phe Ile Leu Phe Thr Leu Leu Gly
                130                 135                 140

Ala Ile Gly Ala Leu Gly Asp Arg Gly Gln Phe Val Asp Asp Pro Pro
145                 150                 155                 160

Thr Gly Leu Glu Lys Ala Val Ile Pro Pro Gly Lys Asn Val Arg Ser
                165                 170                 175

Ala Leu Gly Leu Lys Glu Gln Gly Pro Leu Phe Gly Phe Thr Lys Ala
                180                 185                 190

Asn Glu Leu Phe Val Gly Arg Leu Ala Gln Leu Gly Ile Ala Phe Ser
                195                 200                 205

Leu Ile Gly Glu Ile Ile Thr Gly Lys Gly Ala Leu Ala Gln Leu Asn
210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
                260                 265

<210> SEQ ID NO 15
<211> LENGTH: 265
<212> TYPE: PRT
<213> ORGANISM: Camelina sativa

<400> SEQUENCE: 15
```

Met Ala Gln Thr Met Leu Leu Thr Ser Gly Val Ser Ala Gly Gln Phe
1               5                   10                  15

Leu Arg Asn Lys Asn Pro Leu Ala Gln Pro Lys Val His His Leu Phe
            20                  25                  30

Leu Ser Gly Thr Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys
    50                  55                  60

Val Val Lys Pro Lys Asp Lys Val Glu Asp Gly Ile Phe Gly Thr Ser
65              70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Ala Leu Thr Gly
                100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
            130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
            260                 265

<210> SEQ ID NO 16
<211> LENGTH: 265
<212> TYPE: PRT
<213> ORGANISM: Capsella rubella

<400> SEQUENCE: 16

Met Ala Gln Thr Met Leu Leu Thr Ser Gly Val Ser Ala Gly Gln Phe
1               5                   10                  15

Leu Arg Asn Lys Asn Pro Leu Ala Gln Pro Lys Val His Gln Leu Phe
            20                  25                  30

Leu Ser Gly Thr Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys
    50                  55                  60

Val Glu Lys Val Lys Pro Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Gly Ile Thr Gly

```
            100                 105                 110
Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
        130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
            165                 170                 175

Ala Leu Gly Leu Lys Glu Gln Gly Pro Leu Phe Gly Phe Thr Lys Ala
        180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
        210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
            260                 265

<210> SEQ ID NO 17
<211> LENGTH: 265
<212> TYPE: PRT
<213> ORGANISM: Noccaea caerulescens

<400> SEQUENCE: 17

Met Ala Gln Thr Met Leu Leu Thr Ser Gly Val Ser Ala Asn Gln Phe
1               5                   10                  15

Leu Arg Asn Lys Asn Pro Leu Ala Gln Pro Lys Ile Gln His Leu Phe
            20                  25                  30

Leu Ser Gly Asn Ser Pro Val Ala Leu Pro Ser Arg Arg Pro Ser Phe
        35                  40                  45

Val Pro Leu Ala Leu Phe Lys Pro Lys Thr Lys Ala Ala Pro Lys Lys
50                  55                  60

Val Glu Lys Ala Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
            85                  90                  95

Ala Met Ile Gly Phe Ala Ala Ser Leu Leu Gly Glu Ala Leu Thr Gly
        100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
        130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Ser Val Arg Ser
            165                 170                 175

Ala Leu Gly Leu Lys Glu Gln Gly Pro Leu Phe Gly Phe Thr Lys Ser
        180                 185                 190

Asn Glu Leu Phe Val Gly Arg Leu Ala Gln Leu Gly Ile Ala Phe Ser
            195                 200                 205
```

```
Leu Ile Gly Glu Ile Ile Thr Gly Lys Gly Ala Leu Ala Gln Leu Asn
210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
                260                 265

<210> SEQ ID NO 18
<211> LENGTH: 265
<212> TYPE: PRT
<213> ORGANISM: Brassica napus

<400> SEQUENCE: 18

Met Ala Gln Thr Met Leu Leu Thr Ser Gly Ile Ser Ala Asn His Phe
1               5                   10                  15

Leu Arg Asn Lys Asn Pro Leu Ala Gln Pro Lys Val His His Leu Phe
            20                  25                  30

Leu Ser Gly Asn Ser Pro Val Thr Leu Pro Ser Arg Ile Pro Ser Leu
        35                  40                  45

Val Pro Leu Ala Ile Phe Lys Pro Lys Thr Lys Ala Ala Pro Lys Lys
    50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
    130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
                260                 265

<210> SEQ ID NO 19
<211> LENGTH: 265
<212> TYPE: PRT
<213> ORGANISM: Raphanus sativus

<400> SEQUENCE: 19
```

```
Met Ala Gln Thr Met Leu Leu Thr Ser Gly Ile Ser Ala Asn His Phe
1               5                   10                  15

Leu Arg Asn Lys Asn Pro Leu Ala Gln Pro Lys Val His His Leu Phe
            20                  25                  30

Leu Ser Gly Asn Ser Pro Val Thr Leu Pro Ser Arg Arg Pro Ser Leu
        35                  40                  45

Val Pro Leu Ala Ile Phe Lys Pro Lys Thr Lys Ala Ala Pro Lys Lys
50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Phe Phe Ile Leu Phe Thr Leu Leu Gly
130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
            165                 170                 175

Ala Leu Gly Leu Lys Glu Gln Gly Pro Leu Phe Gly Phe Thr Lys Ala
        180                 185                 190

Asn Glu Leu Phe Val Gly Arg Leu Ala Gln Leu Gly Ile Ala Phe Ser
    195                 200                 205

Leu Ile Gly Glu Ile Ile Thr Gly Lys Gly Ala Leu Ala Gln Leu Asn
210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
            260                 265

<210> SEQ ID NO 20
<211> LENGTH: 265
<212> TYPE: PRT
<213> ORGANISM: Brassica rapa

<400> SEQUENCE: 20

Met Ala Gln Thr Met Leu Leu Thr Ser Gly Ile Ser Ala Asn His Phe
1               5                   10                  15

Leu Arg Asn Lys Asn Pro Leu Ala Gln Pro Lys Val His His Leu Phe
            20                  25                  30

Leu Ser Gly Asn Ser Pro Val Thr Leu Pro Ser Arg Arg Pro Ser Leu
        35                  40                  45

Val Pro Leu Ala Ile Phe Lys Pro Lys Thr Lys Ala Ala Pro Lys Lys
50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
            100                 105                 110
```

-continued

Lys Gly Ile Leu Ala Gln Leu Asn Leu Glu Thr Gly Ile Pro Ile Tyr
            115                 120                 125

Glu Ala Glu Pro Leu Leu Phe Phe Ile Leu Phe Thr Leu Leu Gly
        130                 135                 140

Ala Ile Gly Ala Leu Gly Asp Arg Gly Lys Phe Val Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
                180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
        210                 215                 220

Ile Glu Thr Gly Ile Pro Ile Gln Asp Ile Glu Pro Leu Val Leu Leu
225                 230                 235                 240

Asn Val Ala Phe Phe Ala Ala Ala Ile Asn Pro Gly Asn Gly Lys
                245                 250                 255

Phe Ile Thr Asp Asp Gly Glu Glu Ser
            260                 265

<210> SEQ ID NO 21
<211> LENGTH: 265
<212> TYPE: PRT
<213> ORGANISM: Raphanus sativus

<400> SEQUENCE: 21

Met Ala Gln Thr Met Leu Leu Thr Ser Gly Val Ser Ala Asn Thr Phe
1               5                   10                  15

Leu Arg Asn Lys Asn Pro Leu Ala Gln Pro Lys Val His His Leu Phe
            20                  25                  30

Leu Ser Gly Asn Ser His Val Ile Leu Pro Ser Arg Arg Pro Ser Leu
        35                  40                  45

Val Pro Leu Ala Ile Phe Lys Pro Lys Thr Lys Ala Ala Pro Lys Lys
50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
            115                 120                 125

Glu Ala Glu Pro Leu Leu Phe Phe Ile Leu Phe Thr Leu Leu Gly
        130                 135                 140

Ala Ile Gly Ala Leu Gly Asp Arg Gly Lys Phe Val Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
                180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
            260                 265

<210> SEQ ID NO 22
<211> LENGTH: 265
<212> TYPE: PRT
<213> ORGANISM: Brassica napus

<400> SEQUENCE: 22

Met Ala Gln Thr Met Leu Leu Thr Ser Gly Val Ser Ala Asn Gln Phe
1               5                   10                  15

Leu Arg Asn Lys Asn Pro Leu Ala Gln Pro Lys Val His His Phe Phe
                20                  25                  30

Leu Ser Gly Asn Ser His Val Val Leu Pro Ser Arg Pro Ser Leu
            35                  40                  45

Val Pro Leu Ala Ile Phe Lys Pro Lys Thr Lys Ala Ala Pro Lys Lys
50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
            85                  90                  95

Ala Met Ile Gly Phe Ala Ala Ser Leu Leu Gly Glu Ala Leu Thr Gly
                100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
            260                 265

<210> SEQ ID NO 23
<211> LENGTH: 265
<212> TYPE: PRT
<213> ORGANISM: Brassica rapa

<400> SEQUENCE: 23

Met Ala Gln Thr Met Leu Leu Thr Ser Gly Val Ser Ala Asn Gln Phe

```
                1               5              10              15
            Leu Arg Asn Lys Asn Pro Leu Ala Gln Pro Lys Val His His Phe Phe
                           20                  25                  30
            Leu Ser Gly Asn Ser His Val Val Leu Pro Ser Arg Arg Pro Ser Leu
                           35                  40                  45
            Val Pro Leu Ala Ile Phe Lys Pro Lys Thr Lys Ala Ala Pro Lys Lys
             50                  55                  60
            Val Glu Lys Val Lys Pro Lys Val Glu Asp Gly Ile Phe Gly Thr Ser
             65                  70                  75                  80
            Gly Gly Ile Gly Phe Thr Lys Gln Asn Glu Leu Phe Val Gly Arg Val
                           85                  90                  95
            Ala Met Ile Gly Phe Ala Ala Ser Leu Leu Gly Glu Ala Leu Thr Gly
                          100                 105                 110
            Lys Gly Ile Leu Ala Gln Leu Asn Leu Glu Thr Gly Ile Pro Ile Tyr
                          115                 120                 125
            Glu Ala Glu Pro Leu Leu Leu Phe Phe Ile Leu Phe Thr Leu Leu Gly
                          130                 135                 140
            Ala Ile Gly Ala Leu Gly Asp Arg Gly Lys Phe Val Asp Asp Pro Pro
            145                 150                 155                 160
            Thr Gly Leu Glu Lys Ala Val Ile Pro Pro Gly Lys Gly Val Arg Ser
                          165                 170                 175
            Ala Leu Gly Leu Lys Glu Gln Gly Pro Leu Phe Gly Phe Thr Lys Ala
                          180                 185                 190
            Asn Glu Leu Phe Val Gly Arg Leu Ala Gln Leu Gly Ile Ala Phe Ser
                          195                 200                 205
            Leu Ile Gly Glu Ile Ile Thr Gly Lys Gly Ala Leu Ala Gln Leu Asn
                          210                 215                 220
            Ile Glu Thr Gly Ile Pro Ile Gln Asp Ile Glu Pro Leu Val Leu Leu
            225                 230                 235                 240
            Asn Val Ala Phe Phe Phe Phe Ala Ala Ile Asn Pro Gly Asn Gly Lys
                          245                 250                 255
            Phe Ile Thr Asp Asp Gly Glu Glu Arg
                          260                 265

<210> SEQ ID NO 24
<211> LENGTH: 274
<212> TYPE: PRT
<213> ORGANISM: Phoenix dactylifera

<400> SEQUENCE: 24

Met Val His Ala Val Phe Thr Ser Gly Leu Gly Ala His Leu Pro Asp
1               5                   10                  15
Ser Lys Arg Glu Pro Leu Leu Gln Ser Gln Leu Arg Arg Leu Arg Pro
                20                  25                  30
Thr Pro Phe Ser His Leu Leu Leu Ser Gln Pro Ser His Lys Gln Leu
                35                  40                  45
Pro Ser Pro Ser Tyr Ser Ser Tyr Thr Pro Val Leu Ala Leu Phe Lys
            50                  55                  60
Ser Lys Thr Lys Ala Pro Pro Lys Lys Val Glu Lys Ala Lys Pro Lys
65                  70                  75                  80
Val Glu Asp Gly Ile Phe Gly Thr Ser Gly Gly Ile Gly Phe Thr Lys
                85                  90                  95
Gln Asn Glu Leu Phe Val Gly Arg Val Ala Met Ile Gly Phe Ala Ala
                100                 105                 110
```

```
Ser Leu Leu Gly Glu Ala Ile Thr Gly Lys Gly Ile Leu Ala Gln Leu
            115                 120                 125

Asn Leu Glu Thr Gly Ile Pro Ile Tyr Glu Ala Glu Pro Leu Leu Leu
130                 135                 140

Phe Phe Ile Leu Phe Thr Leu Leu Gly Ala Ile Gly Ala Leu Gly Asp
145                 150                 155                 160

Arg Gly Arg Phe Val Asp Asp Pro Thr Gly Leu Asp Lys Ala Val
                165                 170                 175

Ile Pro Pro Gly Lys Gly Ile Arg Ser Ala Leu Gly Leu Lys Glu Gly
            180                 185                 190

Gly Pro Leu Phe Gly Phe Thr Lys Ser Asn Glu Leu Phe Val Gly Arg
            195                 200                 205

Leu Ala Gln Leu Gly Ile Ala Phe Ser Ile Ile Gly Glu Ile Val Thr
            210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Phe Asn Val Ile Phe Phe Ile
            245                 250                 255

Ala Ala Leu Asn Pro Gly Asn Gly Lys Phe Val Thr Asp Val Asp Glu
            260                 265                 270

Glu Glu

<210> SEQ ID NO 25
<211> LENGTH: 270
<212> TYPE: PRT
<213> ORGANISM: Anthurium amnicola

<400> SEQUENCE: 25

Met Ala Gln Ser Met Leu Met Ser Ser Leu Gly Ser Arg Leu Val Glu
1               5                   10                  15

Thr Lys Gly Glu Pro Leu Leu Gln Phe Gln Ile Arg Arg Leu Arg Pro
            20                  25                  30

Thr Pro Ala Thr His Leu Leu Leu Pro Pro Thr Arg Arg His Pro
        35                  40                  45

Leu Pro Pro Ser Tyr Ala Pro Thr Leu Ala Ala Phe Lys Ser Lys Thr
    50                  55                  60

Lys Ala Ala Pro Lys Lys Val Glu Lys Gly Asn Phe Lys Val Glu Asp
65                  70                  75                  80

Gly Ile Phe Gly Thr Ser Gly Ile Gly Phe Thr Lys Gln Asn Glu
            85                  90                  95

Leu Phe Val Gly Arg Val Ala Met Ile Gly Phe Ala Ala Ser Leu Leu
            100                 105                 110

Gly Glu Ala Ile Thr Gly Lys Gly Ile Leu Ala Gln Leu Asn Leu Glu
            115                 120                 125

Thr Gly Ile Pro Ile Tyr Glu Ala Glu Pro Leu Leu Leu Phe Phe Ile
        130                 135                 140

Leu Phe Thr Leu Leu Gly Ala Ile Gly Ala Leu Gly Asp Arg Gly Arg
145                 150                 155                 160

Phe Val Asp Asp Pro Thr Gly Leu Asp Lys Ala Val Val Pro Pro
                165                 170                 175

Gly Lys Gly Phe Arg Ser Ser Leu Gly Leu Lys Glu Gly Gly Pro Leu
            180                 185                 190

Phe Gly Phe Thr Lys Ser Asn Glu Leu Phe Val Gly Arg Leu Ala Gln
            195                 200                 205
```

```
Leu Gly Ile Ala Phe Ser Ile Ile Gly Glu Ile Ile Thr Gly Lys Gly
    210                 215                 220

Ala Leu Ala Gln Leu Asn Ile Glu Thr Gly Val Pro Ile Ser Asp Ile
225                 230                 235                 240

Glu Pro Leu Val Leu Asn Val Val Phe Phe Leu Ala Ala Leu
            245                 250                 255

Asn Pro Gly Thr Gly Gln Phe Val Thr Asp Asp Gly Glu Asp
            260                 265                 270
```

<210> SEQ ID NO 26
<211> LENGTH: 269
<212> TYPE: PRT
<213> ORGANISM: Trifolium subterraneum

<400> SEQUENCE: 26

```
Met Ala Gln Thr Met Leu Leu Met Ser Ser Val Ser Ser Thr Tyr Ser
1               5                   10                  15

Val Glu Leu Lys Lys Asp Pro Leu Leu Gln Leu Gln Cys Gln Arg Leu
            20                  25                  30

Arg Ser Arg Ile Ser Asp Val Ser Phe Asn Pro Leu Ser Ser Asn Ser
        35                  40                  45

Lys Ser Leu Ser Ser Arg Thr Phe Thr Thr Leu Ala Leu Phe Lys Ser
    50                  55                  60

Lys Thr Lys Ala Pro Ala Lys Val Val Lys Pro Lys Pro Lys Val Glu
65                  70                  75                  80

Asp Gly Ile Phe Gly Thr Ser Gly Phe Gly Phe Thr Lys Gln Asn
                85                  90                  95

Glu Leu Phe Val Gly Arg Val Ala Met Ile Gly Phe Ala Ala Ser Ile
            100                 105                 110

Leu Gly Glu Ala Leu Thr Gly Lys Gly Ile Leu Ala Gln Leu Asn Leu
        115                 120                 125

Glu Thr Gly Ile Pro Ile Tyr Glu Ala Glu Pro Leu Leu Leu Phe Phe
    130                 135                 140

Ile Ile Phe Thr Leu Leu Gly Ala Ile Gly Ala Leu Gly Asp Arg Gly
145                 150                 155                 160

Lys Phe Val Asp Asp Glu Pro Thr Thr Gly Val Ile Pro Pro Gly
                165                 170                 175

Lys Gly Phe Arg Ala Ala Leu Gly Leu Arg Glu Gly Pro Leu Phe
            180                 185                 190

Gly Phe Thr Lys Ser Asn Glu Leu Phe Val Gly Arg Leu Ala Gln Leu
        195                 200                 205

Gly Phe Val Phe Ser Leu Ile Gly Glu Ile Ile Thr Gly Lys Gly Ala
    210                 215                 220

Leu Ala Gln Leu Asn Val Glu Thr Gly Val Pro Ile Thr Glu Ile Glu
225                 230                 235                 240

Pro Leu Val Leu Phe Asn Val Ile Phe Phe Ile Ala Ala Leu Asn
                245                 250                 255

Pro Gly Thr Gly Thr Phe Val Thr Asp Glu Glu Glu Asp
            260                 265
```

<210> SEQ ID NO 27
<211> LENGTH: 270
<212> TYPE: PRT
<213> ORGANISM: Pisum sativum

<400> SEQUENCE: 27

Met Ala Gln Thr Met Leu Leu Met Ser Ser Val Ser Thr Tyr Ser
1               5                   10                  15

Val Pro Leu Asn Lys Asp Pro Leu Leu Gln Leu Gln Cys Gln Arg Leu
                20                  25                  30

Lys Pro Arg Phe Ser Asp Ile Ser Phe Ser Pro Leu Ser Ser Asn Ser
            35                  40                  45

Lys Ser Phe Ser Ser Arg Thr Phe Lys Thr Leu Ala Leu Phe Lys Ser
        50                  55                  60

Lys Thr Lys Ala Pro Ala Lys Val Val Pro Lys Gln Lys Pro Lys Val
65                  70                  75                  80

Glu Asp Gly Val Phe Gly Thr Ser Gly Gly Phe Gly Phe Thr Lys Gln
                85                  90                  95

Asn Glu Leu Phe Val Gly Arg Val Ala Met Ile Gly Phe Ala Ala Ser
                100                 105                 110

Ile Leu Gly Glu Gly Ile Thr Gly Lys Gly Ile Leu Ser Gln Leu Asn
            115                 120                 125

Leu Glu Thr Gly Ile Pro Ile Tyr Glu Ala Glu Pro Leu Leu Leu Phe
        130                 135                 140

Phe Ile Ile Phe Thr Leu Leu Gly Ala Ile Gly Ala Leu Gly Asp Arg
145                 150                 155                 160

Gly Lys Phe Val Asp Asp Glu Pro Thr Thr Gly Gly Val Ile Pro Pro
                165                 170                 175

Gly Lys Gly Phe Arg Gln Ala Leu Gly Leu Ser Glu Gly Gly Pro Leu
                180                 185                 190

Phe Gly Phe Thr Lys Ser Asn Glu Leu Phe Val Gly Arg Leu Ala Gln
            195                 200                 205

Leu Gly Phe Ala Phe Ser Leu Ile Gly Glu Ile Ile Thr Gly Lys Gly
        210                 215                 220

Ala Leu Ala Gln Leu Asn Ile Glu Thr Gly Val Pro Ile Asn Glu Ile
225                 230                 235                 240

Glu Pro Leu Val Leu Phe Asn Val Ala Phe Phe Ile Ala Ala Leu
                245                 250                 255

Asn Pro Gly Thr Gly Lys Phe Val Thr Asp Glu Glu Glu Asp
                260                 265                 270

<210> SEQ ID NO 28
<211> LENGTH: 271
<212> TYPE: PRT
<213> ORGANISM: Beta vulgaris

<400> SEQUENCE: 28

Met Ala Gln Ala Met Leu Leu Met Pro Ser Val Ser Thr Thr Asn Thr
1               5                   10                  15

Ile Asp Leu Lys Arg Asn Ala Leu Leu Lys Ile Gln Ile Gln Lys Ile
                20                  25                  30

Lys Pro Lys Ser Ser Ser Ser His Leu Phe Phe Ser Pro Leu Ser Ser
            35                  40                  45

Ser Ser Ser Ser Ser Ser Thr Phe Lys Thr Leu Ala Leu Phe Lys Pro
        50                  55                  60

Lys Thr Lys Ala Pro Val Lys Lys Val Glu Lys Pro Lys Leu Lys Val
65                  70                  75                  80

Glu Asp Gly Leu Phe Gly Thr Ser Gly Gly Ile Gly Phe Thr Lys Glu
                85                  90                  95

Asn Glu Leu Phe Val Gly Arg Val Ala Met Ile Gly Phe Ala Ala Ser
                100                 105                 110

```
Leu Leu Gly Glu Gly Leu Thr Gly Lys Gly Ile Ala Gln Leu Asn
            115                 120                 125

Leu Glu Thr Gly Ile Pro Ile Tyr Glu Ala Glu Pro Leu Leu Leu
130                 135                 140

Phe Ile Leu Phe Thr Leu Leu Gly Ala Ile Gly Ala Leu Gly Asp Arg
145                 150                 155                 160

Gly Arg Phe Val Asp Asp Pro Pro Thr Gly Leu Glu Lys Ala Val Ile
                165                 170                 175

Pro Pro Gly Lys Asn Val Arg Ser Ala Leu Gly Leu Arg Glu Gly Gly
            180                 185                 190

Pro Leu Phe Gly Phe Thr Lys Ser Asn Glu Leu Phe Val Gly Arg Leu
            195                 200                 205

Ala Gln Leu Gly Phe Ala Phe Ser Leu Ile Gly Glu Ile Ile Thr Gly
            210                 215                 220

Lys Gly Ala Leu Ala Gln Leu Asn Ile Glu Thr Gly Val Pro Val Asn
225                 230                 235                 240

Glu Ile Glu Pro Leu Val Leu Asn Val Leu Phe Phe Phe Ile Ala
                245                 250                 255

Ala Ile Asn Pro Gly Thr Gly Lys Phe Ile Thr Asp Glu Glu Glu
            260                 265                 270

<210> SEQ ID NO 29
<211> LENGTH: 274
<212> TYPE: PRT
<213> ORGANISM: Cephalotus follicularis

<400> SEQUENCE: 29

Met Ala Gln Thr Met Leu Leu Met Cys Gly Ile Ser Thr Ser His Val
1               5                   10                  15

Val Asp Leu Arg Arg Asp Pro Leu Phe His Val Gln Ile Gln Lys Leu
                20                  25                  30

Arg Pro Lys Ser Phe Ser His Leu Phe Phe Asn Pro Leu Ser Asn Asn
            35                  40                  45

Gly Phe Ser Leu Ala Gln Lys Phe Asn Thr Leu Ala Leu Phe Lys Ser
50                  55                  60

Lys Thr Lys Ala Ala Pro Lys Val Ala Thr Thr Ala Lys Pro Lys
65                  70                  75                  80

Val Glu Asp Gly Leu Phe Gly Thr Ser Gly Ile Gly Phe Thr Lys
                        85                  90                  95

Gln Asn Glu Leu Phe Val Gly Arg Val Ala Met Ile Gly Phe Ala Ala
            100                 105                 110

Ser Leu Leu Gly Glu Ala Val Thr Gly Lys Gly Ile Leu Ser Gln Leu
            115                 120                 125

Asn Leu Glu Thr Gly Ile Pro Ile Tyr Glu Ala Glu Pro Leu Leu Leu
            130                 135                 140

Phe Phe Ile Leu Phe Thr Leu Leu Gly Ala Ile Gly Ala Leu Gly Asp
145                 150                 155                 160

Arg Gly Arg Phe Val Asp Asp Glu Pro Thr Gly Leu Glu Arg Ala Val
                165                 170                 175

Ile Pro Pro Gly Lys Gly Ile Arg Gly Ala Leu Gly Leu Arg Glu Gly
            180                 185                 190

Gly Pro Leu Phe Gly Phe Thr Lys Ser Asn Glu Leu Phe Val Gly Arg
            195                 200                 205

Leu Ala Gln Leu Gly Ile Ala Phe Ser Leu Ile Gly Glu Ile Ile Thr
```

```
            210                 215                 220
Gly Lys Gly Ala Leu Ala Gln Leu Asn Ile Glu Thr Gly Ile Pro Ile
225                 230                 235                 240

Asn Glu Ile Glu Pro Leu Val Leu Phe Asn Val Ile Phe Phe Phe Phe
                245                 250                 255

Ala Ala Leu Asn Pro Gly Thr Gly Lys Phe Val Thr Asp Glu Glu Ala
                260                 265                 270

Glu Asp

<210> SEQ ID NO 30
<211> LENGTH: 665
<212> TYPE: PRT
<213> ORGANISM: Tarenaya hassleriana

<400> SEQUENCE: 30

Met Gly Ser Thr Leu Phe Cys Ser Pro Val Asn Pro Ser Leu Ser Lys
1               5                   10                  15

Leu Asp Phe Ser Arg Thr His Leu Leu Ser Pro Ala Asp Lys His Phe
                20                  25                  30

Phe Leu Asp Leu Pro Ser Phe Met Gly Lys Val Arg Gly Lys Ser Ser
            35                  40                  45

Val Met Ser Arg Arg Val Val Gly Val Lys Ala Thr Ala Ala Val
50                  55                  60

Glu Glu Glu Arg Arg Glu Thr Ala Ala Glu Lys Glu Lys Leu Arg Val
65                  70                  75                  80

Leu Val Ala Gly Gly Gly Ile Gly Gly Leu Val Phe Ala Leu Ala Ala
                85                  90                  95

Lys Arg Lys Gly Phe Asp Val Ala Val Phe Glu Lys Asp Leu Ser Ala
                100                 105                 110

Ile Arg Gly Glu Gly Gln Tyr Arg Gly Pro Ile Gln Ile Gln Ser Asn
            115                 120                 125

Ala Leu Ala Ala Leu Glu Ala Ile Asp Met Gly Val Ala Glu Glu Val
            130                 135                 140

Met Glu Ala Gly Cys Ile Thr Gly Asp Arg Ile Asn Gly Leu Val Asp
145                 150                 155                 160

Gly Val Ser Gly Ser Trp Tyr Val Lys Phe Asp Thr Phe Thr Pro Ala
                165                 170                 175

Ala Glu Arg Gly Leu Pro Val Thr Arg Val Ile Ser Arg Met Thr Leu
            180                 185                 190

Gln Gln Ile Leu Ala Arg Ala Val Gly Glu Asp Val Ile Gln Asn Glu
        195                 200                 205

Ser Asn Val Val Ser Phe Ser Glu Ser Glu Asp Lys Val Thr Val Val
    210                 215                 220

Leu Glu Asn Gly Glu Cys Tyr Gln Gly Asp Leu Leu Val Gly Ala Asp
225                 230                 235                 240

Gly Ile Trp Ser Lys Val Arg Ser Gln Leu Phe Gly His Glu Glu Ala
                245                 250                 255

Thr Tyr Ser Gly Tyr Thr Cys Tyr Thr Gly Ile Ala Asp Phe Val Pro
            260                 265                 270

Ala Asp Ile Glu Ser Val Gly Tyr Arg Val Phe Leu Gly His Lys Gln
        275                 280                 285

Tyr Phe Val Ser Ser Asp Val Gly Gly Gly Lys Met Gln Trp Tyr Ala
    290                 295                 300

Phe His Glu Glu Pro Ala Gly Gly Arg Asp Ala Pro Asp Gly Arg Lys
```

```
            305                 310                 315                 320
        Lys Arg Leu Leu Glu Ile Phe Gln Gly Trp Cys Asp Asn Val Ile Asp
                        325                 330                 335

Leu Leu His Ala Thr Glu Asp Ala Ile Leu Arg Arg Asp Ile Tyr
                    340                 345                 350

Asp Arg Thr Pro Ser Phe Thr Trp Gly Lys Gly Arg Val Thr Leu Leu
                        355                 360                 365

Gly Asp Ser Ile His Ala Met Gln Pro Asn Met Gly Gln Gly Gly Cys
                370                 375                 380

Met Ala Ile Glu Asp Ser Tyr Gln Leu Ala Trp Glu Leu Glu His Ala
        385                 390                 395                 400

Trp Arg Arg Ser Val Glu Thr Asp Lys Pro Ile Asp Ile Val Ser Ser
                        405                 410                 415

Leu Arg Ser Tyr Glu Glu Ala Arg Lys Leu Arg Val Ala Ile Ile His
                    420                 425                 430

Gly Met Ala Arg Met Ala Ala Ile Met Ala Ser Thr Tyr Lys Gly Tyr
                435                 440                 445

Leu Gly Val Gly Leu Gly Pro Leu Ser Phe Leu Thr Met Leu Arg Ile
            450                 455                 460

Pro His Pro Gly Thr Val Gly Gly Arg Phe Phe Ile Asp Val Ala Met
        465                 470                 475                 480

Pro Leu Met Leu Asn Trp Val Leu Gly Gly Asn Ser Ser Lys Leu Glu
                        485                 490                 495

Gly Arg Leu Pro Cys Cys Arg Leu Ser Asp Lys Ala Asp Gln Leu
                    500                 505                 510

Gln Arg Trp Phe Gln Asp Asn Asp Ala Leu Glu Arg Thr Val Ile Gly
                515                 520                 525

Asp Trp Tyr Leu Ile Pro Tyr Gly Asn Asp Ser Ile Val Ser Glu Thr
            530                 535                 540

Val Arg Leu Asp Lys Asp Glu Asp Gln Pro Cys Ile Ile Gly Ser Glu
        545                 550                 555                 560

Pro Asp Glu Asp Phe Pro Gly Met Arg Ile Glu Ile Pro Ser Ser Gln
                        565                 570                 575

Val Ser Lys Val His Ala Arg Ile Ile Tyr Lys Asp Gly Ala Phe Phe
                    580                 585                 590

Val Met Asp Leu Arg Ser Glu Tyr Gly Thr Tyr Ile Thr Asp Asn Glu
                595                 600                 605

Gly Arg Arg Tyr Arg Val Thr Pro Asn Phe Pro Ala Arg Phe Arg Pro
            610                 615                 620

Ser Asp Ile Ile Glu Leu Gly Ser Asp Lys Lys Ala Ala Phe Arg Val
        625                 630                 635                 640

Lys Val Ile Arg Lys Thr Pro Lys Met Thr Arg Arg Asp Arg Glu
                        645                 650                 655

Ser Ser Ser Lys Leu Leu Gln Ala Ala
                    660                 665

<210> SEQ ID NO 31
<211> LENGTH: 663
<212> TYPE: PRT
<213> ORGANISM: Arabis alpina

<400> SEQUENCE: 31

Met Gly Ser Thr Pro Phe Cys Tyr Thr Ile Asn Pro Pro Ser Lys
        1               5                   10                  15
```

```
Leu Asp Phe Thr Lys Thr His Leu Ala Lys Gln Phe Tyr Leu Asp Leu
             20                  25                  30

Ser Ser Phe Thr Gly Lys Ser Gly Ala Gly Leu Ser Gly Ile Lys Asn
         35                  40                  45

Arg Arg Gly Val Val Gly Val Lys Ala Ser Ala Thr Ala Leu Val Glu
     50                  55                  60

Glu Glu Lys Arg Glu Thr Val Thr Glu Lys Lys Lys Ser Arg Val
 65                  70                  75                  80

Leu Val Ala Gly Gly Ile Gly Gly Leu Val Phe Ala Leu Ala Ala
                 85                  90                  95

Lys Lys Lys Gly Phe Asp Val Leu Val Phe Glu Lys Asp Leu Ser Ala
                100                 105                 110

Ile Arg Gly Glu Gly Gln Tyr Arg Gly Pro Ile Gln Ile Gln Ser Asn
             115                 120                 125

Ala Leu Ala Ala Leu Glu Ala Ile Asp Ile Ala Val Ala Glu Glu Val
         130                 135                 140

Met Glu Ala Gly Cys Ile Thr Gly Asp Arg Ile Asn Gly Leu Val Asp
145                 150                 155                 160

Gly Val Ser Gly Thr Trp Tyr Val Lys Phe Asp Thr Phe Thr Pro Ala
                 165                 170                 175

Ala Ser Arg Gly Leu Pro Val Thr Arg Val Ile Ser Arg Met Thr Leu
             180                 185                 190

Gln Gln Ile Leu Ala Arg Ala Val Gly Glu Val Ile Arg Asn Glu
         195                 200                 205

Ser Asn Val Val Asp Phe Glu Asp Ser Gly Asp Lys Val Thr Val Val
210                 215                 220

Leu Glu Asn Gly Gln Arg Tyr Glu Gly Asp Leu Leu Val Gly Ala Asp
225                 230                 235                 240

Gly Ile Trp Ser Lys Val Arg Asn Asn Leu Phe Gly Arg Ser Glu Ala
                 245                 250                 255

Thr Tyr Ser Gly Tyr Thr Cys Tyr Thr Gly Ile Ala Asp Phe Ile Pro
             260                 265                 270

Ala Asp Ile Glu Ser Val Gly Tyr Arg Val Phe Leu Gly His Lys Gln
         275                 280                 285

Tyr Phe Val Ser Ser Asp Val Gly Gly Gly Lys Met Gln Trp Tyr Ala
290                 295                 300

Phe Tyr Glu Glu Pro Ala Gly Gly Val Asp Ala Pro Asn Gly Met Lys
305                 310                 315                 320

Lys Arg Leu Phe Asp Ile Phe Glu Gly Trp Cys Asp Asn Val Leu Asp
             325                 330                 335

Leu Leu His Ala Thr Glu Glu Ala Ile Leu Arg Arg Asp Ile Tyr
         340                 345                 350

Asp Arg Ser Pro Ser Phe Thr Trp Gly Lys Gly Arg Val Thr Leu Leu
             355                 360                 365

Gly Asp Ser Ile His Ala Met Gln Pro Asn Met Gly Gln Gly Gly Cys
         370                 375                 380

Met Ala Ile Glu Asp Ser Tyr Gln Leu Ala Ser Glu Leu Glu Asp Ala
385                 390                 395                 400

Trp Lys Gln Ser Val Asp Thr Asn Arg Pro Val Asp Val Ser Ser
                 405                 410                 415

Leu Lys Arg Tyr Glu Glu Ser Arg Arg Leu Arg Val Ala Ile Ile His
             420                 425                 430

Gly Met Ala Arg Met Ala Ala Ile Met Ala Ser Thr Tyr Lys Ala Tyr
```

```
                435                 440                 445
Leu Gly Val Gly Leu Gly Pro Leu Ser Phe Leu Thr Lys Phe Arg Val
    450                 455                 460

Pro His Pro Gly Arg Val Gly Gly Arg Phe Phe Ile Asp Ile Ala Met
465                 470                 475                 480

Pro Leu Met Leu Asn Trp Val Leu Gly Gly Asn Ser Glu Lys Leu Glu
                485                 490                 495

Gly Arg Ala Pro Ser Cys Arg Leu Thr Asp Arg Ala Asp Asp Arg Leu
            500                 505                 510

Arg Glu Trp Phe Asp Asp Asn Glu Ala Leu Glu Arg Thr Ile Ser Gly
        515                 520                 525

Glu Trp Tyr Leu Ile Pro Gln Gly Asp Asp Cys Cys Val Ser Glu Thr
    530                 535                 540

Leu Cys Leu Thr Lys Asp Glu Asp Gln Pro Cys Ile Ile Gly Ser Glu
545                 550                 555                 560

Pro Asp Lys Asp Phe Pro Gly Met His Ile Val Ile Pro Ser Ser Gln
                565                 570                 575

Val Ser Lys Met His Ala Arg Ile Ile Tyr Lys Asp Gly Ala Phe Phe
            580                 585                 590

Val Met Asp Leu Arg Ser Glu His Gly Thr Tyr Val Val Asp Asn Glu
        595                 600                 605

Gly Gly Arg Tyr Arg Ala Thr Pro Asn Phe Pro Ala Arg Phe Arg Pro
    610                 615                 620

Ser Asp Ile Leu Glu Phe Gly Ser Asp Lys Lys Ala Ala Phe Lys Val
625                 630                 635                 640

Lys Val Ile Arg Lys Thr Pro Lys Ser Thr Lys Asn Glu Ser Asn
                645                 650                 655

Gly Lys Leu Leu Gln Ala Ala
            660

<210> SEQ ID NO 32
<211> LENGTH: 665
<212> TYPE: PRT
<213> ORGANISM: Camelina sativa

<400> SEQUENCE: 32

Met Gly Ser Thr Pro Phe Cys Tyr Ser Ile Asn Pro Ser Pro Ser Lys
1               5                   10                  15

Leu Asp Phe Thr Arg Thr His Val Phe Ser Pro Val Ser Lys Gln Phe
                20                  25                  30

Tyr Leu Asp Leu Ser Ser Phe Thr Gly Lys Ser Ala Gly Gly Gly Gly
            35                  40                  45

Gly Phe Arg Ser Arg Arg Ala Leu Val Gly Val Lys Ala Ala Thr Ala
        50                  55                  60

Leu Val Glu Glu Lys Arg Glu Ser Gly Thr Glu Lys Lys Lys Lys Ser
65                  70                  75                  80

Arg Val Leu Val Ala Gly Gly Ile Gly Gly Leu Val Phe Ala Leu
                85                  90                  95

Ala Ala Lys Lys Lys Gly Phe Asp Val Leu Val Phe Glu Lys Asp Leu
            100                 105                 110

Ser Ala Ile Arg Gly Glu Gly Gln Tyr Arg Gly Pro Ile Gln Ile Gln
        115                 120                 125

Ser Asn Ala Leu Ala Ala Leu Glu Ala Ile Asp Thr Asp Val Ala Glu
    130                 135                 140
```

Gln Val Met Glu Ala Gly Cys Ile Thr Gly Asp Arg Ile Asn Gly Leu
145                 150                 155                 160

Val Asp Gly Ile Ser Gly Thr Trp Tyr Val Lys Phe Asp Thr Phe Thr
            165                 170                 175

Pro Ala Ala Ser Arg Gly Leu Pro Val Thr Arg Val Ile Ser Arg Met
                180                 185                 190

Thr Leu Gln Gln Ile Leu Ala Arg Ala Val Gly Glu Val Ile Arg
        195                 200                 205

Asn Glu Ser Asn Val Val Asp Phe Glu Asp Ser Gly Asp Lys Val Thr
    210                 215                 220

Val Val Leu Glu Asn Gly Glu Arg Tyr Glu Gly Asp Leu Leu Val Gly
225                 230                 235                 240

Ala Asp Gly Ile Trp Ser Lys Val Arg Asn Asn Leu Phe Gly Arg Ser
            245                 250                 255

Glu Ala Ser Tyr Ser Gly Tyr Thr Cys Tyr Thr Gly Ile Ala Asp Phe
                260                 265                 270

Ile Pro Ala Asp Ile Glu Ser Val Gly Tyr Arg Val Phe Leu Gly Asn
        275                 280                 285

Lys Gln Tyr Phe Val Ser Ser Asp Val Gly Gly Lys Met Gln Trp
    290                 295                 300

Tyr Ala Phe His Glu Glu Pro Ala Gly Gly Ala Asp Ala Pro Asn Gly
305                 310                 315                 320

Met Lys Lys Arg Leu Phe Glu Ile Phe Asp Gly Trp Cys Asp Asn Val
            325                 330                 335

Leu Asp Leu Leu His Ala Thr Glu Glu Asp Ala Ile Leu Arg Arg Asp
                340                 345                 350

Ile Tyr Asp Arg Asn Pro Ser Phe Thr Trp Gly Lys Gly Arg Val Thr
        355                 360                 365

Leu Leu Gly Asp Ser Ile His Ala Met Gln Pro Asn Met Gly Gln Gly
    370                 375                 380

Gly Cys Met Ala Ile Glu Asp Ser Phe Gln Leu Ala Leu Glu Leu Asp
385                 390                 395                 400

Glu Ala Trp Lys Gln Ser Val Glu Thr Lys Thr Pro Val Asp Val Val
            405                 410                 415

Ser Ser Leu Lys Arg Tyr Glu Glu Ser Arg Arg Leu Arg Val Ala Leu
                420                 425                 430

Ile His Gly Met Ala Arg Met Ala Ala Ile Met Ala Ser Thr Tyr Lys
        435                 440                 445

Ala Tyr Leu Gly Val Gly Leu Gly Pro Leu Ser Phe Leu Thr Lys Phe
    450                 455                 460

Arg Val Pro His Pro Gly Arg Val Gly Gly Arg Phe Phe Ile Asp Ile
465                 470                 475                 480

Ala Met Pro Met Met Leu Asn Trp Val Leu Gly Gly Asn Ser Glu Lys
            485                 490                 495

Leu Glu Gly Arg Ser Pro Ser Cys Arg Leu Thr Asp Lys Ala Asp Asp
                500                 505                 510

Arg Leu Arg Glu Trp Phe Glu Asp Asp Ala Leu Glu Arg Thr Ile
        515                 520                 525

Lys Gly Glu Trp Tyr Leu Ile Pro His Gly Asp Cys Cys Ile Ser
    530                 535                 540

Glu Thr Leu Cys Leu Thr Lys Asp Glu Asp Gln Pro Cys Ile Ile Gly
545                 550                 555                 560

Ser Glu Pro Asp Gln Asp Leu Pro Gly Lys His Ile Val Ile Pro Ser

```
                    565                 570                 575
Ser Gln Val Ser Lys Met His Ala Arg Val Ile Tyr Lys Asp Gly Ala
                580                 585                 590

Phe Phe Leu Met Asp Leu Arg Ser Glu His Gly Thr Tyr Val Thr Asp
            595                 600                 605

Asn Glu Gly Arg Arg Tyr Arg Ala Thr Pro Asn Ser Pro Ala Arg Phe
        610                 615                 620

Arg Thr Ser Asp Ile Ile Glu Phe Gly Ser Asp Lys Lys Ala Ala Phe
625                 630                 635                 640

Arg Val Lys Val Ile Arg Thr Thr Pro Lys Ser Thr Arg Lys Asn Glu
                645                 650                 655

Ser Asn Asp Lys Leu Leu Gln Ala Ala
            660                 665

<210> SEQ ID NO 33
<211> LENGTH: 668
<212> TYPE: PRT
<213> ORGANISM: Camelina sativa

<400> SEQUENCE: 33

Met Gly Ser Thr Pro Phe Cys Tyr Ser Ile Asn Pro Thr Pro Ser Lys
1               5                   10                  15

Leu Asp Phe Thr Arg Thr His Val Phe Ser Pro Val Ser Lys Gln Phe
            20                  25                  30

Tyr Leu Asp Leu Ser Ser Phe Thr Gly Lys Ser Gly Val Gly Ala Gly
        35                  40                  45

Gly Phe Arg Ser Leu Arg Ala Leu Val Gly Val Lys Ala Ala Thr Ala
    50                  55                  60

Leu Val Glu Glu Gln Lys Arg Glu Ser Val Thr Asp Lys Thr Lys
65                  70                  75                  80

Lys Lys Ser Arg Val Leu Val Ala Gly Gly Ile Gly Gly Leu Val
                85                  90                  95

Phe Ala Leu Ala Ala Lys Lys Lys Gly Phe Asp Val Leu Val Phe Glu
            100                 105                 110

Lys Asp Leu Ser Ala Ile Arg Gly Glu Gly Gln Tyr Arg Gly Pro Ile
        115                 120                 125

Gln Ile Gln Ser Asn Ala Leu Ala Ala Leu Glu Ala Ile Asp Thr Asp
    130                 135                 140

Val Ala Glu Gln Val Met Val Ala Gly Cys Ile Thr Gly Asp Arg Ile
145                 150                 155                 160

Asn Gly Leu Val Asp Gly Ile Ser Gly Thr Trp Tyr Val Lys Phe Asp
                165                 170                 175

Thr Phe Thr Pro Ala Ala Ser Arg Gly Leu Pro Val Thr Arg Val Ile
            180                 185                 190

Ser Arg Met Thr Leu Gln Gln Ile Leu Ala Arg Ala Val Gly Glu Glu
        195                 200                 205

Leu Ile Arg Asn Glu Ser Asn Val Val Asp Phe Glu Asp Ser Gly Asp
    210                 215                 220

Lys Val Thr Val Val Leu Glu Asn Gly Glu Arg Tyr Glu Gly Asp Leu
225                 230                 235                 240

Leu Val Gly Ala Asp Gly Ile Trp Ser Lys Val Arg Asn Asn Leu Phe
                245                 250                 255

Gly Arg Ser Glu Ala Ser Tyr Ser Gly Tyr Thr Cys Tyr Thr Gly Ile
            260                 265                 270
```

Ala Asp Phe Ile Pro Ala Asp Ile Glu Ser Val Gly Tyr Arg Val Phe
        275                 280                 285

Leu Gly Asn Lys Gln Tyr Phe Val Ser Ser Asp Val Gly Gly Gly Lys
    290                 295                 300

Met Gln Trp Tyr Ala Phe His Glu Glu Pro Ala Gly Gly Ala Asp Ala
305                 310                 315                 320

Pro Asn Gly Met Lys Lys Arg Leu Phe Glu Ile Phe Asp Gly Trp Cys
                325                 330                 335

Asp Asn Val Leu Asp Leu Leu His Ala Thr Glu Glu Asp Ala Ile Leu
            340                 345                 350

Arg Arg Asp Ile Tyr Asp Arg Asn Pro Ser Phe Thr Trp Gly Lys Gly
        355                 360                 365

Arg Val Thr Leu Leu Gly Asp Ser Ile His Ala Met Gln Pro Asn Met
    370                 375                 380

Gly Gln Gly Gly Cys Met Ala Ile Glu Asp Ser Phe Gln Leu Ala Leu
385                 390                 395                 400

Glu Leu Asp Glu Ala Trp Lys Gln Ser Val Lys Thr Lys Thr Pro Val
                405                 410                 415

Asp Val Val Ser Ser Leu Lys Arg Tyr Glu Glu Ser Arg Arg Leu Arg
            420                 425                 430

Val Ala Leu Ile His Gly Met Ala Arg Met Ala Ala Ile Met Ala Ser
        435                 440                 445

Thr Tyr Lys Ala Tyr Leu Gly Val Gly Leu Gly Pro Leu Ser Phe Leu
    450                 455                 460

Thr Lys Phe Arg Val Pro His Pro Gly Arg Val Gly Gly Arg Phe Phe
465                 470                 475                 480

Ile Asp Ile Ala Met Pro Met Met Leu Asn Trp Val Leu Gly Gly Asn
                485                 490                 495

Ser Glu Lys Leu Glu Gly Arg Ser Pro Ser Cys Arg Leu Thr Asp Lys
            500                 505                 510

Ala Asp Asp Arg Leu Arg Glu Trp Phe Glu Asp Asp Ala Leu Glu
        515                 520                 525

Arg Thr Ile Lys Gly Glu Trp Tyr Leu Ile Pro His Gly Asp Glu Cys
    530                 535                 540

Cys Ile Ser Glu Thr Leu Cys Leu Thr Lys Asp Glu Asp Gln Pro Cys
545                 550                 555                 560

Ile Ile Gly Ser Lys Pro Asp Gln Asp Leu Pro Gly Lys His Ile Val
                565                 570                 575

Ile Pro Ser Ser Gln Val Ser Lys Met His Ala Arg Val Ile Tyr Lys
            580                 585                 590

Asp Gly Ala Phe Phe Leu Met Asp Leu Arg Ser Glu His Gly Thr Tyr
        595                 600                 605

Val Thr Asp Asn Glu Gly Arg Arg Tyr Arg Ala Thr Pro Asn Ser Pro
    610                 615                 620

Ala Arg Phe Arg Thr Ser Asp Ile Ile Glu Phe Gly Ser Asp Lys Lys
625                 630                 635                 640

Ala Ala Phe Arg Val Lys Val Ile Arg Thr Thr Pro Lys Ser Thr Arg
                645                 650                 655

Lys Asn Glu Ser Asn Asp Lys Leu Leu Gln Ala Ala
            660                 665

<210> SEQ ID NO 34
<211> LENGTH: 669
<212> TYPE: PRT

<213> ORGANISM: Capsella rubella

<400> SEQUENCE: 34

Met Gly Ser Thr Pro Phe Cys Tyr Ser Ile Asn Pro Ser Pro Ser Lys
1               5                   10                  15

Leu Asp Phe Thr Arg Thr His Val Phe Ser Pro Val Ala Lys Gln Phe
            20                  25                  30

Tyr Leu Asp Leu Ser Ser Phe Thr Gly Lys Ser Gly Val Gly Gly Gly
        35                  40                  45

Leu Ser Gly Phe Arg Ser Arg Arg Thr Leu Val Gly Val Lys Ala Ala
    50                  55                  60

Thr Ala Leu Val Glu Glu Gln Lys Pro Gly Glu Val Thr Glu Arg
65                  70                  75                  80

Lys Lys Lys Ser Arg Val Leu Val Ala Gly Gly Ile Gly Gly Leu
                85                  90                  95

Val Phe Ala Leu Ala Ala Lys Lys Gly Phe Asp Val Leu Val Phe
            100                 105                 110

Glu Lys Asp Leu Ser Ala Ile Arg Gly Glu Gly Gln Tyr Arg Gly Pro
        115                 120                 125

Ile Gln Ile Gln Ser Asn Ala Leu Ala Ala Leu Glu Ala Ile Asp Asn
    130                 135                 140

Asp Val Ala Glu Gln Val Met Glu Ala Gly Cys Ile Thr Gly Asp Arg
145                 150                 155                 160

Ile Asn Gly Leu Val Asp Gly Val Ser Gly Thr Trp Tyr Val Lys Phe
                165                 170                 175

Asp Thr Phe Thr Pro Ala Ala Ser Arg Gly Leu Pro Val Thr Arg Val
            180                 185                 190

Ile Ser Arg Met Thr Leu Gln Gln Ile Leu Ala Arg Ala Val Gly Glu
        195                 200                 205

Glu Val Ile Arg Asn Glu Ser Asn Val Val Asp Phe Glu Asp Ser Gly
    210                 215                 220

Asp Lys Val Thr Val Val Leu Glu Asn Gly Gln Arg Tyr Glu Gly Asp
225                 230                 235                 240

Leu Leu Val Gly Ala Asp Gly Ile Trp Ser Lys Val Arg Asn Asn Leu
                245                 250                 255

Phe Gly Arg Ser Glu Ala Glu Tyr Ser Gly Tyr Thr Cys Tyr Thr Gly
            260                 265                 270

Ile Ala Asp Phe Ile Pro Ala Asp Ile Glu Ser Val Gly Tyr Arg Val
        275                 280                 285

Phe Leu Gly His Lys Gln Tyr Phe Val Ser Ser Asp Val Gly Gly Gly
    290                 295                 300

Lys Met Gln Trp Tyr Ala Phe His Glu Glu Pro Ala Gly Gly Thr Asp
305                 310                 315                 320

Ala Pro Asn Gly Met Lys Lys Arg Leu Phe Glu Ile Phe Asp Gly Trp
                325                 330                 335

Cys Asp Asn Val Leu Asp Leu Leu His Ala Thr Glu Glu Asp Ala Ile
            340                 345                 350

Leu Arg Arg Asp Ile Tyr Asp Arg Ser Pro Ser Phe Thr Trp Gly Lys
        355                 360                 365

Gly Arg Val Thr Leu Leu Gly Asp Ser Ile His Ala Met Gln Pro Asn
    370                 375                 380

Met Gly Gln Gly Gly Cys Met Ala Ile Glu Asp Ser Phe Gln Leu Ala
385                 390                 395                 400

```
Leu Glu Leu Glu Glu Ala Trp Lys Gln Ser Val Glu Thr Asn Thr Ser
                405                 410                 415

Val Asp Val Val Ser Ser Leu Lys Lys Tyr Glu Glu Ser Arg Arg Leu
            420                 425                 430

Arg Val Ala Ile Ile His Gly Met Ala Arg Met Ala Ala Ile Met Ala
        435                 440                 445

Ser Thr Tyr Lys Ala Tyr Leu Gly Val Gly Leu Gly Pro Leu Ser Phe
    450                 455                 460

Leu Thr Lys Phe Arg Val Pro His Pro Gly Arg Val Gly Gly Arg Phe
465                 470                 475                 480

Phe Ile Asp Ile Ala Met Pro Leu Met Leu Asn Trp Val Leu Gly Gly
                485                 490                 495

Asn Ser Glu Lys Leu Glu Gly Arg Pro Pro Ser Cys Arg Leu Thr Asp
            500                 505                 510

Lys Ala Asp Asp Arg Leu Arg Glu Trp Phe Glu Asn Asp Asp Ala Leu
        515                 520                 525

Glu Arg Thr Ile Asn Gly Glu Trp Tyr Leu Ile Pro His Gly Asp Glu
    530                 535                 540

Cys Cys Val Ser Glu Thr Leu Cys Leu Thr Lys Asp Glu Asp Gln Pro
545                 550                 555                 560

Cys Ile Val Gly Ser Glu Pro Asp Gln Asp Leu Pro Gly Lys His Ile
                565                 570                 575

Val Ile Pro Ser Ser Gln Val Ser Lys Met His Ala Arg Val Ile Tyr
            580                 585                 590

Lys Asp Gly Ala Phe Phe Leu Met Asp Leu Gly Ser Glu His Gly Thr
        595                 600                 605

Phe Val Thr Asp Asn Glu Gly Arg Arg Tyr Arg Ala Thr Pro Asn Phe
    610                 615                 620

Pro Gly Arg Phe Arg Ser Ser Asp Ile Ile Glu Phe Gly Ser Asp Lys
625                 630                 635                 640

Lys Ala Ala Phe Arg Val Lys Val Ile Arg Lys Thr Pro Lys Ala Thr
                645                 650                 655

Arg Lys Asn Glu Ser Asn Asp Lys Leu Leu Gln Ala Ala
            660                 665

<210> SEQ ID NO 35
<211> LENGTH: 667
<212> TYPE: PRT
<213> ORGANISM: Arabidopsis thaliana

<400> SEQUENCE: 35

Met Gly Ser Thr Pro Phe Cys Tyr Ser Ile Asn Pro Ser Pro Ser Lys
1               5                   10                  15

Leu Asp Phe Thr Arg Thr His Val Phe Ser Pro Val Ser Lys Gln Phe
            20                  25                  30

Tyr Leu Asp Leu Ser Ser Phe Ser Gly Lys Pro Gly Gly Val Ser Gly
        35                  40                  45

Phe Arg Ser Arg Arg Ala Leu Leu Gly Val Lys Ala Ala Thr Ala Leu
    50                  55                  60

Val Glu Lys Glu Glu Lys Arg Glu Ala Val Thr Glu Lys Lys Lys Lys
65                  70                  75                  80

Ser Arg Val Leu Val Ala Gly Gly Ile Gly Gly Leu Val Phe Ala
                85                  90                  95

Leu Ala Ala Lys Lys Lys Gly Phe Asp Val Leu Val Phe Glu Lys Asp
            100                 105                 110
```

```
Leu Ser Ala Ile Arg Gly Glu Gly Lys Tyr Arg Gly Pro Ile Gln Ile
        115                 120                 125

Gln Ser Asn Ala Leu Ala Ala Leu Glu Ala Ile Asp Ile Glu Val Ala
        130                 135                 140

Glu Gln Val Met Glu Ala Gly Cys Ile Thr Gly Asp Arg Ile Asn Gly
145                 150                 155                 160

Leu Val Asp Gly Ile Ser Gly Thr Trp Tyr Val Lys Phe Asp Thr Phe
                165                 170                 175

Thr Pro Ala Ala Ser Arg Gly Leu Pro Val Thr Arg Val Ile Ser Arg
                180                 185                 190

Met Thr Leu Gln Gln Ile Leu Ala Arg Ala Val Gly Glu Asp Val Ile
        195                 200                 205

Arg Asn Glu Ser Asn Val Val Asp Phe Glu Asp Ser Gly Asp Lys Val
210                 215                 220

Thr Val Val Leu Glu Asn Gly Gln Arg Tyr Glu Gly Asp Leu Leu Val
225                 230                 235                 240

Gly Ala Asp Gly Ile Trp Ser Lys Val Arg Asn Asn Leu Phe Gly Arg
                245                 250                 255

Ser Glu Ala Thr Tyr Ser Gly Tyr Thr Cys Tyr Thr Gly Ile Ala Asp
                260                 265                 270

Phe Ile Pro Ala Asp Ile Glu Ser Val Gly Tyr Arg Val Phe Leu Gly
        275                 280                 285

His Lys Gln Tyr Phe Val Ser Ser Asp Val Gly Gly Lys Met Gln
        290                 295                 300

Trp Tyr Ala Phe His Glu Pro Ala Gly Ala Asp Ala Pro Asn
305                 310                 315                 320

Gly Met Lys Lys Arg Leu Phe Glu Ile Phe Asp Gly Trp Cys Asp Asn
                325                 330                 335

Val Leu Asp Leu Leu His Ala Thr Glu Glu Ala Ile Leu Arg Arg
                340                 345                 350

Asp Ile Tyr Asp Arg Ser Pro Gly Phe Thr Trp Gly Lys Gly Arg Val
        355                 360                 365

Thr Leu Leu Gly Asp Ser Ile His Ala Met Gln Pro Asn Met Gly Gln
        370                 375                 380

Gly Gly Cys Met Ala Ile Glu Asp Ser Phe Gln Leu Ala Leu Glu Leu
385                 390                 395                 400

Asp Glu Ala Trp Lys Gln Ser Val Glu Thr Thr Pro Val Asp Val
                405                 410                 415

Val Ser Ser Leu Lys Arg Tyr Glu Glu Ser Arg Arg Leu Arg Val Ala
                420                 425                 430

Ile Ile His Ala Met Ala Arg Met Ala Ile Met Ala Ser Thr Tyr
        435                 440                 445

Lys Ala Tyr Leu Gly Val Gly Leu Gly Pro Leu Ser Phe Leu Thr Lys
        450                 455                 460

Phe Arg Val Pro His Pro Gly Arg Val Gly Arg Phe Phe Val Asp
465                 470                 475                 480

Ile Ala Met Pro Ser Met Leu Asp Trp Val Leu Gly Gly Asn Ser Glu
                485                 490                 495

Lys Leu Gln Gly Arg Pro Pro Ser Cys Arg Leu Thr Asp Lys Ala Asp
                500                 505                 510

Asp Arg Leu Arg Glu Trp Phe Glu Asp Asp Ala Leu Glu Arg Thr
        515                 520                 525
```

```
Ile Lys Gly Glu Trp Tyr Leu Ile Pro His Gly Asp Cys Cys Val
    530                 535                 540

Ser Glu Thr Leu Cys Leu Thr Lys Asp Glu Asp Gln Pro Cys Ile Val
545                 550                 555                 560

Gly Ser Glu Pro Asp Gln Asp Phe Pro Gly Met Arg Ile Val Ile Pro
                565                 570                 575

Ser Ser Gln Val Ser Lys Met His Ala Arg Val Ile Tyr Lys Asp Gly
                580                 585                 590

Ala Phe Phe Leu Met Asp Leu Arg Ser Glu His Gly Thr Tyr Val Thr
            595                 600                 605

Asp Asn Glu Gly Arg Arg Tyr Arg Ala Thr Pro Asn Phe Pro Ala Arg
            610                 615                 620

Phe Arg Ser Ser Asp Ile Ile Glu Phe Gly Ser Asp Lys Lys Ala Ala
625                 630                 635                 640

Phe Arg Val Lys Val Ile Arg Lys Thr Pro Lys Ser Thr Arg Lys Asn
                645                 650                 655

Glu Ser Asn Asn Asp Lys Leu Leu Gln Thr Ala
                660                 665

<210> SEQ ID NO 36
<211> LENGTH: 667
<212> TYPE: PRT
<213> ORGANISM: Arabidopsis lyrata

<400> SEQUENCE: 36

Met Gly Ser Thr Leu Phe Cys Tyr Ser Ile Asn Pro Ser Pro Ser Lys
1               5                   10                  15

Leu Asp Phe Thr Arg Thr His Val Val Ser Pro Val Ala Lys Gln Phe
                20                  25                  30

Tyr Leu Asp Leu Ser Ser Phe Ser Gly Lys Ser Gly Gly Gly Leu Ser
            35                  40                  45

Gly Phe Arg Ser Arg Lys Thr Leu Val Gly Val Lys Ala Ala Thr Ala
        50                  55                  60

Leu Val Glu Lys Glu Glu Lys Arg Glu Ala Val Thr Glu Lys Lys Lys
65                  70                  75                  80

Lys Ser Arg Val Leu Val Ala Gly Gly Ile Gly Gly Leu Val Phe
                85                  90                  95

Ala Leu Ala Ala Lys Lys Lys Gly Phe Asp Val Val Phe Glu Lys
                100                 105                 110

Asp Leu Ser Ala Ile Arg Gly Glu Gly Gln Tyr Arg Gly Pro Ile Gln
            115                 120                 125

Ile Gln Ser Asn Ala Leu Ala Ala Leu Glu Ala Ile Asp Thr Asp Val
        130                 135                 140

Ala Glu Gln Val Met Glu Ala Gly Cys Ile Thr Gly Asp Arg Ile Asn
145                 150                 155                 160

Gly Leu Val Asp Gly Val Ser Gly Ser Trp Tyr Val Lys Phe Asp Thr
                165                 170                 175

Phe Thr Pro Ala Ala Ser Arg Gly Leu Pro Val Thr Arg Val Ile Ser
                180                 185                 190

Arg Met Thr Leu Gln Gln Ile Leu Ala Arg Ala Val Gly Glu Asp Val
            195                 200                 205

Ile Arg Asn Glu Ser Asn Val Val Asp Phe Glu Asp Ser Gly Asp Lys
        210                 215                 220

Val Thr Val Val Leu Glu Asn Gly Gln Arg Tyr Glu Gly Asp Leu Leu
225                 230                 235                 240
```

```
Val Gly Ala Asp Gly Ile Trp Ser Lys Val Arg Asn Leu Phe Gly
            245                 250                 255

Arg Ser Glu Ala Thr Tyr Ser Gly Tyr Thr Cys Tyr Thr Gly Ile Ala
        260                 265                 270

Asp Phe Val Pro Ala Asp Ile Glu Ser Val Gly Tyr Arg Val Phe Leu
            275                 280                 285

Gly His Lys Gln Tyr Phe Val Ser Ser Asp Val Gly Gly Lys Met
            290                 295                 300

Gln Trp Tyr Ala Phe His Glu Glu Pro Ala Gly Val Asp Ala Pro
305                 310                 315                 320

Asn Gly Met Lys Lys Arg Leu Phe Glu Ile Phe Asp Gly Trp Cys Asp
                325                 330                 335

Asn Val Leu Asp Leu Leu His Ala Thr Glu Glu Asp Ala Ile Leu Arg
            340                 345                 350

Arg Asp Ile Tyr Asp Arg Ser Pro Ser Phe Thr Trp Gly Lys Gly Arg
        355                 360                 365

Val Thr Leu Leu Gly Asp Ser Ile His Ala Met Gln Pro Asn Met Gly
    370                 375                 380

Gln Gly Gly Cys Met Ala Ile Glu Asp Ser Phe Gln Leu Ala Leu Glu
385                 390                 395                 400

Leu Glu Glu Ala Trp Lys Gln Ser Val Gly Thr Asn Thr Pro Val Asp
                405                 410                 415

Val Val Ser Ser Leu Lys Arg Tyr Glu Glu Ser Arg Arg Leu Arg Val
            420                 425                 430

Ala Ile Ile His Gly Met Ala Arg Met Ala Ala Ile Met Ala Ser Thr
            435                 440                 445

Tyr Lys Ala Tyr Leu Gly Val Gly Leu Gly Pro Leu Ser Phe Leu Thr
    450                 455                 460

Lys Phe Arg Val Pro His Pro Gly Arg Val Gly Gly Arg Phe Phe Val
465                 470                 475                 480

Asp Ile Ala Met Pro Leu Met Leu Asp Trp Val Leu Gly Gly Asn Ser
                485                 490                 495

Glu Lys Leu Glu Gly Arg Pro Ser Cys Arg Leu Thr Asp Lys Ala
            500                 505                 510

Asp Asp Arg Leu Arg Glu Trp Phe Glu Asp Asp Ala Leu Glu Arg
        515                 520                 525

Thr Ile Lys Gly Glu Trp Tyr Leu Ile Pro His Gly Glu Asp Cys Cys
    530                 535                 540

Val Ser Glu Thr Leu Cys Leu Thr Asn Asp Glu Asp Gln Pro Cys Ile
545                 550                 555                 560

Val Gly Ser Glu Pro Asp Gln Asp Phe Pro Gly Met Arg Ile Val Ile
                565                 570                 575

Pro Ser Ser Gln Val Ser Lys Met His Ala Arg Val Ile Tyr Lys Asp
            580                 585                 590

Gly Val Phe Phe Leu Met Asp Leu Arg Ser Glu His Gly Thr Tyr Val
        595                 600                 605

Thr Asp Asn Glu Gly Arg Arg Tyr Arg Ala Thr Pro Asn Phe Pro Ala
    610                 615                 620

Arg Phe Arg Ser Ser Asp Ile Ile Glu Phe Gly Ser Asp Lys Lys Ala
625                 630                 635                 640

Ala Phe Arg Val Lys Val Ile Arg Lys Thr Pro Lys Ser Thr Arg Lys
                645                 650                 655
```

```
Asn Glu Ser Asn Asp Lys Leu Leu Gln Thr Ala
        660                 665

<210> SEQ ID NO 37
<211> LENGTH: 662
<212> TYPE: PRT
<213> ORGANISM: Raphanus sativus

<400> SEQUENCE: 37

Met Gly Ser Ser Thr Leu Phe Cys Tyr Ser Ile Asn Pro Ser Pro Ser
1               5                   10                  15

Lys Leu Asp Phe Thr Lys Thr His Val Phe Ser Pro Val Ala Lys Gln
            20                  25                  30

Phe Tyr Leu Asp Phe Pro Ser Phe Ala Ala Gly Lys Leu Arg Leu Arg
        35                  40                  45

Lys Arg Arg Ala Leu Val Gly Ala Lys Ala Glu Thr Leu Leu Glu Glu
50                  55                  60

Lys Arg Glu Thr Val Thr Glu Lys Lys Lys Pro Arg Val Leu Val
65                  70                  75                  80

Ala Gly Gly Gly Ile Gly Gly Leu Val Phe Ala Leu Ala Ala Lys Lys
                85                  90                  95

Lys Gly Phe Asp Val Leu Val Phe Glu Lys Asp Leu Ser Ala Ile Arg
            100                 105                 110

Gly Glu Gly Gln Tyr Arg Gly Pro Ile Gln Ile Gln Ser Asn Ala Leu
        115                 120                 125

Ala Ala Leu Glu Ala Ile Asp Ile Gly Val Ala Glu Glu Val Met Glu
130                 135                 140

Ala Gly Cys Ile Thr Gly Asp Arg Ile Asn Gly Leu Val Asp Gly Val
145                 150                 155                 160

Ser Gly Thr Trp Tyr Val Lys Phe Asp Thr Phe Thr Pro Ala Ala Ser
                165                 170                 175

Arg Gly Leu Pro Val Thr Arg Val Ile Ser Arg Met Thr Leu Gln Gln
            180                 185                 190

Ile Leu Ala Arg Ala Val Gly Glu Glu Ile Ile Arg Asn Glu Ser Asn
        195                 200                 205

Val Val Asp Phe Gln Asp Ser Gly Asp Lys Val Thr Val Val Leu Glu
210                 215                 220

Asn Gly Glu Arg Tyr Asp Gly Asp Leu Leu Val Gly Ala Asp Gly Ile
225                 230                 235                 240

Trp Ser Lys Val Arg Asn Asn Leu Phe Gly Arg Ser Glu Ala Thr Tyr
                245                 250                 255

Ser Gly Tyr Thr Cys Tyr Thr Gly Ile Ala Asp Phe Val Pro Ala Asp
            260                 265                 270

Ile Glu Ser Val Gly Tyr Arg Val Phe Leu Gly His Lys Gln Tyr Phe
        275                 280                 285

Val Ser Ser Asp Val Gly Gly Gly Lys Met Gln Trp Tyr Ala Phe His
290                 295                 300

Glu Glu Ala Ala Gly Gly Val Asp Ala Pro Asn Gly Met Lys Lys Arg
305                 310                 315                 320

Leu Phe Asp Ile Phe Glu Gly Trp Cys Asp Asn Val Leu Asp Leu Leu
                325                 330                 335

Gln Ala Thr Glu Glu Glu Ala Ile Leu Arg Arg Asp Ile Tyr Asp Lys
            340                 345                 350

Ser Pro Ser Phe Thr Trp Gly Lys Gly Arg Val Thr Leu Leu Gly Asp
        355                 360                 365
```

```
Ser Ile His Ala Met Gln Pro Asn Met Gly Gln Gly Gly Cys Met Ala
        370                 375                 380

Ile Glu Asp Ser Phe Gln Leu Gly Leu Glu Leu Ala Ala Trp Lys
385                 390                 395                 400

Gln Ser Val Glu Thr Asn Thr Pro Val Asp Val Val Ser Ser Leu Arg
                405                 410                 415

Arg Tyr Glu Glu Ser Arg Arg Leu Arg Val Ala Ile Ile His Gly Met
            420                 425                 430

Ala Arg Met Ala Ala Ile Met Ala Ser Thr Tyr Lys Ala Tyr Leu Gly
        435                 440                 445

Val Gly Leu Gly Pro Leu Ser Phe Leu Thr Lys Phe Arg Val Pro His
450                 455                 460

Pro Gly Arg Val Gly Gly Arg Phe Phe Ile Asp Ile Ala Met Pro Leu
465                 470                 475                 480

Met Leu Asn Trp Val Leu Gly Gly Asn Ser Glu Lys Leu Glu Gly Arg
                485                 490                 495

Pro Pro Ser Cys Arg Leu Thr Asp Lys Ala Asp Arg Leu Arg Glu
            500                 505                 510

Trp Phe Glu Asp Glu Ala Leu Glu Arg Thr Ile Asn Gly Glu Trp
        515                 520                 525

Tyr Leu Ile Pro His Gly Asn Glu Cys Ser Val Ser Glu Thr Leu Arg
            530                 535                 540

Leu Thr Lys Asp Glu Glu Gln Pro Cys Ile Val Gly Ser Glu Pro Asp
545                 550                 555                 560

Gln Asp Phe Pro Gly Thr His Ile Val Ile Pro Ser Pro Gln Val Ser
                565                 570                 575

Lys Met His Ala Arg Val Ile Tyr Lys Asp Gly Ala Phe Phe Leu Met
            580                 585                 590

Asp Leu Arg Ser Glu His Gly Thr Tyr Leu Thr Asp Asn Glu Gly Gly
        595                 600                 605

Lys Tyr Arg Val Thr Pro Asn Phe Pro Thr Arg Phe Arg Ser Ser Asp
            610                 615                 620

Ile Ile Glu Phe Gly Ser Asp Lys Lys Ala Ala Phe Arg Val Lys Val
625                 630                 635                 640

Ile Arg Thr Thr Pro Lys Leu Thr Arg Arg Asp Glu Lys Ser Asp Gly
                645                 650                 655

Lys Leu Leu Gln Ala Ala
            660

<210> SEQ ID NO 38
<211> LENGTH: 687
<212> TYPE: PRT
<213> ORGANISM: Brassica napus

<400> SEQUENCE: 38

Met Lys Cys Thr Ser His Ile Lys Leu Pro Leu Arg Ala Ser Arg Ile
1               5                   10                  15

Glu Met Gly Ser Ser Thr Pro Phe Cys Tyr Ser Ile Asn Pro Ser Pro
                20                  25                  30

Ser Lys Leu Asp Phe Thr Arg Thr His Ala Phe Ser Pro Val Ala Lys
            35                  40                  45

Gln Phe Tyr Leu Asp Leu Pro Ser Phe Ala Gly Lys Ser Gly Gly Gly
        50                  55                  60

Leu Ser Gly Leu Arg Lys Arg Arg Thr Leu Ile Gly Val Lys Ala Ala
```

-continued

```
              65                  70                  75                  80
Ala Ala Thr Leu Val Ala Glu Glu Lys Arg Glu Thr Val Thr Glu
                 85                  90                  95
Ser Lys Lys Lys Pro Arg Val Leu Val Ala Gly Gly Ile Gly Gly
                100                 105                 110
Leu Val Phe Ala Leu Ala Ala Lys Lys Gly Phe Asp Val Leu Val
                115                 120                 125
Phe Glu Lys Asp Leu Ser Ala Ile Arg Gly Gly Gln Tyr Arg Gly
                130                 135                 140
Pro Ile Gln Ile Gln Ser Asn Ala Leu Ala Ala Leu Glu Ala Ile Asp
145                 150                 155                 160
Ile Gly Val Ala Glu Glu Val Met Glu Ala Gly Cys Ile Thr Gly Asp
                165                 170                 175
Arg Ile Asn Gly Leu Val Asp Gly Val Ser Gly Thr Trp Tyr Val Lys
                180                 185                 190
Phe Asp Thr Phe Thr Pro Ala Ala Ser Arg Gly Leu Pro Val Thr Arg
                195                 200                 205
Val Ile Ser Arg Met Thr Leu Gln Gln Ile Leu Ala Arg Ala Val Gly
                210                 215                 220
Glu Glu Ile Ile Arg Asn Glu Ser Asn Val Val Asp Phe Glu Asp Ser
225                 230                 235                 240
Gly Asp Lys Val Thr Val Val Leu Glu Asn Gly Gln Arg Tyr Asp Gly
                245                 250                 255
Asp Leu Leu Val Gly Ala Asp Gly Ile Trp Ser Lys Val Arg Asn Asn
                260                 265                 270
Leu Phe Gly Arg Ser Glu Ala Thr Tyr Ser Gly Tyr Thr Cys Tyr Thr
                275                 280                 285
Gly Ile Ala Asp Phe Val Pro Ala Asp Ile Glu Ser Val Gly Tyr Arg
                290                 295                 300
Val Phe Leu Gly His Lys Gln Tyr Phe Val Ser Ser Asp Val Gly Gly
305                 310                 315                 320
Gly Lys Met Gln Trp Tyr Ala Phe His Glu Glu Ala Ala Gly Gly Val
                325                 330                 335
Asp Ala Pro Asn Gly Met Lys Lys Arg Leu Phe Asp Ile Phe Glu Gly
                340                 345                 350
Trp Cys Asp Asn Val Leu Asp Leu Leu Gln Ala Thr Glu Glu Glu Ala
                355                 360                 365
Ile Leu Arg Arg Asp Ile Tyr Asp Arg Ser Pro Ser Phe Thr Trp Gly
                370                 375                 380
Lys Gly Arg Val Thr Leu Leu Gly Asp Ser Ile His Ala Met Gln Pro
385                 390                 395                 400
Asn Met Gly Gln Gly Gly Cys Met Ala Ile Glu Asp Ser Phe Gln Leu
                405                 410                 415
Gly Leu Glu Leu Glu Gln Ala Trp Lys Gln Ser Val Glu Thr Asn Thr
                420                 425                 430
Pro Val Asp Val Val Ser Ser Leu Arg Arg Tyr Glu Glu Ser Arg Arg
                435                 440                 445
Leu Arg Val Ala Ile Ile His Gly Met Ala Arg Met Ala Ala Ile Met
                450                 455                 460
Ala Ser Thr Tyr Lys Ala Tyr Leu Gly Val Gly Leu Gly Pro Leu Ser
465                 470                 475                 480
Phe Leu Thr Lys Phe Arg Val Pro His Pro Gly Arg Val Gly Gly Arg
                485                 490                 495
```

```
Phe Phe Ile Asp Ile Ala Met Pro Leu Met Leu Asn Trp Val Leu Gly
            500                 505                 510

Gly Asn Ser Glu Lys Leu Glu Gly Arg Pro Pro Ser Cys Arg Leu Thr
            515                 520                 525

Asp Lys Ala Asp Asp Arg Leu Arg Glu Trp Phe Glu Asp Asp Glu Ala
            530                 535                 540

Leu Glu Arg Thr Ile Asn Gly Glu Trp Tyr Leu Ile Pro His Gly Asn
545                 550                 555                 560

Glu Cys Ser Val Ser Glu Thr Leu Arg Leu Thr Lys Asp Glu Asp Gln
                565                 570                 575

Pro Cys Ile Val Gly Ser Glu Pro Asp Gln Asp Phe Pro Gly Met His
            580                 585                 590

Ile Val Ile Pro Ser Pro Gln Val Ser Lys Met His Ala Arg Val Ile
            595                 600                 605

Tyr Lys Asp Gly Ala Phe Phe Val Met Asp Leu Arg Ser Glu His Gly
            610                 615                 620

Thr Tyr Leu Thr Asp Asn Glu Gly Gly Lys Tyr Arg Val Thr Pro Asn
625                 630                 635                 640

Phe Pro Ala Arg Phe Arg Pro Ser Asp Ile Ile Glu Phe Gly Ser Asp
            645                 650                 655

Lys Lys Ala Ala Phe Arg Val Lys Val Ile Arg Thr Thr Pro Lys Leu
            660                 665                 670

Thr Arg Arg Asp Glu Lys Ser Asp Gly Lys Leu Leu Gln Ala Ala
            675                 680                 685

<210> SEQ ID NO 39
<211> LENGTH: 668
<212> TYPE: PRT
<213> ORGANISM: Brassica rapa

<400> SEQUENCE: 39

Met Gly Cys Ser Thr Pro Phe Cys Tyr Ser Ile Asn Pro Ser Pro Ser
1               5                   10                  15

Lys Leu Asp Phe Thr Lys Thr His Ala Phe Ser Pro Val Ala Lys Gln
            20                  25                  30

Phe Tyr Leu Asp Leu Pro Ser Phe Ala Gly Lys Ser Gly Gly Gly Leu
            35                  40                  45

Ser Gly Leu Arg Lys Arg Arg Ala Leu Val Gly Val Lys Ala Ala Thr
        50                  55                  60

Leu Leu Ala Glu Glu Glu Lys Arg Glu Thr Val Thr Glu Ser Lys Lys
65                  70                  75                  80

Lys Pro Arg Val Leu Val Ala Gly Gly Ile Gly Gly Leu Val Phe
            85                  90                  95

Ala Leu Ala Ala Lys Lys Lys Gly Phe Asp Val Leu Val Phe Glu Lys
            100                 105                 110

Asp Leu Ser Ala Ile Arg Gly Gly Gln Tyr Arg Gly Pro Ile Gln
            115                 120                 125

Ile Gln Ser Asn Ala Leu Ala Ala Leu Glu Ala Ile Asp Ile Gly Val
            130                 135                 140

Ala Glu Glu Val Met Glu Ala Gly Cys Ile Thr Gly Asp Arg Ile Asn
145                 150                 155                 160

Gly Leu Val Asp Gly Val Ser Gly Thr Trp Tyr Val Lys Phe Asp Thr
                165                 170                 175

Phe Thr Pro Ala Ala Ser Arg Gly Leu Pro Val Thr Arg Val Ile Ser
```

```
                180             185             190
Arg Met Thr Leu Gln Gln Ile Leu Ala Arg Ala Val Gly Glu Glu Ile
            195                 200                 205
Ile Arg Asn Glu Ser Asn Val Val Asp Phe Glu Asp Ser Gly Asp Lys
    210                 215                 220
Val Thr Val Val Leu Glu Asn Gly Gln Arg Tyr Asp Gly Asp Leu Leu
225                 230                 235                 240
Val Gly Ala Asp Gly Ile Trp Ser Lys Val Arg Asn Asn Leu Phe Gly
                245                 250                 255
Arg Ser Glu Ala Thr Tyr Ser Gly Tyr Thr Cys Tyr Thr Gly Ile Ala
            260                 265                 270
Asp Phe Val Pro Ala Asp Ile Glu Ser Val Gly Tyr Arg Val Phe Leu
        275                 280                 285
Gly His Lys Gln Tyr Phe Val Ser Ser Asp Val Gly Gly Gly Lys Met
    290                 295                 300
Gln Trp Tyr Ala Phe His Glu Glu Ala Ala Gly Gly Val Asp Ala Pro
305                 310                 315                 320
Asn Gly Met Lys Lys Arg Leu Phe Asp Ile Phe Glu Gly Trp Cys Asp
                325                 330                 335
Asn Val Leu Asp Leu Leu Gln Ala Thr Glu Glu Ala Ile Leu Arg
            340                 345                 350
Arg Asp Ile Tyr Asp Arg Ser Pro Ser Phe Thr Trp Gly Lys Gly Arg
        355                 360                 365
Val Thr Leu Leu Gly Asp Ser Ile His Ala Met Gln Pro Asn Met Gly
    370                 375                 380
Gln Gly Gly Cys Met Ala Ile Glu Asp Ser Phe Gln Leu Gly Leu Glu
385                 390                 395                 400
Leu Glu Gln Ala Trp Lys Gln Ser Val Glu Thr Asn Thr Pro Val Asp
                405                 410                 415
Val Val Ser Ser Leu Arg Arg Tyr Glu Glu Ser Arg Arg Leu Arg Val
            420                 425                 430
Ala Ile Ile His Gly Met Ala Arg Met Ala Ala Ile Met Ala Ser Thr
        435                 440                 445
Tyr Lys Ala Tyr Leu Gly Val Gly Leu Gly Pro Leu Ser Phe Leu Thr
    450                 455                 460
Lys Phe Arg Val Pro His Pro Gly Arg Val Gly Gly Arg Phe Phe Ile
465                 470                 475                 480
Asp Ile Ala Met Pro Leu Met Leu Asn Trp Val Leu Gly Gly Asn Ser
                485                 490                 495
Glu Lys Leu Glu Gly Arg Pro Pro Ser Cys Arg Leu Thr Asp Lys Ala
            500                 505                 510
Asp Asp Arg Leu Arg Glu Trp Phe Glu Asp Glu Ala Leu Glu Arg
        515                 520                 525
Thr Ile Asn Gly Glu Trp Tyr Leu Ile Pro His Gly Asn Glu Cys Ser
    530                 535                 540
Val Ser Glu Thr Leu Arg Leu Thr Lys Asp Glu Gln Pro Cys Ile
545                 550                 555                 560
Val Gly Ser Glu Pro Asp Gln Asp Phe Pro Gly Thr His Ile Val Ile
                565                 570                 575
Pro Ser Pro Gln Val Ser Lys Met His Ala Arg Val Ile Tyr Lys Asp
            580                 585                 590
Gly Ala Phe Phe Val Met Asp Leu Arg Ser Glu His Gly Thr Tyr Leu
        595                 600                 605
```

```
Thr Asp Asn Glu Gly Gly Lys Tyr Arg Val Thr Pro Asn Phe Pro Ala
    610                 615                 620

Arg Phe Arg Pro Ser Asp Ile Ile Glu Phe Gly Ser Asp Lys Lys Ala
625                 630                 635                 640

Ala Phe Arg Val Lys Val Ile Arg Thr Thr Pro Lys Leu Thr Arg Arg
                645                 650                 655

Asp Glu Lys Ser Asp Gly Lys Leu Leu Gln Ala Ala
                660                 665

<210> SEQ ID NO 40
<211> LENGTH: 668
<212> TYPE: PRT
<213> ORGANISM: Brassica rapa

<400> SEQUENCE: 40

Met Gly Cys Ser Thr Pro Phe Cys Tyr Ser Ile Asn Pro Ser Pro Ser
1               5                   10                  15

Lys Leu Asp Phe Thr Lys Thr His Ala Phe Ser Pro Val Ala Lys Gln
            20                  25                  30

Phe Tyr Leu Asp Leu Pro Ser Phe Ala Gly Lys Ser Gly Gly Gly Leu
        35                  40                  45

Ser Gly Leu Arg Lys Arg Arg Ala Leu Val Gly Val Lys Ala Ala Thr
    50                  55                  60

Leu Leu Ala Glu Glu Lys Arg Glu Thr Val Thr Glu Ser Lys Lys
65                  70                  75                  80

Lys Pro Arg Val Leu Val Ala Gly Gly Ile Gly Gly Leu Val Phe
                85                  90                  95

Ala Leu Ala Ala Lys Lys Lys Gly Phe Asp Val Leu Val Phe Glu Lys
            100                 105                 110

Asp Leu Ser Ala Ile Arg Gly Glu Gly Gln Tyr Arg Gly Pro Ile Gln
        115                 120                 125

Ile Gln Ser Asn Ala Leu Ala Ala Leu Glu Ala Ile Asp Ile Gly Val
    130                 135                 140

Ala Glu Glu Val Met Glu Ala Gly Cys Ile Thr Gly Asp Arg Ile Asn
145                 150                 155                 160

Gly Leu Val Asp Gly Val Ser Gly Thr Trp Tyr Val Lys Phe Asp Thr
                165                 170                 175

Phe Thr Pro Ala Ala Ser Arg Gly Leu Pro Val Thr Arg Val Ile Ser
            180                 185                 190

Arg Met Thr Leu Gln Gln Ile Leu Ala Arg Ala Val Gly Glu Glu Ile
        195                 200                 205

Ile Arg Asn Glu Ser Asn Val Val Asp Phe Glu Asp Ser Gly Asp Lys
    210                 215                 220

Val Thr Val Val Leu Glu Asn Gly Gln Arg Tyr Asp Gly Asp Leu Leu
225                 230                 235                 240

Val Gly Ala Asp Gly Ile Trp Ser Lys Val Arg Asn Asn Leu Phe Gly
                245                 250                 255

Arg Ser Glu Ala Thr Tyr Ser Gly Tyr Thr Cys Tyr Thr Gly Ile Ala
            260                 265                 270

Asp Phe Val Pro Ala Asp Ile Glu Ser Val Gly Tyr Arg Val Phe Leu
        275                 280                 285

Gly His Lys Gln Tyr Phe Val Ser Ser Asp Val Gly Gly Gly Lys Met
    290                 295                 300

Gln Trp Tyr Ala Phe His Glu Glu Ala Ala Gly Gly Val Asp Ala Pro
```

```
            305                 310                 315                 320
Asn Gly Met Lys Lys Arg Leu Phe Asp Ile Phe Glu Gly Trp Cys Asp
                325                 330                 335

Asn Val Leu Asp Leu Leu Gln Ala Thr Glu Glu Ala Ile Leu Arg
                340                 345                 350

Arg Asp Ile Tyr Asp Arg Ser Pro Ser Phe Thr Trp Gly Lys Gly Arg
                355                 360                 365

Val Thr Leu Leu Gly Asp Ser Ile His Ala Met Gln Pro Asn Met Gly
            370                 375                 380

Gln Gly Gly Cys Met Ala Ile Glu Asp Ser Phe Gln Leu Gly Leu Glu
385                 390                 395                 400

Leu Glu Gln Ala Trp Lys Gln Ser Val Glu Thr Asn Thr Pro Val Asp
                405                 410                 415

Val Val Ser Ser Leu Arg Arg Tyr Glu Glu Ser Arg Arg Leu Arg Val
                420                 425                 430

Ala Ile Ile His Gly Met Ala Arg Met Ala Ala Ile Met Ala Ser Thr
                435                 440                 445

Tyr Lys Ala Tyr Leu Gly Val Gly Leu Gly Pro Leu Ser Phe Leu Thr
            450                 455                 460

Lys Phe Arg Val Pro His Pro Gly Arg Val Gly Arg Phe Phe Ile
465                 470                 475                 480

Asp Ile Ala Met Pro Leu Met Leu Asn Trp Val Leu Gly Ser Asn Ser
                485                 490                 495

Glu Lys Leu Glu Gly Arg Pro Pro Ser Cys Arg Leu Thr Asp Lys Ala
                500                 505                 510

Asp Asp Arg Leu Arg Glu Trp Phe Glu Asp Glu Ala Leu Glu Arg
            515                 520                 525

Thr Ile Asn Gly Glu Trp Tyr Leu Ile Pro His Gly Asn Glu Cys Ser
            530                 535                 540

Val Ser Glu Thr Leu Arg Leu Thr Lys Asp Glu Glu Gln Pro Cys Ile
545                 550                 555                 560

Val Gly Ser Glu Pro Asp Gln Asp Phe Pro Gly Thr His Ile Val Ile
                565                 570                 575

Pro Ser Pro Gln Val Ser Lys Met His Ala Arg Val Ile Tyr Lys Asp
                580                 585                 590

Gly Ala Phe Phe Val Met Asp Leu Arg Ser Glu His Gly Thr Tyr Leu
                595                 600                 605

Thr Asp Asn Glu Gly Gly Lys Tyr Arg Val Thr Pro Asn Phe Pro Ala
            610                 615                 620

Arg Phe Arg Pro Ser Asp Ile Ile Glu Phe Gly Ser Asp Lys Lys Ala
625                 630                 635                 640

Ala Phe Arg Val Lys Val Ile Arg Thr Thr Pro Lys Leu Thr Arg Arg
                645                 650                 655

Asp Glu Lys Ser Asp Gly Lys Leu Leu Gln Ala Ala
                660                 665

<210> SEQ ID NO 41
<211> LENGTH: 667
<212> TYPE: PRT
<213> ORGANISM: Noccaea caerulescens

<400> SEQUENCE: 41

Met Gly Ser Thr Pro Phe Cys Tyr Ser Thr Asn Pro Pro Ser Lys
1               5                   10                  15
```

```
Leu Asp Phe Thr Arg Thr His Ala Phe Ser Pro Leu Ala Lys Gln Phe
         20                  25                  30

Tyr Leu Asp Leu Ser Ser Leu Ala Gly Lys Ser Gly Gly Gly Leu Ser
             35                  40                  45

Gly Phe Arg Ser Pro Arg Thr Leu Val Gly Val Lys Ala Ala Ala Ala
     50                  55                  60

Thr Ala Leu Val Glu Glu Lys Arg Glu Val Val Ala Glu Lys Lys
65                  70                  75                  80

Lys Ser Arg Val Leu Val Ala Gly Gly Ile Gly Gly Leu Val Phe
             85                  90                  95

Ala Leu Ala Ala Lys Lys Lys Gly Phe Asp Val Leu Val Phe Glu Lys
             100                 105                 110

Asp Leu Ser Ala Ile Arg Gly Glu Gly Gln Tyr Arg Gly Pro Ile Gln
             115                 120                 125

Ile Gln Ser Asn Ala Leu Ala Ala Leu Glu Ala Ile Asp Thr Asp Val
     130                 135                 140

Ala Glu Glu Val Met Glu Ala Gly Cys Ile Thr Gly Asp Arg Ile Asn
145                 150                 155                 160

Gly Leu Val Asp Gly Val Ser Gly Thr Trp Tyr Val Lys Phe Asp Thr
             165                 170                 175

Phe Thr Pro Ala Ala Ser Arg Gly Leu Pro Val Thr Arg Val Ile Ser
             180                 185                 190

Arg Met Thr Leu Gln Gln Ile Leu Ala Arg Ala Val Gly Glu Glu Ile
         195                 200                 205

Ile Arg Asn Glu Ser Asn Val Val Asp Phe Glu Asp Ser Gly Asp Lys
     210                 215                 220

Val Thr Val Val Leu Glu Asn Gly Glu Arg Tyr Glu Gly Asp Leu Leu
225                 230                 235                 240

Val Gly Ala Asp Gly Ile Trp Ser Lys Val Arg Asn Asn Leu Phe Gly
             245                 250                 255

Arg Ser Glu Ala Thr Tyr Ser Gly Tyr Thr Cys Tyr Thr Gly Ile Ala
             260                 265                 270

Asp Phe Val Pro Ala Asp Ile Glu Ser Val Gly Tyr Arg Val Phe Leu
             275                 280                 285

Gly His Lys Gln Tyr Phe Val Ser Ser Asp Val Gly Gly Lys Met
         290                 295                 300

Gln Trp Tyr Ala Phe His Glu Glu Pro Ala Gly Val Asp Pro Pro
305                 310                 315                 320

Asn Gly Met Lys Lys Arg Leu Phe Asp Ile Phe Glu Gly Trp Cys Asp
             325                 330                 335

Asn Val Leu Asp Leu Leu His Ala Thr Glu Glu Asp Ala Ile Leu Arg
             340                 345                 350

Arg Asp Ile Tyr Asp Arg Thr Pro Ser Phe Thr Trp Gly Lys Gly Arg
         355                 360                 365

Val Thr Leu Leu Gly Asp Ser Ile His Ala Met Gln Pro Asn Met Gly
         370                 375                 380

Gln Gly Gly Cys Met Ala Ile Glu Asp Ser Tyr Gln Leu Ala Met Glu
385                 390                 395                 400

Leu Glu Gly Ala Trp Lys Gln Ser Val Glu Thr Asn Thr Pro Val Asp
                 405                 410                 415

Val Val Ser Ser Leu Lys Lys Tyr Glu Glu Ser Arg Arg Leu Arg Val
                 420                 425                 430

Ala Ile Ile His Gly Met Ala Arg Met Ala Ala Ile Met Ala Ser Thr
```

```
                    435                 440                 445
Tyr Lys Ala Tyr Leu Gly Val Gly Leu Gly Pro Leu Ser Phe Leu Thr
    450                 455                 460
Lys Phe Arg Val Pro His Pro Gly Arg Val Gly Gly Arg Phe Phe Ile
465                 470                 475                 480
Asp Ile Ala Met Pro Leu Met Leu Asn Trp Val Leu Gly Gly Asn Ser
                485                 490                 495
Glu Lys Leu Glu Gly Arg Ser Pro Ser Cys Arg Leu Thr Asp Lys Ala
            500                 505                 510
Asp Asp Arg Leu Arg Glu Trp Phe Glu Asp Asn Asp Ala Leu Glu Arg
            515                 520                 525
Thr Ile Asn Gly Glu Trp Tyr Leu Ile Pro His Gly Asp Asp Ser Ser
        530                 535                 540
Val Lys Glu Thr Ile Ser Leu Thr Lys Asp Asp Gln Pro Cys Ile
545                 550                 555                 560
Ile Gly Ser Glu Pro Asp Gln Asp Leu Pro Gly Met His Ile Val Ile
                565                 570                 575
Pro Ser Ser Gln Val Ser Lys Met His Ala Arg Val Thr Tyr Lys Asp
            580                 585                 590
Gly Ala Phe Phe Leu Met Asp Leu Gly Ser Glu His Gly Thr Tyr Val
                595                 600                 605
Val Asp Asn Glu Gly Arg Arg Tyr Arg Ala Ser Pro Asn Tyr Pro Ala
610                 615                 620
Arg Phe Arg Ser Ser Asp Ile Ile Glu Phe Gly Ser Asp Lys Lys Ala
625                 630                 635                 640
Ala Phe Arg Val Lys Val Ile Arg Thr Thr Pro Lys Ser Thr Ser Lys
                645                 650                 655
Asn Glu Ser Asn Gly Lys Leu Leu Gln Ala Ala
            660                 665

<210> SEQ ID NO 42
<211> LENGTH: 666
<212> TYPE: PRT
<213> ORGANISM: Eutrema salsugineum

<400> SEQUENCE: 42

Met Gly Ser Thr Pro Phe Cys Tyr Ser Ile Asn Pro Ser Pro Ser Lys
1               5                   10                  15
Leu Asp Phe Thr Arg Thr His Val Phe Ser Pro Val Ala Lys Gln Phe
                20                  25                  30
Tyr Leu Asp Leu Ser Ser Cys Ala Gly Lys Ser Gly Gly Gly Leu Ser
            35                  40                  45
Gly Phe Arg Ser Arg Arg Ala Leu Val Gly Val Arg Ala Ala Thr Ala
        50                  55                  60
Leu Val Glu Glu Glu Lys Arg Glu Ile Ala Lys Glu Lys Lys Pro
65                  70                  75                  80
Arg Val Leu Val Ala Gly Gly Gly Ile Gly Leu Val Phe Ala Leu
                85                  90                  95
Ala Ala Lys Lys Lys Gly Phe Asp Val Leu Val Phe Glu Lys Asp Leu
            100                 105                 110
Ser Ala Ile Arg Gly Glu Gly Gln Tyr Arg Gly Pro Ile Gln Ile Gln
        115                 120                 125
Ser Asn Ala Leu Ala Ala Leu Glu Ala Ile Asp Ile Asp Val Ala Glu
    130                 135                 140
```

```
Glu Val Met Glu Ala Gly Cys Ile Thr Gly Asp Arg Ile Asn Gly Leu
145                 150                 155                 160

Val Asp Gly Val Ser Gly Thr Trp Tyr Val Lys Phe Asp Thr Phe Thr
                165                 170                 175

Pro Ala Ala Ser Arg Gly Leu Pro Val Thr Arg Val Ile Ser Arg Met
            180                 185                 190

Thr Leu Gln Gln Ile Leu Ala Arg Ala Val Gly Glu Val Ile Arg
        195                 200                 205

Asn Glu Ser Asn Val Val Asp Phe Glu Asp Ser Gly Asp Lys Val Thr
    210                 215                 220

Val Val Leu Glu Asn Gly Glu Arg Tyr Glu Gly Asp Leu Leu Val Gly
225                 230                 235                 240

Ala Asp Gly Ile Trp Ser Lys Val Arg Asn Asn Leu Phe Gly Arg Ser
                245                 250                 255

Glu Ala Thr Tyr Ser Gly Tyr Thr Cys Tyr Thr Gly Ile Ala Asp Phe
            260                 265                 270

Val Pro Ala Asp Ile Glu Ser Val Gly Tyr Arg Val Phe Leu Gly His
        275                 280                 285

Lys Gln Tyr Phe Val Ser Ser Asp Val Gly Gly Lys Met Gln Trp
    290                 295                 300

Tyr Ala Phe His Glu Glu Pro Ala Gly Gly Val Asp Ala Pro Asn Gly
305                 310                 315                 320

Met Lys Lys Arg Leu Phe Asp Ile Phe Glu Gly Trp Cys Asp Asn Val
                325                 330                 335

Leu Asp Leu Leu His Ala Thr Glu Glu Glu Ala Ile Leu Arg Arg Asp
            340                 345                 350

Ile Tyr Asp Arg Thr Pro Ser Phe Asn Trp Gly Lys Gly Arg Val Thr
        355                 360                 365

Leu Leu Gly Asp Ser Ile His Ala Met Gln Pro Asn Met Gly Gln Gly
    370                 375                 380

Gly Cys Met Ala Ile Glu Asp Ser Tyr Gln Leu Ala Leu Glu Leu Glu
385                 390                 395                 400

Glu Ala Trp Glu Arg Ser Val Glu Thr Asn Ala Pro Val Asp Val Val
                405                 410                 415

Ser Ser Leu Arg Arg Tyr Glu Glu Ser Arg Arg Leu Arg Val Ala Ile
            420                 425                 430

Ile His Gly Met Ala Arg Met Ala Ala Ile Met Ala Ser Thr Tyr Lys
        435                 440                 445

Ala Tyr Leu Gly Val Gly Leu Gly Pro Leu Ser Phe Leu Thr Lys Phe
    450                 455                 460

Arg Val Pro His Pro Gly Arg Val Gly Gly Arg Phe Phe Ile Asp Ile
465                 470                 475                 480

Ala Met Pro Leu Met Leu Asn Trp Val Leu Gly Gly Asn Ser Glu Lys
                485                 490                 495

Leu Glu Gly Arg Pro Pro Ser Cys Arg Leu Thr Asp Lys Ala Asp Asp
            500                 505                 510

Arg Leu Arg Glu Trp Phe Glu Asp Asp Ala Leu Glu Arg Thr Ile
        515                 520                 525

Asn Gly Glu Trp Tyr Leu Ile Pro Tyr Gly Asn Glu Cys Ser Val Ser
    530                 535                 540

Glu Thr Leu Cys Leu Thr Lys Asp Glu Asp Gln Pro Cys Ile Ile Gly
545                 550                 555                 560

Ser Glu Pro Asp Gln Asp Phe Pro Gly Met His Ile Val Ile Pro Ala
```

-continued

```
                565                 570                 575
Pro Gln Val Ser Lys Met His Ala Arg Val Thr Tyr Lys Asp Gly Ala
                580                 585                 590

Phe Phe Leu Met Asp Leu Arg Ser Glu His Gly Thr Tyr Val Thr Asp
                595                 600                 605

Asn Glu Gly Arg Arg Tyr Arg Val Thr Pro Asn Phe Pro Ala Arg Phe
            610                 615                 620

Arg Ser Ser Asp Ile Ile Glu Phe Gly Ser Asp Lys Lys Ala Ala Phe
625                 630                 635                 640

Arg Val Lys Val Ile Arg Thr Thr Pro Lys Ser Thr Ser Lys Asn Lys
                645                 650                 655

Glu Ser Asn Gly Lys Leu Leu Gln Ala Val
            660                 665

<210> SEQ ID NO 43
<211> LENGTH: 666
<212> TYPE: PRT
<213> ORGANISM: Eutrema halophilum
<220> FEATURE:
<221> NAME/KEY: MISC_FEATURE
<222> LOCATION: (492)..(492)
<223> OTHER INFORMATION: Xaa = Any Amino Acid

<400> SEQUENCE: 43

Met Gly Ser Thr Pro Phe Cys Tyr Ser Ile Asn Pro Ser Pro Ser Lys
1               5                   10                  15

Leu Asp Phe Thr Arg Thr His Val Phe Ser Pro Val Ala Lys Gln Phe
                20                  25                  30

Tyr Leu Asp Leu Ser Ser Cys Ala Gly Lys Ser Gly Gly Gly Leu Ser
            35                  40                  45

Gly Phe Arg Ser Arg Arg Ala Leu Val Gly Val Arg Ala Ala Thr Ala
        50                  55                  60

Leu Val Glu Glu Lys Arg Glu Ile Ala Lys Glu Lys Lys Pro
65                  70                  75                  80

Arg Val Leu Val Ala Gly Gly Ile Gly Gly Leu Val Phe Ala Leu
                85                  90                  95

Ala Ala Lys Lys Lys Gly Phe Asp Val Leu Val Phe Glu Lys Asp Leu
                100                 105                 110

Ser Ala Ile Arg Gly Glu Gly Gln Tyr Arg Gly Pro Ile Gln Ile Gln
            115                 120                 125

Ser Asn Ala Leu Ala Ala Leu Glu Ala Ile Asp Ile Asp Val Ala Glu
130                 135                 140

Glu Val Met Glu Ala Gly Cys Ile Thr Gly Asp Arg Ile Asn Gly Leu
145                 150                 155                 160

Val Asp Gly Val Ser Gly Thr Trp Tyr Val Lys Phe Asp Thr Phe Thr
                165                 170                 175

Pro Ala Ala Ser Arg Gly Leu Pro Val Thr Arg Val Ile Ser Arg Met
            180                 185                 190

Thr Leu Gln Gln Ile Leu Ala Arg Ala Val Gly Glu Val Ile Arg
        195                 200                 205

Asn Glu Ser Asn Val Val Asp Phe Glu Asp Ser Gly Asp Lys Val Thr
    210                 215                 220

Val Val Leu Glu Asn Gly Glu Arg Tyr Glu Gly Asp Leu Leu Val Gly
225                 230                 235                 240

Ala Asp Gly Ile Trp Ser Lys Val Arg Asn Asn Leu Phe Gly Arg Ser
                245                 250                 255
```

```
Glu Ala Thr Tyr Ser Gly Tyr Thr Cys Tyr Thr Gly Ile Ala Asp Phe
            260                 265                 270

Val Pro Ala Asp Ile Glu Ser Val Gly Tyr Arg Val Phe Leu Gly His
            275                 280                 285

Lys Gln Tyr Phe Val Ser Ser Asp Val Gly Gly Lys Met Gln Trp
            290                 295                 300

Tyr Ala Phe His Glu Glu Pro Ala Gly Gly Val Asp Ala Pro Asn Gly
305                 310                 315                 320

Met Lys Lys Arg Leu Phe Asp Ile Phe Glu Gly Trp Cys Asp Asn Val
            325                 330                 335

Leu Asp Leu Leu His Ala Thr Glu Glu Ala Ile Leu Arg Arg Asp
            340                 345                 350

Ile Tyr Asp Arg Thr Pro Ser Phe Asn Trp Gly Lys Gly Arg Val Thr
            355                 360                 365

Leu Leu Gly Asp Ser Ile His Ala Met Gln Pro Asn Met Gly Gln Gly
            370                 375                 380

Gly Cys Met Ala Ile Glu Asp Ser Tyr Gln Leu Ala Leu Glu Leu Glu
385                 390                 395                 400

Glu Ala Trp Glu Arg Ser Val Glu Thr Asn Ala Pro Val Asp Val Val
            405                 410                 415

Ser Ser Leu Arg Arg Tyr Glu Glu Ser Arg Arg Leu Arg Val Ala Ile
            420                 425                 430

Ile His Gly Met Ala Arg Met Ala Ala Ile Met Ala Ser Thr Tyr Lys
            435                 440                 445

Ala Tyr Leu Gly Val Gly Leu Gly Pro Leu Ser Phe Leu Thr Lys Phe
            450                 455                 460

Arg Val Pro His Pro Gly Arg Val Gly Gly Arg Phe Phe Ile Asp Ile
465                 470                 475                 480

Ala Met Pro Leu Met Leu Asn Trp Val Leu Gly Xaa Asn Ser Glu Lys
            485                 490                 495

Leu Glu Gly Arg Pro Pro Ser Cys Arg Leu Thr Asp Lys Ala Asp Asp
            500                 505                 510

Arg Leu Arg Glu Trp Phe Glu Asp Asp Ala Leu Glu Arg Thr Ile
            515                 520                 525

Asn Gly Glu Trp Tyr Leu Ile Pro Tyr Gly Asn Glu Cys Ser Val Ser
            530                 535                 540

Glu Thr Leu Cys Leu Thr Lys Asp Glu Asp Gln Pro Cys Ile Ile Gly
545                 550                 555                 560

Ser Glu Pro Asp Gln Asp Phe Pro Gly Met His Ile Val Ile Pro Ala
            565                 570                 575

Pro Gln Val Ser Lys Met His Ala Arg Val Thr Tyr Lys Asp Gly Ala
            580                 585                 590

Phe Phe Leu Met Asp Leu Arg Ser Glu His Gly Thr Tyr Val Thr Asp
            595                 600                 605

Asn Glu Gly Arg Arg Tyr Arg Val Thr Pro Asn Phe Pro Ala Arg Phe
            610                 615                 620

Arg Ser Ser Asp Ile Ile Glu Phe Gly Ser Asp Lys Lys Ala Ala Phe
625                 630                 635                 640

Arg Val Lys Val Ile Arg Thr Thr Pro Lys Ser Thr Ser Lys Asn Lys
            645                 650                 655

Glu Ser Asn Gly Lys Leu Leu Gln Ala Val
            660                 665
```

<210> SEQ ID NO 44
<211> LENGTH: 665
<212> TYPE: PRT
<213> ORGANISM: Cucumis sativus

<400> SEQUENCE: 44

| | | | | | | | | | | | | | | |
|---|---|---|---|---|---|---|---|---|---|---|---|---|---|---|
| Met | Ala | Leu | Thr | Arg | Phe | His | Asn | Pro | Phe | Asn | Leu | Ser | Ser | Ser |
| 1 | | | | 5 | | | | | 10 | | | | | 15 |
| Leu | Ser | Arg | Thr | Cys | Phe | Pro | Val | Pro | Ala | Phe | Arg | Glu | Tyr | Leu | Val |
| | | | 20 | | | | | 25 | | | | | 30 | | |
| Glu | Ile | Ser | Pro | Cys | Gln | Arg | Ile | Gly | Cys | Asn | Phe | Gly | Gly | Lys | Ser |
| | | 35 | | | | | 40 | | | | | 45 | | | |
| Ala | Cys | Gly | Arg | Arg | Lys | Lys | Leu | Thr | Gln | Val | Lys | Ala | Ala | Val | Thr |
| | 50 | | | | | 55 | | | | | 60 | | | | |
| Glu | Ala | Pro | Pro | Ala | Glu | Gly | Ala | Ala | Gly | Ile | Ser | Arg | Ser | Leu |
| 65 | | | | | 70 | | | | | 75 | | | | | 80 |
| Pro | Thr | Lys | Asn | Val | Arg | Ile | Leu | Val | Ala | Gly | Gly | Ile | Gly | Gly |
| | | | | 85 | | | | | 90 | | | | | 95 |
| Leu | Val | Phe | Ala | Leu | Ala | Ala | Lys | Arg | Lys | Gly | Phe | Asp | Val | Val |
| | | | 100 | | | | | 105 | | | | | 110 | | |
| Phe | Glu | Lys | Asp | Ile | Ser | Ala | Ile | Arg | Gly | Glu | Gly | Gln | Tyr | Arg | Gly |
| | | 115 | | | | | 120 | | | | | 125 | | | |
| Pro | Ile | Gln | Ile | Gln | Ser | Asn | Ala | Leu | Ala | Ala | Leu | Glu | Ala | Ile | Asp |
| | 130 | | | | | 135 | | | | | 140 | | | | |
| Leu | Asp | Val | Ala | Glu | Glu | Val | Met | Arg | Val | Gly | Cys | Ile | Thr | Gly | Asp |
| 145 | | | | | 150 | | | | | 155 | | | | | 160 |
| Arg | Ile | Asn | Gly | Leu | Val | Asp | Gly | Val | Ser | Gly | Asn | Trp | Tyr | Ile | Lys |
| | | | | 165 | | | | | 170 | | | | | 175 |
| Phe | Asp | Thr | Phe | Thr | Pro | Ala | Ala | Glu | Arg | Gly | Leu | Pro | Val | Thr | Arg |
| | | | 180 | | | | | 185 | | | | | 190 | | |
| Val | Ile | Ser | Arg | Met | Ser | Leu | Gln | Gln | Ile | Leu | Ala | Arg | Ala | Val | Gly |
| | | 195 | | | | | 200 | | | | | 205 | | | |
| Asp | Asp | Val | Ile | Ile | Asn | Asp | Ser | Asn | Val | Val | Asp | Phe | Glu | Asp | Ser |
| | 210 | | | | | 215 | | | | | 220 | | | | |
| Gly | Glu | Lys | Val | Lys | Val | Thr | Leu | Glu | Asn | Gly | Gln | Gln | His | Glu | Gly |
| 225 | | | | | 230 | | | | | 235 | | | | | 240 |
| Asp | Leu | Leu | Val | Gly | Ala | Asp | Gly | Ile | Trp | Ser | Lys | Val | Arg | Lys | Asn |
| | | | | 245 | | | | | 250 | | | | | 255 |
| Leu | Phe | Gly | His | Ser | Glu | Ala | Val | Tyr | Ser | Gly | Tyr | Thr | Cys | Tyr | Thr |
| | | | 260 | | | | | 265 | | | | | 270 | | |
| Gly | Ile | Ala | Asp | Phe | Ile | Pro | Ala | Asp | Ile | Glu | Thr | Val | Gly | Tyr | Arg |
| | | 275 | | | | | 280 | | | | | 285 | | | |
| Val | Phe | Leu | Gly | His | Lys | Gln | Tyr | Phe | Val | Ser | Asp | Val | Gly | Ala |
| | 290 | | | | | 295 | | | | | 300 | | | | |
| Gly | Lys | Met | Gln | Trp | Tyr | Ala | Phe | His | Lys | Glu | Pro | Pro | Gly | Gly | Ala |
| 305 | | | | | 310 | | | | | 315 | | | | | 320 |
| Asp | Ala | Pro | Asn | Gly | Lys | Lys | Glu | Arg | Leu | Phe | Lys | Ile | Phe | Glu | Gly |
| | | | | 325 | | | | | 330 | | | | | 335 |
| Trp | Cys | Asp | Asn | Val | Thr | Asp | Leu | Ile | Gln | Ala | Thr | Glu | Asp | Ser |
| | | | 340 | | | | | 345 | | | | | 350 | | |
| Val | Leu | Arg | Arg | Asp | Ile | Tyr | Asp | Arg | Thr | Pro | Ile | Phe | Thr | Trp | Gly |
| | | 355 | | | | | 360 | | | | | 365 | | | |
| Lys | Gly | Arg | Val | Thr | Leu | Leu | Gly | Asp | Ser | Val | His | Ala | Met | Gln | Pro |
| | 370 | | | | | 375 | | | | | 380 | | | | |

```
Asn Met Gly Gln Gly Gly Cys Met Ala Ile Glu Asp Gly Tyr Gln Leu
385                 390                 395                 400

Ala Leu Glu Leu Asp Lys Ala Trp Asn Glu Ser Val Ala Ser Gly Ser
            405                 410                 415

Pro Ile Asp Ile Val Ser Ser Leu Lys Ser Tyr Glu Ser Arg Arg
        420                 425                 430

Ile Arg Val Ala Val Ile His Gly Met Ala Arg Met Ala Ala Leu Met
        435                 440                 445

Ala Ser Thr Tyr Lys Ala Tyr Leu Gly Val Gly Leu Gly Pro Leu Ser
    450                 455                 460

Phe Leu Thr Gln Phe Arg Ile Pro His Pro Gly Thr Phe Gly Gly Arg
465                 470                 475                 480

Phe Phe Ile Asp Leu Ala Met Pro Leu Met Leu Asn Trp Val Leu Gly
                485                 490                 495

Gly Asn Ser Ser Lys Leu Glu Gly Arg Pro Pro Ala Cys Arg Leu Ser
                500                 505                 510

Asp Lys Ala Asn Asp Gln Leu Arg Lys Trp Phe Glu Asp Asp Ala
        515                 520                 525

Leu Glu Arg Ala Ile Asn Gly Asp Trp Phe Leu Leu Pro Gln Gly Gly
    530                 535                 540

Glu Ala Ser Val Ser Gln Pro Ile Cys Leu Arg Lys Asp Glu Asn Gln
545                 550                 555                 560

Pro Cys Leu Ile Gly Ser Val Glu Lys Glu Val Asp Ser Gly Leu Ser
                565                 570                 575

Val Ala Ile Pro Leu Pro Gln Val Ser Glu Lys His Ala Arg Ile Tyr
                580                 585                 590

Tyr Lys Asp Gly Ala Phe Phe Leu Thr Asp Leu Arg Ser Glu His Gly
            595                 600                 605

Thr Trp Leu Ser Asp His Glu Gly Arg Arg Tyr Arg Ala Pro Pro Asn
        610                 615                 620

Phe Pro Val Arg Phe His Gln Ser Asp Leu Ile Glu Phe Gly Ser Asp
625                 630                 635                 640

Lys Lys Ala Arg Phe Arg Val Lys Val Ile Arg Ser Ser Val Glu Asn
                645                 650                 655

Asp Arg Glu Lys Val Glu Met Asn Ser
            660                 665

<210> SEQ ID NO 45
<211> LENGTH: 658
<212> TYPE: PRT
<213> ORGANISM: Vitis vinifera

<400> SEQUENCE: 45

Met Ala Ser Ala Val Phe Tyr Ser Ser Val Gln Pro Ser Ile Phe Ser
1               5                   10                  15

Arg Thr His Ile Pro Ile Pro Ile Ser Lys Asp Ser Phe Glu Glu Phe
            20                  25                  30

Gly His Ser Ile Asn Tyr Lys His Tyr Phe Arg Ser Asn Pro Cys Gly
        35                  40                  45

Gln Lys Lys Arg Val Ala Gln Val Lys Ala Thr Leu Ala Glu Ala Thr
    50                  55                  60

Pro Ala Pro Pro Ala Pro Ser Leu Pro Ser Lys Lys Val Arg Ile Leu
65                  70                  75                  80

Val Ala Gly Gly Gly Ile Gly Gly Leu Val Leu Ala Leu Ala Ala Lys
```

```
                85                  90                  95
Lys Lys Gly Phe Asp Val Val Phe Glu Lys Asp Met Ser Ala Ile
            100                 105                 110

Arg Gly Glu Gly Gln Tyr Arg Gly Pro Ile Gln Ile Gln Ser Asn Ala
            115                 120                 125

Leu Ala Ala Leu Glu Ala Val Asp Met Glu Val Ala Glu Glu Val Met
        130                 135                 140

Arg Ala Gly Cys Ile Thr Gly Asp Arg Ile Asn Gly Leu Val Asp Gly
145                 150                 155                 160

Val Ser Gly Asp Trp Tyr Val Lys Phe Asp Thr Phe Thr Pro Ala Ala
                165                 170                 175

Glu Arg Gly Leu Pro Val Thr Arg Val Ile Ser Arg Met Thr Leu Gln
            180                 185                 190

Gln Ile Leu Ala Arg Ala Val Gly Glu Asp Ile Ile Met Asn Gly Ser
        195                 200                 205

Asn Val Val Asp Phe Glu Asp Asp Gly Asn Lys Val Thr Val Ile Leu
210                 215                 220

Glu Asn Gly Gln Arg Tyr Glu Gly Asp Leu Leu Ile Gly Ala Asp Gly
225                 230                 235                 240

Ile Trp Ser Lys Val Arg Lys Ser Leu Phe Gly Pro Lys Glu Ala Thr
                245                 250                 255

Tyr Ser Gly Tyr Thr Cys Tyr Thr Gly Ile Ala Asp Phe Val Pro Ala
            260                 265                 270

Asp Ile Asp Ser Val Gly Tyr Arg Val Phe Leu Gly His Lys Gln Tyr
        275                 280                 285

Phe Val Ser Ser Asp Val Gly Ala Gly Lys Met Gln Trp Tyr Ala Phe
290                 295                 300

Tyr Asn Glu Pro Ala Gly Gly Val Asp Gly Pro Glu Gly Lys Lys Glu
305                 310                 315                 320

Arg Leu Leu Lys Ile Phe Gly Gly Trp Cys Asp Asn Val Ile Asp Leu
                325                 330                 335

Ile Leu Ala Thr Asp Glu Glu Ala Ile Leu Arg Arg Asp Ile Tyr Asp
            340                 345                 350

Arg Thr Pro Thr Phe Thr Trp Gly Arg Gly Arg Val Thr Leu Leu Gly
        355                 360                 365

Asp Ser Val His Ala Met Gln Pro Asn Met Gly Gln Gly Gly Cys Met
370                 375                 380

Ala Ile Glu Asp Ser Tyr Gln Leu Ala Met Glu Leu Asp Lys Ala Trp
385                 390                 395                 400

Glu Gln Ser Ile Lys Ser Gly Thr Pro Ile Asp Val Val Ser Cys Leu
                405                 410                 415

Lys Ser Tyr Glu Lys Ala Arg Arg Ile Arg Val Ala Val Ile His Gly
            420                 425                 430

Met Ala Arg Met Ala Ala Ile Met Ala Ser Thr Tyr Lys Ala Tyr Leu
        435                 440                 445

Gly Val Gly Leu Gly Pro Leu Ser Phe Leu Thr Lys Leu Arg Ile Pro
450                 455                 460

His Pro Gly Arg Val Gly Gly Arg Phe Phe Ile Asp Ile Ala Met Pro
465                 470                 475                 480

Leu Met Leu Ser Trp Val Leu Gly Gly Asn Ser Ser Lys Leu Glu Gly
                485                 490                 495

Arg Pro Pro Ser Cys Arg Leu Ser Asp Lys Ala Asn Asp Gln Leu Arg
            500                 505                 510
```

-continued

```
Arg Trp Phe Glu Asp Asp Ala Leu Glu Arg Ala Ile Gly Gly Glu
        515                 520                 525

Trp Phe Leu Leu Pro Ser Gly Glu Ser Gly Leu Gln Pro Ile Cys Leu
    530                 535                 540

Ser Lys Asp Glu Asn Lys Pro Cys Ile Ile Gly Ser Val Ser His Thr
545                 550                 555                 560

Asp Phe Pro Gly Ile Ser Thr Val Ile Pro Ser Pro Lys Val Ser Lys
                565                 570                 575

Met His Ala Arg Ile Ser Cys Lys Asp Gly Ala Phe Phe Leu Thr Asp
            580                 585                 590

Leu Gln Ser Glu His Gly Thr Trp Ile Thr Asp Asn Val Gly Arg Arg
        595                 600                 605

Gln Arg Val Ser Pro Asn Phe Pro Thr Arg Phe His Pro Ser Glu Val
    610                 615                 620

Ile Asp Phe Gly Ser Glu Lys Ala Ser Phe Arg Val Lys Val Val Arg
625                 630                 635                 640

Thr Pro Pro Asp Asn Ala Ala Lys Asn Glu Ser Lys Leu Phe Gln
                645                 650                 655

Ala Val

<210> SEQ ID NO 46
<211> LENGTH: 664
<212> TYPE: PRT
<213> ORGANISM: Corchorus olitorius

<400> SEQUENCE: 46

Met Ala Thr Thr Leu Phe Gln Asn Pro Ser Thr Phe Phe Thr Gly Thr
1               5                   10                  15

Gln Phe Pro Val Ser Ile Pro Lys Tyr Val Pro Thr Glu Ser Ser Ala
            20                  25                  30

Cys Leu His Cys Asn Tyr His Phe Arg Gly Lys Ala Ser Lys Gln Lys
        35                  40                  45

Lys Arg Phe Leu Gln Val Lys Ala Thr Val Ala Gly Thr Gln Ser Asp
    50                  55                  60

Ser Lys Ser Asp Glu Lys Asn Lys Val Asp Ala Asn Gln Gln Glu Lys
65                  70                  75                  80

Lys Lys Ala Arg Ile Leu Val Ala Gly Gly Ile Gly Gly Leu Val
                85                  90                  95

Phe Ala Leu Ala Ala Lys Asn Lys Gly Phe Asp Val Val Val Phe Glu
            100                 105                 110

Lys Asp Leu Ser Ala Ile Arg Gly Glu Gly Gln Tyr Arg Gly Pro Ile
        115                 120                 125

Gln Ile Gln Ser Asn Ala Leu Ala Ala Leu Glu Ala Ile Asp Met Glu
    130                 135                 140

Val Ala Glu Lys Val Met Glu Ala Gly Cys Ile Thr Gly Asp Arg Ile
145                 150                 155                 160

Asn Gly Leu Val Asp Gly Val Ser Gly Ser Trp Tyr Ile Lys Phe Asp
                165                 170                 175

Thr Phe Thr Pro Ala Ala Glu Arg Gly Leu Pro Val Thr Arg Val Ile
            180                 185                 190

Ser Arg Met Thr Leu Gln Gln Ile Leu Ala Arg Ala Val Gly Glu Asp
        195                 200                 205

Ile Ile Phe Asn Glu Ser Asn Val Val Asp Phe Glu Asp Gly Asn
    210                 215                 220
```

-continued

```
Lys Val Ser Val Val Leu Glu Asn Gly Lys Arg Phe Glu Gly Asp Leu
225                 230                 235                 240

Leu Val Gly Ala Asp Gly Ile Trp Ser Lys Val Arg Lys Asn Leu Phe
            245                 250                 255

Gly Pro Lys Asp Ala Val Tyr Ser Gly Tyr Thr Cys Tyr Thr Gly Ile
        260                 265                 270

Ala Asp Phe Val Pro Ala Asp Ile Asp Ser Val Gly Tyr Arg Val Phe
            275                 280                 285

Leu Gly His Lys Gln Tyr Phe Val Ser Ser Asp Val Gly Gly Gly Lys
        290                 295                 300

Met Gln Trp Tyr Ala Phe His Lys Glu Pro Ala Gly Gly Val Asp Thr
305                 310                 315                 320

Gln Gly Lys Lys Glu Arg Leu Leu Lys Ile Phe Glu Gly Trp Cys Asp
            325                 330                 335

Asn Val Ile Asp Leu Leu Leu Ala Thr Asp Glu Glu Ala Ile Leu Arg
                340                 345                 350

Arg Asp Ile Tyr Asp Arg Thr Pro Ser Leu Thr Trp Gly Lys Gly Arg
            355                 360                 365

Val Thr Leu Leu Gly Asp Ser Ile His Ala Met Gln Pro Asn Leu Gly
        370                 375                 380

Gln Gly Gly Cys Met Ala Ile Glu Asp Gly Tyr Gln Leu Ala Leu Glu
385                 390                 395                 400

Leu Asp Lys Ala Trp Lys Gln Ser Val Glu Ser Gly Thr Pro Ile Asp
            405                 410                 415

Val Val Ser Ser Leu Arg Ser Tyr Glu Ser Ala Arg Arg Leu Arg Val
                420                 425                 430

Ala Ile Ile His Gly Met Ala Arg Met Ala Ala Ile Met Ala Ser Thr
            435                 440                 445

Tyr Lys Ala Tyr Leu Gly Val Gly Leu Gly Pro Leu Ser Phe Leu Thr
    450                 455                 460

Lys Tyr Arg Ile Pro His Pro Gly Arg Val Gly Gly Arg Phe Phe Ile
465                 470                 475                 480

Asp Ile Ala Met Pro Leu Met Leu Ser Trp Val Leu Gly Gly Asn Ser
                485                 490                 495

Ser Lys Leu Glu Gly Arg Ser Leu Thr Cys Arg Leu Ser Asp Lys Ala
        500                 505                 510

Ser Asp Gln Leu Arg Glu Trp Phe Glu Asp Asn Asp Ala Leu Glu Arg
            515                 520                 525

Ala Ile Ser Gly Glu Trp Phe Leu Phe Pro Ala Gly Asp Gly Val Ser
        530                 535                 540

Ser Gln Pro Ile Cys Leu Ser Arg Asp Glu Asn Asn Pro Phe Met Ile
545                 550                 555                 560

Gly Ser Glu Lys Lys Glu Asp Phe Pro Gly Thr Ser Val Val Ile Pro
            565                 570                 575

Ser Ser Gln Val Ser Lys Thr His Ala Gln Ile Thr Tyr Lys Asp Gly
                580                 585                 590

Ala Phe Phe Val Thr Asp Leu Gln Ser Glu His Gly Thr Tyr Ile Ile
            595                 600                 605

Asn Gln Glu Gly Lys Lys Ser Arg Val Thr Pro Asn Val Pro Thr Arg
        610                 615                 620

Ile Arg Pro Ser Asp Val Ile Glu Phe Gly Ser Asp Lys Lys Ala Ala
625                 630                 635                 640
```

```
Phe Arg Val Lys Ala Ile Lys Ser Ala Pro Lys Ile Ala Glu Lys Glu
                645                 650                 655

Gly Ser Gly Val Leu Gln Ala Ala
        660
```

<210> SEQ ID NO 47
<211> LENGTH: 661
<212> TYPE: PRT
<213> ORGANISM: Populus euphratica

<400> SEQUENCE: 47

```
Met Ala Ser Ser Thr Leu Phe Gly Asn Thr Leu Thr Ala Val Ser Ser
1               5                   10                  15

Arg Thr His Phe Pro Thr Pro Ile Phe Asn Asn Ser Leu Glu Leu Leu
            20                  25                  30

Ser Ser Thr His Ser Asn Tyr Asn Phe Lys Thr Lys Ser Thr Ser Ser
        35                  40                  45

Ala Lys Lys Leu Lys Val Glu Ala Val Val Thr Glu Thr Pro Ala Val
    50                  55                  60

Ser Lys Ser Glu Gly Lys Gln Ser Glu Gln Arg Lys Leu Lys Val Leu
65                  70                  75                  80

Val Ala Gly Gly Gly Ile Gly Gly Leu Val Phe Ala Leu Ala Ala Lys
                85                  90                  95

Asn Lys Gly Phe Asp Val Met Val Phe Glu Lys Asp Leu Ser Ala Val
            100                 105                 110

Arg Gly Glu Gly Gln Tyr Arg Gly Pro Ile Gln Ile Gln Ser Asn Ala
        115                 120                 125

Leu Ala Ala Leu Glu Ala Ile Asp Leu Asp Val Ala Glu Glu Val Met
    130                 135                 140

Arg Ala Gly Cys Ile Thr Gly Asp Arg Ile Asn Gly Leu Val Asp Gly
145                 150                 155                 160

Ile Ser Gly Thr Trp Tyr Val Lys Phe Asp Thr Phe Thr Pro Ala Ala
                165                 170                 175

Glu Arg Gly Leu Pro Val Thr Arg Val Ile Ser Arg Met Thr Leu Gln
            180                 185                 190

Gln Ile Leu Ala Arg Ser Val Gly Asp Asp Thr Ile Leu Asn Asp Ser
        195                 200                 205

Asn Val Val Ser Phe Gln Asp Asp Gly Asp Lys Val Thr Val Val Leu
    210                 215                 220

Glu Asn Gly Gln Gln Tyr Glu Gly Asp Leu Leu Val Gly Ala Asp Gly
225                 230                 235                 240

Ile Trp Ser Lys Val Arg Lys Asn Leu Phe Gly Pro Lys Glu Ala Val
                245                 250                 255

Tyr Ser Gly Tyr Thr Cys Tyr Thr Gly Ile Ala Asp Phe Val Pro Val
            260                 265                 270

Asp Ile Glu Thr Val Gly Tyr Arg Val Phe Leu Gly His Lys Gln Tyr
        275                 280                 285

Phe Val Ser Ser Asp Val Gly Ala Gly Lys Met Gln Trp Tyr Ala Phe
    290                 295                 300

His Lys Glu Ser Pro Gly Gly Met Asp Ala Pro His Gly Lys Lys Asp
305                 310                 315                 320

Arg Leu Leu Lys Ile Phe Glu Gly Trp Cys Asp Asn Val Ile Asp Leu
                325                 330                 335

Leu Leu Thr Thr Asp Glu Asp Ser Ile Leu Arg Arg Asp Ile Tyr Asp
            340                 345                 350
```

Arg Glu Pro Ile Ile Thr Trp Gly Lys Gly Arg Val Thr Leu Leu Gly
            355                 360                 365

Asp Ser Val His Ala Met Gln Pro Asn Met Gly Gln Gly Gly Cys Met
        370                 375                 380

Ala Ile Glu Asp Ser Tyr Gln Leu Ala Ser Glu Leu Glu Arg Ala Trp
385                 390                 395                 400

Lys Gln Ser Ile Glu Ser Gly Thr Pro Val Asp Val Leu Ser Ser Leu
                405                 410                 415

Arg Ser Tyr Glu Asn Ala Arg Arg Leu Arg Val Ala Ile Ile His Gly
            420                 425                 430

Met Ala Arg Met Ala Ala Ile Met Ala Ser Thr Tyr Lys Ala Tyr Leu
        435                 440                 445

Gly Val Gly Leu Gly Pro Leu Ser Phe Leu Thr Asn Phe Arg Ile Pro
450                 455                 460

His Pro Gly Arg Val Gly Gly Arg Phe Phe Ile Asp Ile Ala Met Pro
465                 470                 475                 480

Val Met Leu Asp Trp Val Leu Gly Gly Asn Ser Ser Lys Leu Glu Gly
                485                 490                 495

Arg Ser Leu Ser Cys Arg Leu Ser Asp Lys Ala Ser Asp Gln Leu Arg
            500                 505                 510

Arg Trp Phe Val Asp Asp Ala Leu Glu Arg Ser Leu Asn Gly Glu
        515                 520                 525

Trp Phe Leu Leu Pro Cys Gly Asn Asp Ala Val Ala Ser Gln Pro Ile
530                 535                 540

Gly Leu Ser Arg Asp Glu Asn Lys Pro Cys Val Val Gly Ser Val Ser
545                 550                 555                 560

Gln Glu Asp Phe Pro Gly Met Ser Ile Val Ile Pro Ala Pro Gln Val
                565                 570                 575

Ser Lys Thr His Ala Arg Ile Thr Cys Lys Asp Gly Ala Phe Tyr Leu
            580                 585                 590

Ile Asp Leu Arg Ser Glu His Gly Thr Phe Ile Thr Asp Ile Glu Gly
        595                 600                 605

Arg Arg Tyr Arg Ala Pro Pro Asn Phe Pro Thr Arg Phe His Pro Ser
610                 615                 620

Asp Met Ile Glu Phe Gly Ser Asp Lys Lys Val Ile Phe Arg Val Lys
625                 630                 635                 640

Val Met Arg Ser Pro Pro Lys Ile Ser Glu Lys Lys Asp Glu Gly Gln
                645                 650                 655

Val Leu Gln Ser Val
            660

<210> SEQ ID NO 48
<211> LENGTH: 665
<212> TYPE: PRT
<213> ORGANISM: Ricinus communis

<400> SEQUENCE: 48

Met Ala Ser Ser Ala Phe Phe Cys Asn Ser Ile Asn Pro Ser Thr Ser
1               5                   10                  15

Val Phe Ser Arg Thr His Phe Ser Pro Ile Phe Ser Thr Ser Thr
            20                  25                  30

Val Glu Phe Ser Ser Phe Ala Gln Tyr Asn Phe His Phe Lys Thr Lys
        35                  40                  45

Lys Ser Asp His Gln Asn Lys Arg Phe Thr Gln Val Lys Ala Val Val

```
              50                  55                  60
Thr Glu Ser Pro Thr Val Ala Glu Ser Asn Gly Lys Leu Ser Glu Gln
65                  70                  75                  80

Lys Lys Leu Arg Ile Leu Val Ala Gly Gly Ile Gly Gly Leu Val
                85                  90                  95

Phe Ala Leu Ala Ala Lys Arg Lys Gly Phe Glu Val Leu Val Phe Glu
                100                 105                 110

Lys Asp Leu Ser Ala Ile Arg Gly Glu Gly Gln Tyr Arg Gly Pro Ile
                115                 120                 125

Gln Val Gln Ser Asn Ala Leu Ala Ala Leu Glu Ala Ile Asp Leu Glu
                130                 135                 140

Val Ala Glu Glu Val Met Arg Ala Gly Cys Ile Thr Gly Asp Arg Ile
145                 150                 155                 160

Asn Gly Leu Val Asp Gly Val Ser Gly Thr Trp Tyr Cys Lys Phe Asp
                165                 170                 175

Thr Phe Thr Pro Ala Ala Glu Arg Gly Leu Pro Val Thr Arg Val Ile
                180                 185                 190

Ser Arg Met Thr Leu Gln Gln Ile Leu Ala Cys Ala Val Gly Glu Asp
                195                 200                 205

Val Ile Met Asn Ala Ser Asn Val Ile Asn Phe Gln Asp Asn Glu Asp
                210                 215                 220

Lys Val Thr Val Thr Leu Glu Asn Gly Gln Gln Phe Glu Gly Asp Leu
225                 230                 235                 240

Leu Val Gly Ala Asp Gly Ile Trp Ser Lys Val Arg Lys Asn Leu Phe
                245                 250                 255

Gly Pro Lys Glu Ala Thr Tyr Ser Gly Tyr Thr Cys Tyr Thr Gly Ile
                260                 265                 270

Ala Asp Phe Val Pro Val Asp Ile Glu Ser Val Gly Tyr Arg Val Phe
                275                 280                 285

Leu Gly His Lys Gln Tyr Phe Val Ser Ser Asp Val Gly Ala Gly Lys
                290                 295                 300

Met Gln Trp Tyr Ala Phe His Asn Glu Pro Pro Gly Gly Val Asp Ser
305                 310                 315                 320

Pro Asn Gly Lys Lys Glu Arg Leu Leu Lys Ile Phe Glu Gly Trp Cys
                325                 330                 335

Asp Asn Val Ile Asp Leu Leu His Ala Thr Asp Glu Asp Ala Ile Leu
                340                 345                 350

Arg Arg Asp Ile Tyr Asp Arg Glu Pro Val Phe Thr Trp Gly Lys Gly
                355                 360                 365

Arg Val Thr Leu Leu Gly Asp Ser Ile His Ala Met Gln Pro Asn Met
370                 375                 380

Gly Gln Gly Gly Cys Met Ala Ile Glu Asp Ser Tyr Gln Leu Ala Leu
385                 390                 395                 400

Glu Leu Asp Lys Ala Trp Lys Gln Ser Ile Glu Ser Gly Thr Pro Val
                405                 410                 415

Asp Val Val Ser Ser Leu Lys Ser Tyr Glu Arg Thr Arg Arg Leu Arg
                420                 425                 430

Val Ala Ile Ile His Gly Met Ala Arg Met Ala Ala Ile Met Ala Ser
                435                 440                 445

Thr Tyr Lys Ala Tyr Leu Gly Val Gly Leu Gly Pro Leu Ser Phe Leu
450                 455                 460

Thr Lys Tyr Arg Ile Pro His Pro Gly Arg Val Gly Gly Arg Phe Phe
465                 470                 475                 480
```

```
Ile Asp Ile Ala Met Pro Val Met Leu Asn Trp Val Leu Gly Gly Asn
            485                 490                 495

Ser Ser Lys Leu Glu Gly Arg Pro Leu Ser Cys Arg Leu Ser Asp Lys
            500                 505                 510

Ala Ser Asp Gln Leu Gln Thr Trp Phe Glu Asp Asn Ala Leu Glu
            515                 520                 525

Arg Ala Leu Asn Gly Glu Trp Phe Leu Leu Pro Phe Gly Asp Asp Ala
            530                 535                 540

Val Gln Glu Pro Ile Cys Leu Ser Arg Asp Glu Asn Ile Pro Cys Met
545                 550                 555                 560

Val Gly Ser Glu Ser Gln Glu Asp Phe Pro Gly Lys Ser Ile Val Ile
            565                 570                 575

Ser Ser Pro Gln Val Ser Lys Met His Ala Arg Ile Ser Tyr Lys Asp
            580                 585                 590

Gly Gly Phe Tyr Val Ile Asp Leu Gln Ser Glu His Gly Thr Phe Ile
            595                 600                 605

Thr Asp Asn Asp Gly Arg Arg Ser Arg Val Pro Pro Asn Phe Pro Thr
            610                 615                 620

Leu Phe His Pro Ser Glu Ala Ile Glu Phe Gly Ser Ala Gly Lys Ala
625                 630                 635                 640

Lys Phe Arg Val Lys Val Met Lys Ser Pro Ala Lys Ile Lys Glu Lys
            645                 650                 655

Gly Gly Asn Glu Ile Leu Gln Ser Val
            660                 665

<210> SEQ ID NO 49
<211> LENGTH: 665
<212> TYPE: PRT
<213> ORGANISM: Jatropha curcas

<400> SEQUENCE: 49

Met Ala Ser Ser Thr Leu Phe Cys Asn Leu Ile Asn Pro Ser Ile Ser
1               5                   10                  15

Val Phe Ser Arg Thr His Leu Pro Phe Pro Ile Val Ser Ser Ser Ser
            20                  25                  30

Met Glu Leu Ser Ser Ser Ala His Cys Asn Phe His Phe Arg Ser Lys
            35                  40                  45

Lys Ser Glu Gln Asn Lys Lys Leu Thr Gln Val Lys Ala Val Val Thr
        50                  55                  60

Glu Ser Thr Ser Val Ala Gln Ser Asp Glu Lys Gln Pro Glu Gln Arg
65                  70                  75                  80

Lys Pro Arg Ile Leu Val Ala Gly Gly Ile Gly Gly Leu Val Phe
            85                  90                  95

Ala Leu Ala Ala Lys Arg Lys Gly Phe Glu Val Leu Val Phe Glu Lys
            100                 105                 110

Asp Leu Ser Ala Val Arg Gly Glu Gly Gln Tyr Arg Gly Pro Ile Gln
            115                 120                 125

Ile Gln Ser Asn Ala Leu Ala Ala Leu Glu Ala Ile Asp Leu Glu Val
        130                 135                 140

Ala Glu Glu Val Met Glu Ala Gly Cys Ile Thr Gly Asp Arg Ile Asn
145                 150                 155                 160

Gly Leu Val Asp Gly Val Ser Gly Thr Trp Tyr Val Lys Phe Asp Thr
            165                 170                 175

Phe Thr Pro Ala Ala Glu Arg Gly Leu Pro Val Thr Arg Val Ile Ser
```

```
              180                 185                 190
Arg Met Thr Leu Gln Gln Ile Leu Ala Leu Ala Val Gly Glu Asp Val
            195                 200                 205

Ile Arg Asn Glu Ser Asn Val Val Ser Phe Gln Asp Asp Gly Asp Lys
        210                 215                 220

Val Thr Val Thr Leu Glu Asn Gly Gln His Phe Glu Gly Asp Leu Leu
225                 230                 235                 240

Val Gly Ala Asp Gly Ile Trp Ser Lys Val Arg Lys Asn Leu Phe Gly
                245                 250                 255

Pro Lys Asp Ala Thr Tyr Ser Asp Tyr Thr Cys Tyr Thr Gly Ile Ala
            260                 265                 270

Asp Phe Val Pro Ala Asp Ile Glu Ser Val Gly Tyr Arg Val Phe Leu
        275                 280                 285

Gly His Lys Gln Tyr Phe Val Ser Ser Asp Val Gly Ala Gly Lys Met
    290                 295                 300

Gln Trp Tyr Ala Phe His Lys Glu Pro Pro Gly Gly Val Asp Arg Pro
305                 310                 315                 320

Asn Gly Lys Lys Glu Arg Leu Leu Lys Ile Phe Glu Gly Trp Cys Asp
                325                 330                 335

Asn Val Ile Asp Leu Leu Ala Thr Asp Glu Asp Ala Ile Leu Arg
            340                 345                 350

Arg Asp Ile Tyr Asp Arg Thr Pro Thr Leu Thr Trp Gly Arg Gly Arg
        355                 360                 365

Val Thr Leu Leu Gly Asp Ser Val His Ala Met Gln Pro Asn Met Gly
    370                 375                 380

Gln Gly Gly Cys Met Ala Ile Glu Asp Gly Tyr Gln Leu Ala Leu Glu
385                 390                 395                 400

Ile Glu Lys Ala Trp Lys Gln Ser Ile Glu Ser Gly Thr Pro Ile Asp
                405                 410                 415

Ile Val Ser Ser Leu Lys Ser Tyr Glu Arg Ala Arg Arg Leu Arg Val
            420                 425                 430

Ala Ile Ile His Gly Met Ala Arg Met Ala Ala Ile Met Ala Ser Thr
        435                 440                 445

Tyr Lys Ala Tyr Leu Gly Val Gly Leu Gly Pro Leu Ser Phe Leu Thr
    450                 455                 460

Lys Tyr Arg Ile Pro His Pro Gly Arg Val Gly Gly Arg Phe Phe Ile
465                 470                 475                 480

Asp Ile Ala Met Pro Val Met Leu Ser Trp Val Leu Gly Gly Asn Ser
                485                 490                 495

Ser Lys Leu Glu Gly Arg Ser Gln Cys Cys Arg Leu Ser Asp Lys Ala
            500                 505                 510

Ser Asp Gln Leu Arg Thr Trp Phe Glu Asp Asp Ala Leu Glu Arg
        515                 520                 525

Ala Leu Asn Ala Glu Trp Phe Leu Leu Pro Leu Gly Asn Lys Val Val
    530                 535                 540

Val Ser Glu Pro Ile Cys Leu Ser Arg Asn Glu Asn Thr Pro Cys Val
545                 550                 555                 560

Val Gly Lys Val Ser His Lys Asp Phe Pro Gly Met Ser Ile Val Ile
                565                 570                 575

Pro Ser Pro Gln Val Ser Glu Met His Ala Arg Ile Ser Tyr Lys Asp
            580                 585                 590

Gly Ala Phe Tyr Val Ile Asp Leu Gln Ser Glu His Gly Thr Tyr Ile
        595                 600                 605
```

```
Ser Asp Ala Asp Gly Arg Arg Tyr Arg Val Pro Gln Asn Ser Pro Thr
    610                 615                 620

Arg Phe His Pro Ser Asp Val Ile Glu Phe Gly Ser Asp Glu Lys Ala
625                 630                 635                 640

Lys Phe Arg Val Lys Val Met Lys Ser Pro Ser Arg Ile Lys Glu Lys
                645                 650                 655

Glu Gly Ser Glu Ile Leu Gln Ser Val
            660                 665

<210> SEQ ID NO 50
<211> LENGTH: 480
<212> TYPE: PRT
<213> ORGANISM: Eucalyptus grandis

<400> SEQUENCE: 50

Met Ala Ser Met Ala Ala Gly Ser Ile Cys Leu Phe Arg Asp Glu Ser
1               5                   10                  15

Ile Gly Ala Ala Ser Ile Ala Val Thr Ile Leu Ala Asn Arg Ser Ser
            20                  25                  30

His Met Ala Lys Leu Leu Cys Tyr Arg Gly Lys Ala Arg Ala Thr Met
        35                  40                  45

Trp Met Gly Ile Lys Thr Thr Arg Arg Leu Ala Met Lys Cys Ser Leu
    50                  55                  60

Glu Ser His Cys Arg Ser Glu Ser Ser Cys Ser Gly Phe Pro Leu Pro
65                  70                  75                  80

Arg Lys Glu Glu Val Thr Ser Ser Arg Gly Ser Arg Ser Gly Val Pro
                85                  90                  95

Lys Val Thr Glu Ser Ala Arg Glu Ile Phe His Leu Val Arg Glu Trp
            100                 105                 110

Ser Gln Arg Arg Val Ile Gln Leu Ala Ala Leu Ala Ala Cys Thr Phe
        115                 120                 125

Leu Ile Ile Pro Ser Ala Asp Ala Val Asp Ala Leu Lys Thr Cys Ala
    130                 135                 140

Cys Leu Leu Lys Glu Cys Arg Ile Glu Leu Ala Lys Cys Val Ala Asn
145                 150                 155                 160

Pro Ser Cys Ala Ala Asn Val Ala Cys Leu Gln Thr Cys Asn Asn Arg
                165                 170                 175

Pro Asp Glu Thr Glu Cys Gln Ile Lys Cys Gly Asp Leu Phe Glu Asn
            180                 185                 190

Ser Val Val Asp Glu Phe Asn Glu Cys Ala Val Ser Arg Lys Lys Cys
        195                 200                 205

Val Pro Arg Lys Ser Asp Val Gly Glu Phe Pro Val Pro Asp Pro Ala
    210                 215                 220

Val Leu Val Lys Ser Phe Asn Met Ala Asp Phe Thr Gly Lys Trp Phe
225                 230                 235                 240

Ile Ser Ser Gly Leu Asn Pro Thr Phe Asp Thr Phe Asp Cys Gln Leu
                245                 250                 255

His Glu Phe His Thr Glu Ser Asn Lys Leu Met Gly Asn Leu Thr Trp
            260                 265                 270

Arg Ile Arg Thr Pro Asp Ser Gly Phe Phe Thr Arg Thr Ala Val Gln
        275                 280                 285

Arg Phe Val Gln Asp Pro Glu Gln Pro Gly Ile Leu Tyr Asn His Asp
    290                 295                 300

Asn Glu Tyr Leu His Tyr Gln Asp Asp Trp Tyr Ile Leu Ser Ser Lys
```

```
            305                 310                 315                 320
Thr Glu Asn Lys Pro Asp Asp Tyr Val Phe Val Tyr Tyr Arg Gly Arg
                    325                 330                 335

Asn Asp Ala Trp Asp Gly Tyr Gly Ala Val Val Tyr Thr Arg Ser
            340                 345                 350

Ala Val Leu Pro Asp Ser Ile Val Pro Glu Leu Glu Arg Ala Ala Lys
            355                 360                 365

Ser Val Gly Arg Asp Phe Lys Asp Phe Ile Arg Thr Asp Asn Thr Cys
370                 375                 380

Gly Pro Glu Pro Pro Leu Val Glu Arg Ile Glu Lys Thr Val Glu Glu
385                 390                 395                 400

Gly Glu Lys Thr Ile Val Arg Glu Val Glu Gln Ile Glu Asp Glu Val
                    405                 410                 415

Gln Lys Val Gly Lys Thr Glu Met Thr Leu Phe Gln Arg Leu Thr Glu
                    420                 425                 430

Gly Phe Arg Glu Leu Arg Gln Asp Glu Glu Asn Phe Leu Arg Arg Leu
            435                 440                 445

Ser Gln Glu Glu Met Glu Val Leu Asn Glu Leu Lys Met Glu Ala Thr
            450                 455                 460

Glu Val Glu Lys Leu Phe Gly Arg Ala Leu Pro Ile Arg Lys Leu Arg
465                 470                 475                 480

<210> SEQ ID NO 51
<211> LENGTH: 458
<212> TYPE: PRT
<213> ORGANISM: Tarenaya hassleriana

<400> SEQUENCE: 51

Met Ala Val Ala Val Gln Ser Phe Ser Ser Pro Cys Tyr Arg Asp Thr
1               5                   10                  15

Gln Phe Ile Ser Gly Asn Arg Ser Asn Arg Lys Leu Leu Arg Lys Arg
                20                  25                  30

Met Val Asp Ser Asp Thr Ile Val Leu Val Lys Ile Cys Ser Gly Ala
            35                  40                  45

Arg Gly Lys Ile His Cys Ser Leu Lys Ala Arg Phe Ser Ser Pro Ser
50                  55                  60

Ser Gly Tyr Lys Ser Gly Leu Ser Lys Gly Arg Pro Pro Phe Glu Ala
65                  70                  75                  80

Leu Thr Leu Trp Asn Lys Leu Lys Glu Gln Ser Arg Gln Ser Leu Leu
                85                  90                  95

Lys Leu Val Gly Ile Leu Ala Cys Thr Phe Leu Ile Val Pro Ser Val
                100                 105                 110

Asp Ala Val Asp Ala Leu Lys Thr Cys Ala Cys Leu Leu Lys Glu Cys
            115                 120                 125

Arg Ile Glu Leu Ala Lys Cys Ile Ser Asn Pro Ser Cys Ala Ala Asn
130                 135                 140

Val Ala Cys Leu Gln Thr Cys Asn Asn Arg Pro Asp Glu Thr Glu Cys
145                 150                 155                 160

Gln Ile Lys Cys Gly Asp Leu Phe Glu Asn Ser Val Val Asp Glu Phe
                165                 170                 175

Asn Glu Cys Ala Val Ser Arg Lys Lys Cys Val Pro Arg Lys Ser Asp
                180                 185                 190

Leu Gly Glu Phe Pro Ala Pro Asp Pro Ala Val Leu Val Lys Arg Phe
            195                 200                 205
```

```
Asn Ile Gly Asp Phe Ser Gly Lys Trp Tyr Ile Ser Ser Gly Leu Asn
    210                 215                 220
Pro Thr Phe Asp Thr Phe Asp Cys Gln Leu His Glu Phe His Thr Glu
225                 230                 235                 240
Ser Asp Lys Leu Val Gly Asn Leu Ser Trp Arg Ile Arg Thr Pro Asp
                245                 250                 255
Gly Gly Phe Phe Thr Arg Ser Thr Val Gln Lys Phe Val Gln Asp Pro
            260                 265                 270
Asn Gln Pro Gly Ile Leu Tyr Asn His Asp Asn Glu Tyr Leu His Tyr
        275                 280                 285
Gln Asp Asp Trp Tyr Ile Leu Ser Ser Lys Val Glu Asn Gly Pro Asp
290                 295                 300
Asp Tyr Val Phe Val Tyr Tyr Arg Gly Arg Asn Asp Ala Trp Asp Gly
305                 310                 315                 320
Tyr Gly Gly Ala Val Val Tyr Thr Arg Ser Ala Val Leu Pro Asn Asn
                325                 330                 335
Ile Val Pro Glu Leu Glu Arg Ala Ala Lys Ser Val Gly Arg Asp Phe
            340                 345                 350
Ser Lys Phe Ile Arg Thr Asp Asn Thr Cys Gly Pro Glu Pro Pro Leu
        355                 360                 365
Val Glu Arg Ile Glu Lys Thr Val Glu Glu Gly Glu Arg Thr Ile Ile
370                 375                 380
Arg Glu Val Glu Gln Ile Glu Gly Glu Val Ala Lys Val Gly Glu Thr
385                 390                 395                 400
Glu Met Thr Leu Leu Gln Arg Leu Val Glu Gly Phe Lys Glu Leu Lys
                405                 410                 415
Gln Asp Glu Glu Asn Phe Leu Gln Gly Leu Asn Lys Glu Glu Met Glu
            420                 425                 430
Leu Leu Ser Glu Leu Lys Met Glu Ala Ser Glu Val Glu Lys Leu Phe
        435                 440                 445
Gly Lys Ala Leu Pro Ile Arg Lys Leu Arg
    450                 455

<210> SEQ ID NO 52
<211> LENGTH: 461
<212> TYPE: PRT
<213> ORGANISM: Camelina sativa

<400> SEQUENCE: 52

Met Ala Val Ala Thr His Cys Phe Thr Ser Pro Cys His Asp Arg Ile
1               5                   10                  15
Arg Phe Phe Ser Ser Asp Asp Gly Ile Gly Arg Leu Gly Ile Ser Arg
                20                  25                  30
Lys Arg Ile Asn Gly Thr Phe Leu Val Lys Ile Leu Pro Pro Ile Gln
            35                  40                  45
Asn Val Asp Leu Arg Thr Asn Gly Arg Ser Ser Arg Pro Leu Ser Ala
        50                  55                  60
Phe Arg Ser Gly Ile Ser Lys Gly Val Phe Asp Ile Leu Ser Leu Pro
65                  70                  75                  80
Ser Lys Asp Glu Leu Lys Glu Leu Ser Thr Pro Leu Leu Leu Lys Leu
                85                  90                  95
Val Gly Val Phe Ala Cys Ala Phe Leu Ile Val Pro Ser Ala Glu Ala
            100                 105                 110
Val Asp Ala Leu Lys Thr Cys Ala Cys Leu Leu Lys Gly Cys Arg Ile
        115                 120                 125
```

Glu Leu Ala Lys Cys Ile Ser Asn Pro Ala Cys Ala Ala Asn Ile Ala
            130                 135                 140

Cys Leu Gln Thr Cys Asn Asn Arg Pro Asp Glu Thr Glu Cys Gln Ile
145                 150                 155                 160

Lys Cys Gly Asp Ile Phe Glu Asn Lys Val Val Asp Glu Phe Asn Glu
                165                 170                 175

Cys Ala Val Thr Arg Lys Lys Cys Val Pro Lys Lys Ser Asp Leu Gly
            180                 185                 190

Glu Phe Pro Ala Pro Asp Pro Ser Val Leu Val Gln Asn Phe Asn Ile
        195                 200                 205

Gly Asp Phe Ser Gly Lys Trp Tyr Ile Thr Ser Gly Leu Asn Pro Thr
    210                 215                 220

Phe Asp Ala Phe Asp Cys Gln Leu His Glu Phe His Thr Glu Gly Glu
225                 230                 235                 240

Asn Lys Leu Val Gly Asn Ile Ser Trp Arg Ile Lys Thr Leu Asp Ser
                245                 250                 255

Gly Phe Phe Thr Arg Ser Ala Val Gln Thr Phe Val Gln Asp Pro Asn
            260                 265                 270

Gln Pro Gly Val Leu Tyr Asn His Asp Asn Glu Tyr Leu His Tyr Gln
        275                 280                 285

Asp Asp Trp Tyr Ile Leu Ser Ser Lys Ile Glu Asn Lys Pro Glu Asp
    290                 295                 300

Tyr Ile Phe Val Tyr Tyr Arg Gly Arg Asn Asp Ala Trp Asp Gly Tyr
305                 310                 315                 320

Gly Gly Ala Val Val Tyr Thr Arg Ser Ser Val Leu Pro Asn Ser Ile
                325                 330                 335

Val Pro Glu Leu Glu Lys Ala Ala Lys Ser Ile Gly Arg Asp Phe Ser
            340                 345                 350

Thr Phe Ile Arg Thr Asp Asn Thr Cys Gly Pro Glu Pro Pro Leu Val
        355                 360                 365

Glu Arg Leu Glu Lys Thr Val Glu Glu Gly Glu Arg Ile Ile Val Lys
    370                 375                 380

Asp Phe Glu Glu Ile Glu Glu Val Glu Lys Glu Val Glu Lys Val
385                 390                 395                 400

Gly Lys Thr Glu Met Thr Leu Phe Gln Arg Leu Ala Glu Gly Phe Asn
                405                 410                 415

Glu Leu Arg Lys Asp Glu Glu Asn Phe Val Arg Glu Leu Ser Lys Glu
            420                 425                 430

Glu Met Glu Phe Leu Asp Glu Ile Lys Met Glu Ala Asn Glu Val Glu
        435                 440                 445

Lys Leu Phe Gly Lys Ala Leu Pro Ile Arg Lys Val Arg
    450                 455                 460

<210> SEQ ID NO 53
<211> LENGTH: 461
<212> TYPE: PRT
<213> ORGANISM: Capsella rubella

<400> SEQUENCE: 53

Met Ala Val Ala Thr His Cys Phe Thr Ser Pro Cys His Asp Arg Ile
1               5                   10                  15

Arg Phe Phe Ser Ser Asp Asp Gly Ile Ala Arg Leu Gly Ile Ser Arg
            20                  25                  30

Lys Arg Ile Asn Gly Thr Phe Leu Val Lys Ile Leu Ser Pro Ile Gln

```
                35                  40                  45
Ser Ala Asp Leu Arg Thr Ser Gly Arg Ser Arg Pro Leu Ser Ala
 50                  55                  60

Phe Arg Ser Gly Phe Ser Lys Arg Val Phe Asp Ile Val Ser Leu Pro
65                   70                  75                  80

Ser Lys Asn Glu Leu Lys Glu Leu Ser Thr Pro Leu Leu Leu Lys Leu
                 85                  90                  95

Val Gly Val Leu Ala Cys Ala Phe Leu Ile Val Pro Ser Ala Glu Ala
                100                 105                 110

Val Asp Ala Leu Lys Thr Cys Ala Cys Leu Leu Glu Gly Cys Arg Ile
                115                 120                 125

Glu Leu Ala Lys Cys Ile Ala Asn Pro Ala Cys Ala Ala Asn Val Ala
                130                 135                 140

Cys Leu Gln Thr Cys Asn Asn Arg Pro Asp Thr Glu Cys Gln Ile
145                 150                 155                 160

Lys Cys Gly Asp Leu Phe Glu Asn Ser Val Val Asp Glu Phe Asn Glu
                165                 170                 175

Cys Ala Val Ser Arg Lys Cys Val Pro Arg Lys Ser Asp Leu Gly
                180                 185                 190

Glu Phe Pro Ala Pro Asp Pro Ser Val Leu Val Gln Asn Phe Asn Ile
                195                 200                 205

Gly Asp Phe Asn Gly Lys Trp Tyr Ile Thr Ser Gly Leu Asn Pro Thr
210                 215                 220

Phe Asp Ala Phe Asp Cys Gln Leu His Glu Phe His Thr Glu Gly Asp
225                 230                 235                 240

Asn Lys Leu Val Gly Asn Ile Ser Trp Arg Ile Lys Thr Leu Asp Ser
                245                 250                 255

Gly Phe Phe Thr Arg Ser Ala Val Gln Thr Phe Val Gln Asp Pro Asn
                260                 265                 270

Gln Pro Gly Val Leu Tyr Asn His Asp Asn Ala Tyr Leu His Tyr Gln
                275                 280                 285

Asp Asp Trp Tyr Ile Leu Ser Ser Lys Ile Glu Asn Lys Pro Glu Asp
290                 295                 300

Tyr Ile Phe Val Tyr Tyr Arg Gly Arg Asn Asp Ala Trp Asp Gly Tyr
305                 310                 315                 320

Gly Gly Ala Val Val Tyr Thr Arg Ser Ser Val Leu Pro Asn Ser Ile
                325                 330                 335

Val Pro Glu Leu Glu Lys Ala Ala Lys Ser Ile Gly Arg Asp Phe Ser
                340                 345                 350

Thr Phe Ile Lys Thr Asp Asn Thr Cys Gly Pro Glu Pro Pro Leu Val
                355                 360                 365

Glu Arg Leu Glu Lys Thr Val Glu Glu Gly Glu Arg Ile Ile Val Lys
                370                 375                 380

Glu Val Glu Glu Ile Glu Glu Val Glu Lys Glu Val Glu Lys Val
385                 390                 395                 400

Gly Lys Thr Glu Met Thr Leu Phe Gln Arg Leu Ala Glu Gly Phe Asn
                405                 410                 415

Glu Leu Lys Gln Asp Glu Glu Asn Phe Val Arg Glu Leu Ser Lys Glu
                420                 425                 430

Glu Met Glu Phe Leu Asp Glu Ile Lys Met Glu Ala Ser Glu Val Glu
                435                 440                 445

Lys Leu Phe Gly Lys Ala Leu Pro Ile Arg Lys Val Arg
450                 455                 460
```

<210> SEQ ID NO 54
<211> LENGTH: 462
<212> TYPE: PRT
<213> ORGANISM: Arabidopsis thaliana

<400> SEQUENCE: 54

```
Met Ala Val Ala Thr His Cys Phe Thr Ser Pro Cys His Asp Arg Ile
1               5                   10                  15

Arg Phe Phe Ser Ser Asp Gly Ile Gly Arg Leu Gly Ile Thr Arg
            20                  25                  30

Lys Arg Ile Asn Gly Thr Phe Leu Leu Lys Ile Leu Pro Pro Ile Gln
        35                  40                  45

Ser Ala Asp Leu Arg Thr Thr Gly Gly Arg Ser Ser Arg Pro Leu Ser
    50                  55                  60

Ala Phe Arg Ser Gly Phe Ser Lys Gly Ile Phe Asp Ile Val Pro Leu
65                  70                  75                  80

Pro Ser Lys Asn Glu Leu Lys Glu Leu Thr Ala Pro Leu Leu Leu Lys
                85                  90                  95

Leu Val Gly Val Leu Ala Cys Ala Phe Leu Ile Val Pro Ser Ala Asp
            100                 105                 110

Ala Val Asp Ala Leu Lys Thr Cys Ala Cys Leu Leu Lys Gly Cys Arg
        115                 120                 125

Ile Glu Leu Ala Lys Cys Ile Ala Asn Pro Ala Cys Ala Ala Asn Val
    130                 135                 140

Ala Cys Leu Gln Thr Cys Asn Asn Arg Pro Asp Glu Thr Glu Cys Gln
145                 150                 155                 160

Ile Lys Cys Gly Asp Leu Phe Glu Asn Ser Val Val Asp Glu Phe Asn
                165                 170                 175

Glu Cys Ala Val Ser Arg Lys Lys Cys Val Pro Arg Lys Ser Asp Leu
            180                 185                 190

Gly Glu Phe Pro Ala Pro Asp Pro Ser Val Leu Val Gln Asn Phe Asn
        195                 200                 205

Ile Ser Asp Phe Asn Gly Lys Trp Tyr Ile Thr Ser Gly Leu Asn Pro
    210                 215                 220

Thr Phe Asp Ala Phe Asp Cys Gln Leu His Glu Phe His Thr Glu Gly
225                 230                 235                 240

Asp Asn Lys Leu Val Gly Asn Ile Ser Trp Arg Ile Lys Thr Leu Asp
                245                 250                 255

Ser Gly Phe Phe Thr Arg Ser Ala Val Gln Lys Phe Val Gln Asp Pro
            260                 265                 270

Asn Gln Pro Gly Val Leu Tyr Asn His Asp Asn Glu Tyr Leu His Tyr
        275                 280                 285

Gln Asp Asp Trp Tyr Ile Leu Ser Ser Lys Ile Glu Asn Lys Pro Glu
    290                 295                 300

Asp Tyr Ile Phe Val Tyr Tyr Arg Gly Arg Asn Asp Ala Trp Asp Gly
305                 310                 315                 320

Tyr Gly Gly Ala Val Val Tyr Thr Arg Ser Ser Val Leu Pro Asn Ser
                325                 330                 335

Ile Ile Pro Glu Leu Glu Lys Ala Ala Lys Ser Ile Gly Arg Asp Phe
            340                 345                 350

Ser Thr Phe Ile Arg Thr Asp Asn Thr Cys Gly Pro Glu Pro Ala Leu
        355                 360                 365

Val Glu Arg Ile Glu Lys Thr Val Glu Glu Gly Glu Arg Ile Ile Val
```

```
                370             375             380
Lys Glu Val Glu Glu Ile Glu Glu Val Glu Lys Val Glu Lys
385                 390             395                 400

Val Gly Arg Thr Glu Met Thr Leu Phe Gln Arg Leu Ala Glu Gly Phe
                405             410                 415

Asn Glu Leu Lys Gln Asp Glu Glu Asn Phe Val Arg Glu Leu Ser Lys
                420             425             430

Glu Glu Met Glu Phe Leu Asp Glu Ile Lys Met Glu Ala Ser Glu Val
            435             440             445

Glu Lys Leu Phe Gly Lys Ala Leu Pro Ile Arg Lys Val Arg
            450             455             460

<210> SEQ ID NO 55
<211> LENGTH: 455
<212> TYPE: PRT
<213> ORGANISM: Arabidopsis lyrata

<400> SEQUENCE: 55

Met Ala Val Ala Thr His Cys Phe Thr Ser Pro Cys His Gly Arg Ile
1               5                   10                  15

Arg Phe Phe Ser Ser Asp Asp Gly Arg Leu Gly Ile Thr Arg Lys Arg
            20                  25                  30

Ile Asn Gly Thr Phe Leu Leu Lys Ile Leu Pro Pro Ile Gln Asn Ala
        35                  40                  45

Gly Gly Arg Ser Ser Arg Pro Ile Ser Ala Phe Arg Ser Gly Phe Ser
    50                  55                  60

Lys Gly Ile Phe Asp Ile Val Ala Leu Pro Ser Lys Asn Glu Leu Lys
65                  70                  75                  80

Glu Leu Thr Thr Pro Leu Leu Leu Lys Leu Val Gly Val Leu Ala Cys
                85                  90                  95

Ala Phe Leu Ile Val Pro Ser Ala Asp Ala Val Asp Ala Leu Lys Thr
            100                 105                 110

Cys Ala Cys Leu Leu Lys Gly Cys Arg Ile Glu Leu Ala Lys Cys Ile
        115                 120                 125

Ala Asn Pro Ala Cys Ala Ala Asn Val Ala Cys Leu Gln Thr Cys Asn
    130                 135                 140

Asn Arg Pro Asp Glu Thr Glu Cys Gln Ile Lys Cys Gly Asp Leu Phe
145                 150                 155                 160

Glu Asn Ser Val Val Asp Glu Phe Asn Glu Cys Ala Val Ser Arg Lys
                165                 170                 175

Lys Cys Val Pro Arg Lys Ser Asp Leu Gly Glu Phe Pro Ala Pro Asp
            180                 185                 190

Pro Ser Val Leu Val Gln Asn Phe Asn Ile Ser Asp Phe Asn Gly Lys
        195                 200                 205

Trp Tyr Ile Thr Ser Gly Leu Asn Pro Thr Phe Asp Ala Phe Asp Cys
    210                 215                 220

Gln Val His Glu Phe His Thr Glu Gly Asp Asn Lys Leu Val Gly Asn
225                 230                 235                 240

Ile Ser Trp Arg Ile Lys Thr Leu Asp Ser Gly Phe Phe Thr Arg Ser
                245                 250                 255

Ala Val Gln Lys Phe Val Gln Asp Pro Asn Gln Pro Gly Val Leu Tyr
            260                 265                 270

Asn His Asp Asn Glu Tyr Leu His Tyr Gln Asp Asp Trp Tyr Ile Leu
        275                 280                 285
```

```
Ser Ser Lys Ile Glu Asn Lys Pro Asp Asp Tyr Ile Phe Val Tyr Tyr
    290                 295                 300

Arg Gly Arg Asn Asp Ala Trp Asp Gly Tyr Gly Gly Ala Val Val Tyr
305                 310                 315                 320

Thr Arg Ser Ser Val Leu Pro Asn Ser Ile Ile Pro Glu Leu Glu Lys
                325                 330                 335

Ala Ala Lys Ser Ile Gly Arg Asp Phe Ser Thr Phe Ile Arg Thr Asp
            340                 345                 350

Asn Thr Cys Gly Pro Glu Pro Pro Leu Val Glu Arg Ile Glu Lys Thr
        355                 360                 365

Val Glu Glu Gly Glu Arg Ile Ile Val Lys Val Glu Glu Ile Glu
370                 375                 380

Glu Glu Val Glu Lys Glu Val Glu Lys Val Gly Lys Thr Glu Met Thr
385                 390                 395                 400

Leu Phe Gln Arg Leu Ala Glu Gly Phe Asn Glu Leu Lys Gln Asp Glu
                405                 410                 415

Glu Asn Phe Val Arg Glu Phe Ser Lys Glu Glu Met Glu Phe Leu Asp
            420                 425                 430

Glu Ile Lys Met Glu Ala Ser Glu Ile Glu Lys Leu Phe Gly Lys Ala
        435                 440                 445

Leu Pro Ile Arg Lys Val Arg
    450                 455

<210> SEQ ID NO 56
<211> LENGTH: 457
<212> TYPE: PRT
<213> ORGANISM: Brassica napus

<400> SEQUENCE: 56

Met Ser Val Ser Thr His Cys Phe Thr Ser Pro Cys His Asp Arg Thr
1               5                   10                  15

Arg Phe Phe Ser Gly Asp Asp Gly Asn Lys Leu Leu Arg Lys Arg Ile
            20                  25                  30

Lys Gly Thr Phe Leu Val Lys Ile Leu Pro Ser Ser Gln Asn Ala Tyr
        35                  40                  45

Leu Arg Ile Thr Ala Lys Ser Ser Arg Pro Leu Ser Gly Phe Arg Ser
50                  55                  60

Gly Ile Ser Lys Gly Val Phe Asp Ile Val Ala Leu Thr Ser Lys Asn
65                  70                  75                  80

Ala Leu Lys Glu Leu Thr Thr Pro Leu Met Leu Lys Leu Val Gly Val
                85                  90                  95

Val Ala Cys Ala Phe Leu Ile Val Pro Ser Ala Asp Ala Val Asp Ala
            100                 105                 110

Leu Lys Thr Cys Ala Cys Leu Leu Lys Gly Cys Arg Ile Glu Leu Ala
        115                 120                 125

Lys Cys Ile Ala Asn Pro Ser Cys Ala Ala Asn Val Ala Cys Leu Gln
    130                 135                 140

Thr Cys Asn Asn Arg Pro Asp Glu Thr Glu Cys Gln Ile Lys Cys Gly
145                 150                 155                 160

Asp Leu Phe Glu Asn Ser Val Asp Glu Phe Asn Glu Cys Ala Val
                165                 170                 175

Ser Arg Lys Lys Cys Val Pro Arg Lys Ser Asp Leu Gly Glu Phe Pro
            180                 185                 190

Ala Pro Asp Pro Ser Val Leu Val Lys Asn Phe Asn Ile Asn Asp Phe
        195                 200                 205
```

Asp Gly Lys Trp Tyr Ile Thr Ser Gly Leu Asn Pro Thr Phe Asp Ala
            210                 215                 220

Phe Asp Cys Gln Leu His Glu Phe His Thr Glu Asp Gly Lys Leu Val
225                 230                 235                 240

Gly Asn Ile Ser Trp Arg Ile Lys Thr Pro Asp Ser Gly Phe Phe Thr
                245                 250                 255

Arg Ser Thr Val Gln Lys Phe Val Gln Asp Pro Asn Gln Pro Ala Val
            260                 265                 270

Phe Tyr Asn His Asp Asn Glu Tyr Leu His Tyr Gln Asp Asp Trp Tyr
        275                 280                 285

Ile Leu Ser Ser Lys Ile Glu Asn Lys Pro Glu Asp Tyr Ile Phe Val
    290                 295                 300

Tyr Tyr Arg Gly Arg Asn Asp Ala Trp Asp Gly Tyr Gly Gly Ala Val
305                 310                 315                 320

Val Tyr Thr Arg Ser Ala Ser Leu Pro Asn Thr Ile Val Pro Glu Leu
            325                 330                 335

Glu Lys Ala Ala Lys Ser Ile Gly Arg Glu Phe Ser Thr Phe Ile Lys
        340                 345                 350

Thr Asp Asn Thr Cys Gly Pro Glu Pro Pro Leu Val Glu Arg Leu Glu
    355                 360                 365

Lys Thr Val Glu Glu Gly Glu Lys Ile Ile Val Lys Glu Val Glu Glu
370                 375                 380

Ile Glu Glu Glu Val Glu Lys Glu Val Glu Lys Val Gly Lys Thr Glu
385                 390                 395                 400

Met Thr Leu Phe Gln Arg Leu Ala Glu Gly Phe Glu Glu Leu Lys Gln
            405                 410                 415

Asp Glu Glu Asn Phe Leu Arg Gly Leu Ser Lys Glu Glu Met Glu Leu
        420                 425                 430

Leu Asp Glu Leu Lys Met Glu Ala Asn Glu Val Glu Lys Leu Phe Gly
    435                 440                 445

Lys Ala Leu Pro Ile Arg Lys Phe Arg
450                 455

<210> SEQ ID NO 57
<211> LENGTH: 491
<212> TYPE: PRT
<213> ORGANISM: Brassica rapa

<400> SEQUENCE: 57

Met Ser Tyr Pro Lys Gly Ile Ser Ser His Pro Tyr Ile Ser Leu Phe
1               5                   10                  15

Leu Phe Ser Leu Tyr Leu Pro Pro Leu Leu Pro Ala Glu Leu Ser Val
            20                  25                  30

Ser Ser Met Ser Val Ser Thr His Cys Phe Thr Ser Pro Cys His Asp
        35                  40                  45

Arg Thr Arg Phe Phe Ser Gly Asp Asp Gly Asn Lys Leu Leu Arg Lys
    50                  55                  60

Arg Ile Lys Gly Thr Phe Leu Val Lys Ile Leu Pro Ser Ser Gln Asn
65                  70                  75                  80

Ala Tyr Leu Arg Val Thr Ala Lys Ser Ser Arg Pro Leu Ser Gly Phe
            85                  90                  95

Arg Ser Gly Ile Ser Lys Gly Val Phe Asp Ile Val Ala Leu Thr Ser
            100                 105                 110

Lys Asn Ala Leu Lys Glu Leu Ser Thr Pro Leu Met Leu Lys Leu Val

```
            115                 120                 125
Gly Val Val Ala Cys Ala Phe Leu Ile Val Pro Ser Ala Asp Ala Val
    130                 135                 140

Asp Ala Leu Lys Thr Cys Ala Cys Leu Leu Lys Gly Cys Arg Ile Glu
145                 150                 155                 160

Leu Ala Lys Cys Ile Ala Asn Pro Ser Cys Ala Asn Val Ala Cys
                165                 170                 175

Leu Gln Thr Cys Asn Asn Arg Pro Asp Glu Thr Glu Cys Gln Ile Lys
                180                 185                 190

Cys Gly Asp Leu Phe Glu Asn Ser Val Val Asp Glu Phe Asn Glu Cys
                195                 200                 205

Ala Val Ser Arg Lys Lys Cys Val Pro Arg Lys Ser Asp Leu Gly Glu
    210                 215                 220

Phe Pro Ala Pro Asp Pro Ser Val Leu Val Lys Asn Phe Asn Val Lys
225                 230                 235                 240

Asp Phe Asp Gly Lys Trp Tyr Ile Thr Ser Gly Leu Asn Pro Thr Phe
                245                 250                 255

Asp Ala Phe Asp Cys Gln Leu His Glu Phe His Thr Glu Asp Gly Lys
                260                 265                 270

Leu Val Gly Asn Ile Ser Trp Arg Ile Lys Thr Pro Asp Ser Gly Phe
                275                 280                 285

Phe Thr Arg Ser Thr Val Gln Lys Phe Val Gln Asp Pro Asn Gln Pro
                290                 295                 300

Ala Val Phe Tyr Asn His Asp Asn Glu Tyr Leu His Tyr Gln Asp Asp
305                 310                 315                 320

Trp Tyr Ile Leu Ser Ser Lys Ile Glu Asn Lys Pro Glu Asp Tyr Ile
                325                 330                 335

Phe Val Tyr Tyr Arg Gly Arg Asn Asp Ala Trp Asp Gly Tyr Gly Gly
                340                 345                 350

Ala Val Val Tyr Thr Arg Ser Ala Ser Leu Pro Asn Thr Ile Val Pro
                355                 360                 365

Glu Leu Glu Lys Ala Ala Lys Ser Ile Gly Arg Glu Phe Ser Thr Phe
    370                 375                 380

Ile Lys Thr Asp Asn Thr Cys Gly Pro Glu Pro Leu Val Glu Arg
385                 390                 395                 400

Leu Glu Lys Thr Val Glu Glu Gly Glu Lys Ile Ile Val Lys Glu Val
                405                 410                 415

Glu Glu Ile Glu Glu Glu Val Glu Lys Val Glu Lys Val Gly Lys
                420                 425                 430

Thr Glu Met Thr Leu Phe Gln Arg Leu Ala Glu Gly Phe Glu Glu Leu
                435                 440                 445

Lys Gln Asp Glu Glu Asn Phe Leu Arg Gly Leu Ser Lys Glu Glu Met
                450                 455                 460

Glu Leu Leu Asp Glu Leu Lys Met Glu Ala Asn Glu Val Glu Lys Leu
465                 470                 475                 480

Phe Gly Lys Ala Leu Pro Ile Arg Lys Phe Arg
                485                 490

<210> SEQ ID NO 58
<211> LENGTH: 493
<212> TYPE: PRT
<213> ORGANISM: Noccaea caerulescens

<400> SEQUENCE: 58
```

-continued

```
Leu Ser Leu Ser Leu Ser Leu Ser Leu Ser Leu Leu Pro Ala
1               5                   10                  15

Glu Leu Ser Ile Phe Gly Ile Ala Ser Gly Arg Leu Ala Thr Glu Ser
            20                  25                  30

Met Ser Val Ala Thr His Cys Phe Thr Ser Pro Thr Cys His Asp Arg
        35                  40                  45

Ile Arg Phe Phe Ser Arg Ile Thr Ser Asp Asp Gly Arg Leu Val Arg
50                  55                  60

Lys Arg Ile Asn Gly Thr Phe Leu Leu Lys Ile Leu Pro Pro Ser Gln
65                  70                  75                  80

Asn Ala His Leu Arg Thr Thr Leu Arg Ser Ser Arg Pro Leu Ser Ala
            85                  90                  95

Gly Phe Arg Ser Gly Ile Ser Lys Gly Val Ile Asp Ile Val Ala Leu
            100                 105                 110

Thr Ser Arg Asn Ala Leu Lys Glu Leu Ser Thr Pro Leu Leu Leu Lys
        115                 120                 125

Leu Val Gly Val Leu Ala Cys Ala Phe Leu Ile Val Pro Ser Ala Asp
        130                 135                 140

Ala Val Asp Ala Leu Lys Thr Cys Ala Cys Leu Leu Lys Glu Cys Arg
145                 150                 155                 160

Ile Glu Leu Ala Lys Cys Ile Ala Asn Pro Ser Cys Ala Ala Asn Val
            165                 170                 175

Ala Cys Leu Gln Thr Cys Asn Asn Arg Pro Asp Glu Thr Glu Cys Gln
            180                 185                 190

Ile Lys Cys Gly Asp Leu Phe Ala Asn Ser Val Val Asp Glu Phe Asn
            195                 200                 205

Glu Cys Ala Val Ser Arg Lys Lys Cys Val Pro Arg Lys Ser Asp Leu
        210                 215                 220

Gly Glu Phe Pro Val Pro Asp Pro Ser Ala Leu Val Lys Asn Phe Asn
225                 230                 235                 240

Ile Gln Asp Phe Asn Gly Lys Trp Tyr Ile Thr Ser Gly Leu Asn Pro
            245                 250                 255

Thr Phe Asp Ile Phe Asp Cys Gln Leu His Glu Phe His Val Gln Gly
            260                 265                 270

Asn Lys Leu Val Gly Asn Ile Ser Trp Arg Ile Lys Thr Pro Asp Thr
        275                 280                 285

Gly Phe Phe Thr Arg Ser Ala Val Gln Thr Phe Lys Gln Asp Pro Asn
        290                 295                 300

Gln Pro Ala Val Leu Tyr Asn His Asp Asn Glu Tyr Leu His Tyr Gln
305                 310                 315                 320

Asp Asp Trp Tyr Ile Leu Ser Ser Lys Ile Glu Asn Lys Pro Glu Asp
            325                 330                 335

Tyr Ile Phe Val Tyr Tyr Arg Gly Arg Asn Asp Ala Trp Asp Gly Tyr
            340                 345                 350

Gly Gly Ala Val Val Tyr Thr Arg Ser Asn Val Leu Pro Asn Ser Ile
            355                 360                 365

Val Pro Glu Leu Glu Lys Ala Ala Lys Ser Ile Gly Arg Asp Phe Asn
        370                 375                 380

Thr Phe Val Arg Thr Asp Asn Thr Cys Gly Pro Glu Pro Pro Leu Val
385                 390                 395                 400

Glu Arg Leu Glu Lys Thr Val Glu Glu Gly Glu Lys Met Ile Glu Lys
            405                 410                 415

Glu Val Glu Glu Ile Glu Glu Glu Val Glu Lys Glu Val Glu Lys Val
```

```
              420                 425                 430
Gly Lys Thr Glu Met Thr Leu Phe Gln Arg Leu Ala Glu Gly Phe Asn
            435                 440                 445

Glu Leu Lys Gln Asp Glu Asn Phe Leu Arg Gly Leu Ser Glu Glu
450                 455                 460

Glu Met Ala Leu Leu Asp Glu Leu Lys Met Glu Ala Gly Glu Val Glu
465                 470                 475                 480

Lys Leu Phe Gly Lys Ala Leu Pro Ile Arg Lys Phe Arg
                485                 490

<210> SEQ ID NO 59
<211> LENGTH: 459
<212> TYPE: PRT
<213> ORGANISM: Eutrema salsugineum

<400> SEQUENCE: 59

Met Ala Val Ala Thr Tyr Cys Phe Thr Ser Pro Cys His Asp Arg Ile
1               5                  10                  15

Arg Phe Phe Ser Gly Val Thr Ser Phe Asp Gly Arg Leu Leu Arg Lys
                20                  25                  30

Arg Ile Asn Gly Thr Phe Leu Val Lys Ile Leu Pro Pro Ser Gln Asn
            35                  40                  45

Ala Asp Leu Arg Thr Thr Ser Arg Ser Ser Arg Pro Leu Ser Gly Phe
50                  55                  60

Arg Ser Gly Thr Ser Lys Gly Val Phe Asp Ile Val Ala Leu Thr Ser
65              70                  75                  80

Arg Asn Ala Leu Lys Glu Leu Ser Thr Pro Met Val Leu Lys Leu Val
                85                  90                  95

Gly Val Leu Ala Cys Ala Phe Leu Ile Val Pro Ser Ala Asp Ala Val
            100                 105                 110

Asp Ala Leu Lys Thr Cys Ala Cys Leu Leu Lys Gly Cys Arg Ile Glu
        115                 120                 125

Leu Ala Lys Cys Ile Ala Asn Pro Ser Cys Ala Ala Asn Val Ala Cys
130                 135                 140

Leu Gln Thr Cys Asn Asn Arg Pro Asp Glu Thr Glu Cys Gln Ile Lys
145                 150                 155                 160

Cys Gly Asp Leu Phe Glu Asn Lys Val Val Asp Glu Phe Asn Glu Cys
                165                 170                 175

Ala Val Ser Arg Lys Lys Cys Val Pro Gln Lys Ser Asp Leu Gly Glu
            180                 185                 190

Phe Pro Val Pro Asp Pro Ser Val Leu Val Lys Asn Phe Asn Ile Ser
        195                 200                 205

Asp Phe Asn Gly Lys Trp Tyr Ile Thr Ser Gly Leu Asn Pro Thr Phe
210                 215                 220

Asp Thr Phe Asp Cys Gln Arg His Glu Phe His Ala Asp Gly Asp Lys
225                 230                 235                 240

Leu Val Gly Asn Ile Ser Trp Arg Ile Lys Thr Leu Asp Ser Gly Phe
                245                 250                 255

Phe Thr Arg Ser Ala Val Gln Lys Phe Val Gln Asp Pro Asn Gln Pro
            260                 265                 270

Ala Ile Leu Tyr Asn His Asp Asn Glu Tyr Leu His Tyr Gln Asp Asp
        275                 280                 285

Trp Tyr Ile Leu Ser Ser Lys Val Glu Asn Lys Pro Asp Asp Tyr Ile
290                 295                 300
```

-continued

```
Phe Val Tyr Tyr Arg Gly Arg Asn Asp Ala Trp Asp Gly Tyr Gly Gly
305                 310                 315                 320

Ala Val Val Tyr Thr Arg Ser Ala Val Leu Pro Asn Ser Ile Val Pro
            325                 330                 335

Glu Leu Glu Lys Ala Ala Lys Ser Ile Gly Arg Asp Phe Ser Thr Phe
        340                 345                 350

Val Arg Thr Asp Asn Thr Cys Gly Pro Glu Pro Pro Leu Val Glu Arg
    355                 360                 365

Phe Glu Lys Thr Val Glu Gly Glu Lys Ile Ile Val Lys Glu Val
370                 375                 380

Glu Glu Ile Glu Glu Glu Val Glu Lys Glu Val Glu Lys Val Gly Lys
385                 390                 395                 400

Thr Glu Met Thr Leu Phe Gln Arg Leu Ala Glu Gly Phe Asn Glu Leu
            405                 410                 415

Lys Gln Asp Glu Glu Asn Phe Leu Arg Gly Leu Ser Glu Glu Glu Met
        420                 425                 430

Glu Leu Leu Asn Glu Leu Lys Met Glu Ala Ser Glu Val Glu Lys Leu
            435                 440                 445

Phe Gly Lys Ser Leu Pro Ile Arg Lys Val Arg
    450                 455

<210> SEQ ID NO 60
<211> LENGTH: 481
<212> TYPE: PRT
<213> ORGANISM: Prunus humilis

<400> SEQUENCE: 60

Met Ala Leu Ala Gly Arg Ser Ile Phe Leu Ser His Asn Asp Ser Ile
1               5                   10                  15

Gly Asn Thr Cys Ile Arg Leu Gly Ile Thr Ser Asp Glu Gly Phe Gln
            20                  25                  30

Lys Arg Arg Met Val Gly Phe His Val Val Lys Phe Pro Ser Asn
        35                  40                  45

Arg Arg Lys Ser Arg Tyr Ser Gln Phe Ile Arg Ser Lys Arg Asn Phe
    50                  55                  60

Cys Val Leu Gly Ser Lys Cys Ser Ser Leu Leu Ser Ser Lys Thr Glu
65                  70                  75                  80

Glu Ala Phe Ser Lys Cys Ser Thr Arg Thr Ser Glu Pro Glu Met Lys
                85                  90                  95

Arg Val Ile Ser Phe Leu Leu Glu Glu Ala Ser Ser Cys Ile Lys Glu
            100                 105                 110

Trp Ser Gln Leu His Phe Met Lys Val Ala Gly Leu Leu Ala Cys Thr
        115                 120                 125

Phe Met Ile Met Pro Ser Ala Asn Ala Ala Asp Ala Leu Lys Thr Cys
130                 135                 140

Ala Cys Leu Leu Lys Glu Cys Arg Val Glu Leu Ala Lys Cys Ile Gly
145                 150                 155                 160

Asn Pro Ser Cys Ala Ala Asn Ile Ala Cys Leu Gln Thr Cys Asn Asn
                165                 170                 175

Arg Pro Asp Glu Thr Cys Gln Ile Lys Cys Gly Asp Leu Phe Glu
            180                 185                 190

Asn Ser Val Val Asp Glu Phe Asn Glu Cys Ala Val Ser Arg Lys Lys
        195                 200                 205

Cys Val Pro Lys Lys Ser Asp Val Gly Glu Phe Pro Ile Pro Asp Pro
    210                 215                 220
```

```
Ala Val Leu Val Lys Ser Phe Asp Ile Glu Lys Phe Asn Gly Lys Trp
225                 230                 235                 240

Phe Ile Thr Ser Gly Leu Asn Pro Thr Phe Asp Ala Phe Asp Cys Gln
                245                 250                 255

Leu His Glu Phe His Thr Glu Ser Ser Lys Leu Val Gly Asn Leu Ser
            260                 265                 270

Trp Arg Ile Arg Thr Pro Asp Gly Phe Phe Thr Arg Ser Ala Val
        275                 280                 285

Gln Lys Phe Val Gln Asp Pro Asn Gln Pro Gly Ile Leu Tyr Asn His
    290                 295                 300

Asp Asn Asp Tyr Leu His Tyr Gln Asp Trp Tyr Ile Leu Ser Ser
305                 310                 315                 320

Lys Met Glu Asn Lys Pro Asp Asp Tyr Ile Phe Val Tyr Tyr Arg Gly
                325                 330                 335

Arg Asn Asp Ala Trp Asp Gly Tyr Gly Gly Ala Val Ile Tyr Thr Arg
                340                 345                 350

Ser Ser Val Leu Pro Ala Ser Ile Val Pro Asp Leu Glu Lys Ala Ala
            355                 360                 365

Ala Ser Val Gly Arg Asp Phe Ser Lys Phe Ile Arg Thr Asp Asn Thr
370                 375                 380

Cys Gly Pro Glu Pro Leu Val Glu Arg Leu Glu Lys Thr Leu Glu
385                 390                 395                 400

Glu Gly Glu Arg Asn Ile Ile Glu Glu Val Lys Gln Ile Glu Gly Glu
                405                 410                 415

Val Glu Lys Val Glu Gln Thr Glu Leu Thr Leu Leu Gln Lys Leu Ala
            420                 425                 430

Glu Gly Phe Asn Glu Leu Lys Gln Asp Glu Glu Asn Phe Leu Arg Gly
            435                 440                 445

Leu Ser Lys Glu Glu Met Asp Ile Leu Ser Glu Leu Lys Met Glu Ala
            450                 455                 460

Gly Glu Val Glu Lys Leu Phe Gly Gln Thr Leu Pro Leu Arg Lys Leu
465                 470                 475                 480

Arg

<210> SEQ ID NO 61
<211> LENGTH: 481
<212> TYPE: PRT
<213> ORGANISM: Pyrus x bretschneideri

<400> SEQUENCE: 61

Met Ala Phe Ala Gly Arg Ser Val Phe Leu Ser His Lys Glu Ser Ile
1                   5                   10                  15

Gly Asn Ala Cys Ile Arg Leu Gly Leu Lys Ser Asp Glu Arg Leu Gln
                20                  25                  30

Lys Gly Arg Met Val Gly Phe His Val Val Lys Phe Ser Ser Gln
            35                  40                  45

Arg Arg Lys Ser Arg Tyr Cys Gln Phe Ile Ser Ala Lys Arg Asn Phe
    50                  55                  60

Ser Gly Leu Gly Ser Lys Arg Ser Ser Leu Leu Ser Arg Thr Glu
65                  70                  75                  80

Glu Ala Phe Ser Glu Arg Ser Thr Lys Thr Ser Glu Pro Glu Met Gly
                85                  90                  95

Arg Ala Ile Asp Leu Met Ile Glu Glu Val Leu Ser Val Ile Lys Glu
                100                 105                 110
```

```
Trp Ser Gln Leu His Phe Met Lys Val Ala Gly Leu Leu Cys Thr
    115                 120                 125
Phe Met Val Met Pro Ser Ala Asn Ala Val Asp Ala Leu Lys Thr Cys
130                 135                 140
Ala Cys Leu Leu Lys Glu Cys Arg Val Glu Leu Ala Lys Cys Ile Gly
145                 150                 155                 160
Asn Pro Ser Cys Ala Ala Asn Ile Ala Cys Leu Gln Thr Cys Asn Asn
                165                 170                 175
Arg Pro Asp Glu Thr Glu Cys Gln Ile Lys Cys Gly Asp Leu Phe Glu
            180                 185                 190
Asn Lys Val Val Asp Glu Phe Asn Glu Cys Ala Val Ser Arg Lys Lys
        195                 200                 205
Cys Val Pro Met Lys Ser Asp Val Gly Glu Phe Pro Ile Pro Asp Pro
    210                 215                 220
Ala Ala Leu Val Lys Ser Phe Asp Met Ser Lys Phe Asn Gly Lys Trp
225                 230                 235                 240
Phe Ile Thr Ser Gly Leu Asn Pro Thr Phe Asp Val Phe Asp Cys Gln
                245                 250                 255
Leu His Glu Phe His Thr Glu Ser Ser Lys Leu Val Gly Asn Leu Ser
            260                 265                 270
Trp Arg Ile Lys Thr Pro Asp Gly Gly Phe Phe Thr Arg Ser Ala Val
        275                 280                 285
Gln Lys Phe Val Gln Asp Pro Asn Gln Pro Gly Ile Leu Tyr Asn His
    290                 295                 300
Asp Asn Glu Tyr Leu His Tyr Gln Asp Asp Tyr Trp Ile Leu Ser Ser
305                 310                 315                 320
Lys Ile Glu Asn Thr Pro Glu Asp Tyr Ile Phe Val Tyr Tyr Arg Gly
                325                 330                 335
Arg Asn Asp Ala Trp Asp Gly Tyr Gly Gly Ala Val Val Tyr Thr Arg
            340                 345                 350
Ser Ser Val Leu Pro Glu Ser Ile Val Pro Glu Leu Glu Arg Ala Ala
        355                 360                 365
Lys Ser Val Gly Arg Asp Phe Ser Lys Phe Ile Arg Thr Asp Asn Thr
    370                 375                 380
Cys Gly Pro Glu Pro Leu Val Glu Arg Leu Glu Lys Thr Ile Glu
385                 390                 395                 400
Glu Gly Glu Arg Thr Ile Ile Glu Gly Val Lys Gln Ile Glu Gly Glu
                405                 410                 415
Val Glu Lys Val Glu Gln Thr Glu Leu Thr Leu Phe Gln Lys Leu Leu
            420                 425                 430
Glu Gly Phe Asn Val Leu Lys Gln Asp Glu Asn Phe Leu Arg Gly
        435                 440                 445
Leu Ser Lys Glu Glu Met Asp Leu Leu Ser Glu Leu Lys Met Glu Ala
    450                 455                 460
Gly Glu Val Gly Lys Leu Phe Gly Lys Thr Leu Pro Leu Arg Lys Leu
465                 470                 475                 480
Arg

<210> SEQ ID NO 62
<211> LENGTH: 471
<212> TYPE: PRT
<213> ORGANISM: Bixa orellana

<400> SEQUENCE: 62
```

```
Met Ala Leu Ala Pro His Ser Thr His Phe Ser Glu Leu Thr Gly Arg
1               5                   10                  15

Arg Phe Leu Ser Arg Lys Val Val His Leu His Gly Met Val Leu Leu
                20                  25                  30

Arg Ile Gln Ser Ser Asp Arg Lys Ser Arg Tyr Ser Lys Ser Ile Asn
            35                  40                  45

Pro Tyr Arg Asn His Ile Val Ser Lys Leu Arg Cys Ser Asp Gln Leu
        50                  55                  60

Ser Glu Gly Thr His Asn Ile Ser Ser Thr Cys Ser Ser Asn Thr Arg
65                  70                  75                  80

Arg Lys His Glu Ala Lys Glu Gly Phe Glu Phe Val Val Pro Asn Leu
                85                  90                  95

Pro Asn Ile Leu Arg Lys Trp Ser Gln Leu Gln Ile Met Lys Val Ala
            100                 105                 110

Gly Val Leu Ala Cys Ala Leu Leu Val Ile Pro Ser Ala Ser Ala Val
        115                 120                 125

Asp Ala Leu Lys Thr Cys Thr Cys Leu Leu Lys Glu Cys Arg Ile Glu
    130                 135                 140

Leu Ala Lys Cys Ile Ala Asn Pro Ser Cys Ala Ala Asn Val Ala Cys
145                 150                 155                 160

Leu Gln Thr Cys Asn Asn Arg Pro Asp Glu Thr Glu Cys Gln Ile Lys
                165                 170                 175

Cys Gly Asp Leu Phe Glu Asn Ser Val Val Asp Val Phe Asn Glu Cys
            180                 185                 190

Ala Val Ser Arg Lys Lys Cys Val Pro Gln Lys Ser Asp Val Gly Glu
        195                 200                 205

Phe Ala Val Pro Asp Pro Ser Val Leu Val Lys Asn Phe Asn Ile Ala
    210                 215                 220

Asp Phe Ser Gly Lys Trp Tyr Ile Ser Ser Gly Leu Asn Pro Ser Phe
225                 230                 235                 240

Asp Thr Phe Asp Cys Gln Leu His Glu Phe His Thr Glu Ser Asn Lys
                245                 250                 255

Leu Val Gly Asn Leu Ser Trp Arg Ile Arg Thr Pro Asp Gly Gly Phe
            260                 265                 270

Phe Thr Arg Ser Thr Leu Gln Lys Phe Val Gln Asp Pro Lys Gln Pro
        275                 280                 285

Gly Ile Leu Tyr Asn His Asp Asn Glu Tyr Leu His Tyr Gln Asp Asp
    290                 295                 300

Trp Tyr Ile Leu Ser Ser Lys Ile Glu Asn Lys Gln Asp Asp Tyr Val
305                 310                 315                 320

Phe Val Tyr Tyr Arg Gly Arg Asn Asp Ala Trp Asp Gly Tyr Gly Gly
                325                 330                 335

Ala Val Val Tyr Thr Arg Ser Ala Val Leu Pro Glu Ser Ile Val Pro
            340                 345                 350

Glu Leu Glu Arg Ala Ala Lys Cys Val Gly Arg Asp Phe Asn Lys Phe
        355                 360                 365

Ile Lys Thr Asp Asn Thr Cys Gly Pro Glu Pro Pro Leu Val Glu Arg
    370                 375                 380

Leu Glu Lys Lys Val Glu Gly Glu Thr Ile Ile Arg Glu Val
385                 390                 395                 400

Glu Gln Leu Glu Gly Gln Val Glu Lys Val Gly Lys Thr Glu Met Thr
                405                 410                 415
```

```
Leu Phe Gln Lys Leu Ala Glu Gly Phe Lys Glu Leu Gln Lys Asp Glu
            420                 425                 430

Glu Asn Phe Leu Glu Glu Leu Ser Lys Glu Met Asp Val Leu Ser
        435                 440                 445

Glu Leu Lys Met Glu Ala Arg Glu Val Glu Lys Leu Phe Gly Gly Ala
    450                 455                 460

Leu Pro Leu Arg Lys Leu Arg
465             470

<210> SEQ ID NO 63
<211> LENGTH: 487
<212> TYPE: PRT
<213> ORGANISM: Theobroma cacao

<400> SEQUENCE: 63

Met Ala Gln Ala Ala Arg Ser Leu Cys Phe Ser His Asp Lys Ser Val
1               5                   10                  15

Gln Val Pro Cys Arg Thr Ser Gly Leu Thr Ser Asn Glu Arg Phe His
            20                  25                  30

Arg Arg Gln Ile Ala His Phe His Gly Ile Met Leu Val Lys Ile Gln
        35                  40                  45

Ser Ser Gly Arg Lys Ala Arg Tyr Ser Gln Leu Asn Lys Ser Asn Pro
    50                  55                  60

Asn Tyr Ser Ala Ser Asp Leu Arg Cys Ser Asn Gln Leu Ser Arg Arg
65                  70                  75                  80

Lys Asp Arg Asn Phe Ser Ser Cys Ser Cys Asn Arg Arg Pro Lys
                85                  90                  95

Ala Glu Glu Ala Phe Ala Phe Leu Val Pro Thr Ile Ser Asn Val Leu
            100                 105                 110

Lys Glu Trp Ser Gln Ser Lys Ile Val Lys Val Gly Leu Leu Ala
        115                 120                 125

Cys Ala Tyr Leu Val Ile Pro Ser Ala Ser Ala Val Asp Ala Leu Lys
130                 135                 140

Thr Cys Thr Cys Leu Leu Lys Glu Cys Arg Ile Glu Leu Ala Lys Cys
145                 150                 155                 160

Ile Ala Asn Pro Ser Cys Ala Ala Asn Ile Ala Cys Leu Gln Thr Cys
                165                 170                 175

Asn Asp Arg Pro Asp Glu Thr Glu Cys Gln Ile Lys Cys Gly Asp Leu
            180                 185                 190

Phe Glu Asn Ser Val Val Asp Glu Phe Asn Glu Cys Ala Val Ser Arg
        195                 200                 205

Lys Lys Cys Val Pro Gln Lys Ser Asp Ile Gly Glu Phe Pro Val Pro
    210                 215                 220

Ser Pro Ala Val Leu Val Lys Asn Phe Asn Ile Ala Asp Phe Ser Gly
225                 230                 235                 240

Lys Trp Phe Ile Ser Ser Gly Leu Asn Pro Thr Phe Asp Thr Phe Asp
                245                 250                 255

Cys Gln Leu His Glu Phe His Thr Glu Ala Gly Lys Leu Val Gly Asn
            260                 265                 270

Leu Ser Trp Arg Ile Gly Thr Pro Asp Gly Phe Phe Thr Arg Ser
        275                 280                 285

Thr Leu Gln Arg Phe Val Gln Asp Pro Asn Tyr Pro Gly Ile Leu Tyr
    290                 295                 300

Asn His Asp Asn Glu Tyr Leu His Tyr Gln Asp Asp Trp Tyr Ile Ile
305                 310                 315                 320
```

-continued

```
Ser Ser Lys Ile Glu Asn Lys Gln Asp Asp Tyr Ile Phe Val Tyr Tyr
            325                 330                 335

Gln Gly Arg Asn Asp Ala Trp Asp Gly Tyr Gly Ala Val Val Tyr
        340                 345                 350

Thr Arg Ser Ala Val Leu Pro Glu Ser Ile Val Pro Glu Leu Glu Lys
            355                 360                 365

Ala Ala Lys Asn Val Gly Arg Asp Phe Asn Lys Phe Ile Arg Thr Asp
        370                 375                 380

Asn Thr Cys Gly Pro Glu Pro Pro Leu Val Glu Arg Leu Glu Lys Lys
385                 390                 395                 400

Val Glu Glu Gly Glu Gln Thr Leu Ile Arg Glu Val Lys Glu Ile Glu
            405                 410                 415

Gly Glu Val Glu Lys Glu Val Lys Arg Val Glu Lys Thr Glu Met Thr
        420                 425                 430

Leu Phe Gln Lys Leu Ala Glu Gly Phe Lys Glu Leu Gln Gln Asp Glu
            435                 440                 445

Glu Asn Phe Leu Arg Gly Leu Ser Lys Glu Glu Met Gly Leu Leu Asn
        450                 455                 460

Glu Leu Lys Met Glu Ala Ser Glu Val Glu Lys Leu Phe Gly Glu Ala
465                 470                 475                 480

Leu Pro Leu Arg Lys Leu Arg
                485

<210> SEQ ID NO 64
<211> LENGTH: 479
<212> TYPE: PRT
<213> ORGANISM: Gossypium arboreum

<400> SEQUENCE: 64

Met Ala Glu Ala Ala Arg Leu Ile Cys Phe Ser His Gly Lys Ser Val
1               5                   10                  15

Lys Val Pro Cys Arg Thr Ser Gly Phe Thr Arg Lys Glu Arg Phe His
            20                  25                  30

Arg Arg Leu Val Ala His Phe His Gly Met Met Leu Leu Lys Leu Gln
        35                  40                  45

Ser Ser Cys Arg Asn Ser Arg Tyr Ser Gln Leu Ile Lys Pro Asn Met
    50                  55                  60

Asn Tyr Ser Ala Ser Lys Leu Arg Cys Ser His Gln Leu Ser Arg Arg
65                  70                  75                  80

Lys Glu Arg Lys Phe Ser Ser Ser Ser Asn Glu Arg Thr Pro Lys
            85                  90                  95

Ile Pro Thr Ile Ser Asn Leu Leu Glu Gln Trp Ser Gln Ser Gln Thr
            100                 105                 110

Val Lys Leu Val Gly Leu Leu Ala Cys Ala Tyr Leu Val Ile Pro Ser
        115                 120                 125

Ala Ala Ala Val Asp Ala Leu Lys Thr Cys Thr Cys Leu Leu Lys Glu
    130                 135                 140

Cys Arg Ile Glu Leu Ala Lys Cys Ile Ala Asn Pro Ser Cys Ala Ala
145                 150                 155                 160

Asn Val Ala Cys Leu Gln Thr Cys Asn Asp Arg Pro Asp Glu Thr Glu
                165                 170                 175

Cys Gln Ile Lys Cys Gly Asp Leu Phe Glu Asn Ser Val Val Asp Glu
            180                 185                 190

Phe Asn Glu Cys Ala Val Ser Arg Lys Lys Cys Val Pro Gln Lys Ser
```

```
                195                 200                 205
Asp Ile Gly Glu Phe Pro Val Pro Asp Pro Ala Val Leu Val Glu Asn
210                 215                 220

Phe Asn Ile Ala Asp Phe Thr Gly Lys Trp Phe Ile Ser Ser Gly Leu
225                 230                 235                 240

Asn Pro Thr Phe Asp Thr Phe Asp Cys Gln Leu His Glu Phe His Ile
                245                 250                 255

Glu Gly Gly Lys Leu Val Gly Asn Leu Ser Trp Arg Ile Arg Thr Pro
            260                 265                 270

Asp Gly Gly Phe Phe Thr Arg Ser Ala Thr Gln Arg Phe Val Gln Asp
        275                 280                 285

Pro Asn His Pro Gly Ile Leu Tyr Asn His Asp Asn Glu Tyr Leu His
    290                 295                 300

Tyr Gln Asp Asp Trp Tyr Ile Ile Ser Lys Ile Glu Asn Lys Pro
305                 310                 315                 320

Asp Asp Tyr Val Phe Val Tyr Arg Gly Arg Asn Asp Ala Trp Asp
                325                 330                 335

Gly Tyr Gly Gly Ala Val Val Tyr Thr Arg Ser Ala Val Leu Pro Glu
            340                 345                 350

Thr Ile Val Pro Glu Leu Lys Arg Ala Ala Gln Asn Val Gly Arg Asn
        355                 360                 365

Phe Asn Lys Phe Ile Arg Thr Asp Asn Ser Cys Gly Pro Glu Pro Pro
    370                 375                 380

Leu Val Glu Arg Leu Glu Lys Lys Val Glu Glu Gly Glu Gln Thr Leu
385                 390                 395                 400

Ile Arg Glu Val Glu Gln Ile Glu Gly Glu Val Lys Gly Val Glu
                405                 410                 415

Lys Val Glu Lys Thr Glu Gln Thr Leu Phe Gln Arg Leu Ala Glu Gly
            420                 425                 430

Phe Lys Glu Leu Gln Gln Asp Glu Glu Asn Phe Leu Arg Gly Leu Ser
        435                 440                 445

Lys Glu Glu Met Glu Leu Leu Asn Asp Leu Lys Met Glu Ala Ser Glu
    450                 455                 460

Val Glu Lys Leu Phe Gly Glu Ala Leu Pro Ile Arg Lys Leu Arg
465                 470                 475

<210> SEQ ID NO 65
<211> LENGTH: 487
<212> TYPE: PRT
<213> ORGANISM: Gossypium hirsutum

<400> SEQUENCE: 65

Met Ala Glu Ala Ala Arg Leu Ile Cys Phe Ser His Gly Lys Ser Val
1               5                   10                  15

Lys Val Pro Cys Arg Thr Ser Gly Phe Thr Arg Lys Glu Arg Phe His
            20                  25                  30

Arg Arg Leu Val Ala His Phe His Gly Met Met Leu Leu Lys Leu Gln
        35                  40                  45

Ser Ser Cys Arg Asn Ser Arg Tyr Ser Gln Leu Ile Lys Pro Asn Met
    50                  55                  60

Asn Tyr Ser Ala Ser Lys Leu Arg Cys Ser His Gln Phe Ser Arg Arg
65                  70                  75                  80

Lys Glu Arg Lys Phe Ser Ser Ser Ser Asn Glu Arg Thr Pro Lys
                85                  90                  95
```

Ala Glu Glu Val Phe Ser Phe Gln Ile Pro Thr Ile Ser Asn Leu Leu
            100                 105                 110

Glu Gln Trp Ser Gln Ser Gln Thr Val Lys Leu Val Gly Leu Leu Ala
        115                 120                 125

Cys Ala Tyr Leu Val Ile Pro Ser Ala Ala Val Asp Ala Leu Lys
130                 135                 140

Thr Cys Thr Cys Leu Leu Lys Glu Cys Arg Ile Glu Leu Ala Lys Cys
145                 150                 155                 160

Ile Ala Asn Pro Ser Cys Ala Ala Asn Val Ala Cys Leu Gln Thr Cys
                165                 170                 175

Asn Asp Arg Pro Asp Glu Thr Glu Cys Gln Ile Lys Cys Gly Asp Leu
            180                 185                 190

Phe Glu Asn Ser Val Val Asp Glu Phe Asn Glu Cys Ala Val Ser Arg
        195                 200                 205

Lys Lys Cys Val Pro Gln Lys Ser Asp Ile Gly Glu Phe Pro Val Pro
    210                 215                 220

Asp Pro Ala Val Leu Val Glu Asn Phe Asn Ile Ala Asp Phe Thr Gly
225                 230                 235                 240

Lys Trp Phe Ile Ser Ser Gly Leu Asn Pro Thr Phe Asp Thr Phe Asp
                245                 250                 255

Cys Gln Leu His Glu Phe His Ile Glu Gly Gly Lys Leu Val Gly Asn
            260                 265                 270

Leu Ser Trp Arg Ile Arg Thr Pro Asp Gly Gly Phe Phe Thr Arg Ser
        275                 280                 285

Ala Thr Gln Arg Phe Leu Gln Asp Pro Asn His Pro Gly Ile Leu Tyr
    290                 295                 300

Asn His Asp Asn Glu Tyr Leu His Tyr Gln Asp Asp Trp Tyr Ile Ile
305                 310                 315                 320

Ser Ser Lys Ile Glu Asn Lys Pro Asp Asp Tyr Val Phe Val Tyr Tyr
                325                 330                 335

Arg Gly Arg Asn Asp Ala Trp Asp Gly Tyr Gly Gly Ala Val Val Tyr
            340                 345                 350

Thr Arg Ser Ala Val Leu Pro Glu Thr Ile Val Pro Glu Leu Lys Arg
        355                 360                 365

Ala Ala Gln Asn Val Gly Arg Asn Phe Asn Lys Phe Ile Arg Thr Asp
    370                 375                 380

Asn Ser Cys Gly Pro Glu Pro Pro Leu Val Glu Arg Leu Glu Lys Lys
385                 390                 395                 400

Val Glu Glu Gly Glu Gln Thr Leu Ile Arg Glu Val Glu Gln Ile Glu
                405                 410                 415

Gly Glu Val Glu Lys Gly Val Glu Lys Val Glu Lys Thr Glu Gln Thr
            420                 425                 430

Leu Phe Gln Arg Leu Ala Glu Gly Phe Lys Glu Leu Gln Gln Asp Glu
        435                 440                 445

Glu Asn Phe Leu Arg Gly Leu Ser Lys Glu Glu Met Glu Leu Leu Asn
    450                 455                 460

Asp Leu Lys Met Glu Ala Ser Glu Val Glu Lys Leu Phe Gly Glu Ala
465                 470                 475                 480

Leu Pro Ile Arg Lys Leu Arg
                485

<210> SEQ ID NO 66
<211> LENGTH: 489
<212> TYPE: PRT

<213> ORGANISM: Populus trichocarpa

<400> SEQUENCE: 66

```
Met Ala Leu Ala Ala Asn Pro Phe Cys Leu Ser Gln Glu Gln Tyr Ile
1               5                   10                  15

Ile Ser Ser Ser Ser Val Ala Lys Ser Gly Leu Ala Ser Asp Gly Arg
            20                  25                  30

Phe His Arg Arg Gln Arg Leu His Phe His Gly Ala Val Leu Ser Gln
        35                  40                  45

Phe Trp Pro Asn Ser Arg Lys Leu Arg Tyr Ile Gln Ser Ile Arg Ser
    50                  55                  60

His Arg His His Tyr Gly Gly Val Ile Arg Cys Ser Asn Gln Leu Ser
65                  70                  75                  80

Asp Trp Thr Lys Lys Phe Ser Ser Leu Cys Ser Ser Ser Arg Ser
                85                  90                  95

Met Pro Lys Ala Ile Glu Arg Leu Asn Phe Val Val Leu Ser Val Thr
            100                 105                 110

Asn Ala Leu Lys Glu Arg Asn Asn Leu Glu Cys Leu Lys Leu Ala Gly
        115                 120                 125

Ile Leu Leu Cys Ala Leu Leu Val Ile Pro Ser Ala Asp Ala Val Asp
    130                 135                 140

Ala Leu Lys Thr Cys Thr Cys Leu Leu Lys Glu Cys Arg Leu Glu Leu
145                 150                 155                 160

Ala Lys Cys Ile Ala Asn Pro Ser Cys Ala Ala Asn Val Ala Cys Leu
                165                 170                 175

Gln Thr Cys Asn Asn Arg Pro Asp Glu Thr Glu Cys Gln Ala Ser Ser
            180                 185                 190

Ile Lys Cys Gly Asp Leu Phe Glu Asn Ser Val Val Asp Glu Phe Asn
        195                 200                 205

Glu Cys Ala Val Ser Arg Lys Lys Cys Val Pro Arg Lys Ser Asp Val
    210                 215                 220

Gly Glu Phe Pro Val Pro Asp Pro Ala Val Leu Val Glu Asn Phe Asn
225                 230                 235                 240

Met Ala Asp Phe Ser Gly Lys Trp Phe Ile Thr Ser Gly Leu Asn Pro
                245                 250                 255

Thr Phe Asp Thr Phe Asp Cys Gln Leu His Glu Phe His Thr Glu Ser
            260                 265                 270

Asn Lys Leu Val Gly Asn Leu Ser Trp Arg Ile Lys Thr Pro Asp Thr
        275                 280                 285

Gly Phe Phe Thr Arg Ser Ala Val Gln Arg Phe Val Gln Asp Pro Val
    290                 295                 300

His Pro Gly Ile Leu Tyr Asn His Asp Asn Glu Tyr Leu His Tyr Gln
305                 310                 315                 320

Asp Asp Trp Tyr Ile Leu Ser Ser Lys Ile Glu Asn Lys Gln Asp Asp
                325                 330                 335

Tyr Val Phe Val Tyr Tyr Gln Gly Arg Asn Asp Ala Trp Asp Gly Tyr
            340                 345                 350

Gly Gly Ala Val Val Tyr Thr Arg Ser Ala Val Leu Pro Glu Ser Ile
        355                 360                 365

Val Pro Glu Leu Glu Lys Ala Ala Lys Ser Val Gly Arg Asp Phe Ser
    370                 375                 380

Lys Phe Ile Arg Thr Asp Asn Thr Cys Gly Pro Glu Pro Pro Leu Val
385                 390                 395                 400
```

```
Glu Arg Leu Glu Lys Thr Val Glu Gly Glu Lys Thr Ile Ile Lys
            405                 410                 415

Glu Val Glu Glu Ile Glu Gln Lys Val Glu Lys Ala Gly Lys Thr Glu
        420                 425                 430

Leu Ser Leu Phe Gln Arg Leu Thr Glu Gly Phe Lys Glu Ile Gln Lys
            435                 440                 445

Asp Glu Glu Asn Phe Leu Arg Glu Leu Ser Lys Glu Glu Thr Asp Leu
450                 455                 460

Leu Asn Asp Leu Arg Met Glu Ala Gly Glu Val Glu Lys Leu Phe Gly
465                 470                 475                 480

Arg Ala Leu Pro Ile Arg Lys Leu Arg
                485

<210> SEQ ID NO 67
<211> LENGTH: 483
<212> TYPE: PRT
<213> ORGANISM: Manihot esculenta

<400> SEQUENCE: 67

Met Ala Ile Ser Ala Asn Ser Val Cys Leu Ser His Glu Glu Ser Ile
1               5                   10                  15

Cys Ser Ser Tyr Phe Arg Pro Gly Ile Ala Ser Tyr Glu Arg Ile His
            20                  25                  30

Gly Arg Arg Gly Leu Asn Tyr Gln Ser Ile Val Val Leu Asn Phe Trp
        35                  40                  45

Pro Asn Ser Arg Lys Ser Arg Tyr Val Gln Leu Met Arg Thr His Lys
    50                  55                  60

Asn Tyr His Gly Ile Lys Leu Arg Cys Ser His Gly Phe Ser Gly Trp
65                  70                  75                  80

Thr Lys Lys Phe Ser Ser Phe Cys Arg Thr Gly Ala Asn Val Thr Lys
                85                  90                  95

Ala Lys Glu Val Leu Asn Phe Leu Met Phe Ser Val Ser Asn Asn Leu
            100                 105                 110

Lys Glu Lys Ser His Leu Gln Phe Leu Lys Val Ala Ser Ile Leu Ala
        115                 120                 125

Cys Val Leu Leu Phe Ile Pro Ser Ala Asp Ala Val Asp Ala Leu Lys
130                 135                 140

Thr Cys Thr Cys Leu Leu Lys Glu Cys Arg Leu Glu Leu Ala Lys Cys
145                 150                 155                 160

Ile Ala Asn Pro Ala Cys Ala Ala Asn Ile Ala Cys Leu Gln Thr Cys
                165                 170                 175

Asn Asn Arg Pro Asp Glu Thr Glu Cys Gln Ile Lys Cys Gly Asp Leu
            180                 185                 190

Phe Glu Asn Thr Val Val Asp Glu Phe Asn Glu Cys Ala Val Ser Arg
        195                 200                 205

Lys Lys Cys Val Pro Lys Lys Ser Asp Val Gly Glu Phe Pro Val Pro
    210                 215                 220

Asp Pro Ala Val Leu Val Lys Ser Phe Asn Ile Ala Asp Phe Asn Gly
225                 230                 235                 240

Lys Trp Tyr Ile Thr Arg Gly Leu Asn Pro Thr Phe Asp Thr Phe Asp
                245                 250                 255

Cys Gln Leu His Glu Phe His Val Glu Ser Asn Lys Leu Val Gly Asn
            260                 265                 270

Ile Ser Trp Arg Ile Arg Thr Pro Asp Ser Gly Phe Phe Thr Arg Ser
        275                 280                 285
```

```
Thr Val Gln Arg Phe Val Gln Asp Pro Met Gln Pro Gly Ile Leu Tyr
            290                 295                 300

Asn His Asp Asn Glu Tyr Leu His Tyr Gln Asp Asp Trp Tyr Ile Leu
305                 310                 315                 320

Ser Ser Lys Val Glu Asn Lys Ser Asp Asp Tyr Ile Phe Val Tyr Tyr
                325                 330                 335

Arg Gly Arg Asn Asp Ala Trp Asp Gly Tyr Gly Gly Ala Val Val Tyr
                340                 345                 350

Thr Arg Ser Ser Val Leu Pro Glu Ser Ile Ala Pro Glu Leu Glu Arg
            355                 360                 365

Ala Ala Lys Ser Val Gly Arg Asp Phe Ser Lys Phe Ile Arg Thr Asp
            370                 375                 380

Asn Thr Cys Gly Pro Glu Pro Pro Leu Val Glu Arg Leu Glu Lys Thr
385                 390                 395                 400

Val Glu Glu Gly Glu Lys Ser Ile Ile Arg Glu Val Gln Glu Ile Glu
                405                 410                 415

Gly Glu Val Glu Lys Val Gly Lys Thr Glu Met Thr Leu Phe Gln Arg
                420                 425                 430

Leu Ala Glu Gly Phe Lys Glu Leu Gln Gln Asp Glu Glu Ile Leu Leu
            435                 440                 445

Arg Lys Leu Ser Lys Glu Glu Met Glu Leu Phe Asn Asp Leu Lys Met
450                 455                 460

Glu Ala Ser Glu Val Glu Lys Leu Phe Gly Gly Ala Leu Pro Leu Arg
465                 470                 475                 480

Lys Leu Arg

<210> SEQ ID NO 68
<211> LENGTH: 481
<212> TYPE: PRT
<213> ORGANISM: Jatropha curcas

<400> SEQUENCE: 68

Met Ala Leu Ala Ala Asn Ser Ile Tyr Leu Ser His Glu Ser Ile
1               5                   10                  15

Ser Ser Ser Tyr Ile Lys Ser Gly Ile Glu Arg Phe His Gly Arg Lys
                20                  25                  30

Gly Leu His Phe Arg Ser Ile Val Val Leu Lys Ile Leu Pro Asn Ser
            35                  40                  45

Arg Lys Ser Arg Arg His Val Gln Leu Ile Arg Ser Tyr Arg Asn Tyr
50                  55                  60

Cys Gly Leu Val Leu Arg Cys Ser His Gln Phe Ser Gly Trp Thr Asn
65                  70                  75                  80

Lys Phe Pro Ser Phe Ser Ser Thr Ala Ala Ser Ile Asn Lys Ala Lys
                85                  90                  95

Glu Val Leu Asn Phe Leu Met Leu Ser Val Ser Asn Asn Leu Lys Glu
                100                 105                 110

Lys Gly Gln Leu Gln Phe Leu Lys Val Ala Gly Ile Leu Ala Cys Ala
            115                 120                 125

Leu Leu Val Ile Pro Ser Ala Asp Ala Val Asp Ala Leu Lys Thr Cys
130                 135                 140

Ala Cys Leu Leu Lys Glu Cys Arg Leu Glu Leu Ala Lys Cys Ile Ala
145                 150                 155                 160

Asn Pro Ala Cys Ala Ala Asn Ile Ala Cys Leu Gln Thr Cys Asn Asn
                165                 170                 175
```

```
Arg Pro Asp Glu Thr Glu Cys Gln Ile Lys Cys Gly Asp Leu Phe Glu
            180                 185                 190
Asn Asn Val Val Asp Glu Phe Asn Glu Cys Ala Val Ser Arg Lys Lys
        195                 200                 205
Cys Val Pro Lys Lys Ser Asp Val Gly Glu Phe Pro Val Pro Asp Pro
        210                 215                 220
Ala Val Leu Val Lys Ser Phe Asn Ile Ala Asp Phe Ser Gly Lys Trp
225                 230                 235                 240
Phe Ile Thr Ser Gly Leu Asn Pro Thr Phe Asp Thr Phe Asp Cys Gln
                245                 250                 255
Leu His Asp Phe His Arg Glu Ser Asn Arg Leu Val Gly Asn Leu Ser
            260                 265                 270
Trp Arg Ile Arg Thr Pro Asp Gly Gly Phe Phe Thr Arg Ser Thr Val
            275                 280                 285
Gln Lys Phe Val Gln Asp Pro Leu Gln Pro Gly Ile Leu Tyr Asn His
        290                 295                 300
Asp Asn Glu Tyr Leu His Tyr Gln Asp Asp Trp Tyr Ile Leu Ser Ser
305                 310                 315                 320
Lys Leu Glu Asn Ser Glu Asn Asp Tyr Ile Phe Val Tyr Tyr Arg Gly
                325                 330                 335
Arg Asn Asp Ala Trp Asp Gly Tyr Gly Gly Ala Val Val Tyr Thr Arg
            340                 345                 350
Ser Ala Val Leu Pro Glu Ser Ile Ile Pro Glu Leu Glu Thr Ala Ala
            355                 360                 365
Lys Lys Val Gly Arg Asp Phe Asn Lys Phe Ile Ile Thr Asp Asn Thr
        370                 375                 380
Cys Gly Pro Glu Pro Pro Leu Ala Glu Arg Ile Glu Lys Thr Val Glu
385                 390                 395                 400
Glu Gly Glu Lys Thr Ile Ile Arg Glu Val Glu Glu Ile Glu Gly Asn
                405                 410                 415
Val Glu Lys Val Gly Lys Thr Glu Met Ala Leu Phe Gln Arg Leu Ala
            420                 425                 430
Glu Gly Phe Lys Glu Leu Gln Gln Asp Glu Glu Phe Phe Val Arg Glu
        435                 440                 445
Leu Ser Lys Glu Glu Met Asp Ile Leu Asn Asp Leu Lys Met Glu Ala
        450                 455                 460
Gly Glu Val Glu Lys Leu Phe Gly Glu Ala Leu Pro Leu Arg Lys Leu
465                 470                 475                 480
Arg
```